US012169123B2

(12) United States Patent
Bernstein et al.

(10) Patent No.: US 12,169,123 B2
(45) Date of Patent: Dec. 17, 2024

(54) GENERATION OF ONE OR MORE EDGES OF LUMINOSITY TO FORM THREE-DIMENSIONAL MODELS OF OBJECTS

(71) Applicant: VISIE Inc., Austin, TX (US)

(72) Inventors: Aaron Charles Bernstein, Austin, TX (US); Jeffrey A. Levine, Manor, TX (US); Patrick C. Edwards, Austin, TX (US)

(73) Assignee: VISIE Inc., Austin, TX (US)

( * ) Notice: Subject to any disclaimer, the term of this patent is extended or adjusted under 35 U.S.C. 154(b) by 0 days.

(21) Appl. No.: 18/505,878

(22) Filed: Nov. 9, 2023

(65) Prior Publication Data

US 2024/0110781 A1  Apr. 4, 2024

Related U.S. Application Data

(63) Continuation of application No. 17/108,527, filed on Dec. 1, 2020, now Pat. No. 11,852,461, which is a
(Continued)

(51) Int. Cl.
*G01B 11/24* (2006.01)
*A61B 1/00* (2006.01)
(Continued)

(52) U.S. Cl.
CPC .... *G01B 11/2433* (2013.01); *A61B 1/000095* (2022.02); *A61B 1/00194* (2022.02);
(Continued)

(58) Field of Classification Search
CPC ............ G01B 11/2433; G01B 11/2527; G01B 11/254; G01B 11/24; G01B 11/25; G01B 11/2518
See application file for complete search history.

(56) References Cited

U.S. PATENT DOCUMENTS 3,051,166 A   8/1962  Hovnanian
4,113,389 A   9/1978  Kaye et al.
(Continued)

FOREIGN PATENT DOCUMENTS

CA        2925620 A1    5/2014
CA      2017214735     12/2017
(Continued)

OTHER PUBLICATIONS

Baker et al: "Reconfigurable Designs for Radiosity"; Published in: 13th Annual IEEE Symposium on Field-Programmable Custom Computing Machines (FCCM'05); Date of Conference: Apr. 18-20, 2005; Date Added to IEEE Xplore: Oct. 17, 2005; Print ISBN:0-7695-2445.
(Continued)

*Primary Examiner* — Michael P Stafira

(57) ABSTRACT

Disclosed herein are various embodiments related generally to computer vision, graphics, image scanning, shadow casters, shadow caster scanners, and image processing as well as associated mechanical, electrical and electronic hardware, computer software and systems, and wired and wireless network communications to form at least three-dimensional models or images of objects and environments.

53 Claims, 77 Drawing Sheets

Related U.S. Application Data continuation of application No. 16/906,675, filed on Jun. 19, 2020, now Pat. No. 10,890,439, which is a continuation of application No. 16/496,338, filed as application No. PCT/US2018/054653 on Oct. 5, 2018, now Pat. No. 10,724,853.

(51) Int. Cl.

| | | |
|---|---|---|
| *A61B 1/06* | (2006.01) | |
| *A61B 34/10* | (2016.01) | |
| *A61B 34/20* | (2016.01) | |
| *A61B 90/00* | (2016.01) | |
| *A61B 90/20* | (2016.01) | |
| *A61B 90/30* | (2016.01) | |
| *F21V 1/08* | (2006.01) | |
| *F21V 1/10* | (2006.01) | |
| *F21V 7/00* | (2006.01) | |
| *F21V 11/12* | (2006.01) | |
| *G06T 15/60* | (2006.01) | |
| *B64U 101/30* | (2023.01) | |
| *F21Y 103/00* | (2016.01) | |

(52) U.S. Cl.
CPC ............ *A61B 1/0605* (2022.02); *A61B 34/10* (2016.02); *A61B 34/20* (2016.02); *A61B 90/20* (2016.02); *A61B 90/30* (2016.02); *A61B 90/37* (2016.02); *F21V 1/08* (2013.01); *F21V 1/10* (2013.01); *F21V 7/005* (2013.01); *F21V 11/12* (2013.01); *G06T 15/60* (2013.01); *A61B 2034/105* (2016.02); *A61B 2034/2051* (2016.02); *A61B 2034/2055* (2016.02); *A61B 2090/306* (2016.02); *A61B 2090/365* (2016.02); *A61B 2090/367* (2016.02); *A61B 2090/373* (2016.02); *A61B 2090/374* (2016.02); *A61B 2090/3762* (2016.02); *B64U 2101/30* (2023.01); *F21Y 2103/00* (2013.01); *G06T 2215/12* (2013.01)

(56) References Cited

U.S. PATENT DOCUMENTS

| | | | |
|---|---|---|---|
| 4,160,587 | A | 7/1979 | Heiniger et al. |
| 5,418,608 | A | 5/1995 | Caimi et al. |
| 5,685,305 | A | 11/1997 | Moonen et al. |
| 5,740,224 | A | 4/1998 | Müller et al. |
| 5,806,521 | A | 9/1998 | Morimoto et al. |
| 5,850,289 | A | 12/1998 | Fowler et al. |
| 5,971,767 | A | 10/1999 | Kaufman et al. |
| 6,014,472 | A | 1/2000 | Minami et al. |
| 6,023,495 | A | 2/2000 | Adler et al. |
| 6,039,457 | A | 3/2000 | O'Neal |
| 6,072,496 | A | 6/2000 | Guenter et al. |
| 6,377,865 | B1 | 4/2002 | Edelsbrunner et al. |
| 6,509,559 | B1 | 1/2003 | Ulrich et al. |
| 6,514,082 | B2 | 2/2003 | Kaufman et al. |
| 6,522,777 | B1 | 2/2003 | Paulsen et al. |
| 6,532,299 | B1 | 3/2003 | Sachdeva et al. |
| 6,592,371 | B2 | 7/2003 | Durbin et al. |
| 6,600,168 | B1 | 7/2003 | Geng |
| 6,600,553 | B1 | 7/2003 | Stone |
| 6,791,542 | B2 | 9/2004 | Matusik et al. |
| 6,803,910 | B2 | 10/2004 | Pfister et al. |
| 6,903,738 | B2 | 6/2005 | Pfister et al. |
| 6,968,075 | B1 | 11/2005 | Chang |
| 7,020,325 | B2 | 3/2006 | Park |
| 7,234,937 | B2 | 6/2007 | Sachdeva et al. |
| 7,286,954 | B2 | 10/2007 | Kopelman et al. |
| 7,305,121 | B2 | 12/2007 | Kaufmann et al. |
| 7,399,220 | B2 | 7/2008 | Kriesel et al. |
| 7,477,359 | B2 | 1/2009 | England et al. |
| 7,494,338 | B2 | 2/2009 | Durbin et al. |
| 7,643,966 | B2 | 1/2010 | Adachi et al. |
| 7,817,823 | B1 | 10/2010 | O'Donnell |
| 8,224,064 | B1 | 7/2012 | Hassebrook et al. |
| 8,284,170 | B2 | 10/2012 | Bernstein |
| 8,872,818 | B2 | 10/2014 | Freeman et al. |
| 9,098,931 | B2 | 8/2015 | Shpunt et al. |
| 9,411,079 | B1 | 8/2016 | Yu |
| 9,432,655 | B2 * | 8/2016 | Lee ...................... H04N 13/254 |
| 9,576,393 | B1 * | 2/2017 | Bethel ................. G06F 3/04815 |
| 9,600,927 | B1 | 3/2017 | Poursohi et al. |
| 9,734,397 | B1 | 8/2017 | Larson et al. |
| 9,754,398 | B1 * | 9/2017 | Cardwell .............. G06F 1/1694 |
| 9,854,155 | B1 | 12/2017 | Sikka et al. |
| 2002/0024593 | A1 | 2/2002 | Bouguet et al. |
| 2002/0057438 | A1 | 5/2002 | Decker |
| 2003/0112237 | A1 * | 6/2003 | Corbetta ................. G06T 15/60 |
| | | | 345/426 |
| 2003/0137673 | A1 | 7/2003 | Cox et al. |
| 2004/0027347 | A1 | 2/2004 | Farsalie |
| 2005/0068523 | A1 | 3/2005 | Wang et al. |
| 2005/0134588 | A1 * | 6/2005 | Aila ........................ G06T 15/60 |
| | | | 345/426 |
| 2005/0148859 | A1 | 7/2005 | Miga et al. |
| 2005/0151839 | A1 | 7/2005 | Ito et al. |
| 2005/0270645 | A1 | 12/2005 | Cossairt et al. |
| 2006/0017720 | A1 | 1/2006 | Li |
| 2006/0020204 | A1 | 1/2006 | Serra et al. |
| 2006/0023197 | A1 | 2/2006 | Joel |
| 2008/0040080 | A1 | 2/2008 | Bae et al. |
| 2009/0123045 | A1 | 5/2009 | Quadling et al. |
| 2009/0238449 | A1 | 9/2009 | Zhang et al. |
| 2010/0111370 | A1 | 5/2010 | Black et al. |
| 2010/0295853 | A1 * | 11/2010 | Diamond .............. G06T 15/405 |
| | | | 345/426 |
| 2011/0007326 | A1 | 1/2011 | Daxauer et al. |
| 2012/0092461 | A1 | 4/2012 | Fisker et al. |
| 2012/0097002 | A1 * | 4/2012 | Thiedig ................ G01B 11/046 |
| | | | 83/365 |
| 2013/0034203 | A1 | 2/2013 | Wang et al. |
| 2013/0109608 | A1 | 7/2013 | Holz |
| 2014/0047724 | A1 | 2/2014 | Winistörfer et al. |
| 2014/0271964 | A1 | 9/2014 | Roberts et al. |
| 2014/0362184 | A1 | 12/2014 | Jovanovski et al. |
| 2015/0003052 | A1 | 1/2015 | Westermarck et al. |
| 2015/0045928 | A1 | 2/2015 | Perez et al. |
| 2015/0054918 | A1 | 2/2015 | Lee et al. |
| 2016/0042552 | A1 | 2/2016 | McNabb |
| 2016/0338803 | A1 | 11/2016 | Pesach |
| 2017/0027651 | A1 | 2/2017 | Esterberg |
| 2018/0097831 | A1 | 5/2018 | Browd et al. |
| 2018/0276877 | A1 | 9/2018 | Mountney et al. |

FOREIGN PATENT DOCUMENTS

| | | | |
|---|---|---|---|
| CH | 2010133966 | | 11/2010 |
| DE | 2009000536 | | 12/2008 |
| DE | 2009115311 | | 9/2009 |
| EP | 0321095 | A2 | 6/1989 |
| EP | 0321095 | A3 | 6/1989 |
| EP | 3054311 | A2 | 8/2016 |
| GB | 2392072 | A * | 2/2004 ............. G06T 15/60 |
| GB | 2453163 | A * | 4/2009 ........... G06T 7/0077 |
| IL | 2016113745 | | 7/2016 |
| WO | 1997013180 | | 4/1997 |

OTHER PUBLICATIONS

Dimitrov: "Cascaded Shadow Maps", 1-5 • Aug. 1, 2007 (Aug. 1, 2007), pp. 1-16, XP055499196, Retrieved from the Internet: URL:http://www.cse.chalmers.se/edu/year/2011/course/TDA361/Advanced%20Computer%20Graphics/cascaded shadow maps.pdf [retrieved on Aug. 13, 2018] figures 2-4.

Vanek et al: "High-Quality Shadows with Improved Paraboloid Mapping", Sep. 26, 2011 (Sep. 26, 2011), ICIAP: International Conference on Image Analysis and Processing, 17th International Conference, Naples, Italy, Sep. 9-13, 2013. Proceedings; [Lecture

(56) References Cited

OTHER PUBLICATIONS

Notes in Computer Science; Lect. Notes Computer], Springer, Berlin, Heidelberg, pp. 421-424, XP047396785, ISBN: 978-3-642-17318-9 paragraph [0002].

* cited by examiner

GENERATION OF ONE OR MORE EDGES OF LUMINOSITY TO FORM THREE-DIMENSIONAL MODELS OF OBJECTS

CROSS-REFERENCE TO RELATED APPLICATIONS

This application is a continuation of U.S. patent application Ser. No. 16/906,675 filed Jun. 19, 2020, which is a continuation of U.S. patent application Ser. No. 16/496,338 filed Sep. 20, 2019, which is the U.S. National Stage Application of International Application No. PCT/US18/54653 filed Oct. 5, 2018, which claims benefit of U.S. Provisional Patent Application No. 62/569,353 filed Oct. 6, 2017. The contents of these applications are hereby incorporated by reference in their entirety.

STATEMENT REGARDING FEDERALLY SPONSORED RESEARCH OR DEVELOPMENT

Not Applicable

REFERENCE TO SEQUENCE LISTING, A TABLE, OR A COMPUTER PROGRAM LISTING COMPACT DISK APPENDIX

Not Applicable

BACKGROUND OF THE INVENTION

1. Field of the Invention

The present invention is in the technical field of scanning devices. More particularly, the preferred embodiments of the present invention relate generally to scanning devices, which generate three-dimensional models of the object being scanned. More particularly, the preferred embodiments of the present invention relate generally to apparatuses, systems and methods, which use shadow casters to generate three-dimensional models of objects or areas being scanned.

2. Description of the Related Art

Advances in computing hardware and software have facilitated the generation of three-dimensional models and digital imagery that convey a shape of an object in three-dimensional space. Conventional computing techniques and devices are implemented as three-dimensional ("3D") scanners to form three-dimensional models of the surface of an object being scanned. Of these, structured-light scanner systems usually use complex patterns of light and one or multiple camera systems to capture images representing a shape of an object in three dimensions. While traditional structured-light scanner systems are functional, they are not well suited to apply to a wide range of applications because these systems typically require materials and resources that make the scanners cost prohibitive. For instance, such scanners employ lasers and/or liquid crystal display ("LCD") projectors, as well as other computing hardware and algorithms that need to process the complicated light patterns and imaging techniques associated with such scanners.

At least in one approach, a scanning technique using "weak-structured" light has been developed to address one of the limitations of the structured-light scanner systems. A traditional weak-structured light-based scanner typically employs simple incandescent lights and/or a rod (e.g., pencil) to capture images from which a surface of an object may be derived. An example of such a scanner system is depicted in FIG. 1. Diagram 100 depicts a simple incandescent light bulb 102 and a rod 114, or any other cylindrical object, such as a pencil, for applying a shadow onto a plane 110 to capture the shape of object 116. Light bulb 102 includes a filament 104 extending between supports at distance ("d") 106 within a glass enclosure, which may be formed of a clear, unfrosted glass. Filament 104 typically generating light along a relatively wide range of distances relative to a width of rod 114. Generally, filament 104 may be positioned in a plane that is not parallel to rod 114. A camera 101 may be used to capture images of points that can be used to compute the surface of 116. To capture the images of points, rod 114 is used to apply a shadow over object 116 to try to determine a relative depth of a pixel on the surface of object 116 as captured by camera 101 (e.g., relative to the pixel at a point in time when object 116 is absent).

The scanner in FIG. 1 suffers a number of drawbacks. While the scanner of FIG. 1 is functional, the system of diagram 100 may not be well suited to model 3D imagery for three-dimensional objects. White light bulb 102 and rod 114 may generate a shadow 120 that includes a zone 121 of minimal illumination from a given light bulb 102. At further distances 122 from rod 114, the boundaries between zone 121 and illuminated portions 111 of plane 110 become increasingly diffuse. An example of increasing illumination diffusivity may be depicted as increasing from line 122 out along line 114 within distance ("b") 126, which illustrates a diffused boundary between zone 121 of minimal illumination and an illuminated portion 111. To counter the deleterious effects of the diffused boundary, conventional approaches to 3D scanning rely on a threshold of illumination in conjunction with temporal or video-frame coordinates and an associated algorithm to define a boundary based on sufficient differences between darkness and lightness. A diffused boundary may reduce accuracy of a surface computed from the captured image of object 116. Also, using a threshold of illumination, while operational, may require disregarding luminous effects of different colors, shades, or textures. For example, the color "yellow" may have a higher luminance that may be distinguishable from the effects of the diffused boundary, whereas the color "blue" may have a relatively lower luminance that may be detected as being part of the diffused boundary. As such, blue portion 117 of object 116 may be disregarded due to the implementation of a traditional threshold of illumination. Hence, colors and other luminous effects often cause this disregarding, an inaccuracy that is manifest in conventional 3D scanning. In some approaches, algorithmic computations are employed to classify whether a pixel is illuminated or not. These known algorithms, however, are usually limited to distinguishing between relatively substantial swings between brightness and darkness. Such thresholding may require resources to customize and adapt the scanner of diagram 100 to specific scanning applications.

Thus, what is needed is a solution for facilitating techniques to generate three-dimensional models or images of objects and environments, without the limitations of conventional techniques.

SUMMARY OF THE INVENTION

Various embodiments relate generally to computer vision, graphics, image scanning, and image processing as well as associated mechanical, electrical and electronic hardware, computer software and systems, and wired and wireless network communications to form at least three-dimensional models or images of objects and environments. The broad embodiments of the present invention relates generally to apparatuses, methods, and systems, for generating one or more edges of luminosity to form three-dimensional models of objects or environments. In broad embodiment, the present invention comprises one or more light sources and one or more shadow casters, which generate one or more edges of luminosity across objects or areas being modeled, one or more means of detecting the one or more edges of luminosity, a means of moving the one or more edges of luminosity relative to the objects or areas being modeled, and a means of generating three-dimensional models of the objects or areas being modeled, as well as related methods and systems. Most of the shadow casters in these embodiments comprise a shape with at least one edge, said edge being contained within a plane, which contains said one or more light sources, or, in other words, a shape with at least one straight edge when said shape is projected by said one or more light sources onto a plane. Some embodiments move the one or more shadow casters, some embodiments move the one or more light sources, and some embodiments move the object through the one or more edges of luminosity. These embodiments are exemplary of the scope and spirit of the present invention; however, the above described embodiments and examples should not limit the present invention, and those of ordinary skill will understand and appreciate the existence of variations, combinations, and equivalents of the specific embodiment, method, and examples herein.

In a preferred embodiment, the present invention relates broadly to apparatuses and methods, which move one or more shadow casters in order to move one or more edges of luminosity relative to the objects or areas being modeled. This embodiment relates generally to an apparatus for generating one or more edges of luminosity to form three-dimensional models of an object, said apparatus comprising: one or more light sources; one or more shadow casters, said one or more shadow casters comprising: a shape with at least one edge, said edge being contained within a plane, which contains said one or more light sources; one or more actuators, said actuators being capable of moving said one or more shadow casters; one or more image capture devices; a memory stored in non-transitory computer-readable medium; a processor, said processor comprising: said computer-readable medium; and a display; wherein said one or more light sources illuminate said one or more shadow casters to project high contrast shadows of known geometry, which form said one or more edges of luminosity on said object; wherein said one or more actuators move said one or more shadow casters in order to sweep said one or more edges of luminosity across said object; wherein said one or more image capture devices capture images of said one or more edges of luminosity on said object and record said images into said memory; wherein said processor forms a three-dimensional data representation from recorded said images; wherein said processor generates said three-dimensional model of said object using said three-dimensional data representation; and wherein said three-dimensional model is displayed on said display using said processor. This preferred embodiment also relates generally to a method for generating one or more edges of luminosity to form three-dimensional models of an object, said method comprising: providing one or more light sources; providing one or more shadow casting elements, said one or more shadow casting elements comprising: a shape with at least one edge, said edge being contained within a plane, which contains said one or more light sources; projecting high contrast shadows of known geometry to form said one or more edges of luminosity on said object using said one or more light sources and said one or more shadow casting elements; moving said one or more shadow casting elements in order to move said one or more edges of luminosity across said object; capturing images of said one or more edges of luminosity on said object; forming a three-dimensional data representation from captured said images; generating said three-dimensional model of said object using said three-dimensional data representation; and displaying said three-dimensional model. Other versions of this broad embodiment have one or more light sources, which are discrete or continuous, linear, or comprise one or more arrays of lights. Other versions of this embodiment base the shape of the one or more shadow casters on the object being scanned and modeled, such as through three-dimensional printing techniques. Additionally, some versions of this embodiment use one or more shadow casters, which further comprise configurable shapes, configurable opacity, or color filters. Other versions of this embodiment use one or more actuators to rotate the one or more shadow casters. Moreover, some versions of this embodiment use a display, which is an augmented reality headset that can overlay the three-dimensional model over the view of a user of the headset.

In another preferred embodiment, the present invention relates broadly to apparatuses and methods, which move one or more light sources in order to move one or more edges of luminosity relative to the objects or areas being modeled. This embodiment relates generally to an apparatus for generating one or more edges of luminosity to form three-dimensional models of an object, said apparatus comprising: one or more light sources; one or more shadow casters, said one or more shadow casters comprising: a shape with at least one edge, said edge being contained within a plane, which contains said one or more light sources; one or more actuators, said actuators being capable of moving said one or more light sources; one or more image capture devices; a memory stored in non-transitory computer-readable medium; a processor, said processor comprising: said computer-readable medium; and a display; wherein said one or more light sources illuminate said one or more shadow casters to project high contrast shadows of known geometry, which form said one or more edges of luminosity on said object; wherein said one or more actuators move said one or more light sources in order to sweep said one or more edges of luminosity across said object; wherein said one or more image capture devices capture images of said one or more edges of luminosity on said object and record said images into said memory; wherein said processor forms a three-dimensional data representation from recorded said images; wherein said processor generates said three-dimensional model of said object using said three-dimensional data representation; and wherein said three-dimensional model is displayed on said display using said processor. This preferred embodiment also relates generally to a method for generating one or more edges of luminosity to form three-dimensional models of an object, said method comprising: providing one or more light sources; providing one or more shadow casting elements, said one or more shadow casting elements comprising: a shape with at least one edge, said edge being contained within a plane, which contains said one or more light sources; projecting high contrast shadows of known geometry to form said one or more edges of luminosity on said object using said one or more light sources and said one or more shadow casting elements;

moving said one or more light sources in order to move said one or more edges of luminosity across said object; capturing images of said one or more edges of luminosity on said object; forming a three-dimensional data representation from captured said images; generating said three-dimensional model of said object using said three-dimensional data representation; and displaying said three-dimensional model. Other versions of this broad embodiment have one or more light sources, which are discrete or continuous, linear, or comprise one or more arrays of lights. Other versions of this embodiment base the shape of the one or more shadow casters on the object being scanned and modeled, such as through three-dimensional printing techniques. Additionally, some versions of this embodiment use one or more shadow casters, which further comprise configurable shapes, configurable opacity, or color filters. Furthermore, other versions of this embodiment use one or more actuators to rotate the one or more shadow casters. Moreover, some versions of this embodiment use a display, which is an augmented reality headset that can overlay the three-dimensional model over the view of a user of the headset.

In another preferred embodiment, the present invention relates broadly to apparatuses and methods, which move the object being modeled through the one or more edges of luminosity. This embodiment relates generally to an apparatus for generating one or more edges of luminosity to form three-dimensional models of an object, said apparatus comprising: one or more light sources; one or more shadow casters, said one or more shadow casters comprising: a shape with at least one edge, said edge being contained within a plane, which contains said one or more light sources; one or more image capture devices; a memory stored in non-transitory computer-readable medium; a processor, said processor comprising: said computer-readable medium; and a display; wherein said one or more light sources illuminate said shadow casters to project high contrast shadows of known geometry, which form said one or more edges of luminosity; wherein said object moves through said one or more edges of luminosity in order to sweep said one or more edges of luminosity across said object; wherein said one or more image capture devices detect the motion of said object moving through said one or more edges of luminosity and records said motion into said memory; wherein said one or more image capture devices capture images of said one or more edges of luminosity on said object moving through said one or more edges of luminosity and record said images into said memory; wherein said processor calculates the velocity of said object moving through said one or more edges of luminosity from recorded said motion; wherein said processor forms a three-dimensional data representation from recorded said images and calculated said velocity; wherein said processor generates said three-dimensional model of said object using said three-dimensional data representation; and wherein said three-dimensional model is displayed on said display. This preferred embodiment also relates generally to a method for generating one or more edges of luminosity to form three-dimensional models of an object, said method comprising: providing one or more light sources; providing one or more shadow casting elements, said one or more shadow casting elements comprising: a shape with at least one edge, said edge being contained within a plane, which contains said one or more light sources; projecting high contrast shadows of known geometry to form said one or more edges of luminosity on said object using said one or more light sources and said one or more shadow casting elements; moving said object through said one or more edges of luminosity; detecting the velocity of said object moving through said one or more edges of luminosity; capturing images of said one or more edges of luminosity on said object moving through said one or more edges of luminosity; forming a three-dimensional data representation from detected said velocity and captured said images; generating said three-dimensional model of said object using said three-dimensional data representation; and displaying said three-dimensional model. Other versions of this broad embodiment have one or more light sources, which are discrete or continuous, linear, or comprise one or more arrays of lights. Other versions of this embodiment base the shape of the one or more shadow casters on the object being scanned and modeled, such as through three-dimensional printing techniques. Additionally, some versions of this embodiment use one or more shadow casters, which further comprise configurable shapes, configurable opacity, or color filters. Other versions of this embodiment use one or more actuators to rotate the one or more shadow casters. Moreover, some versions of this embodiment use a display, which is an augmented reality headset that can overlay the three-dimensional model over the view of a user of the headset. Still other version of this embodiment are installed in a room and mounted on the ceiling with similar versions having the one or more light sources mounted on the ceiling.

In another preferred embodiment, the present invention relates broadly to apparatuses and methods, which model the surroundings of an object. This embodiment relates generally to an apparatus for generating one or more edges of luminosity to form, said apparatus comprising: one or more light sources, said one or more light sources being mounted on said object; one or more shadow casters, said one or more shadow casters being mounted on said object and comprising: a shape with at least one edge, said edge being contained within a plane, which contains said one or more light sources; one or more actuators, said actuators being capable of moving said one or more shadow casters; one or more image capture devices, said one or more image capture devices being mounted on said object; a memory stored in non-transitory computer-readable medium; and a processor, said processor comprising: said computer-readable medium; wherein said one or more light sources illuminate said one or more shadow casters to project high contrast shadows of known geometry, which form said one or more edges of luminosity on said surroundings of said object; wherein said one or more actuators move said one or more shadow casters in order to sweep said one or more edges of luminosity across said surroundings of said object; wherein said one or more image capture devices capture images of said one or more edges of luminosity on said surroundings of said object and record said images into said memory; wherein said processor forms a three-dimensional data representation from recorded said images; wherein said processor generates said three-dimensional model of said surroundings of said object using said three-dimensional data representation; and wherein said three-dimensional model is stored in said memory. This preferred embodiment also relates generally to a method for generating one or more edges of luminosity to form three-dimensional models of the surroundings of an object, said method comprising: providing one or more light sources, said one or more light sources being mounted on said object; providing one or more shadow casting elements, said one or more shadow casting elements being mounted on said object and comprising: a shape with at least one edge, said edge being contained within a plane, which contains said one or more light sources; projecting high contrast shadows of known geometry to form said one or more edges of luminosity on said surroundings of said object using said one or more light sources and said one or more shadow casting elements; moving said one or more shadow casting elements in order to move said one or more edges of luminosity across said surroundings of said object; capturing images of said one or more edges of luminosity on said surroundings of said object; forming a three-dimensional data representation from captured said images; generating said three-dimensional model of said surroundings of said object using said three-dimensional data representation; and storing said three-dimensional model in non-transitory computer-readable medium. Other versions of this broad embodiment have one or more light sources, which are discrete or continuous, linear, or comprise one or more arrays of lights. Additionally, some versions of this embodiment use one or more shadow casters, which further comprise configurable shapes, configurable opacity, or color filters. Furthermore, some versions of this embodiment use an augmented reality headset and display the model overlaid on the surroundings of the object, while similar versions display the model overlaid on the surroundings of the augmented reality headset. Moreover, this embodiment of the present invention may be used on a vehicle, such as for use as artificial vision for an autonomous automobile or submersible vehicle, in which case the apparatus comprises water resistant parts. Similarly, this embodiment may be used for artificial vision for a robot.

In another preferred embodiment, the present invention relates broadly to apparatuses and methods, which model the surroundings of an object using a static shadow caster. This embodiment relates generally to an apparatus for generating one or more edges of luminosity to form three-dimensional models of the surroundings of an object, said apparatus comprising: one or more light sources, said one or more light sources being mounted on said object; one or more shadow casters, said one or more shadow casters being mounted on said object and comprising: a shape with at least one edge, said edge being contained within a plane, which contains said one or more light sources; one or more image capture devices, said one or more image capture devices being mounted on said object; a memory stored in non-transitory computer-readable medium; and a processor, said processor comprising: said computer-readable medium; wherein said one or more light sources illuminate said one or more shadow casters to project high contrast shadows of known geometry, which form said one or more edges of luminosity on said surroundings of said object; wherein said object moves through said surroundings of said object in order to sweep said one or more edges of luminosity across said surroundings of said object; wherein said one or more image capture devices capture images of said one or more edges of luminosity on said surroundings of said object and record said images into said memory; wherein said processor forms a three-dimensional data representation from recorded said images; wherein said processor generates said three-dimensional model of said surroundings of said object using said three-dimensional data representation; and wherein said three-dimensional model is stored in said memory. This preferred embodiment also relates generally to a method for generating one or more edges of luminosity to form three-dimensional models of the surroundings of an object, said method comprising: providing one or more light sources, said one or more light sources being mounted on said object; providing one or more shadow casting elements, said one or more shadow casting elements being mounted on said object and comprising: a shape with at least one edge, said edge being contained within a plane, which contains said one or more light sources; projecting high contrast shadows of known geometry to form said one or more edges of luminosity on said surroundings of said object using said one or more light sources and said one or more shadow casting elements; moving said object in order to move said one or more edges of luminosity across said surroundings of said object; capturing images of said one or more edges of luminosity on said surroundings of said object; forming a three-dimensional data representation from captured said images; generating said three-dimensional model of said surroundings of said object using said three-dimensional data representation; and storing said three-dimensional model in non-transitory computer-readable medium. Other versions of this broad embodiment have one or more light sources, which are discrete or continuous, linear, or comprise one or more arrays of lights. Additionally, some versions of this embodiment use one or more shadow casters, which further comprise configurable shapes, configurable opacity, or color filters. Furthermore, some versions of this embodiment use an augmented reality headset and display the model overlaid on the surroundings of the object, while similar versions display the model overlaid on the surroundings of the augmented reality headset. Moreover, this embodiment of the present invention may be used on a vehicle, such as for use as artificial vision for an autonomous automobile or submersible vehicle, in which case the apparatus comprises water resistant parts. Similarly, this embodiment may be used for artificial vision for a robot.

In the most preferred embodiment, the present invention relates generally to an apparatus for generating one or more edges of luminosity to form three-dimensional models of an object, said apparatus comprising: an outer housing, said outer housing comprising: a back panel, said back panel comprising: a camera opening, a top panel, and two side panels, said side panels comprising: a pivot point; a shadow caster, said shadow caster comprising: a front segment, said front segment being rectangular, two side segments, each said side segment depending perpendicularly from opposite ends of said front segment, each said side segment comprising: a triangular shape, and a shoulder mount, each said shoulder mount comprising: a shoulder screw hole, and a shoulder screw, said shoulder screw being rotatably attached to said side panel using a nut, and a tab, said tab depending from one said side segment; an actuator assembly, said actuator assembly comprising: an actuator arm, said actuator arm depending from said outer housing, an actuator motor, said actuator motor depending from said actuator arm, and an actuator connector, said actuator connector depending from said actuator motor and connecting to said tab of said shadow caster; a light source, said light source being discrete, continuous, linear, and extending between said shoulder screws of said shoulder mounts of said side segments of said shadow caster; a video cameras assembly, said video camera assembly extending through said camera opening of said back panel of said outer housing, said video camera assembly comprising: a video camera support platform, and a video camera, said video camera being mounted on said video camera support platform, said video camera comprising: a camera lens, a camera sync port, a video output port, and a control port; a memory stored in non-transitory computer-readable medium; a processor, said processor comprising: said computer-readable medium; and a display; wherein said light source illuminates said shadow caster to project high contrast shadows of known geometry, which form said one or more edges of luminosity on said object; wherein said actuator motor moves said shadow caster in order to sweep said one or more edges of luminosity across said object; wherein said video camera captures images of said one or more edges of luminosity on said object and record said images into said memory; wherein said processor forms a three-dimensional data representation from recorded said images; wherein said processor generates said three-dimensional model of said object using said three-dimensional data representation; and wherein said three-dimensional model is displayed on said display using said processor. Other versions of this embodiment base the shape of the one or more shadow casters on the object being scanned and modeled, such as through three-dimensional printing techniques. Additionally, some versions of this embodiment use one or more shadow casters, which further comprise configurable shapes, configurable opacity, or color filters. Moreover, some versions of this embodiment use a display, which is an augmented reality headset that can overlay the three-dimensional model over the view of a user of the headset. Other version of this embodiment use a front segment of the shadow caster with multiple front sections and side segments with multiple side sections. Additional versions are used in a room with the apparatus mounted on the ceiling. For a particular application, a version of this embodiment may be used to scan a whole person and generate a three-dimensional model of the skin of the person, such as for use in dermatology for creating a map of moles or skin lesions, or inspecting a patient for skin cancer or similar ailments, or the like. As another specific application of the most preferred embodiment of the present invention, the apparatus may be used during brain surgery of a patient, with the apparatus further comprising a drape, which conforms to said outer housing of the apparatus and is capable of protecting the patient from contamination, and a clamp assembly, which is capable of fixing the position of the apparatus relative to the patient. This preferred embodiment also relates generally to a method of using the apparatus for brain surgery of a patient, said method comprising: draping said apparatus with a drape, said drape conforming to said outer housing of said apparatus and being capable of protecting said patient from contamination; aligning said apparatus with said patient; focusing said video camera of said apparatus on said patient; starting to record video of said patient using said video camera; sweeping said one or more edges of luminosity across said patient using said actuator motor; capturing images of said one or more edges of luminosity on said patient using said video camera; stopping to record video of said patient; collecting and analyzing said images using said processor; forming a three-dimensional data representation from said images using said processor; generating said three-dimensional model of said patient using said three-dimensional data representation using said processor; and displaying said three-dimensional model on said display using said processor. This preferred embodiment also relates generally to a method of using the apparatus for robotic brain surgery of a patient, said method comprising: providing a robot for controlling said apparatus, said robot being capable of controlling said video camera and said actuator motor and of interacting with said processor, said robot comprising: a navigation computer, said navigation computer being capable of navigating said robot, said navigation computer comprising: said memory, and said computer-readable medium, one ore more positioning robotic motors, one or more aligning robotic motors, and one or more focusing robotic motors; draping said apparatus with a drape, said drape conforming to said outer housing of said apparatus and being capable of protecting said patient from contamination; positioning said apparatus over said patient using said one or more positioning robotic motors; aligning said apparatus with said patient using said one or more aligning robotic motors; focusing said video camera of said apparatus on said patient using said one or more focusing robotic motors; recording video of said patient using robotically-controlled said video camera; sweeping said one or more edges of luminosity across said patient using robotically-controlled said actuator motor; capturing images of said one or more edges of luminosity on said patient using robotically-controlled said video camera; collecting and analyzing said images using said processor; forming a three-dimensional data representation from said images using said processor; generating said three-dimensional model of said patient using said three-dimensional data representation using said processor; storing said three-dimensional model to said navigation computer of said robot for use during said robotic brain surgery. Additionally, this preferred embodiment also relates generally to a method of using the apparatus for brain surgery of a patient, said method comprising: scanning the brain of said patient prior to said brain surgery using other scanning techniques to generate a prior model of said brain, said other scanning techniques comprising: an MRI scan, a CT scan, a PET scan, or an ultrasound scan; storing said prior model in said memory using said processor; draping said apparatus with a drape, said drape conforming to said outer housing of said apparatus and being capable of protecting said patient from contamination; aligning said apparatus with said patient; focusing said video camera of said apparatus on said patient; starting to record video of said patient using said video camera; sweeping said one or more edges of luminosity across said patient using said actuator motor; capturing images of said one or more edges of luminosity on said patient using said video camera; stopping to record video of said patient; collecting and analyzing said images using said processor; forming a three-dimensional data representation from said images using said processor; generating said three-dimensional model of said patient using said three-dimensional data representation using said processor; comparing said three-dimensional model to said prior model using said processor; and displaying said three-dimensional model overlaid with said prior model on said display using said processor. This preferred embodiment also relates generally to a method of using the apparatus for brain surgery of a patient with a rhythmically pulsing brain, said method comprising: draping said apparatus with a drape, said drape conforming to said outer housing of said apparatus and being capable of protecting said patient from contamination; aligning said apparatus with said rhythmically pulsing brain of said patient; focusing said video camera of said apparatus on said rhythmically pulsing brain of said patient; starting to record video of said rhythmically pulsing brain of said patient using said video camera; measuring the blood pressure wave profile of said patient, said blood pressure wave profile comprising: the rhythmic pulsing of the blood pressure of said patient; sweeping said one or more edges of luminosity across said rhythmically pulsing brain of said patient using said actuator motor; capturing images of said one or more edges of luminosity on said rhythmically pulsing brain of said patient using said video camera; stopping to record video of said rhythmically pulsing brain of said patient; collecting and analyzing said images using said processor; eliminating the rhythmic motion of said rhythmically pulsing brain of said patient using said blood pressure wave profile and said processor; accounting for the scanning motion of said shadow caster using said processor; forming a three-dimensional data representation from said images and eliminated said rhythmic motion of said rhythmically pulsing brain of said patient using said processor; generating said three-dimensional model of said patient using said three-dimensional data representation using said processor; and displaying said three-dimensional model on said display using said processor.

In another preferred embodiment, the present invention relates generally to endoscope apparatuses. This embodiment relates generally to an apparatus for generating one or more edges of luminosity to form three-dimensional models of an object, said apparatus comprising: an endoscope body, said endoscope body comprising: a proximal end, a distal end, an endoscope sleeve, said endoscope sleeve spanning between said proximal end and said distal end, a tapered fiber optic bundle, said tapered fiber optic bundle being disposed within said endoscope sleeve and tapered towards said distal end, and an endoscope camera, said endoscope camera being disposed within said endoscope sleeve and facing out said distal end; a shadow caster, said shadow caster being mounted on said distal end of said endoscope body over said tapered fiber optic bundle, said shadow caster comprising: a semi-circular piece; a light launch, said light launch comprising: a horizontal platform, a vertical stand, said vertical stand distending from said horizontal platform, a stepper motor linear actuator, said stepper motor linear actuator distending from said horizontal platform, a translating platform, said translating platform being connected to said stepper motor linear actuator, a light source, said light source depending from said translating platform, an optic fiber bundle, said optic fiber bundle depending from said light source, a square-to-round taper, said square-to-round taper depending from said optic fiber bundle, and a slit, said slit being mounted on said square-to-round taper; a memory stored in non-transitory computer-readable medium; a processor, said processor comprising: said computer-readable medium; and a display; wherein said light launch is connected to said proximal end of said endoscope body; wherein said light source illuminates said optic fiber bundle, said square-to-round taper, said slit, said tapered fiber optic bundle, and said shadow caster, to project high contrast shadows of known geometry, which form said one or more edges of luminosity on said object; wherein said stepper motor linear actuator moves said translating platform with said light source in order to sweep said one or more edges of luminosity across said object; wherein said endoscope camera captures images of said one or more edges of luminosity on said object and records said images into said memory; wherein said processor forms a three-dimensional data representation from recorded said images; wherein said processor generates said three-dimensional model of said object using said three-dimensional data representation; and wherein said three-dimensional model is displayed on said display using said processor. This preferred embodiment also relates generally to an apparatus for generating one or more edges of luminosity to form three-dimensional models of an object, said apparatus comprising: an endoscope body, said endoscope body comprising: a proximal end, a distal end, an endoscope sleeve, said endoscope sleeve spanning between said proximal end and said distal end, a tapered fiber optic bundle, said tapered fiber optic bundle being disposed within said endoscope sleeve and tapered towards said distal end, and an endoscope camera, said endoscope camera being disposed within said endoscope sleeve and facing out said distal end; a shadow caster, said shadow caster being mounted on said distal end of said endoscope body over said tapered fiber optic bundle, said shadow caster comprising: a semi-circular piece; a light launch, said light launch comprising: a horizontal platform, a vertical stand, said vertical stand distending from said horizontal platform, a stepper motor linear actuator, said stepper motor linear actuator distending from said horizontal platform, a supporting platform, said supporting platform depending from said vertical stand, a light source, said light source depending from said supporting platform, an optic fiber bundle, said optic fiber bundle depending from said light source, a square-to-round taper, said square-to-round taper depending from said optic fiber bundle, and a slit, said slit being mounted to said stepper motor linear actuator; a memory stored in non-transitory computer-readable medium; a processor, said processor comprising: said computer-readable medium; and a display; wherein said light launch is connected to said proximal end of said endoscope body; wherein said light source illuminates said optic fiber bundle, said square-to-round taper, said slit, said tapered fiber optic bundle, and said shadow caster, to project high contrast shadows of known geometry, which form said one or more edges of luminosity on said object; wherein said stepper motor linear actuator moves slit in order to sweep said one or more edges of luminosity across said object; wherein said endoscope camera captures images of said one or more edges of luminosity on said object and records said images into said memory; wherein said processor forms a three-dimensional data representation from recorded said images; wherein said processor generates said three-dimensional model of said object using said three-dimensional data representation; and wherein said three-dimensional model is displayed on said display using said processor. Other versions of this embodiment use a tapered fiber optic bundle, which is rectangular or rounded-rectangular. Additionally, some versions of this embodiment use one or more shadow casters, which further comprise configurable shapes, configurable opacity, or color filters.

In another preferred embodiment, the present invention relates generally to systems, which use drones to model an area. This embodiment relates generally to a system for generating one or more edges of luminosity to form three-dimensional models of an area, said system comprising: a plurality of shadow drones, each said shadow drones comprising: a drone, said drone comprising: a remote controlled flying vehicle, and a shadow caster, said shadow caster comprising: a panel, said panel depending from said drone; a plurality of camera drones, each said camera drones comprising: said drone, and an image capture device, said image capture device depending from said drone; a memory stored in non-transitory computer-readable medium; a processor, said processor being able to control said shadow drones and said camera drones, said processor comprising: said computer-readable medium; and a display; wherein said plurality of shadow drones are aligned in a flight formation so that said shadow casters form a substantially continuous collective shadow caster, said collective shadow caster comprising aligned said shadow casters; wherein the sun illuminates said collective shadow caster to project high contrast shadows of known geometry, which form said one or more edges of luminosity on said area; wherein aligned said plurality of shadow drones in said flight formation move in formation across said area in order to sweep said one or more edges of luminosity across said area; wherein said image capture devices of said camera drones capture images of said one or more edges of luminosity on said area and record said images into said memory; wherein said processor forms a three-dimensional data representation from recorded said images; wherein said processor generates said three-dimensional model of said area using said three-dimensional data representation; and wherein said three-dimensional model is displayed on said display using said processor. This preferred embodiment also relates generally to a system for generating one or more edges of luminosity to form three-dimensional models of an area, said system comprising: a plurality of shadow drones, each said shadow drones comprising: a drone, said drone comprising: a remote controlled flying vehicle, and a shadow caster, said shadow caster comprising: a panel, said panel depending from said drone; a plurality of light drones, each said light drones comprising: said drone, and a light source, said light source depending from said drone; a plurality of camera drones, each said camera drones comprising: said drone, and an image capture device, said image capture device depending from said drone; a memory stored in non-transitory computer-readable medium; a processor, said processor being able to control said shadow drones, said light drones, and said camera drones, said processor comprising: said computer-readable medium; and a display; wherein said plurality of shadow drones are aligned in a flight formation so that said shadow casters form a substantially continuous collective shadow caster, said collective shadow caster comprising aligned said shadow casters; wherein said light drones illuminate said collective shadow caster to project high contrast shadows of known geometry, which form said one or more edges of luminosity on said area; wherein aligned said plurality of shadow drones in said flight formation move in formation across said area in order to sweep said one or more edges of luminosity across said area; wherein said image capture devices of said camera drones capture images of said one or more edges of luminosity on said area and record said images into said memory; wherein said processor forms a three-dimensional data representation from recorded said images; wherein said processor generates said three-dimensional model of said area using said three-dimensional data representation; and wherein said three-dimensional model is displayed on said display using said processor. Other versions of this embodiment use one or more shadow casters, which further comprise configurable shapes, configurable opacity, or color filters. Additionally, some versions of this embodiment use a display, which is an augmented reality headset that can overlay the three-dimensional model over the view of a user of the headset.

In another preferred embodiment, the present invention relates generally to systems, which model an area, such as a large stadium, or the like. This embodiment relates generally to a system for generating one or more edges of luminosity to form three-dimensional models of an area, said system comprising: a shadow caster platform, said shadow casting platform being horizontal and capable of rotation; a light source, said light source depending from the center of said shadow caster platform; at least one shadow caster, each said shadow caster depending from said shadow caster platform around said light source and comprising: a vertical panel, and an angled panel, said angled panel being angled towards said light source; a plurality of image capture devices, each said image capture device being mounted on a tripod; a memory stored in non-transitory computer-readable medium; a processor, said processor comprising: said computer-readable medium; and a display; wherein said plurality of image capture devices are arranged around said shadow caster platform; wherein said light source illuminates said shadow casters to project high contrast shadows of known geometry, which form said one or more edges of luminosity on said area; wherein said shadow caster platform is rotated, thereby rotating said shadow casters around said light source in order to sweep said one or more edges of luminosity across said area; wherein said plurality of image capture devices capture images of said one or more edges of luminosity on said area and record said images into said memory; wherein said processor forms a three-dimensional data representation from recorded said images; wherein said processor generates said three-dimensional model of said area using said three-dimensional data representation; and wherein said three-dimensional model is displayed on said display using said processor. This preferred embodiment also relates generally to a system for generating one or more edges of luminosity to form three-dimensional models of an area, said system comprising: a shadow caster platform, said shadow casting platform being horizontal; a light source, said light source being directional, being capable of rotation, and depending from the center of said shadow caster platform; at least one shadow caster, each said shadow caster depending from said shadow caster platform around said light source and comprising: a vertical panel, and an angled panel, said angled panel being angled towards said light source; a plurality of image capture devices, each said image capture device being mounted on a tripod; a memory stored in non-transitory computer-readable medium; a processor, said processor comprising: said computer-readable medium; and a display; wherein said plurality of image capture devices are arranged around said shadow caster platform; wherein said light source illuminates said shadow casters to project high contrast shadows of known geometry, which form said one or more edges of luminosity on said area; wherein said light source is moved in order to sweep said one or more edges of luminosity across said area; wherein said plurality of image capture devices capture images of said one or more edges of luminosity on said area and record said images into said memory; wherein said processor forms a three-dimensional data representation from recorded said images; wherein said processor generates said three-dimensional model of said area using said three-dimensional data representation; and wherein said three-dimensional model is displayed on said display using said processor. Other versions of this embodiment use one or more shadow casters, which further comprise configurable shapes, configurable opacity, or color filters. Additionally, some versions of this embodiment use a display, which is an augmented reality headset that can overlay the three-dimensional model over the view of a user of the headset.

In another preferred embodiment, the present invention relates broadly to methods of generating a shaped shadow caster, which is used in many of the above-preferred embodiments. This present embodiment relates generally to a method of creating a custom shadow caster for generating one or more edges of luminosity to form three-dimensional models of an object, said method comprising: providing a three-dimensional printer; determining the profile of said object using photography, video, or shadow projection; three-dimensionally printing said custom shadow caster in the shape of said profile using said three-dimensional printer; and placing said custom shadow caster substantially close to said object when generating said one or more edges of luminosity.

In another preferred embodiment, the present invention relates to an apparatus, a slitted linear light source, which may be used in many of the above-preferred embodiments. This present embodiment relates generally to an apparatus for generating light for a shadow caster, said apparatus comprising: a slitted tube, said slitted tube comprising: an interior, said interior being painted white, an exterior, said exterior being opaque, and a slit, said slit running the length of said slitted tube and comprising: a width; two light sources, said light sources depending on opposite ends of said slitted tube; two heat sinks, said heat sinks depending from said light sources; two clamps, each said clamp wrapping around said slitted tube and comprising: a screw; wherein said clamps are capable of adjusting said width of said slit. Other versions of this embodiment use light sources, which are an assembly of LEDs or provided by fiber optic bundles. Furthermore, additional versions of this embodiment further comprise one or more lens across the slit, which have a negative focal length.

In another preferred embodiment, the present invention relates to an apparatus for generating a sharp shadow, said apparatus comprising: two side shadow casters, each said side shadow caster being triangular and comprising: a base, two sides, said sides extending from said base and meeting at a point, and an apex, said apex comprising: said point at which two said sides meet, and a pivot point; a main shadow caster, said main shadow caster disposed between said bases of said side shadow casters with said side shadow casters depending from said main shadow caster; a rotational axis, said rotational axis intersecting said pivot points of said side shadow casters; and a light source, said light source being linear, spanning between said apexes of said side shadow casters, and disposed along said rotational axis; wherein said side shadow casters and said main shadow caster may rotate around said rotational axis; and wherein said light source projects light across said side shadow casters and said main shadow caster in order to generate said sharp shadow. Other versions of this embodiment use side shadow casters and a main shadow caster, which further comprise configurable shapes. Still other versions of this embodiment use side shadow casters and a main shadow caster, which further comprise configurable opacity. Additional versions of this embodiment use side shadow casters and a main shadow caster, which further comprise color filters. Furthermore, other versions of this embodiment use side shadow casters and a main shadow caster, which further comprise multiple sections. When used with a shadow caster scanner, a camera must be separated from the light source.

Although the foregoing examples have been described in some detail for purposes of clarity of understanding, the above-described inventive techniques are not limited to the details provided. There are many alternative ways of implementing the above-described invention techniques. The disclosed examples are illustrative and not restrictive. These embodiments are not intended to limit the scope of the present invention.

BRIEF DESCRIPTION OF THE DRAWING

Illustrative and preferred embodiments of the present invention are shown in the accompanying drawings in which.

DETAILED DESCRIPTION OF THE PREFERRED EMBODIMENTS

For the purpose of illustration, the present invention is shown in the preferred embodiments of apparatuses, methods, and systems, for generating one or more edges of luminosity to form three-dimensional models of objects or environments. In broad embodiment, the present invention comprises one or more light sources and one or more shadow casters, which generate one or more edges of luminosity across objects or areas being modeled, one or more means of detecting the one or more edges of luminosity, a means of moving the one or more edges of luminosity relative to the objects or areas being modeled, and a means of generating three-dimensional models of the objects or areas being modeled, as well as related methods and systems. Some embodiments move the one or more shadow casters, some embodiments move the one or more light sources, and some embodiments move the object through the one or more edges of luminosity. Various embodiments or examples may be implemented in numerous ways, including as a system, a process, a method, an apparatus, a user interface, or a series of program instructions on a computer readable medium such as a computer readable storage medium or a computer network where the program instructions are sent over optical, electronic, or wireless communication links. In general, operations of disclosed processes may be performed in an arbitrary order, unless otherwise provided in the claims. These embodiments are not intended to limit the scope of the present invention.

A detailed description of one or more examples is provided below along with accompanying figures. The detailed description is provided in connection with such examples, but is not limited to any particular example. The scope is limited only by the claims, and numerous alternatives, modifications, and equivalents thereof. Numerous specific details are set forth in the following description in order to provide a thorough understanding. These details are provided for the purpose of example and the described techniques may be practiced according to the claims without some or all of these specific details. For clarity, technical material that is known in the technical fields related to the examples has not been described in detail to avoid unnecessarily obscuring the description.

Figure 1:
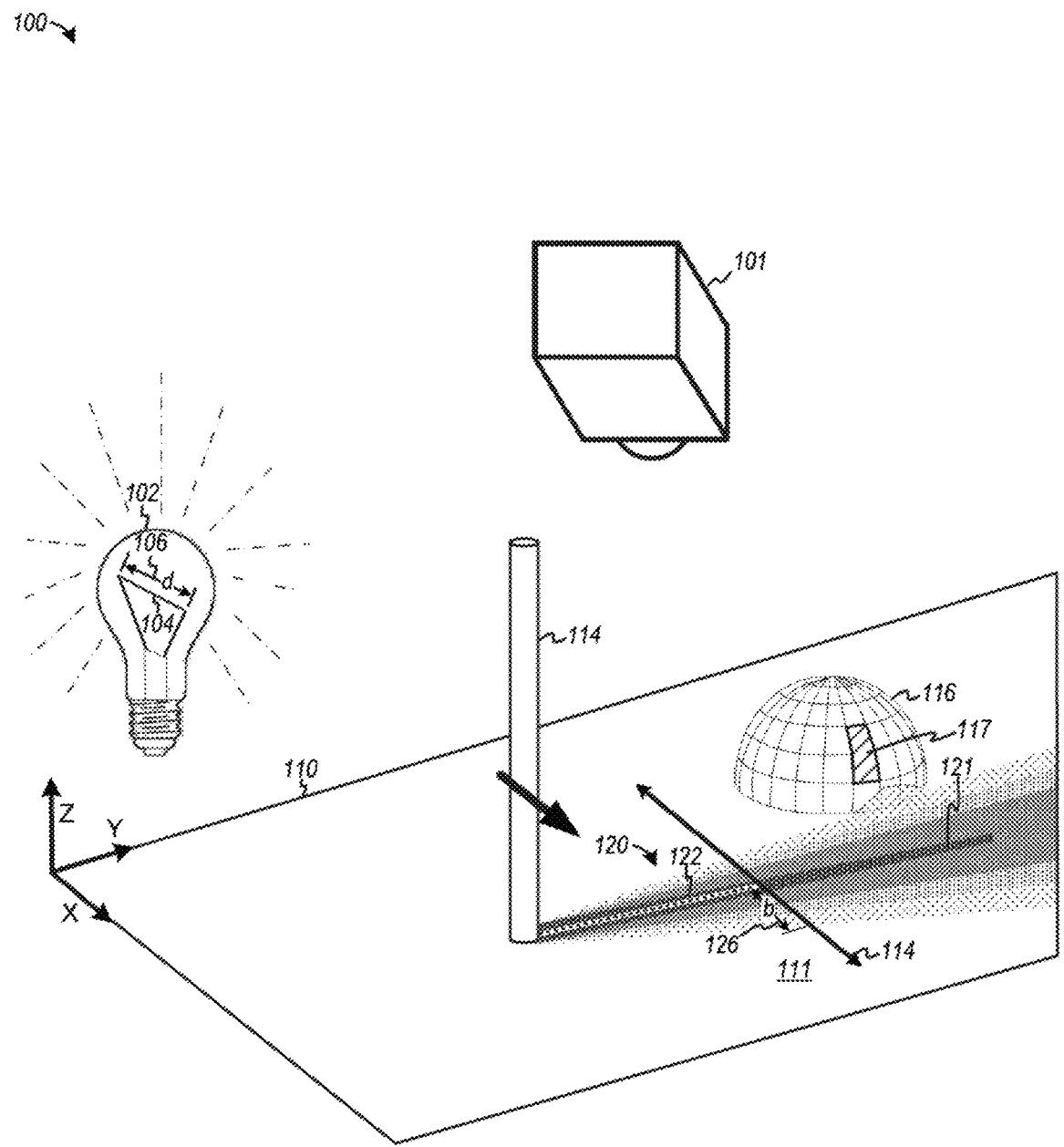
FIG. 1 is a known scanner system.
Figure 2:
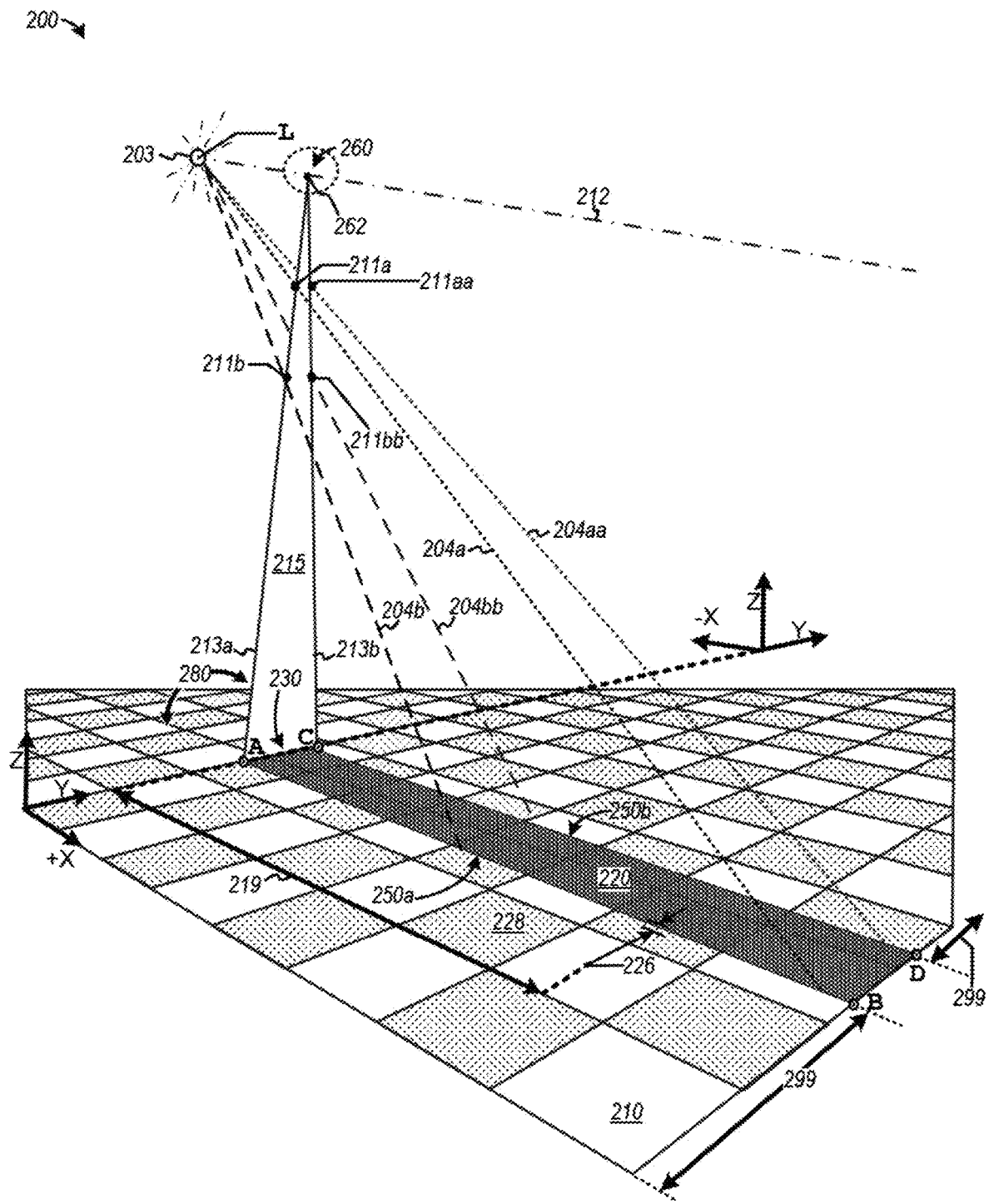
FIG. 2 is a diagram depicting an example of a shadow caster, according to some embodiments.

Referring now to the preferred embodiments of the present invention, FIG. 2 is a diagram depicting an example of a shadow caster, according to some embodiments. Diagram 200 depicts an example of a shadow caster 215 configured to form an edge of luminosity 250a and 250b at or upon a plane of projection or object (not shown) or environment (not shown) to facilitate three-dimensional representations of the shape and image of an object or environment. In some examples, shadow caster 215 may be configured to receive photonic emission (e.g., as light) that may impinge on at least edge portions 211a and 211b of edge 213a of shadow caster 215, which, in turn, may cause projections 204a and 204b of light originating from edge portions 211a and 211b to form an edge of luminosity 250a on plane of projection 210. Similarly, light may also impinge on edge portions 211aa and 211bb of edge 213b, which, in turn, may cause projections 204aa and 204bb of light originating from edge portions 211aa and 211bb to form another edge of luminosity 250b. According to various examples, either edge of luminosity 250a or edge of luminosity 250b, or both, may be used to facilitate three-dimensional scanning and digital replication. In the example shown, shadow caster 215 may be opaque to form an umbra 220 based on the edges of luminosity 250a and 250b. Umbra 220 may be associated with relatively high degrees of darkness (e.g., low to negligible levels of illumination) relative to illuminated portions 299 of plane 210, including illuminated plane portion 228.

In view of the foregoing, shadow caster 215 may be implemented in accordance with various functions and/or structures described herein, to form edges of luminosity to facilitate three-dimensional scanning and digital replication of spatial characteristics associated with surfaces of objects and environments. According to some examples, a shadow caster 215 includes a triangular cross-sectional area that provides a triangular profile, in projection, onto the plane Y-Z, which casts a sharp shadow with each edge maintaining parallelism to line 212 throughout a scan, where that sharp shadow is projected onto any plane parallel to line 212. That is, parallelism of one or both edges to line 212 may be maintained as projected onto plane 210 during a scan (e.g. when one or both edges of luminosity 250a and 250b move over an object, environment, and/or plane of projection 210). The geometries and dimensions of shadow caster 215, light source 203, and an edge of luminosity 250a (or edge of luminosity 250b) facilitates maintenance of parallelism as, for example, one or more of the edge of luminosity move during a scanning process. As an angle of shadow caster 215 may be known a-priori, the parallelism may be maintained as one or more edges of luminosity used in scanning to facilitate accuracy in determination of a shadow plane, which, in turn, may improve accuracy of the coordinates of a 3D object. In at least one example, shadow caster 215 may be implemented to form shadows planes that are parallel to line 212 traversing through light source 203 at point L and apex 262 of shadow caster 215, for either edge 213a or 213b, or both. An example of a shadow plane is formed with points L, A, and B, and an example of a second shadow plane is formed with points L, C, and D. Thus, edge of luminosity 250a between points A and B may be maintained as being parallel to (or substantially parallel to) edge of luminosity 250b between points C and D, according to some examples. Note that line 212 traversing through light source 203 need not traverse through shadow planes in accordance with at least one example. In other examples, line 212 is parallel to the shadow plane, which is extendable to line 212. However, a shadow may not necessarily be cast along this line by a shadow caster.

Edge of luminosity 250a, for example, may be associated with a relatively sharp rate of change from an absence (or relatively low amounts) of reflected light or photonic emissions in umbra 220 (e.g., relatively low levels of brightness or luminosity) to relatively high levels of reflected light or photonic emissions at an illuminated plane portion 228 within a unit 226 of distance. According to some examples, edge of luminosity 250a may be described as being associated with a gradient indicating unit distance 226. Characteristics of pixels may include, but are not limited to, pixel intensities, such as gray pixel intensities, values of brightness, luminosity, etc. In one example, a gradient may specify a distance at which one or more pixel characteristics of associated umbra 220 change from pixel value 000 (e.g., no illumination, or "black") to a pixel value 255 (e.g., fully illuminated, or "white"). In at least some cases, a cross-sectional area associated with shadow caster 215 may produce sharper edges of luminosity and higher contrast than, for example, a cylindrical rod or pencil where such rod or pencil is disposed such that no shadow-casting edge lies entirely in a single plane containing the light source, according to at least some examples. In other words, any edge that lies entirely in a single-plane, where that plane also contains the light source, casts a sharp, high contrast shadow, which is a particular advantage of the embodiments of the present invention.

In some examples, an edge of luminosity may sufficiently provide for relatively sharp contrasts between illuminated surfaces and a generated shadow. As such, examples of edge of luminosity may facilitate capture of spatial characteristics of 3D surfaces as well as color associated with the surfaces where that color may be obtained from the illuminated surface closest to the shadow edge. Therefore, a color determination may be obtained relatively close to an edge of luminosity during a scan for accurately representing a color during a scan than otherwise might be the case. For example, determining a color need not rely on a co-registration of 3D data with separate color information, which may be obtained using a separate camera or at a different time than when data representing 3D information is scanned or otherwise captured.

Referring still to FIG. 2, diagram 200 depicts a light source 203 being disposed in a region associated with a negative X-plane (e.g., "−X") portion of plane of projection 210, with shadow caster 215 (or a projection thereof) being disposed in a plane (e.g., Y-Z plane). A portion 260 of shadow caster 215 may be disposed at or adjacent to a line 212. Line 212 may also include light source 203 positioned thereon. In at least one example, portion 260 may be coextensive with line 212. In one example, line 212 may coincide with one or more points of shadow caster 215, which may include a point at an apex 262 of a triangular-shaped shadow caster 215 shown in diagram 200. Line 212 may be parallel to the X-Y plane and orthogonal to the Y-Z plane, at least in some cases. Another portion of shadow caster 215 may be disposed distally, such as at end portion 230. For example, end portion 230 may be disposed at or adjacent plane of projection 210.

In some examples, the depiction of shadow caster 215 may represent a cross-sectional area, or a projection thereof, in association with a plane (e.g., Y-Z plane) that may form edges of luminosity 250a and 250b. Alternatively, shadow caster 215 (or a cross-sectional area thereof) may be positioned or oriented at an angle relative to a plane (e.g., at an angle 280 relative to a plane coextensive to an X-Y plane). Hence, structures and functions of shadow caster 215 need not be limited to that depicted and described in relation to FIG. 2. For example, a rectangular shadow caster may be implemented with one or more features, functions and/or structures described herein, such as one or more sources of light 203 (e.g., points of light), whereby the rectangular shadow caster may be rotated about a point on its edge (e.g. about a rotation axis parallel to line 212) to form at least one relatively sharp shadow edge (or edge of luminosity). Shadow caster 215 may be opaque, with the opacity being configurable or programmable, according to some examples. Note that, in some examples, a penumbra may be implemented as umbra 220, whereby a partial amount of illumination from light source 203 (or any other light source) may modify or limit a maximum of darkness (e.g., a partial amount of illumination may cause an increase in values of pixel intensities above 000, which may represent total darkness). Regardless, edge of luminosity 250a and 250b may be detected as a transition from a first range of one or more pixel values associated the penumbra 220 to a second range of one or more pixel values associated with an illuminated portion 228 of plane of projection 210, according to some examples. According to some examples, a transition may be detected or determined in a single frame in which adjacent pixels may be compared. Or, a transition may be determined as a change in brightness of a pixel over time (e.g., over multiple frames). In at least one instance, an edge of luminosity (or shadow) may be resolved at dimensions finer than a pixel (e.g., during one or more frames in which a pixel value may change relatively slowly as a shadow edge moves across a pixel during a scan). Thus, an edge of luminosity may be determined at subpixel accuracy.

Figure 3:
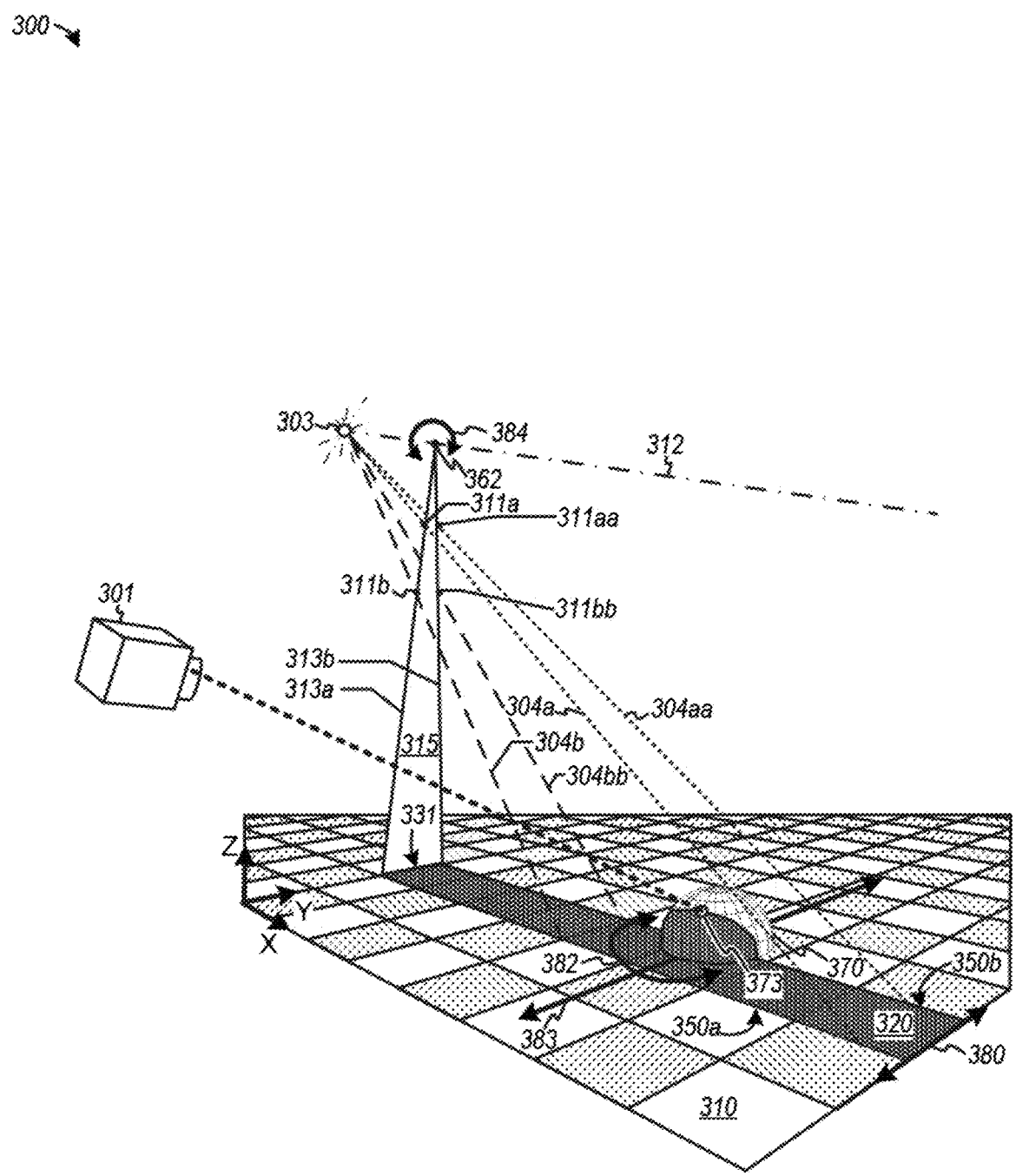
FIG. 3 is a diagram depicting a scanning system, according to some examples.

FIG. 3 is a diagram depicting a scanning system, according to some examples. Diagram 300 depicts another example of a shadow caster 315 as a constituent component of a scanning system also including an image capture device 301 and one source of light 303 or multiple sources of light 303 (not shown) disposed on line 312. Line 312 may extend through an apex 362 of shadow caster 315 and one or more sources of light 303. In some examples, shadow caster 315 may be configured to receive photonic emission (e.g., as light) that may impinge on at least edge portion 311a and 311b of edge 313a of shadow caster 315, which, in turn, may cause projections 304a and 304b, respectively, of light originating from edge portions 311a and 311b to form an edge of luminosity 350a on plane of projection 310. Similarly, light may also impinge on edge portions 311aa and 311bb of edge 313b, which, in turn, may cause projections 304aa and 304bb of light originating from edge portions 311aa and 311bb to form another edge of luminosity 350b. The one or more edges of luminosity 350a and 350b may be formed at or upon a plane of projection 310 to facilitate generation of three-dimensional representations of a shape of an object 370.

According to various functions and structures, an edge of luminosity 350a and 350b may transit or move over a surface of object 370 to determine three-dimensional spatial characteristics of the surface. Any number or type of motive force (not shown) may be generated by a device (not shown), such as an electromechanical motor, or by gravity, to move one of shadow caster 315 and object 370 relative to the other to effectuate movement of edge of luminosity 350 relative to object 370. For example, a motive force may cause angular displacement of shadow caster 315 in a plane (e.g., Y-Z plane) (e.g., rotation 384 that has at least some rotational component about an axis parallel to line 312). In some examples, above-described parallelism may be maintained so as provide parallel edges of luminosity that move (e.g., in synchronicity) throughout a scan by rotating shadow caster 315 about apex 362 of FIG. 3. Similarly, shadow caster 215 of FIG. 2 may rotate about apex 262 to maintain parallelism. Note that width of bottom portion 331 (e.g., in the Y-axis direction) may be depicted as equivalent to a width of one or more squares of a checkerboard pattern depicted in diagram 300. But here, or in any other example described herein, the width of bottom portion 331 may be smaller or larger than a width of any number of checkerboard squares. Thus, dimensions of shadow caster 315 shown in diagram 300 are exemplary. Any number of configurations and widths may be used to form any distance 333 between parallel edges of luminosity 350a and 350b, among various examples.

To implement a scan, an angular displacement of shadow caster 315 in the Y-Z plane may cause edge of luminosity 350 and umbra 320 to move in a direction 380 parallel to, for example, a Y-axis and over plane of projection 310. As another example, a motive force may cause shadow caster 315 to translate (e.g., non-rotationally) in an orientation shown along the Y-axis to cause edge of luminosity 350a and 350b and umbra 320 to move in a direction 380. In yet another example, a motive force may cause object 370 to rotate 382 or translate 383 (e.g., linear displacement parallel to Y-axis) relative to shadow caster 315 to cause edge of luminosity 350a and 350b to contact different portions of object 370 at different points in time. In another example, a motive force may cause object 370 to move relative to shadow caster 315 to cause motion of an edge of luminosity.

In some examples, a motive force may cause one of light source 303, shadow caster 315, and object 370 to move relative to the others to effectuate movement of edge of luminosity 350a and 350b. Note that the motive force on light source 303 or shadow caster 315 may be any type of motive force, examples of which include, but are not limited to, mechanical, electromechanical, electrical, magnetic, electromagnetic, electronic (e.g., currents or voltages to activate elements of a LCD to effectuate motion of a simulated shadow caster 315), or any other motive force. Further, a device that generates a motive force need not be limited to an electromechanical motor, but may be gravity or any known device to cause movement of edge of luminosity 350 relative to a surface of object 370.

Image capture device 301 may be configured to capture images of a scene or environment that includes object 370 as edge of luminosity 350a and 350b travels or moves over plane of projection 310. Examples of image capture device 301 may include any type of camera, such as a digital video camera, a charge-coupled device ("CCD")-based image sensor, etc., as well as analog cameras. In the example shown, image capture device 301 may capture one or more frames of images (e.g., video at a particular frame rate) in which a one or more pixels 373 may be associated edge of luminosity 350a and 350b as shadow 320 (e.g., umbra) passes over object 370. One or more pixels 373 may be pixels on a camera corresponding to a point on object 370, which is depicted as one or more pixels 373. In this example, image capture device 301 can capture for a given edge of luminosity a change in reflected luminosity from either darkness to brightness, or brightness to darkness. The surface of object 370 may cause a portion of edge of luminosity 350a and 350b (e.g., the portion casted upon object 370) to deviate from other straighter line portions of edge of luminosity 350a and 350b (e.g., on the X-Y plane) as detected from a point of view of camera 301. The deviation or deformation of edge of luminosity 350a and 350b may be due to surface dimensions (of object 370) extending in positive values of the Z-axis. In at least one implementation, a single image capture device 301 (e.g., with a single lens) may be sufficient to implement at least some of the scanning functions described herein.

Figure 4:
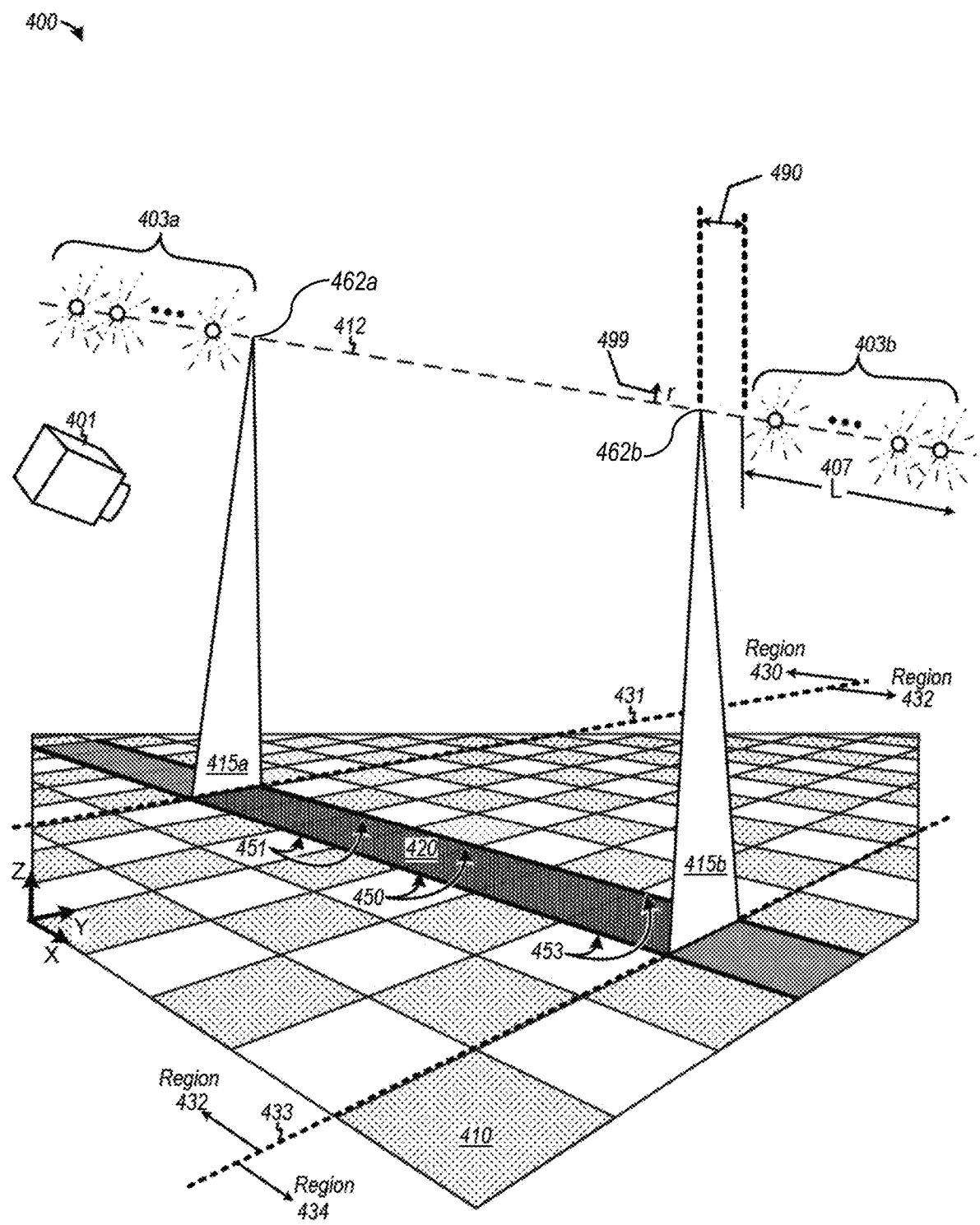
FIG. 4 is a diagram depicting another example of a shadow caster, according to some embodiments.

FIG. 4 is a diagram depicting another example of a shadow caster, according to some embodiments. Diagram 400 depicts a system of shadow casters 415a and 415b configured to form one or more edges of luminosity 450 at or upon a plane 410 of projection to facilitate three-dimensional object scanning. Diagram 400 also depicts an arrangement in which shadow casters 415a and 415b may be configured to cast edges of luminosity 451 and 453 to be coincident with each other to form common edges 450. Diagram 400 also depicts an image capture device 401, a subset 403a of one or more light sources, and a subset 403b of one or more light sources. Subset 403a of one or more light sources are shown to be disposed in region 430 (e.g., on one side of shadow caster 415a), and subset 403b of one or more light sources may be disposed in region 434. Regions 430, 432, and 434 may define two-dimensional or three-dimensional space. The light sources of subsets 403a and 403b may be disposed axially on a line 412, and may be any type of light-generating source that may emit any amount of lumens (e.g., 200 lumens, or less, to 1300 lumens, or greater). Examples of light-generating sources may include, but are not limited to, LED, incandescent, halogen, laser, etc., as well as any type of light pipe, lens (e.g., Fresnel lens), or light guide, such as illuminated optical fibers (e.g., fiber optic, such as fiber optic cables). Each light source in subsets 403a and 403b may emit photon emissions (e.g., light) at a same or different wavelength. For example, one or more light sources in each of subsets 403a and 403b may generate light in the visible light spectrum, as well as other any range of spectra (e.g., ultraviolet spectra, infrared spectra, etc.), and may emit at a relatively narrow spectral range. One or more ranges of wavelengths may be selectably implemented as a function of an application of shadow casters 415a and 415b. In some cases, light sources of subsets 403a and 403b can be implemented to emit wavelengths of light that constitute "white light" or "broad bandwidth light," which may reduce or negate effects of diffraction at edges of a shadow caster (e.g., one or more ranges of wavelengths, in combination, may reduce or negate artifacts associated with light diffracting due to an edge). Also, light sources of subsets 403a and 403b can implement any number of ranges of wavelengths regardless of whether those ranges are in the visible spectra. Light sources of subsets 403a and 403b may be configured to emit light omnidirectionally, unidirectionally, or in any other pattern of light.

In some cases, light sources in subsets 403a and 403b may be relatively narrow or approximate points of light, and/or may have a reduced (or relatively short) radial dimension ("r") 499 about line 412 to, for example, effectuate a relatively sharp transition from "light" to "dark" along edges 450. As a number of sources (e.g., relatively narrow sources) of light increases along a length ("L") 407 of a portion of line 412, edge of luminosity 453 generated by shadow caster 415b may sharpen (e.g., increase a rate of transition from umbra or shadowed area 420 in region 432 to an illuminated portion of plane 410 of projection.). In some examples, sources of light, such as subset 403b, may be disposed at greater distances 490 from the shadow caster 415b to sharpen edges of luminosity 453. Similarly, any number of sources of light may be disposed in subset 403a along a corresponding portion of line 412 to generate an enhanced edge of luminosity 451 in association with shadow caster 415a. In at least one example, a filament (e.g., in a halogen light bulb) may be used to function as a number point sources of light disposed in subset 403a such that they form a continuous set. A radius of a halogen bulb or filament, or any other light source described herein, may be referred to a subset of light sources describing a "narrow source" of light of radius "r" 499, at least in some examples.

According to some examples, shadow caster 415a may be configured to receive photonic emissions (e.g., from subset 403a of one or more light sources) at edge portions to form at least two portions of edges of luminosity 451. At least two portions of edges of luminosity 451 may be parallel or substantially parallel (e.g., non-intersecting on plane of projection 410) to each other as projected on a plane of projection 410. Shadow caster 415b may be configured to receive photonic emissions (e.g., from subset 403b of one or more light sources) at edge portions to form at least two portions of edges of luminosity 453. At least two portions of edges of luminosity 453 may be parallel or substantially parallel to each other as projected onto a plane of projection 410.

Edges of luminosity 453 may coincide coextensive (or substantially coextensive) with edges of luminosity 451 to form edges of luminosity 450 based on shadow casters 415a and 415b. Thus, shadow caster 415b may form edges of luminosity 453 to bolster edges of luminosity 451 (e.g., adjacent shadow caster 415b), and similarly, shadow caster 415a may form edges of luminosity 451 to bolster edges of luminosity 453 (e.g., adjacent shadow caster 415a). A bolstered edge of luminosity 453 may provide for a relatively sharp shadow for a parallel shadow, according to at least one example.

Edges of luminosity 450 may translate, in synchronicity, over plane of projection 410 as shadow casters 415a and 415b have a common component of rotation about line 412 as an axis, where line 412 may be maintained to extend along subsets 403a and 403b of light sources, and to the apexes 462a and 462b of shadow casters 415a and 415b, respectively. In other examples, shadow casters 415a and 415b and subsets 403a and 403b of light sources may translate together with some component along the Y axis, for example along lines 431 and 433, respectively. In other examples, shadow casters 415a and 415b and subsets of 403a and 403b of light sources may rotate together while maintaining a common line 412. In such a case, edges of illumination 450 need not lie along a single axis (e.g., such as an X-axis depicted in FIG. 4). In other examples, shadow casters 415a and 415b and 403a and 403b may both translate and/or rotate in unison while maintaining a common line 412.

Figure 5:
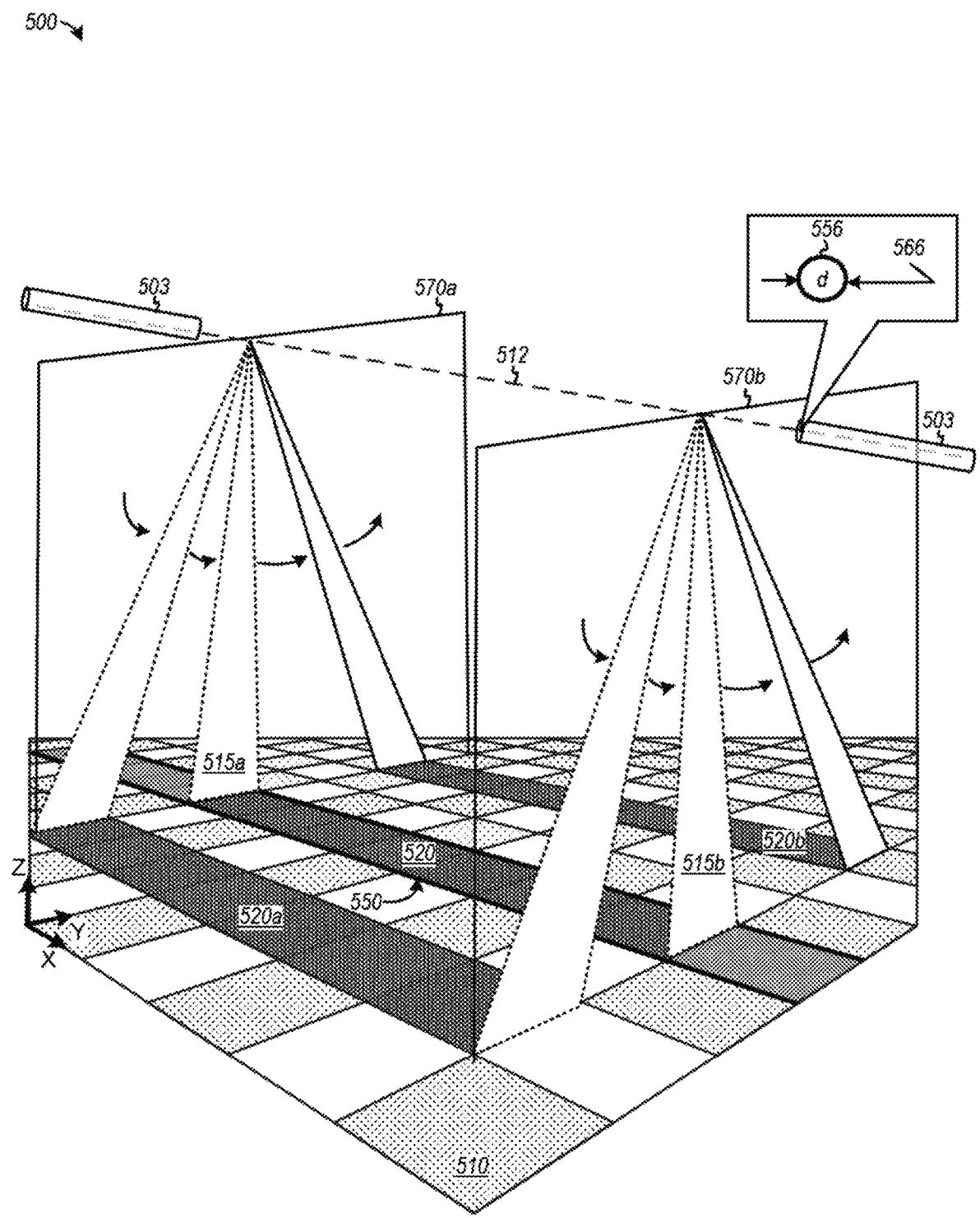
FIG. 5 is a diagram depicting another example of a shadow caster, according to some embodiments.

FIG. 5 is a diagram depicting another example of a shadow caster, according to some embodiments. Diagram 500 depicts a system of shadow casters 515a and 515b configured to form one or more edges of luminosity 550 at or upon a plane 510 of projection to facilitate three-dimensional object scanning. As shown, shadow casters 515a and 515b are depicted at different positions and/or orientations at different points of time as shadow casters 515a and 515b rotate about axis 512 (e.g., the dashed lines representing preceding positions or orientations). Correspondingly, shadow casters 515a and 515b may form moving edges of luminosity 550 as an umbra moves to position 520a at a first point in time, from position 520a to 520 at a second point in time, from position 520 to position 520b at a third point in time, and to other positions at other points in time.

In some examples, sources of light 503 may be implemented as extended sources of light (e.g., elongated sources of light) along axis 512. In some embodiments, halogen lamps may be used with filaments that extend longitudinally along axis 512. As a halogen lamp, light sources 503 may have a diameter ("d") 566, as shown in end view 556, and may be implemented as two times "r" 499 of FIG. 4 (e.g., 2*radius, 'r'). According to the particular implementation, diameter 566 of light source 503 may be two (2) mm, or less. In some cases, diameter 566 may be greater or otherwise dimensioned in accordance with a type of light source implemented. Further, light source 503, in addition to being reflected, may be a real or virtual image of a light source as affected by a positive or negative lens or lens system (not shown), including images of light sources that are magnified or de-magnified images of light sources. Such an image can by extension be considered the light source 503.

In at least one embodiment, shadow casters 515a and 515b may be implemented using liquid crystal displays ("LCDs") 570a and 570b, or other switchable opaque glass, film, or material. For example, LCDs 570a and 570b may be transparent (e.g., normally transparent), and may be activated to form opaque cross-sectional shapes to simulate shadow casters 515a and 515b and/or their movement. LCDs 570a and 570b may have portions selectively activated at different times to cause light emitted from light sources 503 to generate edges of luminosity 550 that move over the surface of the plane of projection 510.

In various examples, multiple shadow casters may be substituted for either shadow caster 515a or 515b, or both. For example, each of the triangular shapes in diagram 500 may represent different physical shadow casters that may move in synchronicity (e.g., in synchronize rotation in relation to axis 512). Hence, each subset of shadow casters 515a (e.g., in a first plane) and 515b (e.g., in a second plane) may generate six (6) edges of luminosity with each shadow caster generating two (2) edges of luminosity. According to various other examples, any number of shadow casters may be used.

Figure 6:
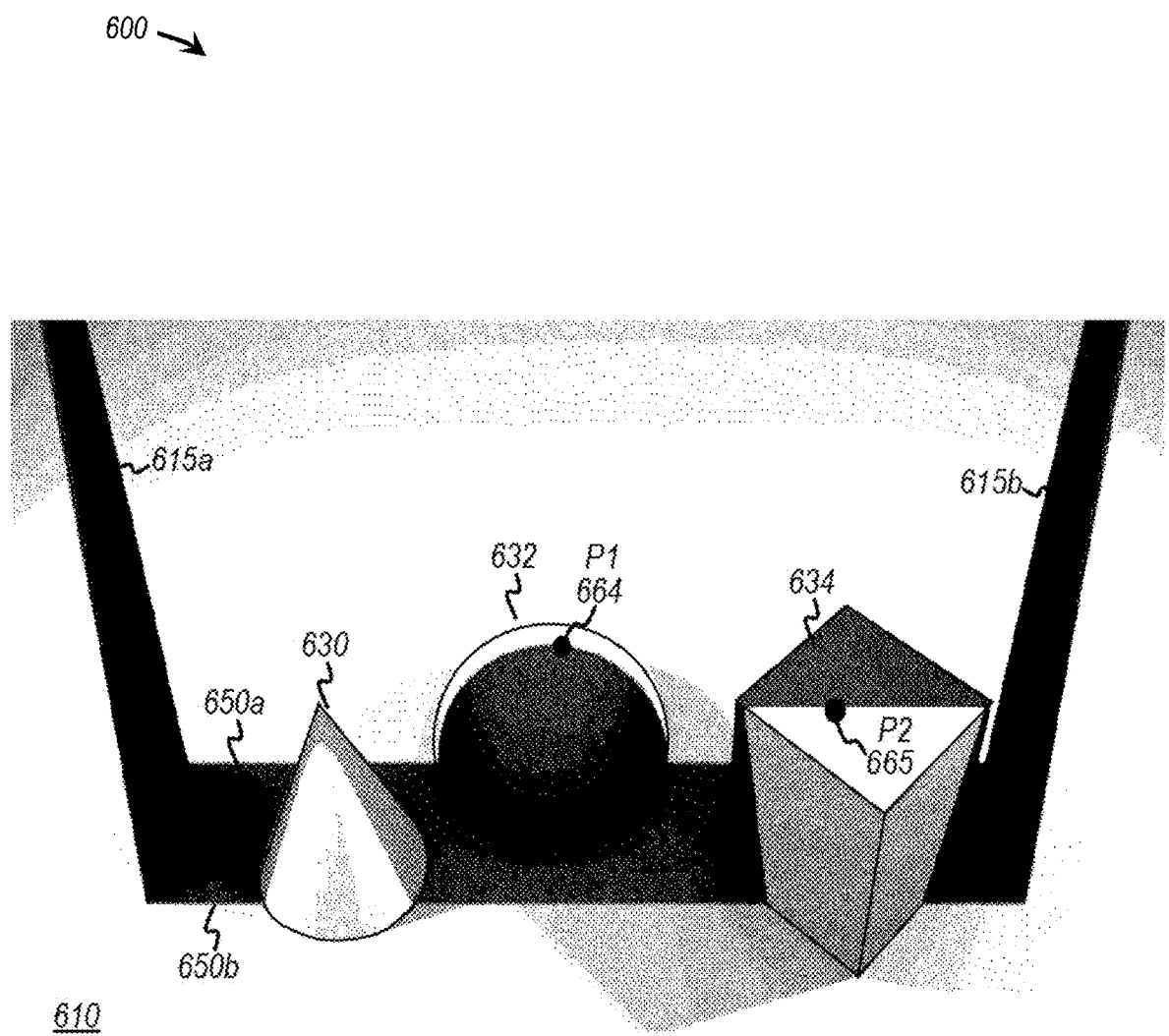
FIG. 6 is a diagram depicting an example of shadow casters generating edges of luminosity to scan multiple objects, according to some examples.

FIG. 6 is a diagram depicting an example of shadow casters generating edges of luminosity to scan multiple objects, according to some examples. Diagram 600 depicts shadows cast by shadow casters 615a and 615b in an illumination arrangement as indicated in FIG. 4 to generate edges of luminosity 650a and 650b. As shown, edges of luminosity 650a and 650b maintain their common edges and a relatively rapid transition from light (e.g., a region of illumination) to dark (e.g., a region of reduced or no illumination) over three-dimensional objects, such as a cone 630, a hemisphere 634, and a rectangular block 634. Further, illuminated regions of the objects are illuminated from the lights corresponding to shadows cast from both 615a and 615b such that they may be illuminated from multiple directions to provide enhanced information during a 3D scan (e.g., based on the multiple directions). Shadow casters 615a and 615b may rotated or moved, as described relative to shadow casters 415a and 415b of FIG. 4, to translate or rotate a shadow over cone 630, hemisphere 632, and a rectangular block 634, to form a three-dimensional data representation or model of each. An image capture device, such as a camera (not shown), may capture pixelated imagery associated with a point ("P1") 664 on the surface of hemisphere 632 at a point in time when edge of luminosity 650a coincides with point 664. Similarly, the image capture device may capture an image of a point ("P2") 665 on the surface of block 634 at a point in time when edge of luminosity 650b coincides with point 665.

Figure 7A:
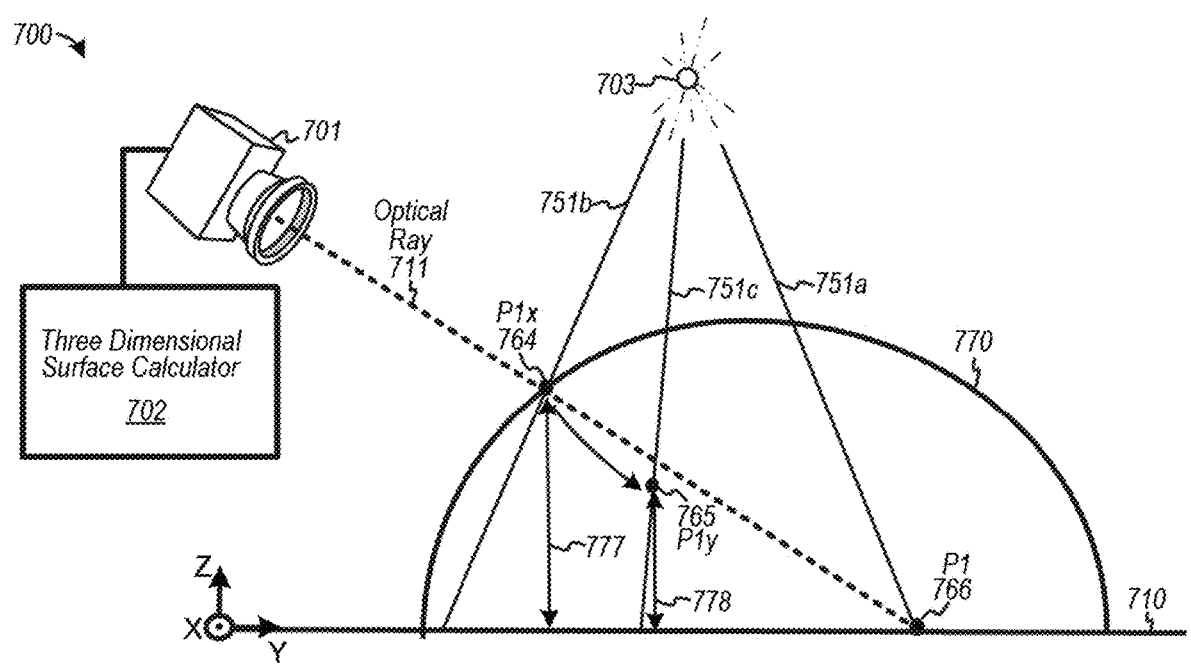
FIG. 7A is a diagram depicting a side view of an object being scanned, according to some examples.

FIG. 7A is a diagram depicting a side view of an object being scanned, according to some examples. Diagram 700 depicts an image capture device 701 and a source of light 703 arranged to capture images of an edge of luminosity as it moves over the surface of an object 770. Image capture device 701 can be calibrated to correlate each pixel with an angular coordinate of an optical ray, relative to a coordinate system common to the camera, light, and plane edge of luminosity. Image capture device 701 can also have its position known relative to a coordinate system common to the camera, light, and pane edge of luminosity. For example, a point ("P 1") 766 on a surface of a plane of projection 710, absent an object 770, may be captured as an edge of luminosity including illuminating ray 751a moves over point 766. One or more pixels of image capture device 701 (and corresponding pixel data), which, for example, may be detected along optical ray 711, can represent image data for point 766. An angular coordinate of point 766 can be determined by image capture device 701, which, along with a position of image capture device 701, may define a line from camera to point 766, which is depicted as optical ray 711 in the example shown. Given that a plane edge of luminosity containing illuminating ray 751a may be identified, a spatial coordinate of point ("P1") 766 can be determined as an intersection of optical ray 711 and edge of luminosity containing illuminating ray 751a. While diagram 700 includes projection plane 710 in an example of a 3D scanning process, projection plane 710 is optional and need not be implemented for a 3D scan.

During scanning of object 770 disposed on plane projection 710, a point ("P1x") 764 may be identified as edge of luminosity containing illuminating ray 751*b* passes over object 770 at a first point in time. At a subsequent point in time, image capture device 701 may capture another point ("P1*y*") 765 as edge of luminosity containing illuminating ray 751*c* passes over object 770. Since other optical rays (not shown) intercept different points on the surface of object 770, portions of an edge of luminosity that are applied to a surface portion of object 770 may be distorted from its shape on plane of projection 710 (in the absence of object 770). Three-dimensional surface calculator 702 includes logic, whether in either hardware or software, or a combination thereof, to compute X and Y positions (not shown), and Z-depths 777 and 778 for points 764 and 765, respectively.

Figure 7B:
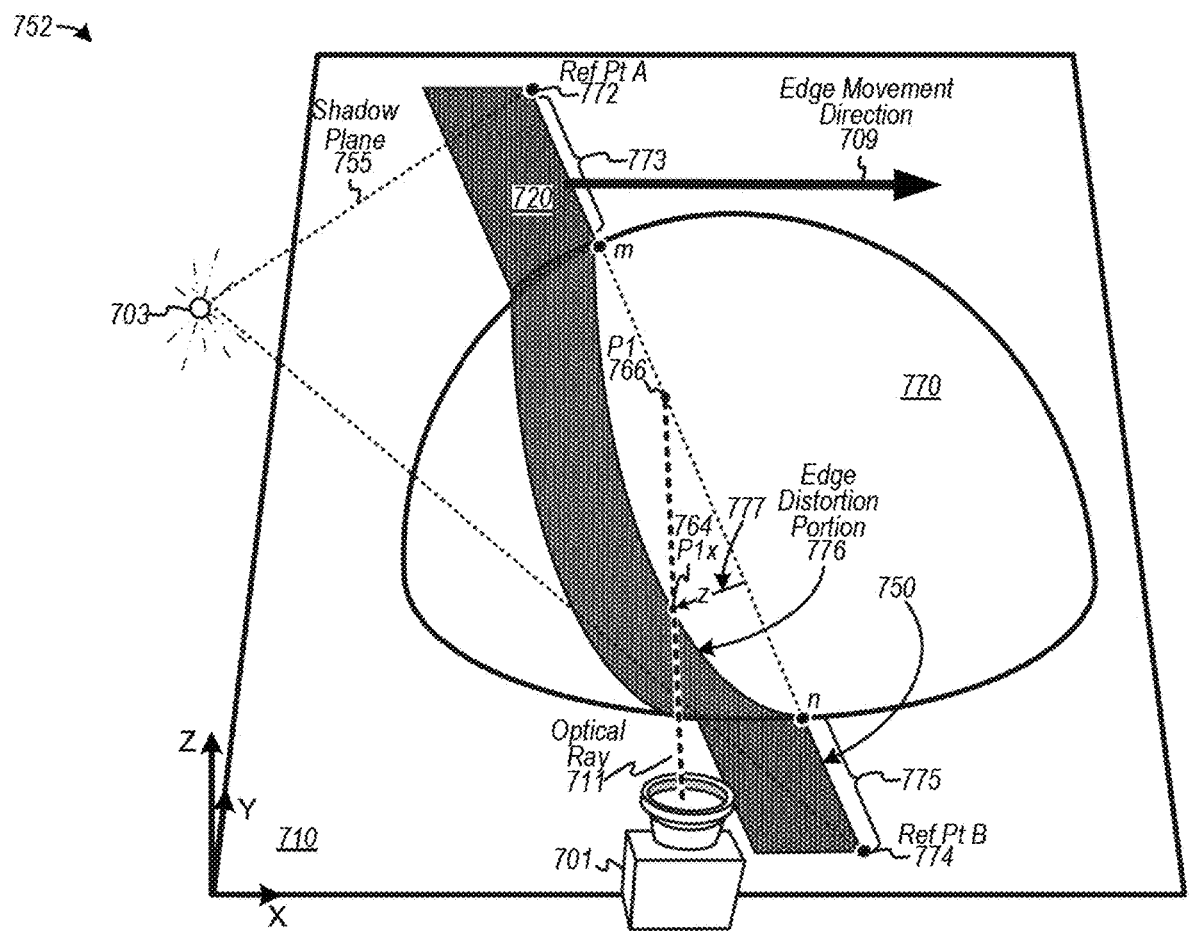
FIG. 7B is a diagram depicting a perspective view of an object being scanned, according to some examples.

FIG. 7B is a diagram depicting a perspective view of an object being scanned, according to some examples. Diagram 752 depicts an image capture device 701 and a source of light 703 arranged to capture images of an edge of luminosity as it moves in direction 709 over the surface of an object 770. Shadow 720 and corresponding edge of luminosity 750 containing illuminating ray 751*c*, labeled 750 of FIG. 7B, is shown projected onto portions of plane of projection 710 and a surface of object 770. Portions 773 and 775 of edge of luminosity 750 are shown projected upon a surface of plane 710. Portion 773 of edge of luminosity 750 includes a reference point ("Ref. Pt. A") 772 and portion 775 of edge of luminosity 750 includes a reference point ("Ref. Pt. B") 774. While portions 773 and 775 are shown coextensive with a straight line, at least in this example, edge distortion portion 776 of edge of luminosity containing illuminating ray 751*c* is depicted as an edge distortion portion 776 between points "m" and "n," whereby the edge intercepts the surface of object 770 at point 764 rather than intercepting plane of projection 710 at point 766. Based on reference points 772 and 774 and either a location of a line (not shown), which may be equivalent of line 512 on FIG. 5, or a location of light source 703, a shadow plane 755 may be derived. According to some examples, a position of one or more shadow casters may be determined in lieu of reference points 772 and 774. For example, a position and angle of a shadow caster may be monitored using linear or angular encoders, or any other detection or monitoring device. Intersections of multiple optical rays (not shown) and shadow plane 775 may be used to determine spatial characteristics of a three dimensional surface.

With introduction of object 770 onto plane of projection 710, optical ray 711 may intercept point 764 on object 770 rather than point 766 on plane of projection 710. Point 764 is shown on edge distortion portion 776 of edge of luminosity 750. Further, shadow edge 750 is shown to have distorted to determined Z-depth 777, indicating a corresponding Z coordinate for point 764, measured from a line on which edge of luminosity 750 intercepts point 766 in plane of projection 710 (in the absence of object 770). Similarly point 764 X and Y positions (not shown) can also be determined from interception of optical ray 711 with edge of luminosity 750. Various lines, segments, triangles, planes, and other geometric relationships, as well as dimensions thereof, obtained from multiple positions of edge of luminosity 750 measured using multiple images may be used to compute an estimation of subsets of points on the surface of object 770 to form a three-dimensional model or representation of the object surface.

Figure 7C:
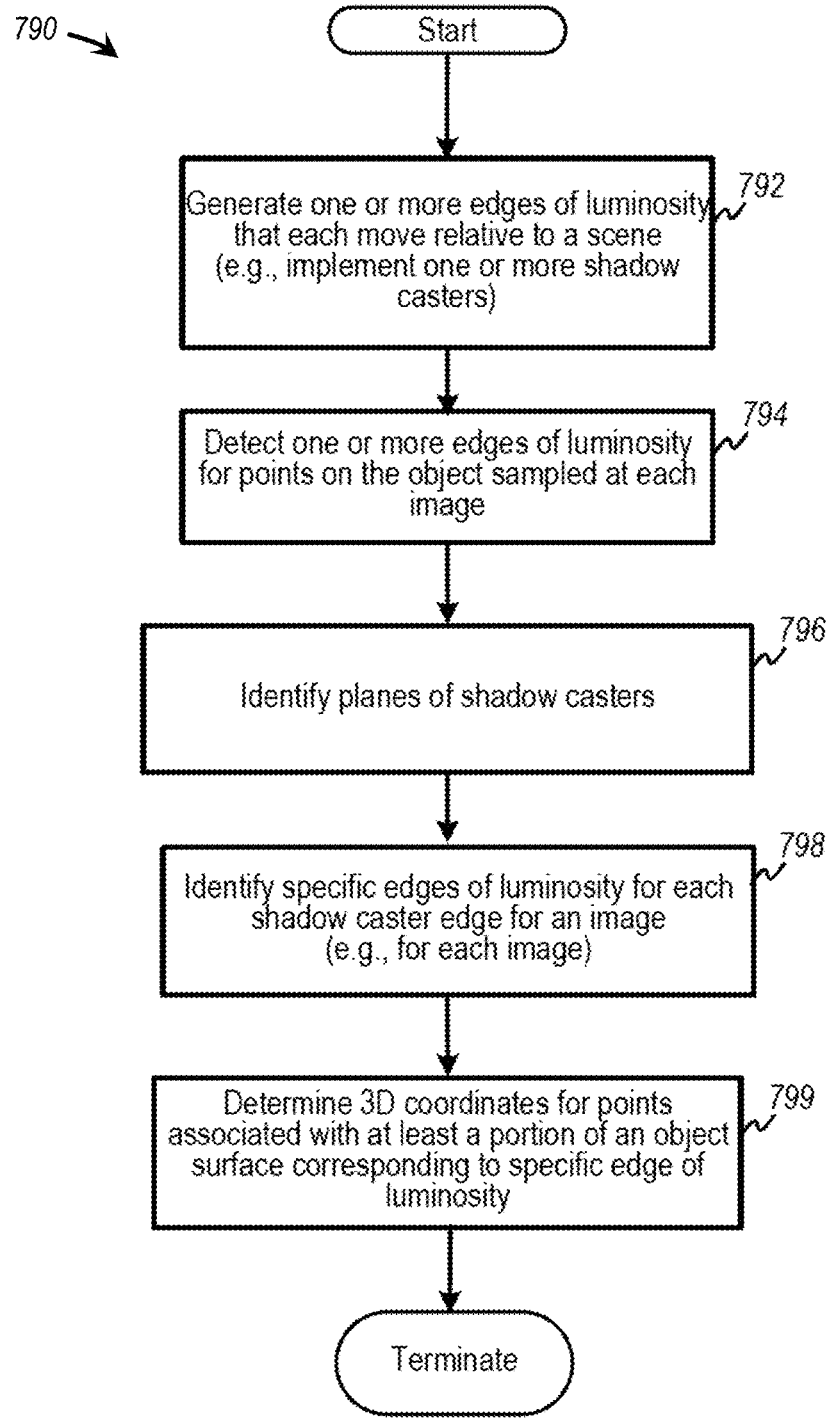
FIG. 7C is an example flow chart for determining spatial locations of points on an object surface, according to some examples.
Figure 8:
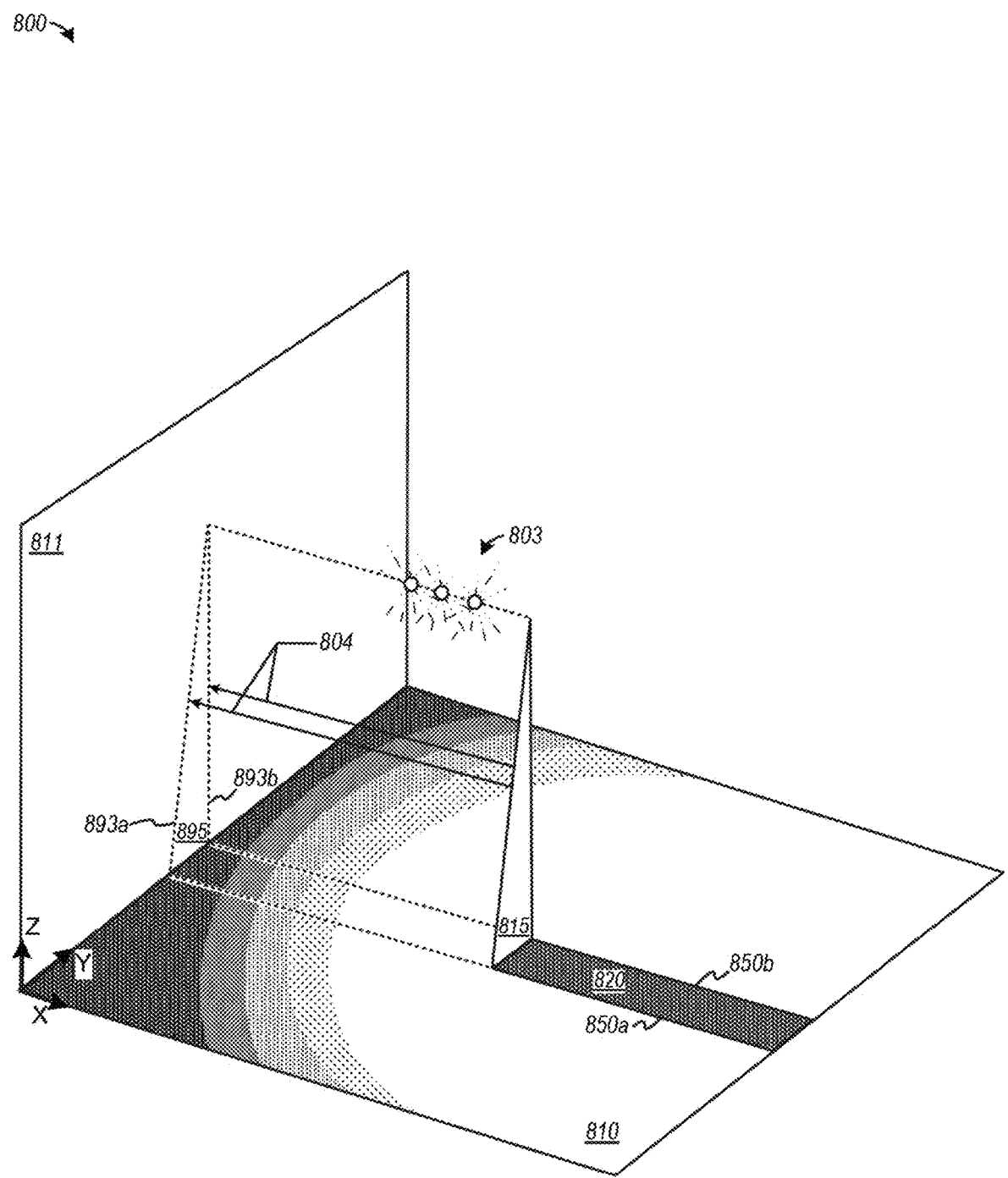
FIG. 8 is a diagram depicting an example of a shadow caster, according to various embodiments.

FIG. 7C is an example flow to determine spatial locations of points on an object surface, according to some examples. Flow 790 may compute spatial locations in three dimensions for points having X, Y, and Z coordinates, the points being coextensive with a surface of an object. At 792, one or more shadow casters may be used to project edges of the luminosity that move across a scene. At 794, edges of luminosity may be detected for points on the object sampled at each image. For example, an image capture device may capture a set of edges of luminosity relative to an object disposed on the plane of projection with each image, and, using multiple images, may sample multiple portions of the object. Each edge of luminosity for each image may be stored as a data representation or processed in real-time (substantially in real-time) to determine data representing 3D points along an edge, which may be aggregated with other 3D points to describe a three-dimensional portion of a surface. At 796, a plane associated with a position of each shadow caster may be determined for each image. For each point at edge of luminosity on the surface, a shadow plane may be determined from, for example, mechanical or optical measurements of a position of a shadow caster together with a location of a source of light, which may be predetermined. Further, a shadow plane may be computed relative to the reference points and a location of lights or equivalent of line 512 of FIG. 5. At 798, points along a specific edge of luminosity may be determined as distinguished from all points corresponding to other edges of luminosity, for each image. In some examples, each point may be associated with one or more pixels in an image frame. Further, a shadow plane associated with the specific point can be identified. The specific edge of luminosity and corresponding shadow plane can be captured for a particular image frame during a scanning process. A "specific frame" for a specific point may be derived based on a sequence number of a frame. At 799, an optical ray to any specific point may be identified, and an estimated coordinate X, Y, and Z for the point can be computed based on the intersection of the optical ray and the shadow plane of the particular edge of luminosity of the point. An optical ray may be determined based on one or more coordinates and an angle of a calibrated camera. Further, based on the estimated coordinates of points coextensive with a surface, a three-dimensional model of the surface may be formed. Note that in some examples, the reference "each image" may describe each image in a subset of images. Note, too, a color of a point on the three-dimensional model of the surface may be derived from the image used to derive its three-dimensional coordinate, according to some examples. In some examples, an image obtained near a sequence number of the frame used to derive a three-dimensional coordinate.

FIG. 8, FIG. 9, FIG. 10, and FIG. 10A, are diagrams depicting various examples of shadow casters, according to various embodiments. Diagram 800 of FIG. 8 includes shadow caster 815 and a light source 803 (e.g., one or more point or relatively narrow light sources) configured to form a shadow 820 and edges of luminosity 850*a* and 850*b* on a plane of projection 810. Diagram 800 also shows a projected cross-sectional area 895 of shadow caster 815, whereby the dimensions and/or boundaries of shadow caster 815 may be projected along direction 804 to form projected cross-sectional area 895. For example, edges of shadow caster 815 may be projected 804 onto a plane 811 parallel to a Y-Z plane to form projected edges 893*a* and 893*b*.

Figure 9:
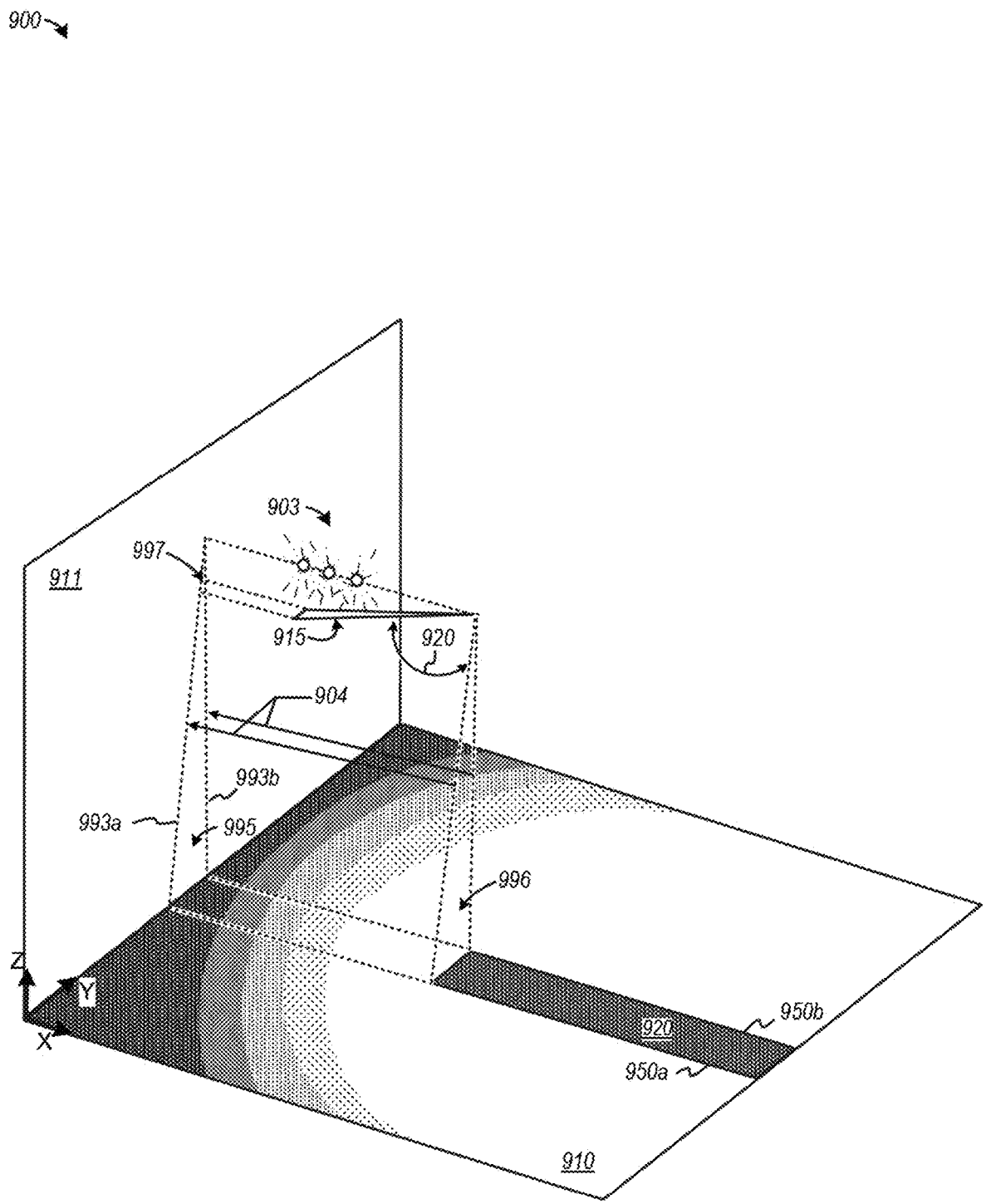
FIG. 9 is a diagram depicting an example of a shadow caster, according to various embodiments.

Diagram 900 of FIG. 9 includes shadow caster 915 and a light source 903 (e.g., one or more point light sources) configured to form a shadow 920 and edges of luminosity 950*a* and 950*b* on a plane of projection 910. As shown, shadow caster 915 may be oriented at angle 920 relative to, for example, a cross-sectional area 996 (e.g., of shadow caster 815 of FIG. 8) that may be parallel to plane 911.

According to this example, a cross-sectional area of a physical form of shadow caster 915 may be reduced in association with reduced dimensions (e.g., a reduced distance between an apex portion and a distal portion of shadow caster 915). FIG. 9 depicts cross-sectional area 996 projected onto plane 911 as a projected cross-sectional area 995 having projected edges 993a and 993b. Plane 911 may be parallel to a Y-Z plane. As shown, a smaller sized shadow caster 915, which may reduce a form factor of a 3D scanner, may simulate implementation of cross-sectional area 996 to form edges of luminosity 950a and 950b, with its profile boundaries, which are shown projected onto plane 911, overlapping over a sufficient region of profile 995. Scanning in this configuration may be achieved by rotating shadow caster 915 with a component of rotation about the line containing lights 903, while maintaining its apex (not shown) upon this line.

Figure 10:
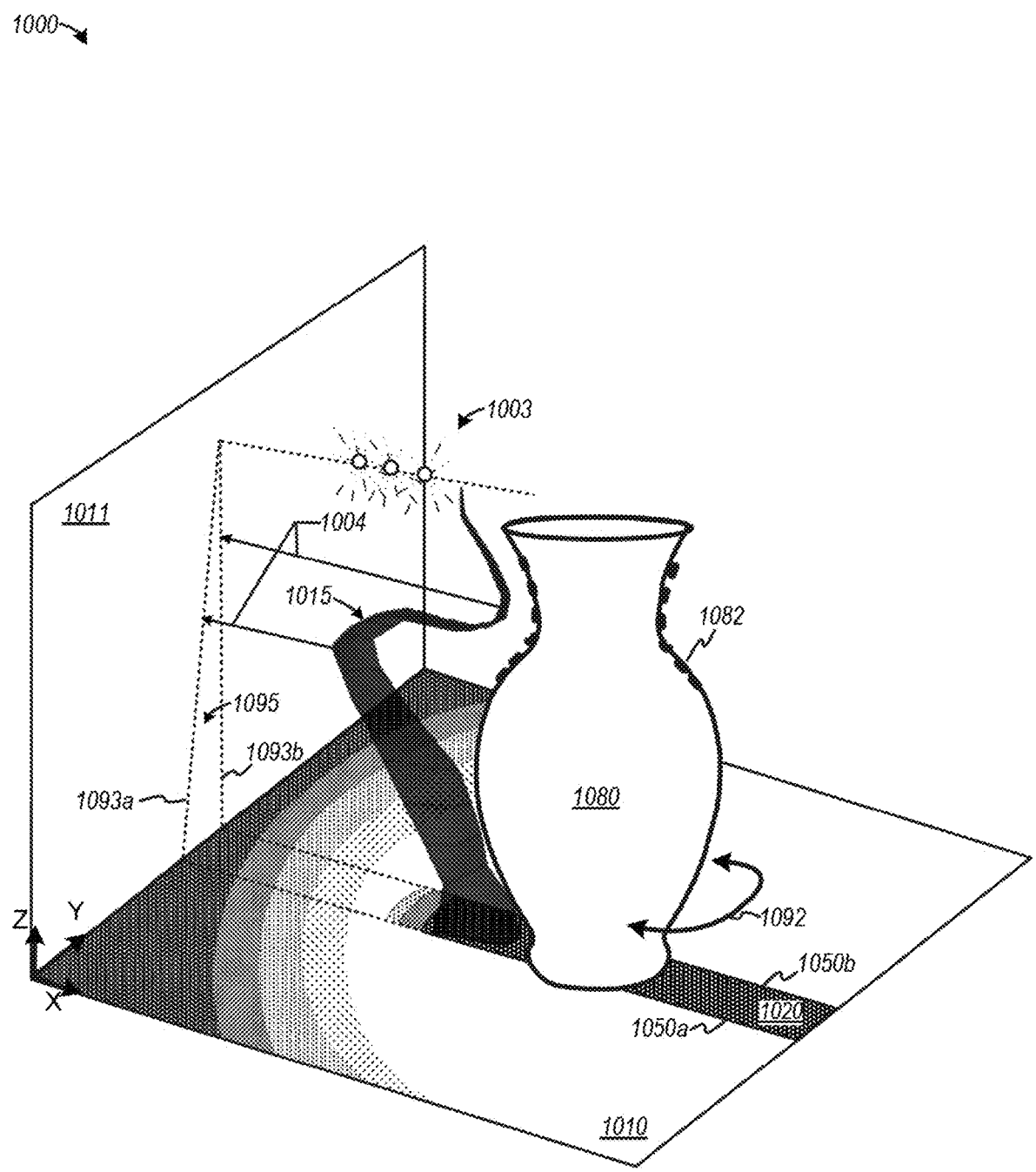
FIG. 10 is a diagram depicting an example of a shadow caster, according to various embodiments.
Figure 10A:
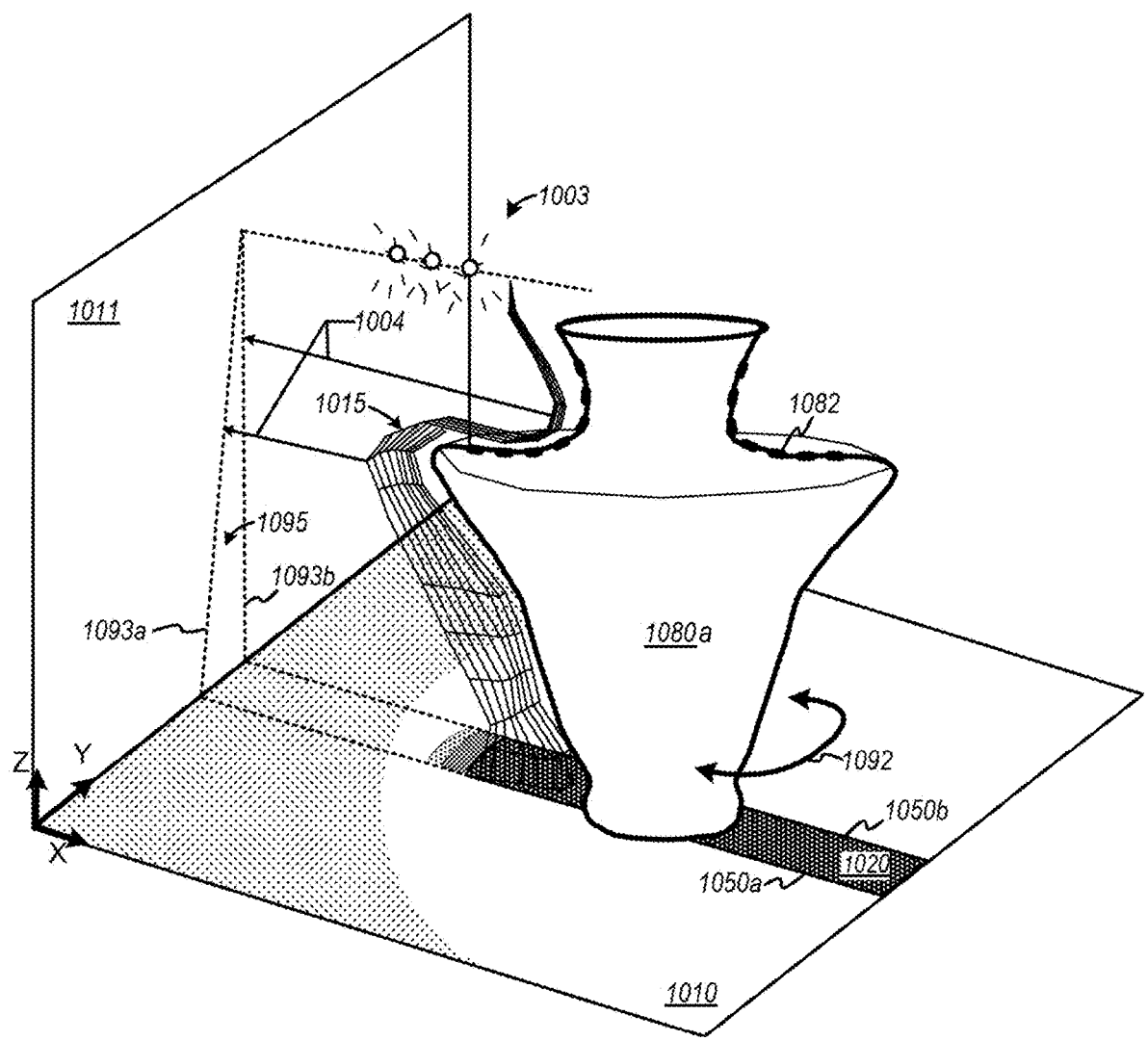
FIG. 10A is a diagram depicting an example of a shadow caster, according to various embodiments.

Diagram 1000 of FIG. 10 and FIG. 10A includes shadow caster 1015 and a light source 1003 (e.g., one or more point light sources) configured to form a shadow 1020 and edges of luminosity 1050a and 1050b on a plane of projection 1010. Note that a cross-sectional area of a physical form of shadow caster 1015 may be projected onto plane 1011 to form a projected cross-sectional area 1095. For example, edges of shadow caster 1015 may be projected 1004 onto a plane 1011 parallel to a Y-Z plane to form projected edges 1093a and 1093b. In one example, projected cross-section 1095 may be equivalent to projected cross-sectional area 895 of shadow caster 815 in FIG. 8. As shown, shadow caster 1015 may be non-planar, for example, when as its deformation from a plane is along the direction 1004, which is parallel to the line along the lights. As such, shadow casters 815 (FIG. 8) and 1015 (FIG. 10 and FIG. 10A) may form similar or equivalent edges of luminosity, according to various examples.

Shadow caster 1015 may be flexibly deformable or may be rigidly formed. Shadow caster 1015 may be formed of any material (e.g., opaque material), such as plastic, metal, wood, etc. Shadow caster 1015 may be formed of a colored transparent material such that shadow is specifically of one or more wavelengths of one or more wavelength ranges. In the case of a colored transparent material used for the shadow caster, edges of luminosity may be determined using an image detection device (not shown) with color filtering employed that enables detect of transitions of light of one or more particular colors, according to some examples. For making improved iterations of a shadow caster 1015, a rough shadow caster may be used to make a rough three-dimensional scan, which may then be used to make other closer shadow casters.

In one example, shadow caster 1015 may be formed from material used in three-dimensional ("3D") printing techniques. As such, shadow caster 1015 may be formed to conform, mimic, or replicate dimensions and contours of a surface of an object subjected to initial profile measurement using a series of photographs (or digitized images), or, for example, a prior 3D scanning. In the example shown, shadow caster 1015 has been formed to replicate surface features of a vase 1080 (FIG. 10), and, for comparison, a differently shaped vase 1080b (FIG. 10A), including surface contour 1082. Shadow caster 1015 may be formed to establish a gap having a relatively reduced distance (or a constant or substantially constant distance) between a surface of shadow caster 1015 and a surface of vase 1080 or differently shaped vase 1080b. The gap distance may be expressed relative to the X-Y plane.

Figure 11A:
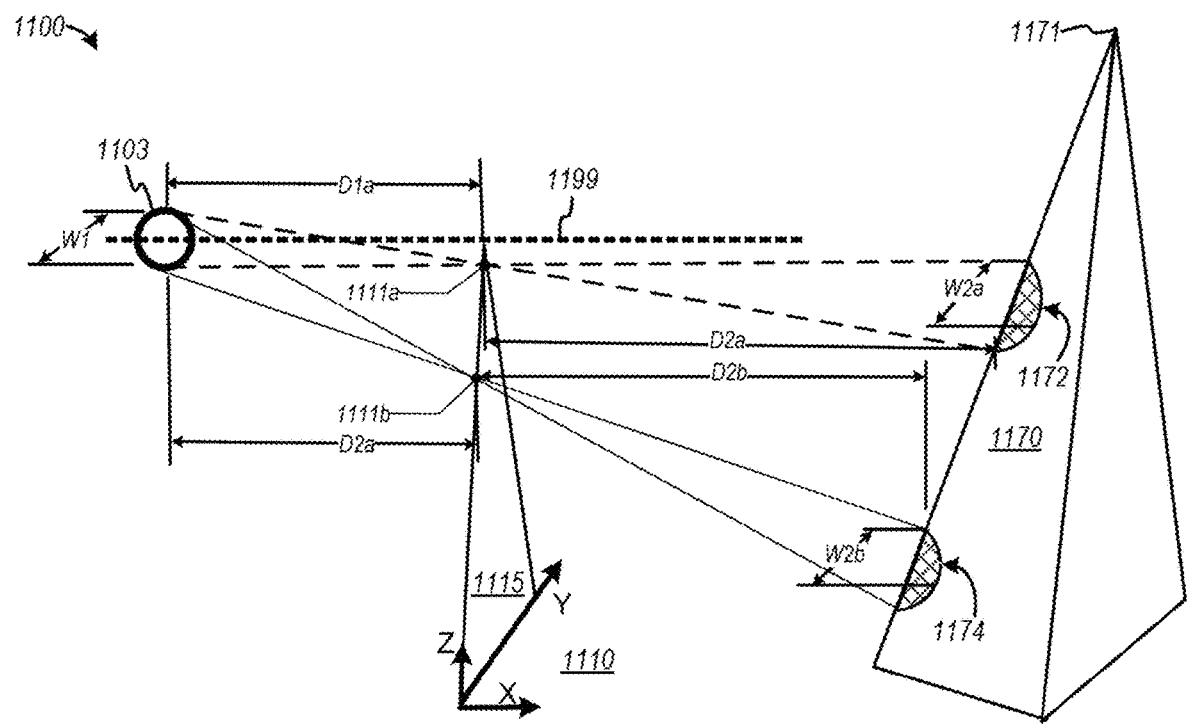
FIG. 11A is a diagram depicting examples of adaptable structural characteristics of a shadow caster for scanning three-dimensional objects, according to some examples.
Figure 11B:
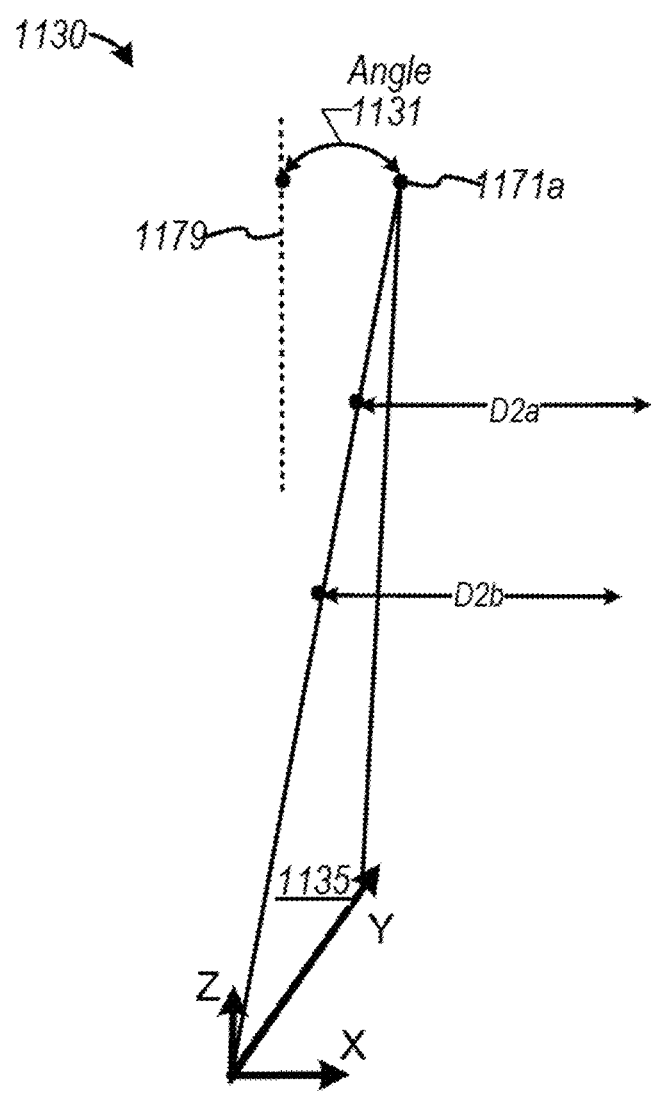
FIG. 11B is a diagram depicting examples of adaptable structural characteristics of a shadow caster for scanning three-dimensional objects, according to some examples.
Figure 11C:
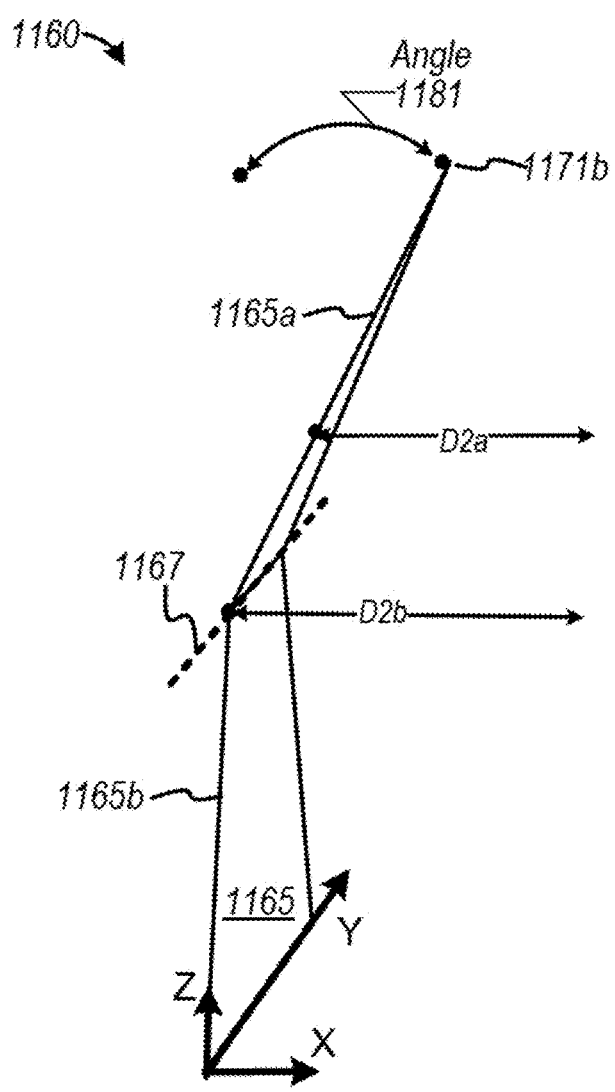
FIG. 11C is a diagram depicting examples of adaptable structural characteristics of a shadow caster for scanning three-dimensional objects, according to some examples.

Also, implementation of a gap having a relatively small distance may provide for enhanced accuracy and resolution of a 3D scan of object 1080 or 1080a, as described in association with FIGS. 11A to 11C. According to some examples, shadow caster 1015 may provide accuracies in determining edges of luminosity and points on a surface of an object (e.g., including pixels) in a range of millimeters, as well as ranges in the sub millimeters (e.g., resolutions may be expressed in units of microns or smaller). According to some embodiments, surfaces of vase 1080 or differently-shaped vase 1080b may be scanned with application of a motive force (not shown) to rotate 1092 vase 1080 or differently-shaped vase 1080b about a line in a Z-direction (and perpendicular to the X-Y plane).

FIGS. 11A to 11C are diagrams depicting examples of adaptable structural characteristics of a shadow caster for scanning three-dimensional objects, according to some examples. FIG. 11A is a diagram 1100 depicting a light source 1103, a shadow caster 1115, and a three-dimensional object 1170. In the example shown, shadow caster 1115 is depicted as being disposed in a plane (e.g., a Y-Z plane). Light source 1103 is shown to have a width W1, such as a diameter or distance parallel to a Y axis. Also, light source 1103 may be located at distance D1a from point 1111a at an edge of shadow caster 1115, and located at distance D1b from point 1111b at the edge of shadow caster 1115. Object 1170 is a pyramid having a surface portion 1172 and a surface portion 1174, which are regions of shadow cast by points 1111a and 1111b, respectively. Surface portions 1172 and 1174 are disposed at distances (e.g., average distances) D2a and D2b, relative to points 1111a and 1111b, respectively, and shadow caster 1115. Pyramid surface portions 1172 and 1174 have widths W2a and W2b, respectively. Note that FIG. 11A does not show the entire regions of 1172 and 1174 as they may be partially obscured by pyramid 1170, however, their widths along the Y axis are depicted as W2a and W2b, respectively. For example, W2a may represent a width, as measured along the Y-axis direction, of a penumbra or a width of an edge of luminosity formed in the shadow of shadow caster 1115 and light source 1103, according to some embodiments. As the height of pyramid 1170 extends in a Z-direction from a plane of projection 1110 (e.g., coextensive with an X-Y plane) to apex 1171, surface portions are located at increased distances from shadow caster 1115. Thus, distance D2a may be greater than distance D2b.

In various examples, structures described herein may be associated with characteristics that may be adapted to, for example, enhance one or more functions thereof. One or more structural characteristics of shadow caster 1115 and/or light source 1103 may be modified to enhance, for example, an edge of luminosity (e.g., sharpness). Structural characteristics may be adapted based on a relationship in which a product of width W2a and distance D1a may be proportional to a product of width W1 and distance D2a. Also, a product of width W2b and distance D1b may be proportional to a product of width W1 and D2b. As an example, a relationship may be expressed as $W2a \cdot D1a = W1 \cdot D2a$. In some examples, an accuracy of three-dimensional scanning may be enhanced with increased resolution of an edge of luminosity by, for example, reducing values of W2a and W2b, which, in turn, may be influenced by reducing a distance between shadow caster 1115 and a surface of object 1170 (e.g., reducing one or more of distances D2a and D2b, with D1a and D1b remaining constant). Width W2 may represent or otherwise influence a width of a penumbra or, for example, a width of an edge of luminosity, according to some embodiments.

In various examples, width W1 of light source 1103 may be reduced to reduce W2a and W2b in accordance, for example, to the following relationship: W2a=(D2a/D1a)·W1 (for W2a). In one instance, width W2a, for example, may reduce to less than 1 millimeter, such as to 250 microns or less by, for example, implementing a light source having a diameter (or width W1) at two (2) millimeters or less and implementing a ratio of D2/D1 as ¼ or less. Light source 1103 may be a halogen light bulb or the like, according to one example, where its linear extent (not shown) is along a line 1199 connecting light source 1103 to the apex of shadow caster 1115.

FIGS. 11B and 11C depict examples of adjusting at least a subset of distances D1 and D2 as a function of locations of surface portions, such as surface portion 1172 (e.g., relative to surface portion 1174). According to some examples, shadow caster 1115 may be configured, adapted, or formed to reduce a subset of distances D2, including distance D2a, while increasing a subset of distances D1, including distance D1a of FIG. 11A, affecting a scan of greater resolution as described in the equation above associated with FIG. 11A. Diagram 1130 of FIG. 11B depicts shadow caster 1135 having an apex 1171a oriented at an angle 1131 from a line 1179 (e.g., orthogonal to X-Y plane). At angle 1131, distances D2a and D2b may be approximately equalized to provide for a substantially constant gap between a surface of shadow caster 1135 and one or more surface portions of object 1170 of FIG. 11A. Diagram 1160 of FIG. 11C depicts shadow caster 1165 including a portion 1165a adapted to vary in the X-direction, which is the direction between a light source (not shown) and apex of 1171b, such that shadow caster 1165 has portion 1165a that is oriented about axis 1167 by an angle 1181 relative to a portion 1165b. This change maintains the profile of the shadow caster as projected along the direction of the line between light 1103 of FIG. 11A and apex 1171b of shadow caster 1165, onto, for example, a plane of projection parallel to the Y-Z plane (not shown). This change is an example that maintains that there is a single plane containing the light 1103 of FIG. 11A, and both portions 1165a and 1165b. At angle 1181, distance D2a may be reduced to approach or approximate distance D2b. According to some cases, multiple portions 1165a (not shown) may be implemented to approximate a curvature of an object to be scanned, or the shadow caster can be similarly distorted in a continuous manner along a Y direction to effectuate smooth profiles.

Figure 12:
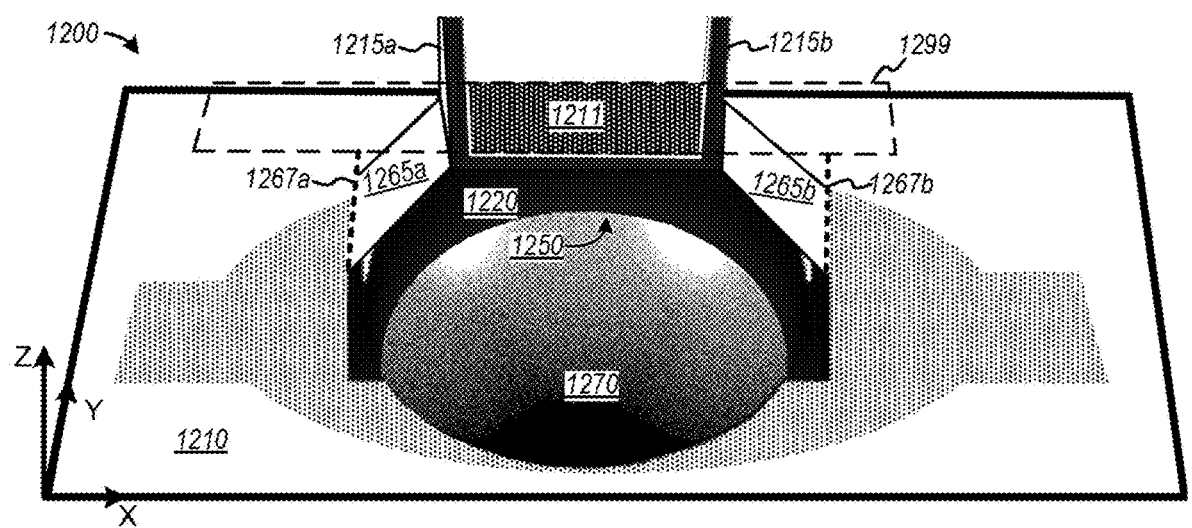
FIG. 12 is a diagram depicting an example of configurable shadow casters, according to some examples.

FIG. 12 is a diagram depicting an example of configurable shadow casters, according to some examples. Diagram 1200 includes shadow casters 1215a and 1215b having adaptable portions 1265a and 1265b, respectively, to approximate shapes of an object surface to reduce or equalize magnitudes of gap variation between shadow casters 1215a and 1215b and an example scanned object 1270. Object 1270 is a hemisphere disposed on a plane of projection 1210. Adaptable portions 1265a and 1265b are depicted in this example as portions angled about axes 1267a and 1267b, respectively. In some examples, shadow casters 1215a and 1215b may be implemented to constitute a system of shadow casters that optionally may include an adaptable opaque top portion 1211 coupled between shadow casters 1215a and 1215b to contribute to the generation of shadow 1220 (or umbra) and one or more edges of luminosity 1250. A light source (not shown) collinear with the line defined by, for example, lines 312, 412, or 512 of FIG. 3, 4, or 5, respectively, may lie above shadow casters 1215a and 1215b, and between them with implementation of top portion 1211 (or portions 1265a and 1265b), at least in some cases. Note that adaptable portions 1211, 1265a, and 1265b may be subdivided in any number of planar portions to approximate a curvature. Alternatively, adaptable portions 1265a and 1265b may be formed as, or configured to include, one or more curved portions.

According to some embodiments, shadow caster portions 1215a and 1215b may be detected by an image-capturing device (not shown) to, for example, determine geometry of a plane of an edge of illumination. This determined plane of edge of illumination may then be used in conjunction with a deformation of the edge of illumination to determine the shape of object 1270. Shadow caster portions 1215a and 1215b may be similar to 815, 915, and 1015 in having a triangular profile in order to define a single plane edge of illumination on each edge. Alternatively, shadow caster portions 1215a and 1215b may be structural and supportive of portions 1211, 1265a and 1265b and not in itself cast a shadow edge onto object 1270. Note while object 1270 is depicted as a smooth-surfaced hemisphere, any shaped object may be used. In some cases, object 1270 may include surface topologies and textures that include convex and concave surface portions, including, but not limited to, protruding or ridge-like features and depressions, fissures, or grooves, and the like. In some examples, object 1270 may be representative of a surface of a brain, or any other organic structure.

In at least one example, a shadow caster may include section 1211, which may have one or more straight edges parallel to a line containing a light source (not shown), and section 1211 may extend longitudinally (e.g., having a perimeter 1299) so as to cast a shadow over each dimension of object 1210. Thus, portions 1265a and 1265b may be omitted. In such a case, there may also be multiple light sources (not shown) parallel to each other and to 1211. The multiple parallel light sources may be illuminated sequentially (and/or spatially) to generate a sequence of straight shadows. A parallel light source or the shadow caster, or both, may be moved to effectuate a scan across a surface of object 1210 and may have multiple rows of lights that need not be disposed on an axis of rotation. Such a configuration may generate one or more shadow planes with a geometry that may be used in conjunction with a deformation of an edge of luminosity to determine the three-dimensional shape of object 1270. Parallel light sources may extend to regions above section 1211 to generate the edge of illumination of object 1270. According to at least one example, one or more light sources may be limited in extent so as to extend above section 1211 without (or with minimal or negligible) extensions longitudinally to either side along an X-direction, which may sufficiently illuminate object 1270 (e.g., evenly illuminate object 1270) on its illuminated portion while also producing an edge of luminosity with enhanced contrast.

According to various examples, selectably-opaque shadow casters may be formed such that a shadow caster may implement one or more portions that are opaque to white light, or they may include colored portions that may be configured to selectably reduce or negate transmission of certain wavelengths of light (e.g., implementing color filtering). Edges of luminosity may then be determined by illuminated regions transitioning to relatively darker regions of illumination (e.g., region of less illumination) at wavelengths variously transmitted by the shadow casters. Alternatively, an edge of luminosity may be determined by regions illuminated at one wavelength range transitioning to regions illuminated by one or more other wavelength ranges.

Shadow casters may contain multiple wavelength transmission regions arranged in a pattern that may also have opaque regions in combination.

Selectably-opaque shadow casters may be configured to be opaque relative to one or more ranges or bands of wavelengths of light. Thus, a selectably opaque shadow caster may selectably filter out one or more ranges of wavelengths of light to allow selected wavelengths to pass through. In one example, different selectably opaque shadow casters may be implemented as colored transparent shadow casters that cast light that transitions from blue light to red light, whereby an example of a set of colored transparent shadow casters may include at least two flat color-filters abutting each other. One transparent shadow caster may be red and the other may be blue. When scanning, a scene transition from blue to red may constitute an edge of illumination, and may be filtered to identify the blue-to-red transition from other changes in the scene. Keeping track of this color change provides a technique to track shadow motion, even if other things in the scene change. As such, a particular color change (regardless of the colors) may be processed to identify an edge of illumination. According to various examples, the above-described selectably-opaque shadow casters may facilitate 3D scanning when object 1210 (or any other object) may move relative to an image capture device (e.g., in a controllable way). A mobile computing device, such as a mobile phone with a camera or any other mobile device, may implement the above-described selectably-opaque shadow casters, according to some embodiments.

Figure 13:
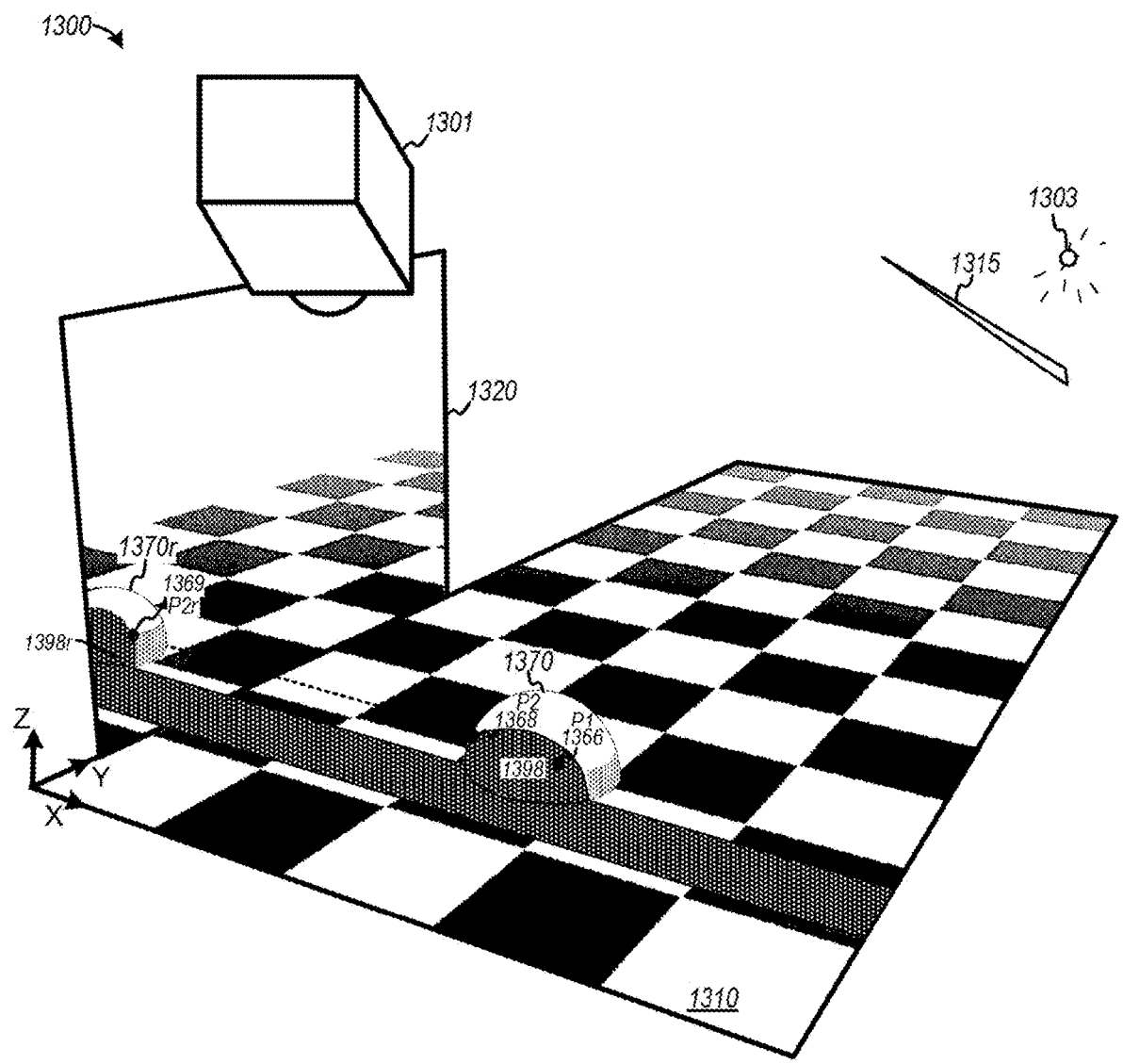
FIG. 13 is a diagram depicting an example of a scanning system, according to some examples.

FIG. 13 is a diagram depicting an example of a scanning system, according to some examples. Diagram 1300 depicts another example of a shadow caster 1315 as a constituent component of a scanning system including an image capture device 1301, one or more sources of light 1303, a reflective surface 1320 (e.g., a reflective plane or mirror). Reflective surface 1320 may obviate implementation of another set of a shadow caster and a light source opposite shadow caster 1315. Object 1370 is disposed on planar projection 1310 and its reflection 1370r is depicted in reflective surface 1320. Further, diagram 1300 depicts a point ("P2") 1368 on the surface of object 1370 as reflected point ("P2r") 1369 in reflective surface 1320. As shown, casted shadow 1398 on object 1370 may be reflected as shadow 1398r on reflection of object 1370r. Note that photonic emission, including light, may travel a farther distance to illuminate point 1368 (via reflected light) than that may travel to point 1366. Thus, light reflected by reflective surface 1320 into image capture device 1301 from a surface portion including point 1368 may be less bright and less accurate than reflected light from another surface portion including point 1366. However, distance D1 of the relationship W2=(D2/D1)·W1 may be modified relatively (e.g., increased) to enhance contrast, among other things, associated with an edge of luminosity at point 1368.

Image capture device 1301 may observe the reflected object 1370 as 1370r and may thereby observe portions of 1370 not otherwise visible through the unreflected or direct observation of object 1370. In this way, other reflective surfaces (not shown) may be disposed within the field of view of image capture device 1301 such that image capture device 1301 may observe one or more portions of 1370 in reflection not otherwise visible through unreflected or direct observation of object 1370. For example, one may make the plane of projection 1310 a reflective surface that would reflect the underside of objects disposed upon them to image capture device 1301. A shadow caster may then be moved, for example, to effectuate a scan such that edges of luminosity may also reflect from the reflective surface onto regions not otherwise accessed by the shadow through unreflected or direct projection of the shadow edge onto object 1370. Reflective surfaces may be a flat geometry but may also be curved or include curved surfaces or segments of flat surfaces or a combination of both.

Figure 14:
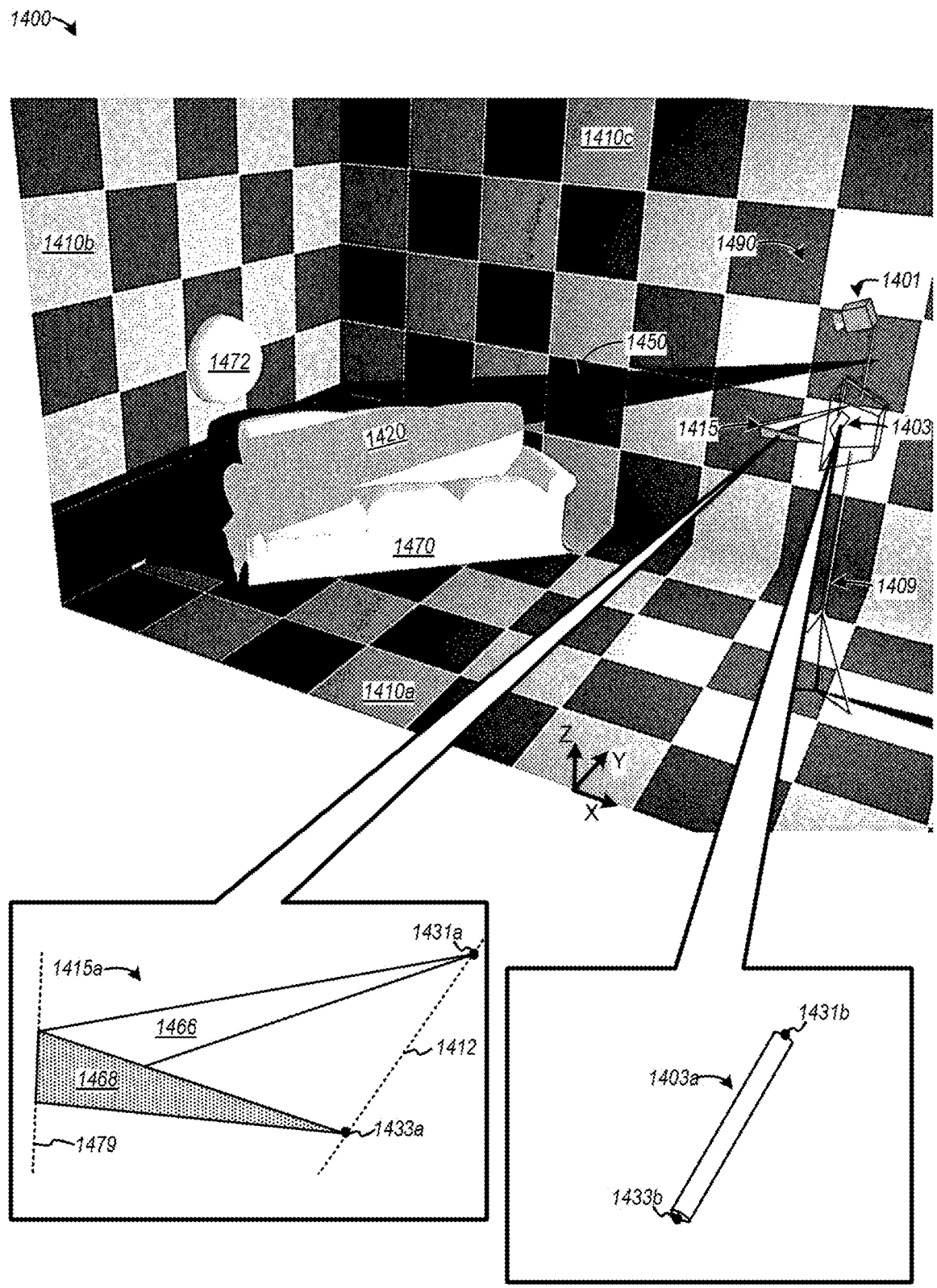
FIG. 14 is a diagram to depicting yet another example of a scanning system, according to some examples.

FIG. 14 is a diagram depicting yet another example of a scanning system, according to some examples. Diagram 1400 illustrates a scanning system 1490 including an image capture device 1401, a shadow caster 1415, one or more light sources 1403, and a stand or structure 1409 configured to implement or integrate the foregoing components. Scanning systems described herein may be scalable to scan relatively small objects and relatively large objects, such as objects in any environment. Examples of an environment include a room (e.g., persons, appliances, furniture, etc.), and outside buildings (e.g., scanning of the building, vehicles, trees, etc.). In the example shown, scanning system 1490 may be configured to scan a couch 1470 and a wall ornament 1472, such as a mirror or painting, in a room defined by planes of projection 1410a (e.g., a floor), 1410b (e.g., a rear wall), and 1410c (e.g., a sidewall).

In the example shown, shadow caster 1415 may be implemented as a diamond-shaped structure, or any equivalent shadow caster having cross-sectional area that may generate similar or equivalent single edge, or sharp shadow, or two edges of luminosity as described in association with, for example, shadow casters in FIGS. 9 and 10. Shadow caster 1415a is shown to be formed as, for example, two (2) triangular shaped structures 1466 and 1468 joined or coupled at line 1479. Apex 1431a and apex 1433a may be disposed on an axis of rotation 1412, whereby rotation of shadow caster 1415a about axis 1412 may generate edge of luminosity 1450. Further, light source 1403 may be implemented as light source 1403a, which may include a light source or a linear arrangement of one or more light sources along an axis spanning from a point 1431b to a point 1433b. One example of light source 1403a may be an elongated halogen bulb. Another example of light source 1403a may be a linear array of light-emitting diodes. Points 1431b and 1433b of light source 1403a may be collinear with points 1431a and 1433a, respectively, on axis 1412. According to various examples, shadow caster 1415 and light source 1403 may be implemented in any number of structures or varieties, and those depicted in diagram 1400 are not intended to be limiting. Furthermore, scanning system 1490 and other scanning systems described herein may be varied and adapted to any number of applications, including medical applications and augmented reality applications, among others.

Figure 15:
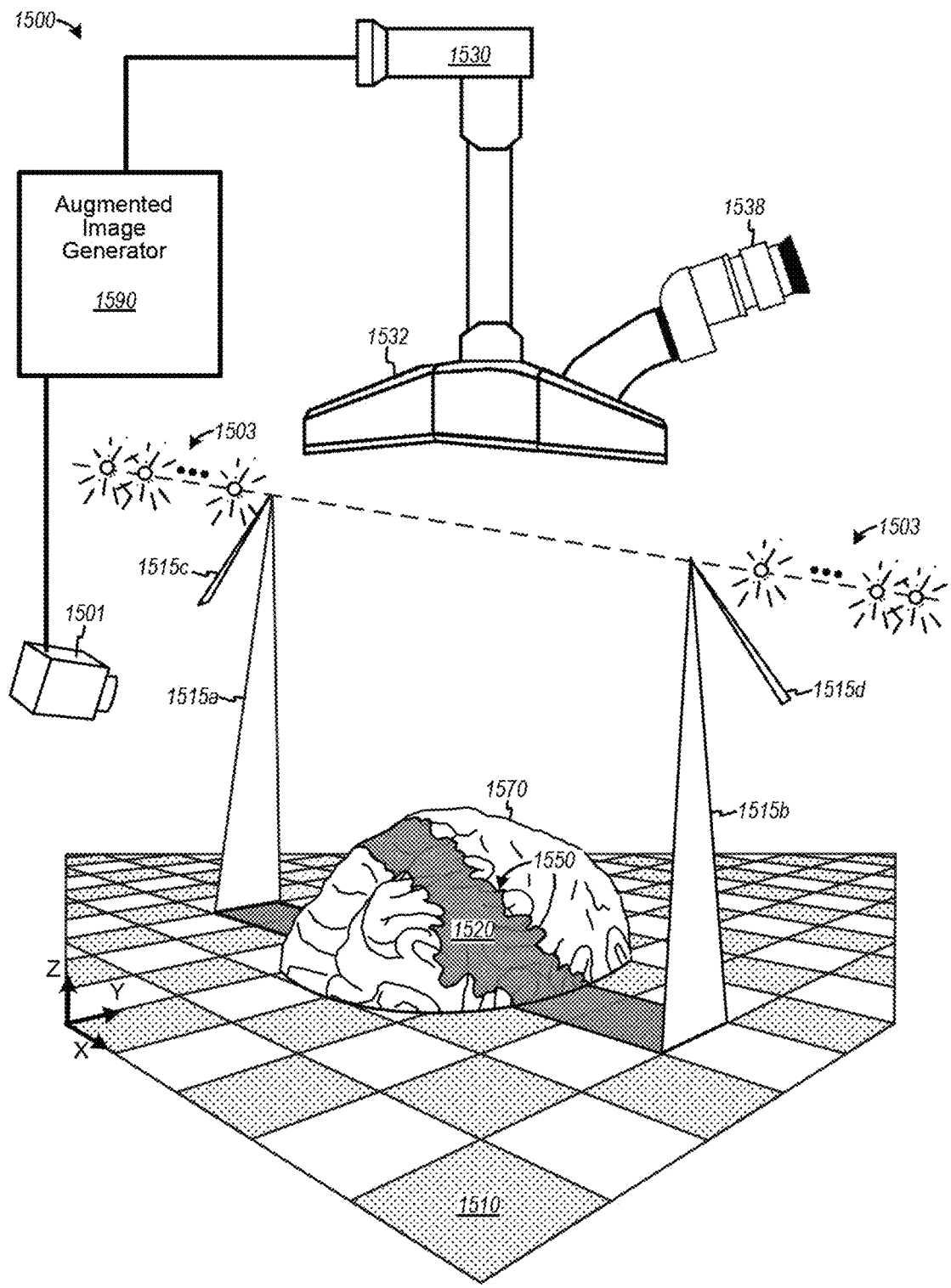
FIG. 15 depicts an example of a scanning system configured to perform medical applications, according to some examples.

FIG. 15 depicts an example of a scanning system configured to perform medical applications, according to some examples. Diagram 1500 includes a medical instrument or tool, such as a surgical microscope 1530. Surgical microscope may be adapted to implement data generated by a scanning system configured to perform three-dimensional scanning of tissue in vivo, such as brain tissue (i.e., as an object 1570), for medical applications. Further, scanning system of diagram 1500 may facilitate in situ three-dimensional scanning of brain tissue during surgery.

Surgical microscope 1530 includes optical components 1538, including eye pieces, which may be configured to magnify relatively small features of interest, including tissue, and may further be configured to integrate digitally-created imagery that may be integrated or overlaid over a magnified view of brain 1570. According to the example shown, surgical microscope 1530 may be coupled electronically or optically to an augmented image generator 1590, which, in turn, may be coupled electronically or optically to an image capture device 1501. In some examples, surgical microscope 1530 may be coupled electronically or optically to image capture device 1501, which, in turn, may be coupled electronically or optically to augmented image generator 1590. In some examples, augmented image generator 1590 may optically augment a view of magnified brain tissue by applying (e.g., overlaying) 3D scanned-based imagery onto a view of the brain tissue. For example, cross-hatching graphics representing a target brain portion (e.g., for repair or removal) may be overlaid in three dimensions onto a view or digital image of the magnified brain tissue so that a surgeon may readily identify the target. Housing 1532 of surgical microscope 1530 may include processors and electronic components configured to execute instructions (e.g., software, firmware, etc.) to optically combine image data generated by augmented image generator 1590.

A scanning system of diagram 1500 may implement any type or number of shadow casters in accordance to a variety of examples. One or more scanning systems may include one or more subsets 1503 of one or more light sources, and a subset of shadow casters configured to form a shadow 1520 and one or more edges of luminosity 1550. A subset of shadow casters may include one or more of shadow casters 1515*a* and 1515*b* in a first exemplary implementation. Another subset of shadow casters may include one or more of shadow casters 1515*c* and 1515*d* in a second exemplary implementation. Other shadow caster and light source structures may be used, as well.

In various applications, including medical application, a scanning system of diagram 1500 may have resolutions of less than 1 millimeter (e.g., 25 microns or less), at least in some cases, to form 3D representations of at least a portion of brain 1570. In some cases, scanning system of diagram 1500 may provide 3D surface information of resolutions finer than that available using magnetic resonance imaging ("MRI") scan data, or other technologies, such as computed tomography ("CT") scan data.

Organic objects consisting of soft tissue, such as brain 1570, may have three-dimensional surface shapes that may change or vary due to altered conditions. For example, flexible soft tissue may have a first three-dimensional surface shape in a first state (e.g., undisturbed, prior to surgery), whereby the surface shape may vary from the first state when transitioned to a second state (e.g., subsequent to a medical or surgical procedure). In one example, the surface shape may vary in state rhythmically (e.g. in response to the rhythmic blood pressure variations due to the heart beating). In at least one state, the surface of brain 1570, or a portion thereof, may be scanned using one or more of shadow casters 1515*a*, 1515*b*, 1515*c*, and 1515*d* to form a three-dimensional model of brain 1570. A camera 1501 may capture images of brain 1570 and augmented image generator 1590 may determine X, Y and Z coordinates of pixels representing points on the surface of brain 1570. In the case where the surface shape is changing in rhythmic response to variations (e.g. heart beating and pulsating blood flow), the scan may be performed over a time period that allows measuring surface 1570 at multiple stages in the rhythmic response, such that surface 1570 may be determined at each of those stages. This may be achieved by correlating stages of the measured surface 1570 with stages in the rhythmic response as the scan is being performed.

In particular, a scanning system of diagram 1500 may be configured to capture digitally the contours and other anatomical features of brain 1570. For example, the surface curvature and contours of a modeled brain surface may include ridges (i.e., gyri) and grooves (i.e., sulci) of the cerebral cortex in three-dimensional space. Further, the scanning system of diagram 1500 may be configured to capture the three-dimensional surface features of a vascular system serving the brain (e.g., veins, arteries, capillaries, etc.), whereby vascular tissue may be used as monuments (or guide posts) to provide a vascular "roadmap" to assist surgeons navigating a blood vessel to a portion of brain 1570. Some of these vessels may be more fine than a resolution of associated MRI or CT scans.

Before the operation, a patient may undergo a diagnostic procedure such as magnetic resonance imaging to obtain MRI scans, which may depict 2D and 3D images of brain 1570, including interior structures. Thereafter, brain 1570 may be exposed subsequent to a craniotomy, or removal of a portion of a bone. A scanning system of diagram 1500 may optionally be used to generate a 3D scan of an exposed portion of brain 1570 (e.g., prior to disturbance of the structure of brain 1570). Augmented image generator 1590 may be configured to receive a first subset of data representing MRI scans of a brain and a second subset of data representing 3D scan data of brain 1570 originating from the scanner system of diagram 1500. Further, augmented image generator 1590 may include processors and electronic components configured to execute instructions (e.g., software, firmware, etc.) to associate the 3D surface of the second subset of data to the MRI-generated surface of the first subset of data. Thus, 3D scan data from the second subset of data may be associated with data representing interior structures of the MRI-generated brain scan data from the first subset of data.

With a portion of a skull removed, brain tissue forming a portion of a cerebral cortex may be accessed via an incision into a membrane (e.g., pia mater, etc., or other fluid barrier tissue). Incisions into the membrane surrounding brain tissue may result in loss of fluid (e.g., cerebrospinal fluid, or CSF), thereby causing a change in a structural state of the brain. With loss of the fluid, brain tissue structures can deflate or otherwise deform due to a change of mechanical properties, which, in turn, may cause brain tissue structures to shift. Therefore, shifted brain tissue introduces error into using MRI data to locate surface and interior structures of brain tissue to identify a targeted location of brain tissue.

Post-incision, the scanner system of diagram 1500 may be used to determine the curvature and contours brain 1570 after brain tissue shape shifts due to decreased internal fluid pressure. Subsequently, augmented image generator 1590 may include logic configured to form a second three-dimensional model of surface of brain 1570, which may include positional deviations in brain tissues and vascular structures relative to MRI scan data. Further, augmented image generator 1590 may include logic configured to identify vascular structures and other landmarks such as specific sulci and gyri, in three-dimensional brain models in both pre-incision and post-incision states, and determine positional deviations for registration and alignment of digital imagery. As vascular tissue (e.g., blood vessels) may be resiliently affixed to adjacent brain tissue, the deviation in vascular structures may be used instead of, or in addition to, the deviation of the specific sulci and gyri to predict post-incision positions of interior brain tissue portion. Further, previously obtained MRI scan data may be adjusted to reflect the predicted post-incision positions of interior brain tissue. Hence, the movement of capillaries and sulci and gyri with associated brain tissue may aid in predicting a location of targeted brain tissue. During a medical procedure, scanner system of diagram 1500 may also be used to determine affected portions of the brain (e.g. after brain tissue has been excised or otherwise changed). Previously-obtained MRI scan data may be adjusted to reflect the predicted post-incision portions of brain tissue thus affected by the medical procedure.

Logic in augmented image generator 1590 may be configured to correlate changes in locations of vascular structures to predict position deviations of interior brain tissue from initial MRI scan data. Additionally, the predicted position deviations of interior brain tissue may be determined by calculating brain deformation that approximates expected changes based on a model of brain deformation data and calculations. According to some examples, a model of brain deformation data may represent expected changes in a brain as a function of various factors (e.g., amount of fluid loss, incision size, gender, age, ethnicity, infirmity, etc.). Such a model may be used to predict how a brain structure may deform due to a loss of cerebrospinal fluid. The brain deformation data may be formed empirically and/or probabilistically (e.g., mathematically) via computing algorithms.

In view of the foregoing, a targeted portion of brain tissue may be localized prior to surgery within a three-dimensional space of brain 1570. An example of a targeted portion of brain tissue may be that which causes pediatric epileptic seizures. Removal of the targeted portion of brain tissue may alleviate symptoms, including seizures. In accordance with the above-described implementation of the scanner system of diagram 1500, augmented image generator 1590 may be configured to identify or predict positional deviations of brain tissue at the surface and within the interior of brain 1570. Thus, augmented image generator 1590 may be configured to identify or predict positional deviations of a targeted portion of brain tissue additionally identified, for example, in an initial MRI.

According to various examples, the above-described techniques implementing the scanner system of diagram 1500 may be applicable to other brain related diagnostics, testing, surgeries, and remedies. Moreover, the above-described techniques may be applicable to any medical application, including hard tissues (e.g., bones, etc.). Another example is the use of the scanner system of diagram 1500 for wound healing. For example, consider a scanner system similar to that of diagram 1500 (excluding surgical microscope 1530) may be disposed at a residence of diabetic patient to monitor a wound (e.g., an ulcer) against infection. The patient may have the wound scanned three dimensionally (e.g., with or without color) to generate wound shape data that may be transmitted via a network to a healthcare provider to monitor the rate of healing of the wound. The above-described examples are non-limiting and may be applicable to any medical or non-medical application.

Figure 16A:
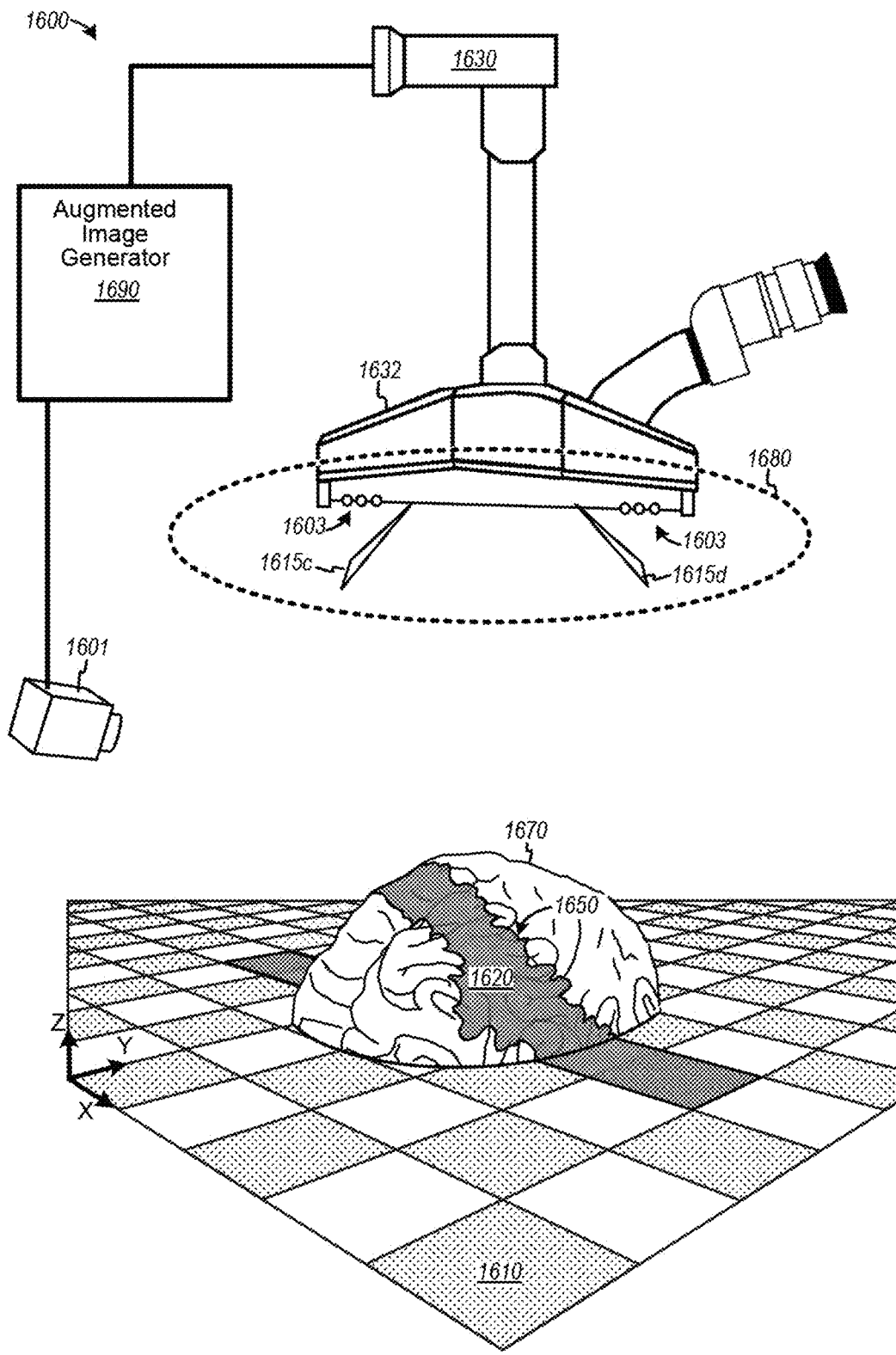
FIG. 16A is a diagram depicting a specialized surgical microscope including a system of shadow casters, according to some examples.

FIG. 16A is a diagram depicting a specialized surgical microscope including a system of shadow casters, according to some examples. Diagram 1600 includes a surgical microscope 1630, an augmented image generator 1650, and an image capture device 1601 configured to facilitate in situ three-dimensional scanning of brain 1670. According to some examples, elements depicted in diagram 1600 of FIG. 16A may include structures and/or functions as similarly-named or similarly-numbered elements depicted in other drawings. In this example, shadow casters 1615c and 1615d and light sources 1603 may interact as a system 1680 to form shadow 1620 and one or more edges of luminosity 1650. In some embodiments, shadow casters 1615c and 1615d and light sources 1603, or equivalents thereof, may be disposed within housing 1632 to form an integrated three-dimensional scanning surgical microscope configured to perform 3D scanning in accordance to examples described herein.

Figure 16B:
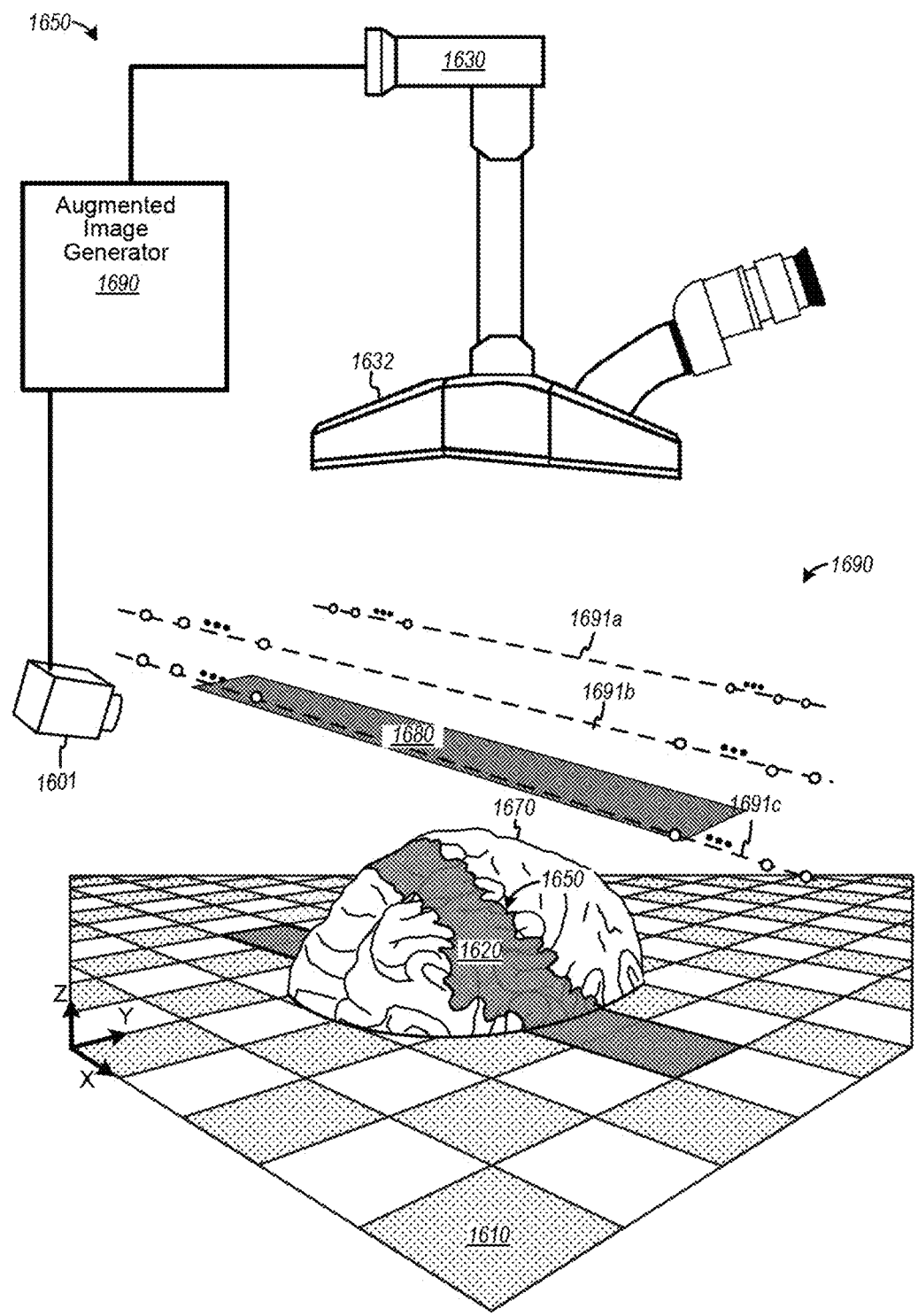
FIG. 16B is a diagram depicting yet another specialized surgical microscope including at least one shadow casters, according to some examples.

FIG. 16B is a diagram depicting yet another specialized surgical microscope including at least one shadow caster, according to some examples. Diagram 1650 includes a surgical microscope 1630 and other elements described herein configured to facilitate in situ three-dimensional scanning of brain 1670. According to some examples, elements depicted in diagram 1650 of FIG. 16B may include structures and/or functions as similarly-named or similarly-numbered elements depicted in other drawings. In this example, shadow caster 1680 and subsets of light sources 1691a, 1691b, and 1691c may interact as a system 1690 to form shadow 1620 and one or more edges of luminosity 1650 as a function of a subset of light sources 1691a, 1691b, and 1691c being illuminated at different points in time. An example of shadow caster 1680 is described in FIG. 12, and light sources 1691a, 1691b, and 1691c may be disposed above shadow caster 1680. According to some examples, subset of light sources 1691a, 1691b, and 1691c are implemented as multiple parallel light sources that may be illuminated sequentially and/or spatially to generate a sequence of shadows (e.g., straight shadows or edges of luminosity). In some embodiments, shadow caster 1680 and light sources 1691a, 1691b, and 1691c, or equivalents thereof, may be disposed within housing 1632 to form an integrated three-dimensional scanning surgical microscope configured to perform 3D scanning in accordance to examples described herein.

Figure 17:
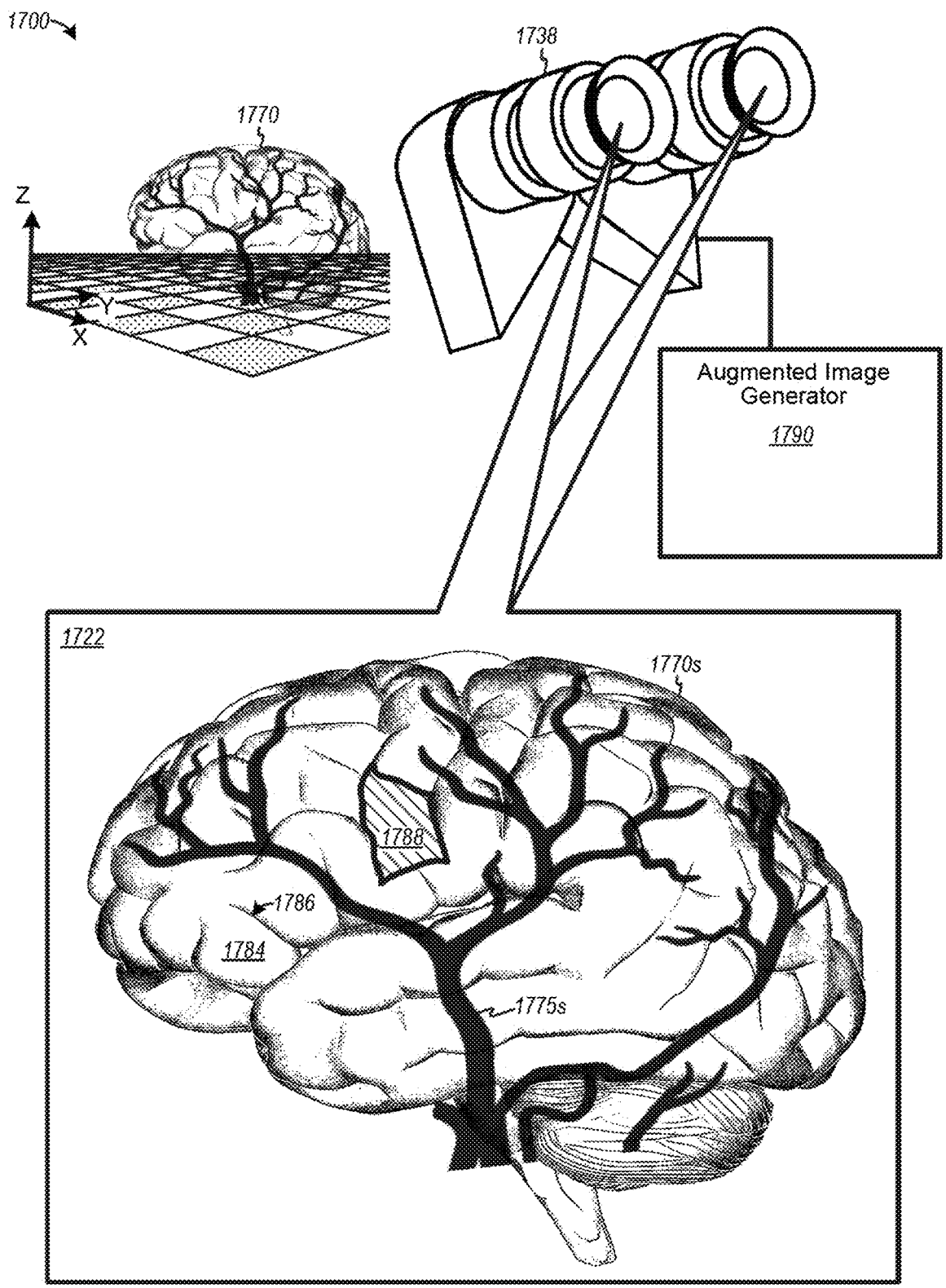
FIG. 17 is a diagram depicting a magnified image based on three-dimensionally scanned features, according to some examples.

FIG. 17 is a diagram depicting a magnified image based on three-dimensionally-scanned features, according to some examples. Diagram 1700 includes optical components 1738 configured to magnify portions of a brain 1770. A surgical microscope to which optical components 1738 couple is not shown. Diagram 1700 also includes an augmented image generator 1790 configured to integrate optical imagery of brain 1770 (based on light reflected from surface of the brain) and digitally-generated image overlay data representing, for example, a surface location of target brain tissue 1788, which may be observable via optical components 1738. In some examples, a surgeon or any other user may view via optical components 1738 an image presented in inset 1722. For example, one may view a brain 1770s, and portions thereof, in eyepieces 1738 relative to gyri or sulci or relative to a vascular system 1775s of blood vessels having various number or size. In some examples, contours of brain 1770s may be captured via three-dimensional scanning as ridges (gyri) 1784 and grooves (sulci) 1786. According to at least one example, inset 1722 may include either real (e.g., directly magnified) imagery or simulated imagery (e.g., based on image processing), or a combination of both.

Figure 18:
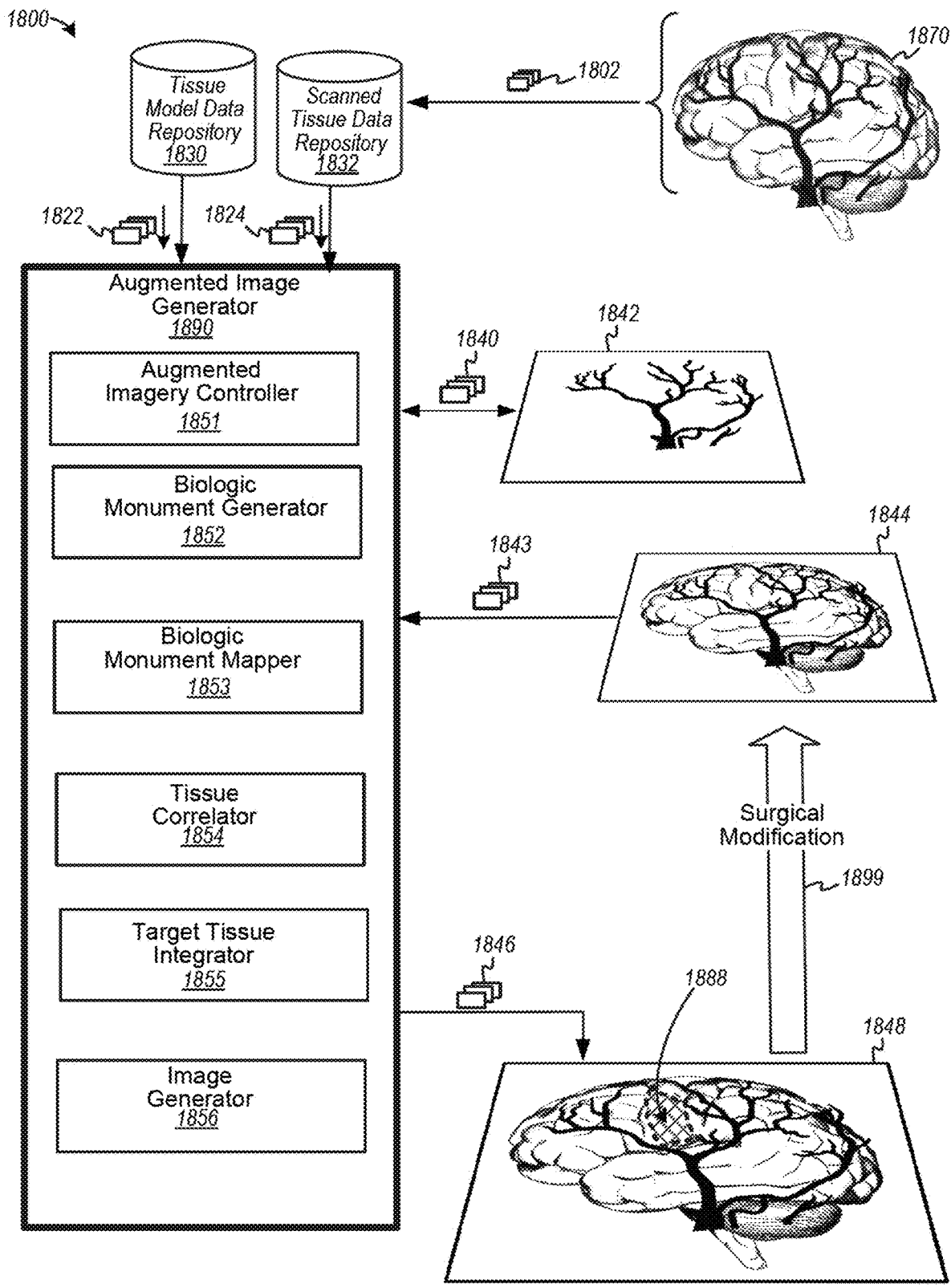
FIG. 18 is a functional block diagram depicting in vivo three dimensional scanning and image integration, according to some examples.

FIG. 18 is a functional block diagram depicting in vivo three-dimensional scanning and image integration, according to some examples. Diagram 1800 includes an augmented image generator 1890, a tissue model data repository 1830, and a scanned tissue data repository 1832, one or more of which may be implemented to form, for example, imagery depicted, for example, in FIG. 17. Scanned tissue data repository 1832 is configured to receive scanned brain data 1802 representing two-dimensional and/or three-dimensional anatomical features and structures of brain 1870. For example, data 1802 may include MRI data, CT data, MEG data, PET data, or any other brain-related data may be stored in scanned tissue data repository 1832 and retrieved by augmented image generator 1890 as data 1824. Tissue model data repository 1830 may be configured to store data models to determine or predict a rate of change in brain deformation or positional deviation in a brain based on a function of various factors (e.g., amount of fluid loss, incision size, gender, age, ethnicity, infirmity, etc.). These data models may be used by augmented image generator 1890 to predict and simulate mathematically (e.g., probabilistically) a degree to which a brain structure may vary (e.g., with respect to size, position, location, etc.) due to a corresponding loss of cerebrospinal fluid or extracted tumor or brain mass. Data 1822 from the data models may be retrieved by augmented image generator 1890. According to some examples, elements depicted in diagram 1800 of FIG. 18 may include structures and/or functions as similarly-named or similarly-numbered elements depicted in other drawings.

Augmented image generator 1890 is shown to include an augmented imagery controller 1851, a biologic monument generator 1852, a biologic monument mapper 1853, a tissue correlator 1854, a target tissue integrator 1855, and an image generator 1856. According to at least some examples, augmented imagery controller 1851 may be configured to control subsidiary functions (e.g., elements 1852 to 1856) of augmented image generator 1890 to facilitate an overall function of augmented image generator 1890.

Biologic monument generator 1852 may be configured to access scanned tissue data 1824 (e.g., MRI data) to generate data 1840 representing characteristics of vascular or brain data 1842, such as spatial dimensions, positions, etc., of blood vessels. Data 1842 represents a data structure including data 1840 specifying, for example, spatial dimensions, positions, etc., of geometric features based on, for example, blood vessels or any other physiological feature, such as features of sulci, gyri, or the like. Vascular data 1842 may originate from data 1824. Data 1840 is an example of data retrieved from data structure 1842, which enables portions of vascular system data 1842 to be used as "monuments" (e.g., survey monuments identifying a "roadmap" to brain portions of interest), or reference points relative to, for example, adjacent brain tissue. According to some examples, geometric features, such as vascular geometric features may be described in vascular system data 1842, which may represent characteristics (e.g., surface features) of a vascular system for brain 1870 prior to surgical or other structural disturbances.

Biological monument mapper 1853 may be configured to map or otherwise correlate an updated subset of data 1844, which includes data representing brain or vascular data (e.g., at the surface of brain 1870 post-incision) derived via three-dimensional scanning by a model generator. In some examples, biological monument mapper 1853 may be able to compute and characterize positional displacement of portions of brain or vascular data 1842 based on structural brain deformation. Positional displacement data 1843 may be received at tissue correlator 1854.

Tissue correlator 1854 may be configured to correlate surface feature data 1843 of a deflated brain to initial MRI surface data 1824 to identify original portions of brain tissue initially detected by MRI. Based on displacement of blood vessels and surface features (e.g., ridges and grooves), the displacement in surfaces portions can be identified, as well as displacement of targeted portion of brain tissue 1888. It may also be configured to access tissue model data repository 1830 to perform calculations that estimate and predict displacement of the surface of interior brain structures.

Target tissue integrator 1855 is configured to identify a portion of targeted brain tissue, which may or may not be associated with a dye, relative to MRI data 1824. The targeted tissue 1888 may represent, for example, brain tissue associated with pediatric epilepsy, or a tumor. Further, target tissue integrator 1855 may be configured to calculate displacement of targeted tissue 1888 in relation to post-incision activities and data from tissue correlator 1854. For example, tissue correlator 1854 may be configured to determine positional deviations with which to adjust target tissue 1888 for identification and extraction.

Image generator 1856 may be configured to generate image data 1846 that depicts an overlaid target tissue 1888 upon an image 1848 of a brain in real-time (or substantially in real-time), as well as in vivo. Image data 1846 is depicted as a real-time 2D or 3D image of an in-vivo view that augments data 1844 providing a view with a view of targeted region 1888 overlaid thereupon. Therefore, a surgeon may be enabled to address targeted tissue 1888, and upon extraction of a brain portion at 1899 (a surgical modification), the remaining brain portions to be extracted may be detected in vivo based on 3D scanning to update subset of data 1844. Augmented image generator 1890 may recalculate graphical overlay data for optical presentation of remaining tissue to a surgeon for subsequent treatment. Thus, a surgeon may view the "peeling away" of extracted tissue based on in situ 3D scanning and presenting via optical microscope or other surgical navigation device or display the remaining tissue to be extracted in vivo. According to various other examples, functional block diagram 1800 may be varied in accordance with the various examples described herein.

Figure 19:
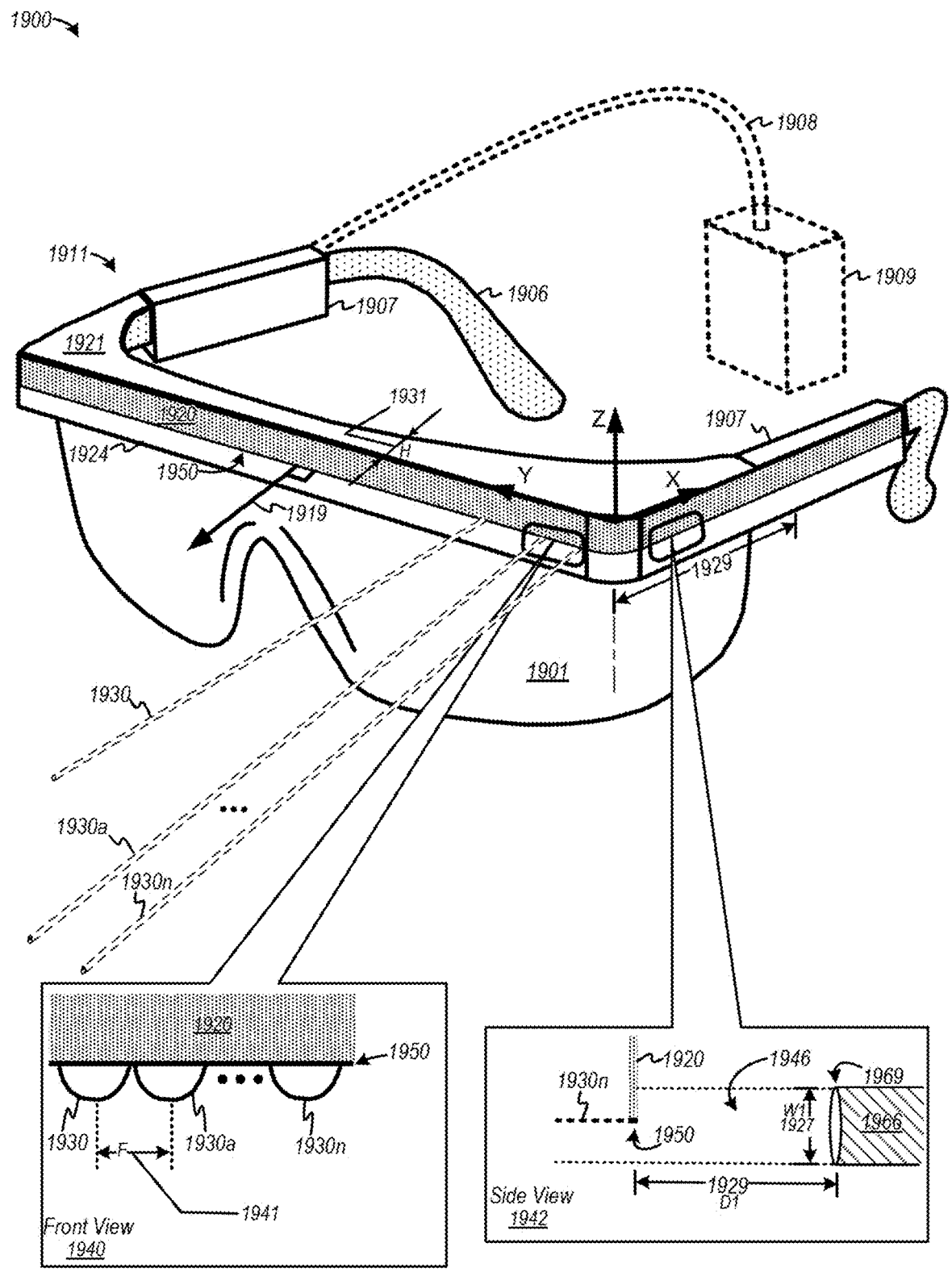
FIG. 19 is a diagram depicting yet another example of one or more shadow casters configured to generate one or more edges of luminosity, according to some examples.

FIG. 19 is a diagram depicting yet another example of one or more shadow casters configured to generate one or more edges of luminosity, according to some examples. Diagram 1900 depicts a wearable shadow caster, such as wearable system 1911 that may be configured to generate at least one edge of luminosity to facilitate three-dimensional scanning. In this example, wearable system 1911 is eyewear that include at least a front housing 1921 having at least one shadow caster 1920 having an edge 1950 configured to generate an edge of luminosity. Shadow caster 1920, at least in some examples, may be an opaque film applied to a transparent surface (e.g., lenses or frame of eyewear). The eyewear may also include earpieces 1906 to secure about a user's ears and temple bar structures 1907 that may include electronics, light guides, etc. to facilitate implementation of the eyewear as three dimensional scanner including a shadow caster disposed therein. The eyewear may receive light and electronic signals via conduit 1908 from a power and light generation module 1909, which may be optional and may be disposed anywhere on a user's person or elsewhere.

Further to wearable system 1911, the eyewear may include an optional transparent structure 1924 through which photonic emissions, including light, may be transmitted. Transparent structure 1924 may implement Fresnel prisms as a layer to control forward transmitted light along the direction parallel to edge 1950. A lens 1901, which may be optional, may be configured to receive projected light (not shown) upon which to form a heads up display, or HUD, at least in some cases. In the example shown, light sources may be implemented as optical fibers (e.g., fiber optic) configured to emit light as, for example, light beams 1930, 1930a, and 1930n (e.g., as formed from a source behind temple bars or similar structures). Many more light beams may be implemented, or beams may be in the shape of a continuous emitted line as would result from the partially overlapping combination of many light beams 1930, 1930*a*, and 1930*n*. Further, the wavelengths of light transmitted via the fiber as light emission or beams 1930, 1930*a*, and 1930*n* may be of any wavelength range. For example, light emitted from the optical fibers may be in a range of wavelengths of light not detectable or perceived by the human eye (e.g., within non-visible spectra of light). In some examples, front view 1940 depicts light emission 1930, 1930*a*, and 1930*n* from fibers, whereby the light emissions may impinge at edge 1950 of shadow caster 1920 to form an edge of luminosity. Front view 1940 in this example is shown to be in a plane parallel to a Y-Z plane (e.g. viewing along the X-axis). Further to front view 1940, light beams may be directed at any distance ("F") 1941 along edge 1950, relative to each other (e.g., next to each other), and the distance between each other need not be the same. Any number of ends of fibers may be implemented to generate any number of light emissions 1930, 1930*a*, and 1930*n*.

According to some examples, light beams 1930, 1930*a*, and 1930*n* may be disposed or oriented such to traverse a common plane, such a plane parallel an X-Y plane. In some examples, light emission 1930, 1930*a*, and 1930*n* from each fiber and/or ends of fibers (not shown) may each emit such that at edge 1950 its direction is parallel to a line 1919 normal surface of shadow caster 1920. Or, light emissions 1930, 1930*a*, and 1930*n* from each fiber and/or ends of fibers may each emit such that at edge 1950 their direction may be at angles relative to 1919 that are parallel to the X-Y plane containing shadow caster 1920. To effectuate a sharp edge of luminosity in the case of a shadow caster 1920 linear in all dimensions X, Y, and Z, one or more fibers may be arranged so that one or more light beams 1930, 1930*a*, and 1930*n* are emitted such that at edge 1950 their directions are at any angle in an X and Y plane, and containing a common component in the Z direction relative to line 1919.

Side view 1942 depicts a side of fiber 1966 emitting light 1946 that is projected against shadow caster 1920 and edge 1950 to form light beam 1930*n*. Light 1946 may be collimated (e.g. straight) as shown in side view 1942, or it may diverge such that it gets wider as it reaches the shadow caster 1950. Side view 1942, in this example, is shown to be in a plane parallel to an X-Z plane. An end 1969 of fiber 1966 from which light is emitted may have a dimension, such as a width ("W1") 1927. End 1969 of fiber 1966 may be disposed in, for example, one or more of a front housing 1921 and a temple bar structure 1907. Further, ends 1969 of fibers 1966 may be disposed at any distance ("D1") 1929 from shadow caster 1920. A depth ("H") of front housing 1921 may be extended to accommodate greater distances 1929. According to some examples, a diameter, or W1, may be in a range of 25 to 50 microns, or less, or in a range up to 400 microns. In another example LEDs or micro-LEDS may be used instead of fibers 1966 with width W1. In addition, a layer of Fresnel prisms may be used to affect light exiting fiber ends 1969 to generate light beams 1930, 1930*a*, and 1930*n* as described above with respect to line 1919.

In operation, wearable system 1911 is configured to generate at least one edge of luminosity that is projected onto an environment, such as a room including appliances, furniture, people, etc. Movement of shadow caster 1920 may coincide with the movement of a user's head when the user is assessing and reviewing its surrounding environment, such as in a room. In some examples, electronics in temple bar structures 1907 may include processors, memory, accelerometers, etc. In one case, one or more accelerometers, tilt meters, compasses, gyroscopes, etc., may determine a rate at which a user is moving its head. Thus, logic in temple bar structures 1907 may detect a rate at which an edge of luminosity is sweeping across an environment or scene for purposes of forming a 3D model of the environment, if desired. The sweep rate may be transmitted via a radio transceiver in eyewear system 1911 or power and light generation module 1909. In another case, external fiducials (e.g. reflective markers or IR LED emitters, which are not shown) may be used by external detectors (not shown) of the position and orientation of 1911. Such external detectors may be, for example, cameras or field proximity sensors.

In some examples, electronics in temple bar structures 1907, or any other portion of wearable shadow caster 1911, may include processors and memory to support video projection onto, for example, one or more lenses 1901 to overlay graphical imagery over a view of three-dimensional objects in an environment provide to create augmented reality imagery. For example, a user wearing wearable shadow caster 1911 may look at a chair in a room, whereby wearable shadow caster 1911 (and an image capture device) may capture the three dimensional spatial dimensions and surfaces of the chair. Further, wearable shadow caster 1911 may receive video or imagery that overlays a different color over the user's view of the chair on lens 1901. Also, wearable shadow caster 1911 may receive video or imagery that overlays a graphical representation of a person sitting in the chair over the user's view of the chair on lens 1901.

Figure 20:
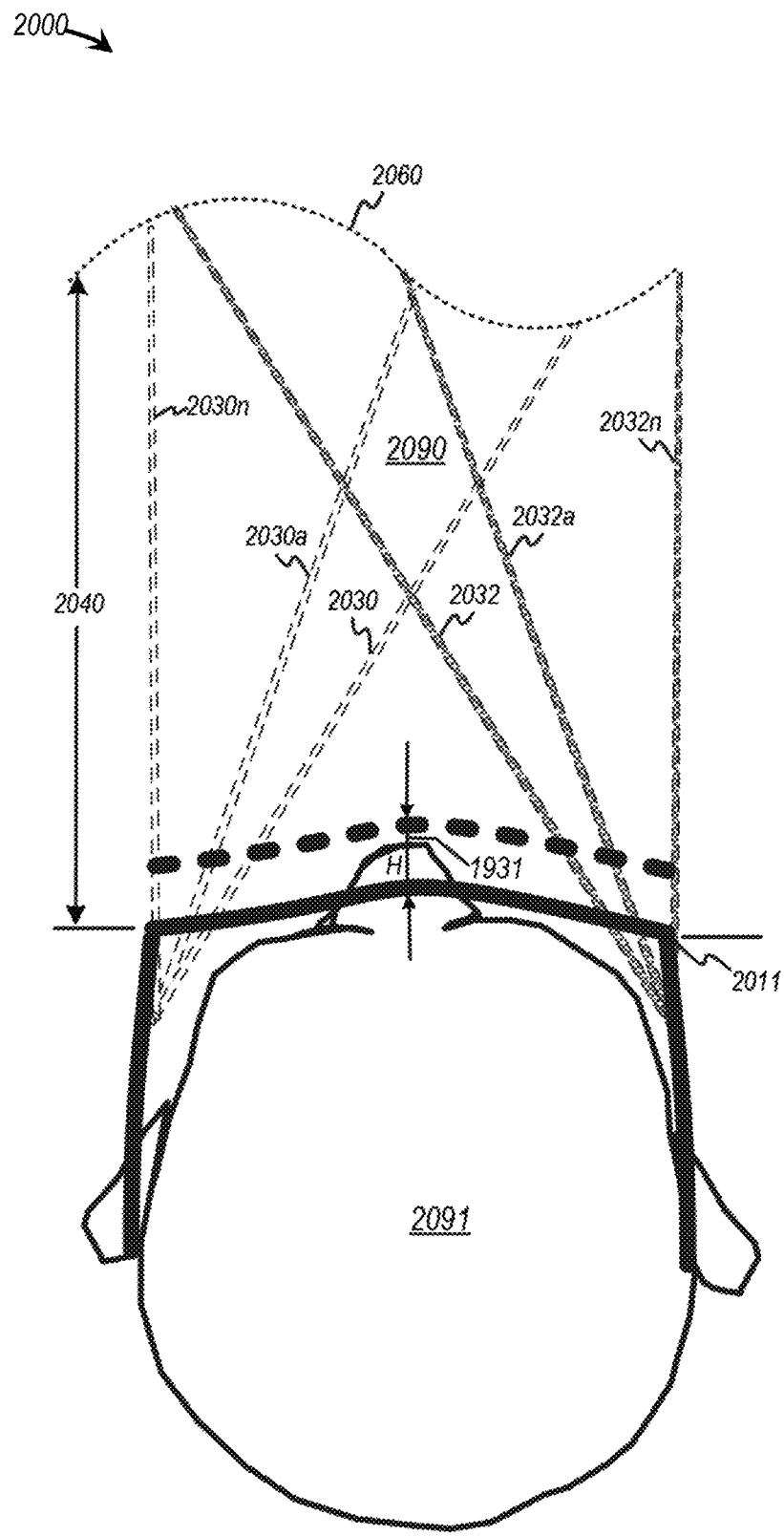
FIG. 20 is a diagram depicting an example of light projection patterns originating at a wearable shadow caster, according to some examples.

FIG. 20 is a diagram depicting an example of light projection direction originating at a wearable system, according to some examples. As shown, the light projection directions may emit from many fiber or LED sources disposed along temple bars of wearable system 2011.

Diagram 2000 includes a user 2091 wearing a wearable system 2011 and a front housing depicted as a dashed line, through which light beams 2030, 2030*a*, 2030*n*, 2032, 2032*a*, and 2032*n* transmit. Front housing may have a depth ("H") 1931 as described in reference to FIG. 19. Referring back to FIG. 20, light beams 2030, 2030*a*, 2030*n*, 2032, 2032*a*, 2032*n* may alternatively partially overlap to affect a continuous distribution of light (not shown). At least light emissions 2030*n* and 2032*n* may be parallel to a line of sight. In some cases, light emissions 2030, 2030*a*, 2030*n*, 2032, 2032*a*, and 2032*n* each may project into environment 2090 parallel to a line of sight (not shown). As shown, a subset of light emissions, such as light emissions 2030, 2030*a*, 2032, and 2032*a* may project at angles to the line of sight (e.g., to illuminate surface features in the environment that may be parallel to the line of sight). In the example shown, light emissions 2030, 2030*a*, 2030*n*, 2032, 2032*a*, and 2032*n* may be used to determine three-dimensional spatial dimensions of a contoured surface 2060 at distance 2040 relative to wearable shadow caster 2011.

Examples of light emissions depicted in diagram 2000 may be varied or adapted based on the suitability of a particular application. For example, wearable shadow caster 2011 may be worn by a surgeon performing brain surgery or any other medical application. According to various examples, wearable shadow caster 2011 may be implemented for purposes of communication, such as three-dimensional web camera communications, and the like. In some cases, wearable shadow caster 2011 may be configured to facilitate virtual reality applications and augmented reality applications. For example, wearable shadow caster 2011 may include one or more lenses or one or more transparent surfaces (not shown) upon which a heads up display ("HUD") or a reduced video image may be projected thereupon.

Figure 21:
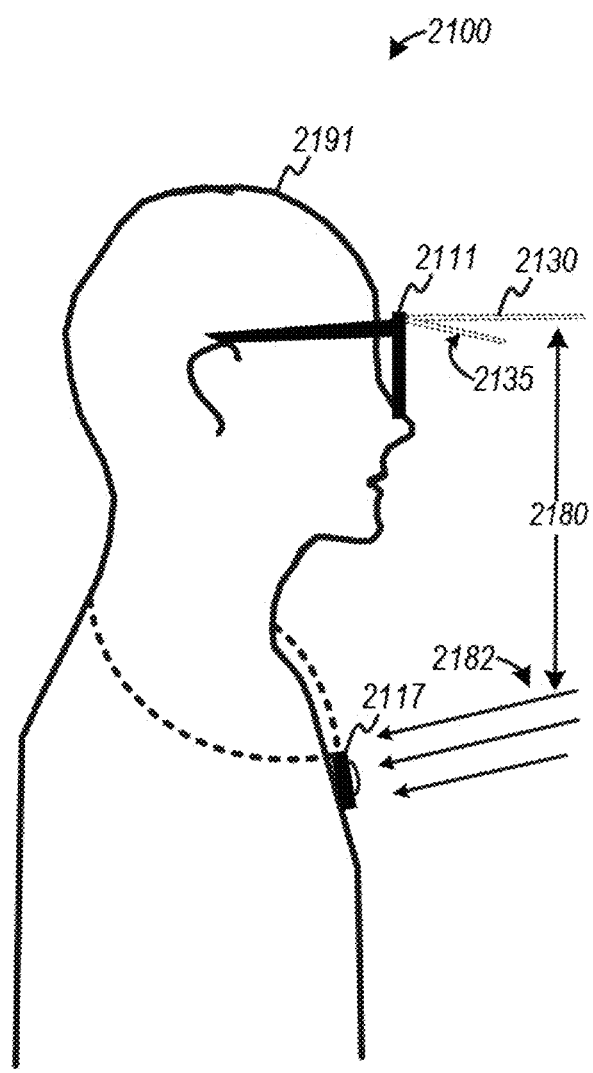
FIG. 21 is a diagram depicting an image capture device implemented with a wearable shadow caster, according to some examples.

FIG. 21 is a diagram depicting an image capture device implemented with a wearable shadow caster, according to some examples. Diagram 2100 includes a user 2191 wearing a wearable system 2111 and a wearable camera 2117, which may include processors, memory, and a radio to transmitted and receive data, including data associated with edges of luminosity projected upon surfaces in an environment. Wearable camera 2117 may also include accelerometers, tilt-detectors, compass, etc., for determining and reporting its location and orientation, especially with respect to the wearable system 2111. As shown, light emissions 2130 may be projected within a plane including a line of sight, or may be projected as light emission 2135 at an angle to the line of sight. As shown, light 2182 reflected back into camera 2117 may be at a distance 2180 from light emissions 2135. According to some examples, distance 2180 may be at 20 centimeters, or within a range that includes 20 centimeters. In this example, as in others, camera location distance 2180 separates that camera from the shadow plane to observe a deformation in the edge of luminosity that results from shape 2060 of FIG. 20. In at least one example, distance 2180 may be reduced without adversely affecting the determination of 3D information of surface 2060 of FIG. 20 by modifying other parameters with which wearable shadow caster 2111 operates. In other various examples, camera 2117 may be disposed off-person (e.g., the camera need not be worn). Thus, another camera 2117 may be co-located in an environment in which wearable shadow caster 2111 is disposed, whereby camera 2117 and 2111 may exchange data with each other wirelessly. According to some examples, elements depicted in diagrams 2000 of FIG. 20 and 2100 of FIG. 21 may include structures and/or functions as similarly-named or similarly-numbered elements depicted in other drawings. In one example, wearable shadow caster 2111 and a wearable camera 2117 may be used interchangeably with scanning system 1490 of FIG. 14.

Figure 22:
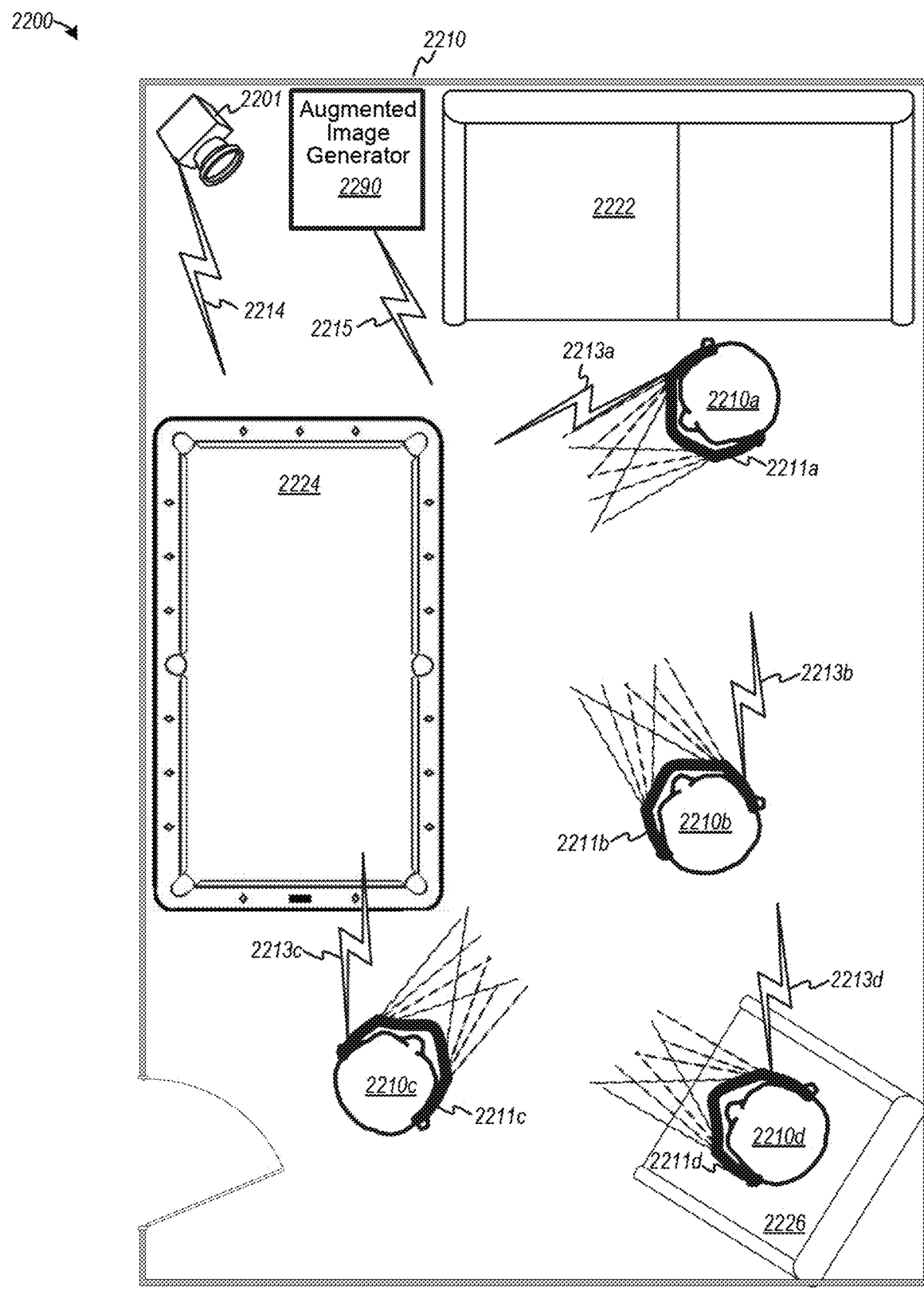
FIG. 22 is a diagram depicting multiple wearable shadow casters collaborating in a common environment, according to some examples.

FIG. 22 is a diagram depicting multiple wearable shadow casters collaborating in a common environment, according to some examples. Diagram 2200 depicts an environment, such as a room 2210, which includes various surface features of a couch 2222, a billiard table 2224, and a chair 2226. Further, room 2210 includes a subset of users 2210a, 2210b, 2210c, and 2210d wearing wearable shadow casters 2211a, 2211b, 2211c and 2211d, respectively. Each of wearable shadow casters 2211a, 2211b, 2211c and 2211d may include processors, memory, and other electronic components, such as accelerometers, video image generators, GPS transmitters, gyroscopes, cameras, radio transceivers (e.g., RF radio transmitters and/or receivers), etc. While not shown, image capture devices or cameras may be associated with each of users 2210a, 2210b, 2210c, and 2210d. According to some examples, elements depicted in diagram 2200 of FIG. 22 may include structures and/or functions as similarly-named or similarly-numbered elements depicted in other drawings.

In some examples, one or more off-person (or remote) cameras 2201 may capture images of multiple edges of luminosity from multiple wearable shadow casters that are reflected off various surfaces. According to various examples, one or more of cameras 2201, augmented image generator 2290, and wearable shadow casters 2211a, 2211b, 2211c, and 2211d may be configured to determine location and orientation of users 2210a, 2210b, 2210c, and 2210d (and cameras). Also, fiducials (e.g. reflective markers or IR LED emitters, which are not shown) may be disposed at any location room 2210 as for detecting position and orientation of wearable shadow casters 2211a, 2211b, 2211c, and 2211d. One or more of cameras 2201, augmented image generator 2290, and wearable shadow casters 2211a, 2211b, 2211c, and 2211d may be configured to determine differences among wearable shadow casters 2211a, 2211b, 2211c, and 2211d, and may be further configured to implement wearable shadow casters 2211b, 2211c, and 2211 in an invisible wavelength or any other wavelength. Also shown is an augmented image generator 2290 that may include logic to combine multiple subsets of 3D scan data to form a unitary, three-dimensional model of room 2210 and its occupants and furniture. Thus, augmented image generator 2290 may perform image registration to align multiple 3D images to form an integrated image or 3D model based on data from wearable shadow casters 2211a to 2211d. Further, augmented image generator 2290 may generate data representing graphical imagery that may be overlaid over 3D surfaces of objects in room 2210. For example, augmented image generator 2290 may generate graphical images of "virtual costumes" that users 2210a, 2210b, 2210c, and 2210d may select for viewing by the others. Consider that user 2210a wishes users 2210b, 2210c, and 2210d to perceive user 2210a wearing a "pirate costume." Augmented image generator 2290 can generate graphical imagery that may be overlaid on lenses in wearable shadow casters 2211b, 2211c, and 2211d. Thus, users 2210b, 2210c, and 2210d may visually perceive user 2210a wearing an overlaid "pirate costume." Hence, these users may organize a virtual costume party.

Wearable shadow casters 2211a, 2211b, 2211c, and 2211d, may include RF radios to generate wireless data links 2213a, 2213b, 2213c, and 2213d, respectively. Further, one or more cameras 2201 and augmented image generator 2290 may include logic (e.g., hardware or software, or a combination thereof) and RF radios to transmit and receive data with one or more wearable shadow casters. In one implementation, wearable shadow casters 2211a, 2211b, 2211c, and 2211d, may form a peer-to-peer network via links 2213a, 2213b, 2213c, and 2213d to exchange 3D scan data and graphically imagery to facilitate augmented reality applications. In another implementation, wearable shadow casters 2211a, 2211b, 2211c and 2211d may implement a client-server network with camera 2201 and augmented image generator 2290 via wireless data links 2214, 2215, 2213a, 2213b, 2213c, and 2213d, each of which may be adapted to implement other network topologies as well.

Figure 23:
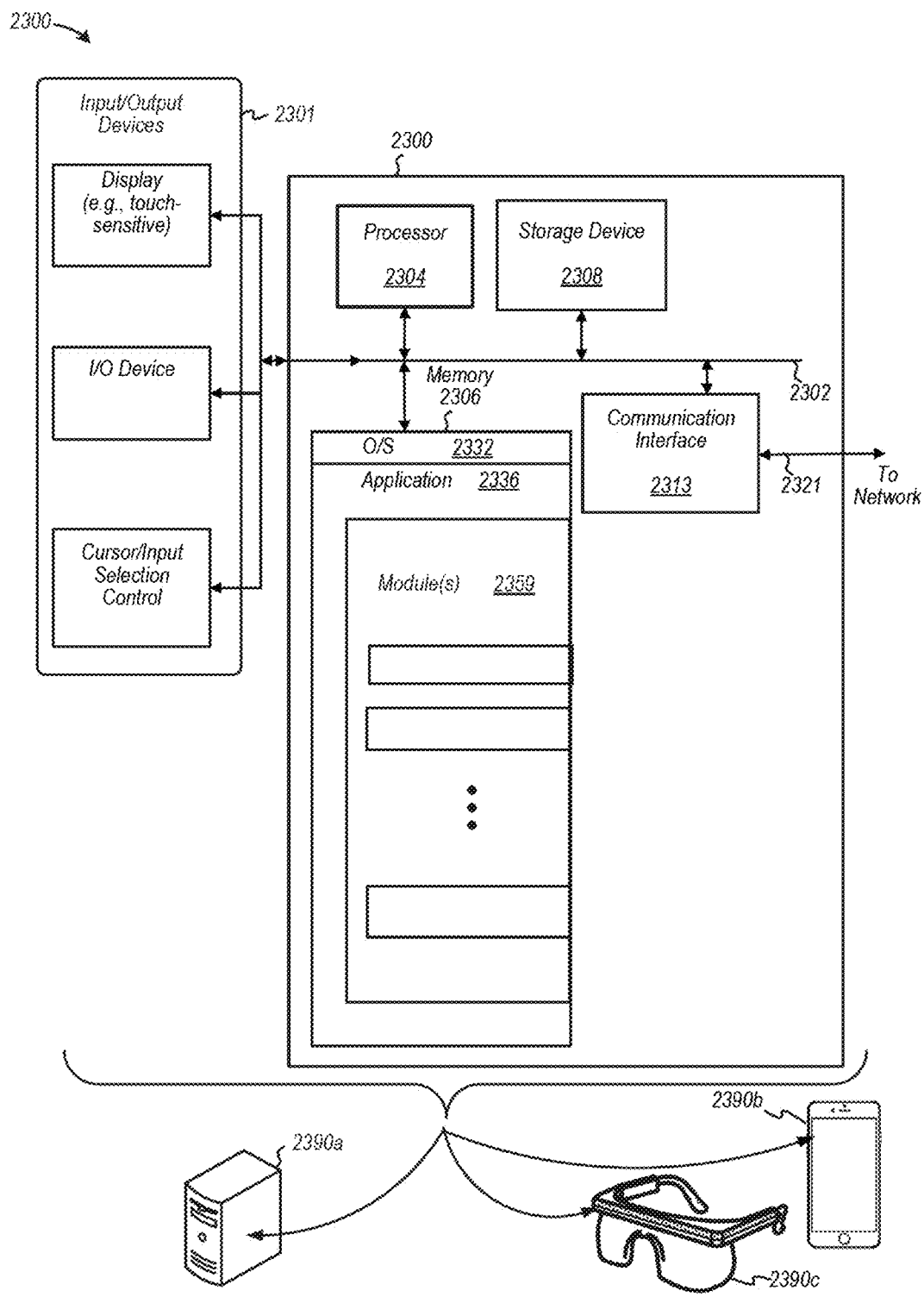
FIG. 23 illustrates examples of various computing platforms configured to provide various functionalities to components to preform three-dimensional scanning, according to various embodiments.

FIG. 23 illustrates examples of various computing platforms configured to provide various functionalities to components to preform three-dimensional scanning, according to various embodiments. In some examples, computing platform 2300 may be used to implement computer programs, applications, methods, processes, algorithms, or other software, as well as any hardware implementation thereof, to perform the above described techniques.

In some cases, computing platform 2300 or any portion (e.g., any structural or functional portion) can be disposed in any device, such as a computing device 2390a, mobile computing device 2390b, wearable device 2390c, and/or a processing circuit to implement various structures and/or functions, according to various examples described herein.

Computing platform 2300 includes a bus 2302 or other communication mechanism for communicating information, which interconnects subsystems and devices, such as processor 2304, system memory 2306 (e.g., RAM, etc.), storage device 2308 (e.g., ROM, etc.), an in-memory cache (which may be implemented in RAM 2306 or other portions of computing platform 2300), a communication interface 2313 (e.g., an Ethernet or wireless controller, a Bluetooth controller, NFC logic, etc.) to facilitate communications via a port on communication link 2321 to communicate, for example, with a computing device, including mobile computing and/or communication devices with processors, including database devices (e.g., storage devices configured to store atomized datasets, including, but not limited to triplestores, etc.). Processor 2304 can be implemented as one or more graphics processing units ("GPUs"), as one or more central processing units ("CPUs"), such as those manufactured by Intel® Corporation, or as one or more virtual processors, as well as any combination of CPUs and virtual processors. Computing platform 2300 exchanges data representing inputs and outputs via input-and-output devices 2301, including, but not limited to, keyboards, mice, audio inputs (e.g., speech-to-text driven devices), user interfaces, displays, monitors, cursors, touch sensitive displays, LCD or LED displays, and other I/O-related devices.

Note that in some examples, input-and-output devices 2301 may be implemented as, or otherwise substituted with, a user interface in a computing device associated with a user account identifier in accordance with the various examples described herein.

According to some examples, computing platform 2300 performs specific operations by processor 2304 executing one or more sequences of one or more instructions stored in system memory 2306, and computing platform 2300 can be implemented in a client-server arrangement, peer-to-peer arrangement, or as any mobile computing device, including smart phones and the like. Such instructions or data may be read into system memory 2306 from another computer readable medium, such as storage device 2308. In some examples, hard-wired circuitry may be used in place of or in combination with software instructions for implementation. Instructions may be embedded in software or firmware. The term "computer readable medium" refers to any tangible medium that participates in providing instructions to processor 2304 for execution. Such a medium may take many forms, including but not limited to, nonvolatile media and volatile media. Non-volatile media includes, for example, optical or magnetic disks and the like. Volatile media includes dynamic memory, such as system memory 2306.

Known forms of computer readable media include, for example, floppy disk, flexible disk, hard disk, magnetic tape, any other magnetic medium, CD-ROM, any other optical medium, punch cards, paper tape (e.g., or patterns of holes), any other physical medium, such as RAM, PROM, EPROM, FLASH-EPROM devices, any other memory chip or cartridge, or any other medium from which a computer can access data. Instructions may further be transmitted or received using a transmission medium. The term "transmission medium" may include any tangible or intangible medium that is capable of storing, encoding or carrying instructions for execution by the machine, and includes digital or analog communications signals or other intangible medium to facilitate communication of such instructions. Transmission media includes coaxial cables, copper wire, and fiber optics, including wires that comprise bus 2302 for transmitting a computer data signal.

In some examples, execution of the sequences of instructions may be performed by computing platform 2300. According to some examples, computing platform 2300 can be coupled by communication link 2321 (e.g., a wired network, such as LAN, PSTN, or any wireless network, including WiFi of various standards and protocols, Bluetooth®, NFC, Zig-Bee, etc.) to any other processor to perform the sequence of instructions in coordination with (or asynchronous to) one another. Computing platform 2300 may transmit and receive messages, data, and instructions, including program code (e.g., application code) through communication link 2321 and communication interface 2313. Received program code may be executed by processor 2304 as it is received, and/or stored in memory 2306 or other non-volatile storage for later execution.

In the example shown, system memory 2306 can include various modules that include executable instructions to implement functionalities described herein. System memory 2306 may include an operating system ("O/S") 2332, as well as an application 2336 and/or logic module(s) 2359. In the example shown in FIG. 23, system memory 2306 may include any number of modules 2359, any of which, or one or more portions of which, can be configured to facilitate any one or more components of a computing system (e.g., a client computing system, a server computing system, etc.) by implementing one or more functions described herein.

The structures and/or functions of any of the above-described features can be implemented in software, hardware, firmware, circuitry, or a combination thereof. Note that the structures and constituent elements above, as well as their functionality, may be aggregated with one or more other structures or elements. Alternatively, the elements and their functionality may be subdivided into constituent sub-elements, if any. As software, the above-described techniques may be implemented using various types of programming or formatting languages, frameworks, syntax, applications, protocols, objects, or techniques. As hardware and/or firmware, the above-described techniques may be implemented using various types of programming or integrated circuit design languages, including hardware description languages, such as any register transfer language ("RTL") configured to design field-programmable gate arrays ("FPGAs"), application-specific integrated circuits ("ASICs"), or any other type of integrated circuit. According to some embodiments, the term "module" can refer, for example, to an algorithm or a portion thereof, and/or logic implemented in either hardware circuitry or software, or a combination thereof. These can be varied and are not limited to the examples or descriptions provided.

In some embodiments, modules 2359 of FIG. 23, or one or more of their components, or any process or device described herein, can be in communication (e.g., wired or wirelessly) with a mobile device, such as a mobile phone, a wearable device, or a computing device, or can be disposed therein.

In some cases, a mobile device, or any networked computing device (not shown) in communication with one or more modules 2359 or one or more of its/their components (or any process or device described herein), can provide at least some of the structures and/or functions of any of the features described herein. As depicted in the above-described figures, the structures and/or functions of any of the above-described features can be implemented in software, hardware, firmware, circuitry, or any combination thereof. Note that the structures and constituent elements above, as well as their functionality, may be aggregated or combined with one or more other structures or elements. Alternatively, the elements and their functionality may be subdivided into constituent sub-elements, if any. As software, at least some of the above-described techniques may be implemented using various types of programming or formatting languages, frameworks, syntax, applications, protocols, objects, or techniques. For example, at least one of the elements depicted in any of the figures can represent one or more algorithms. Or, at least one of the elements can represent a portion of logic including a portion of hardware configured to provide constituent structures and/or functionalities.

For example, modules 2359 or one or more of its/their components, or any process or device described herein, can be implemented in one or more computing devices (i.e., any mobile computing device, such as a wearable device, such as a hat or headband, or mobile phone, whether worn or carried) that include one or more processors configured to execute one or more algorithms in memory. Thus, at least some of the elements in the above-described figures can represent one or more algorithms. Or, at least one of the elements can represent a portion of logic including a portion of hardware configured to provide constituent structures and/or functionalities. These can be varied and are not limited to the examples or descriptions provided.

As hardware and/or firmware, the above-described structures and techniques can be implemented using various types of programming or integrated circuit design languages, including hardware description languages, such as any register transfer language ("RTL") configured to design field-programmable gate arrays ("FPGAs"), application-specific integrated circuits ("ASICs"), multi-chip modules, or any other type of integrated circuit For example, modules 2359 or one or more of its/their components, or any process or device described herein, can be implemented in one or more computing devices that include one or more circuits. Thus, at least one of the elements in the above described figures can represent one or more components of hardware. Or, at least one of the elements can represent a portion of logic including a portion of a circuit configured to provide constituent structures and/or functionalities.

According to some embodiments, the term "circuit" can refer, for example, to any system including a number of components through which current flows to perform one or more functions, the components including discrete and complex components. Examples of discrete components include transistors, resistors, capacitors, inductors, diodes, and the like, and examples of complex components include memory, processors, analog circuits, digital circuits, and the like, including field-programmable gate arrays ("FPGAs"), application-specific integrated circuits ("ASICs"). Therefore, a circuit can include a system of electronic components and logic components (e.g., logic configured to execute instructions, such that a group of executable instructions of an algorithm, for example, and, thus, is a component of a circuit). According to some embodiments, the term "module" can refer, for example, to an algorithm or a portion thereof, and/or logic implemented in either hardware circuitry or software, or a combination thereof (i.e., a module can be implemented as a circuit). In some embodiments, algorithms and/or the memory in which the algorithms are stored are "components" of a circuit. Thus, the term "circuit" can also refer, for example, to a system of components, including algorithms. These can be varied and are not limited to the examples or descriptions provided.

In view of the foregoing, diagrams 200 to 2300 set forth any number of structures and functions that may be applied to any number of applications. For example, any of the above-described structures and functions may be incorporated into a mobile phone having a camera. Thus, a shadow caster and/or light source may be attached to, or integrated within a mobile phone to perform 3D scanning. In another example, any of the above-described structures and functions may be implemented to store surface patterns for identification purposes, such as scanning finger prints three dimensionally as a data for providing secure authorization or identification. Any number of applications may implement the structures and functions described herein.

In one example, a method may include receiving photonic emission at a shadow caster, and forming an edge of luminosity. The method may include receiving the photonic emission as light, and projecting the edge of luminosity onto a plane of projection. The method may include receiving the photonic emission at two edge portions of the shadow caster, and forming two portions of at least two portions of edges of luminosity. At least two portions of edges of luminosity may be substantially parallel as projected on a plane of projection. The method may include receiving other photonic emission at another shadow caster, and forming another edge of luminosity. The other edge of luminosity may be substantially coextensive with the edge of luminosity. The method may include generating photonic emission at source of light disposed (e.g., substantially on an axis) adjacent at an end of the shadow caster at a distance (e.g., a greatest distance) from a plane of projection. In some examples, receiving the photonic emission at the shadow caster may include receiving photonic emission in a first region, and projecting an edge of luminosity onto a plane of projection. The shadow caster may be disposed between one or more sources of light and a plane of projection. The method may include applying a motive force to move an edge of luminosity over a plane of projection.

Figure 24:
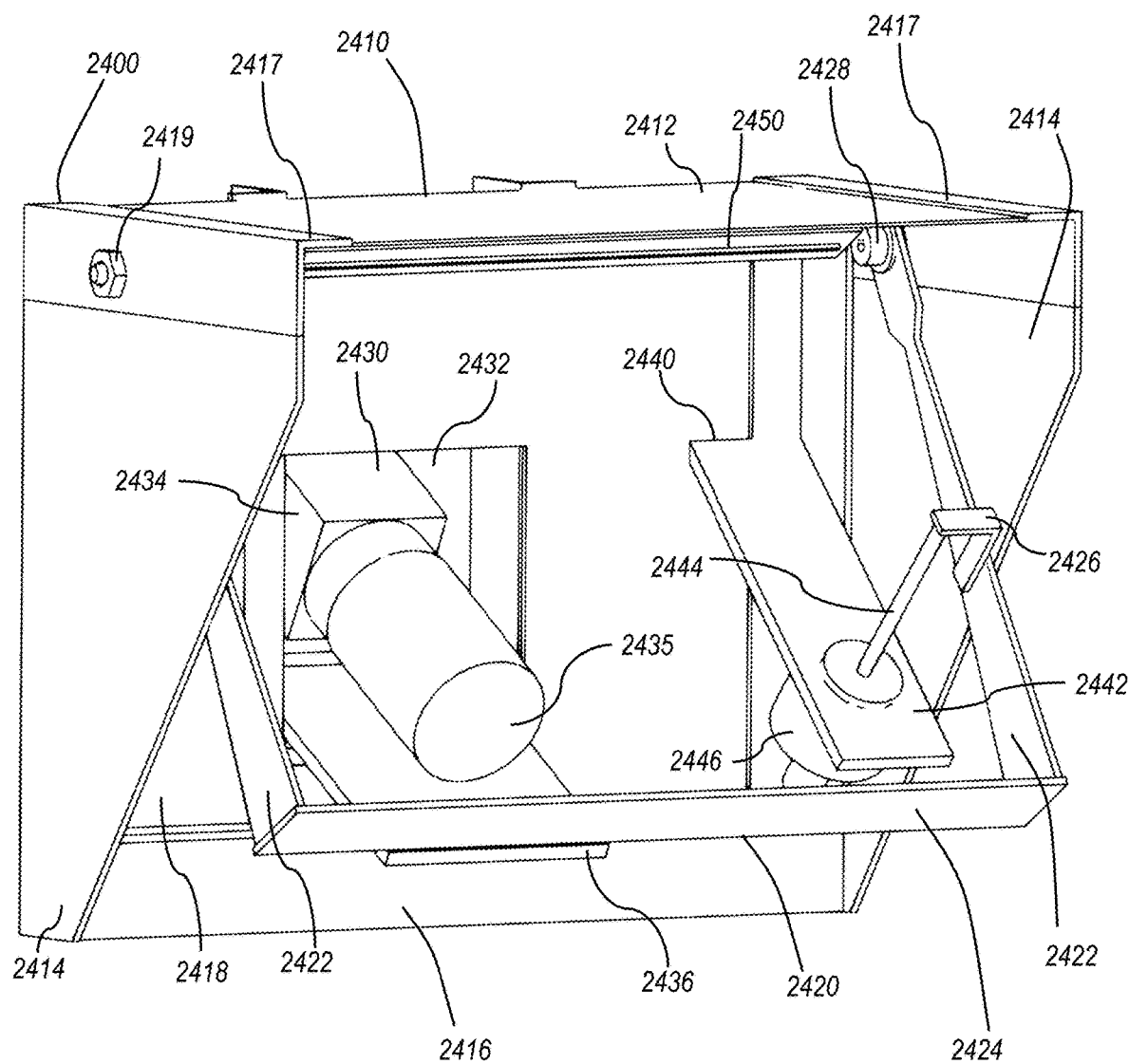
FIG. 24 is a front perspective view of an apparatus of the present invention, according to some examples.
Figure 25:
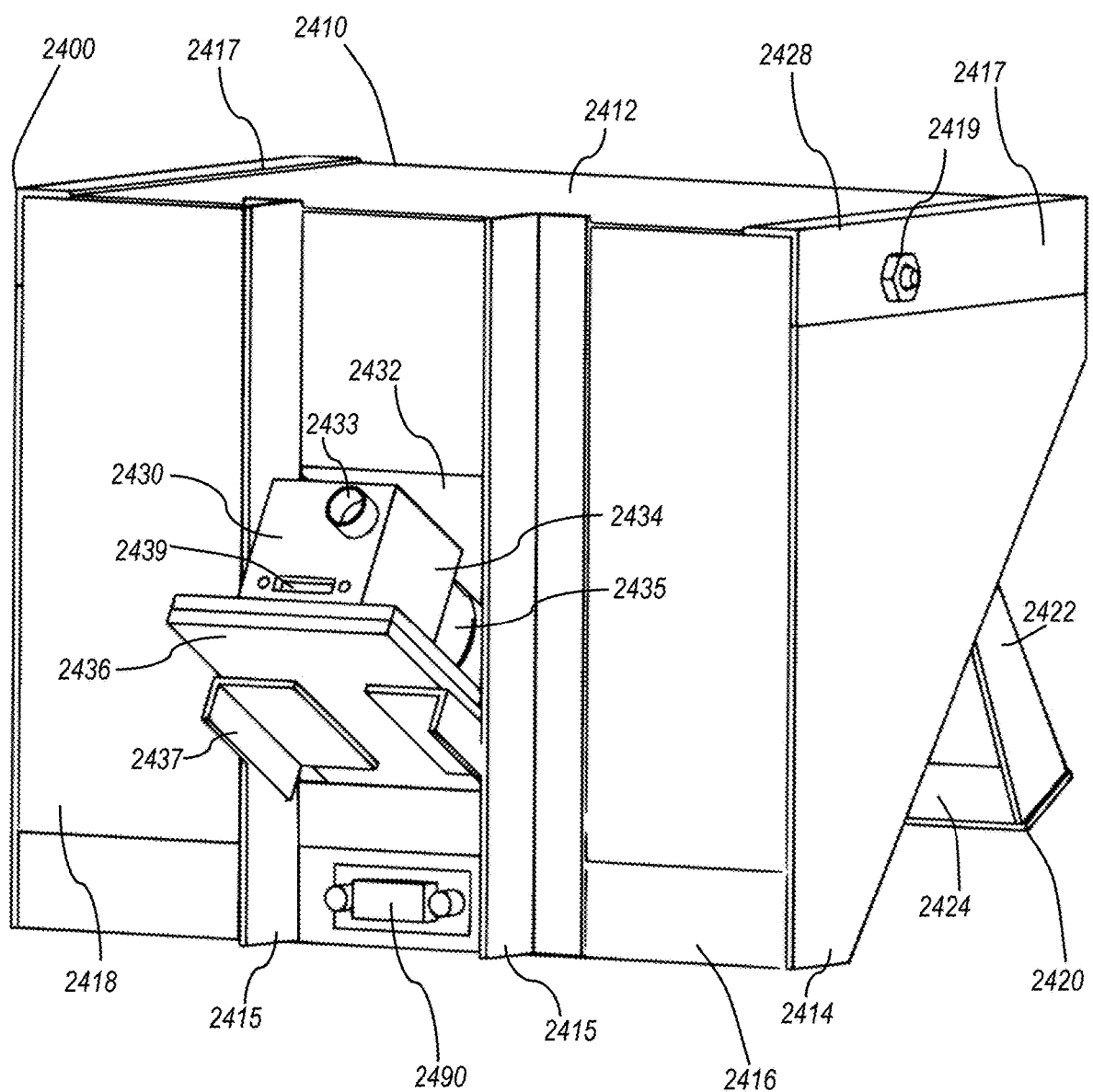
FIG. 25 is a rear perspective view of an apparatus of FIG. 24, according to some examples.
Figure 26:
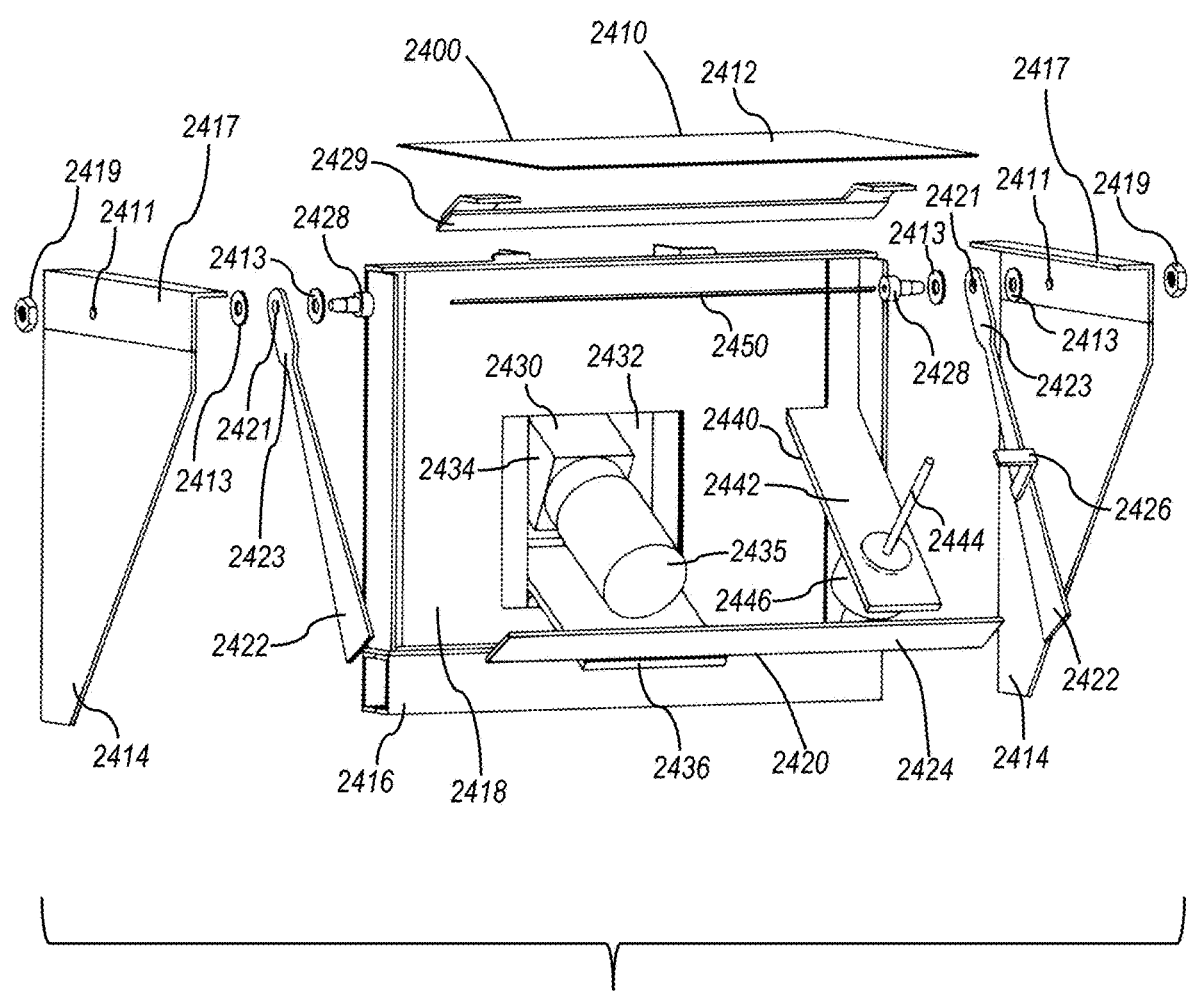
FIG. 26 is an exploded view of an apparatus of FIG. 24, according to some examples.
Figure 27:
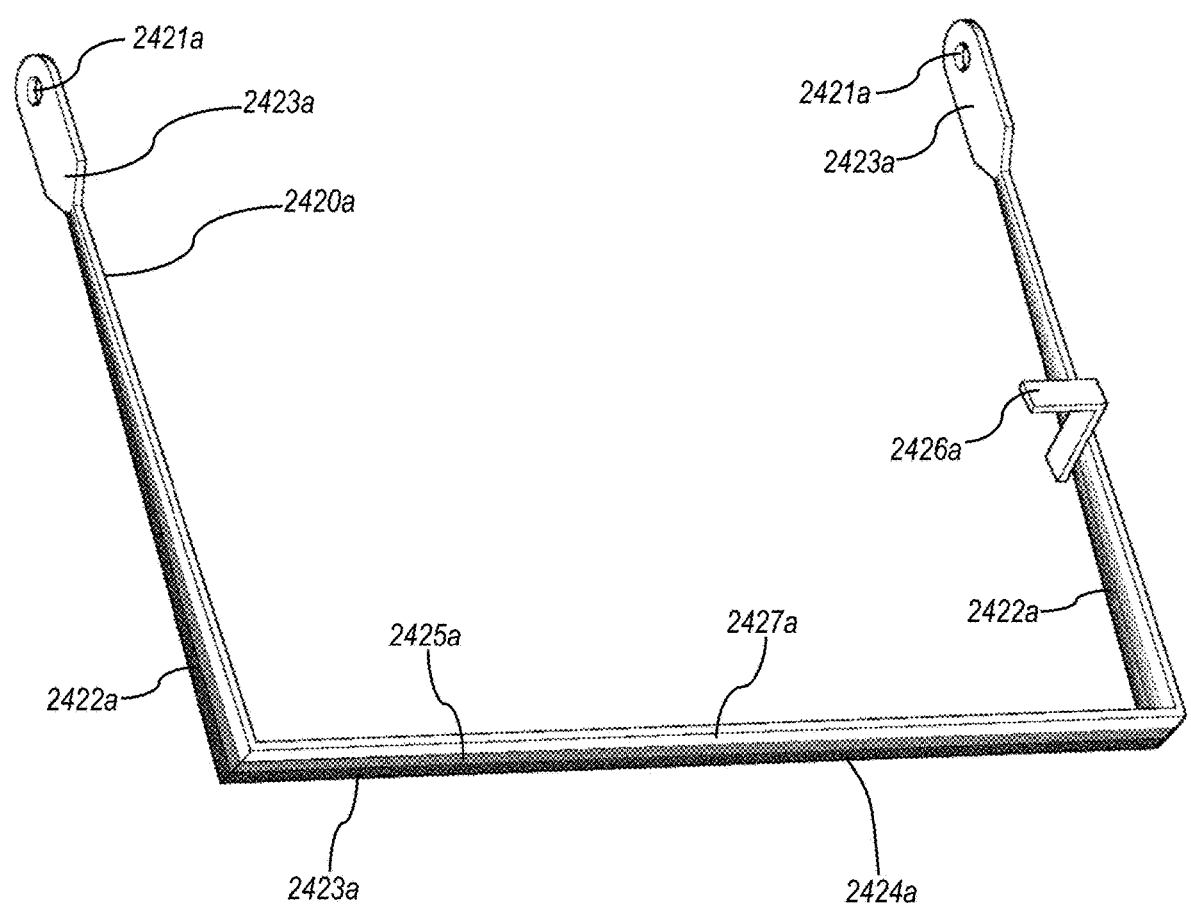
FIG. 27 is a front perspective view of a shadow caster of the present invention, according to various embodiments.
Figure 28:
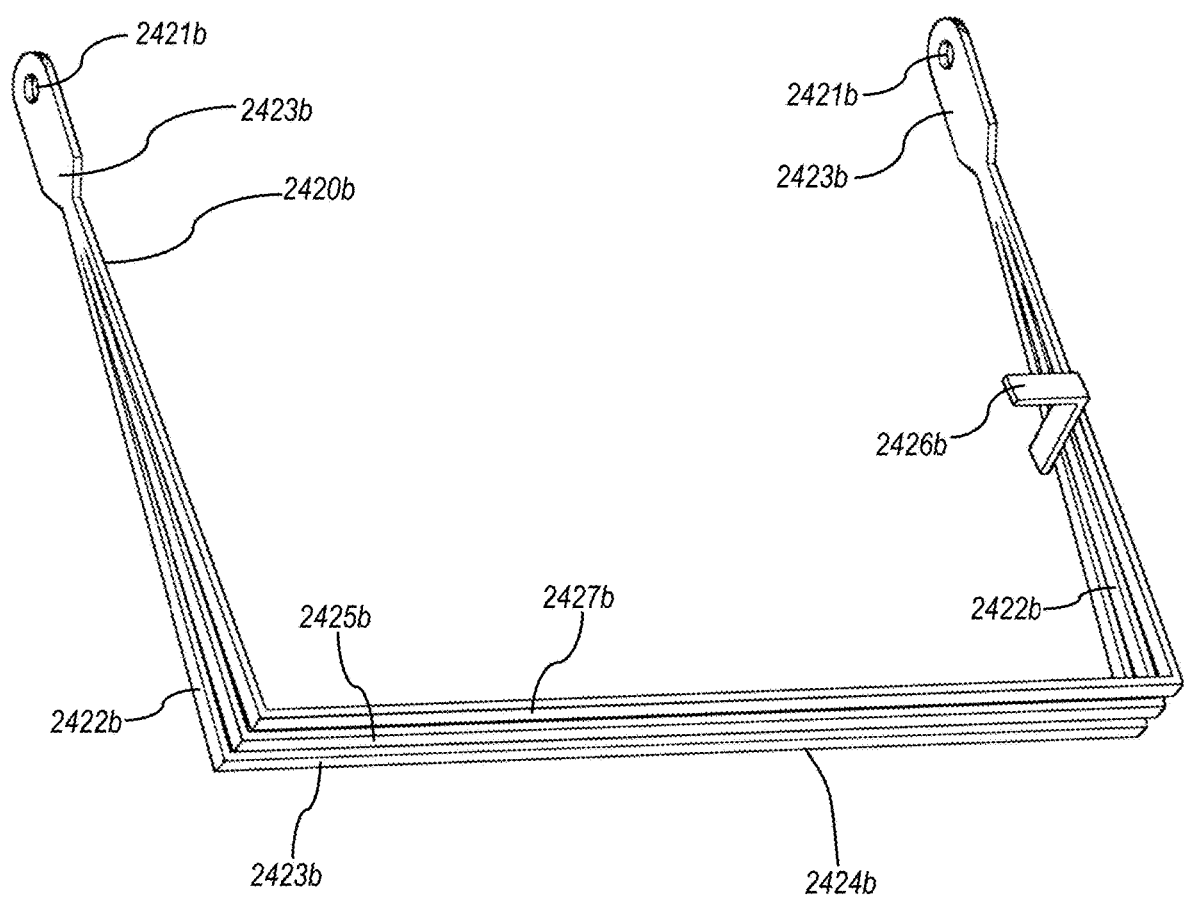
FIG. 28 is a front perspective view of another shadow caster of the present invention, according to various embodiments.
Figure 29:
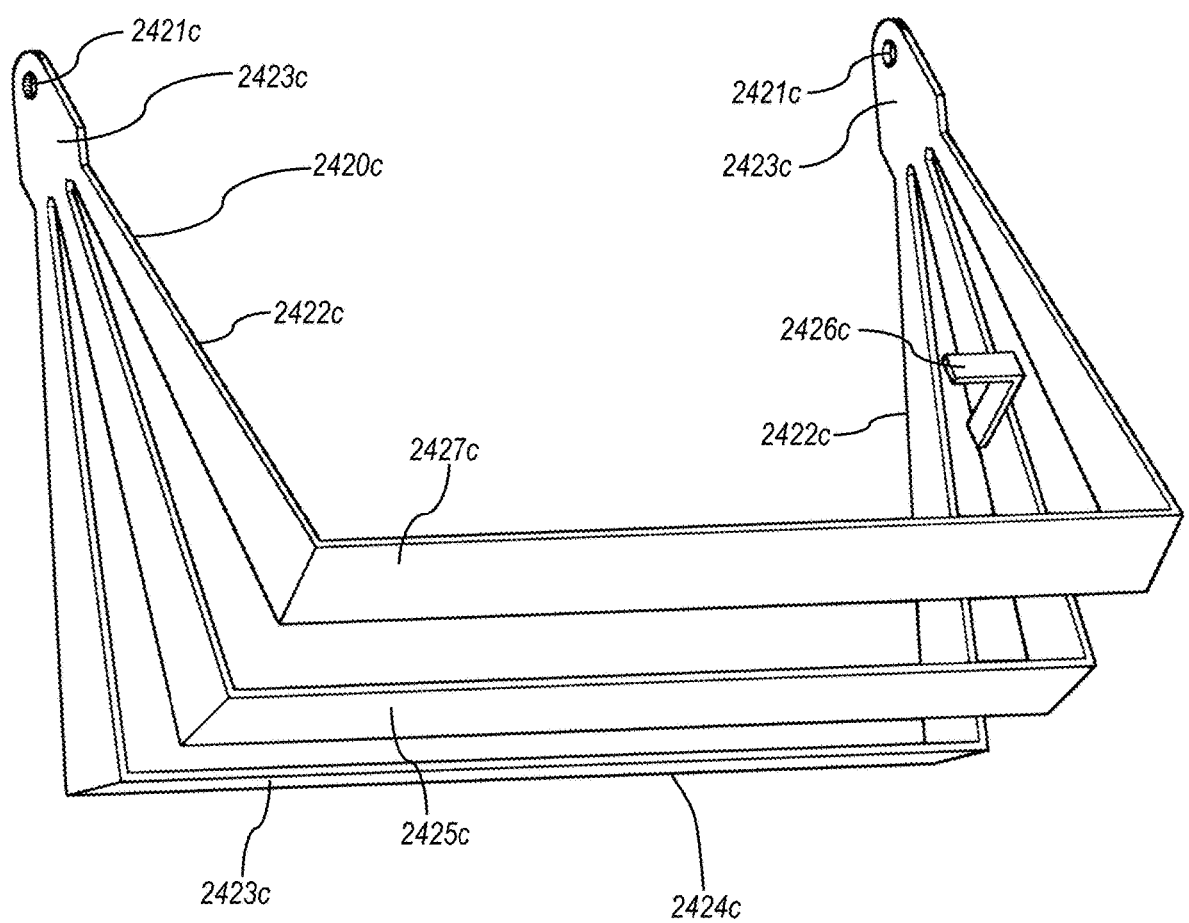
FIG. 29 is a front perspective view of another shadow caster of the present invention, according to various embodiments.
Figure 30:
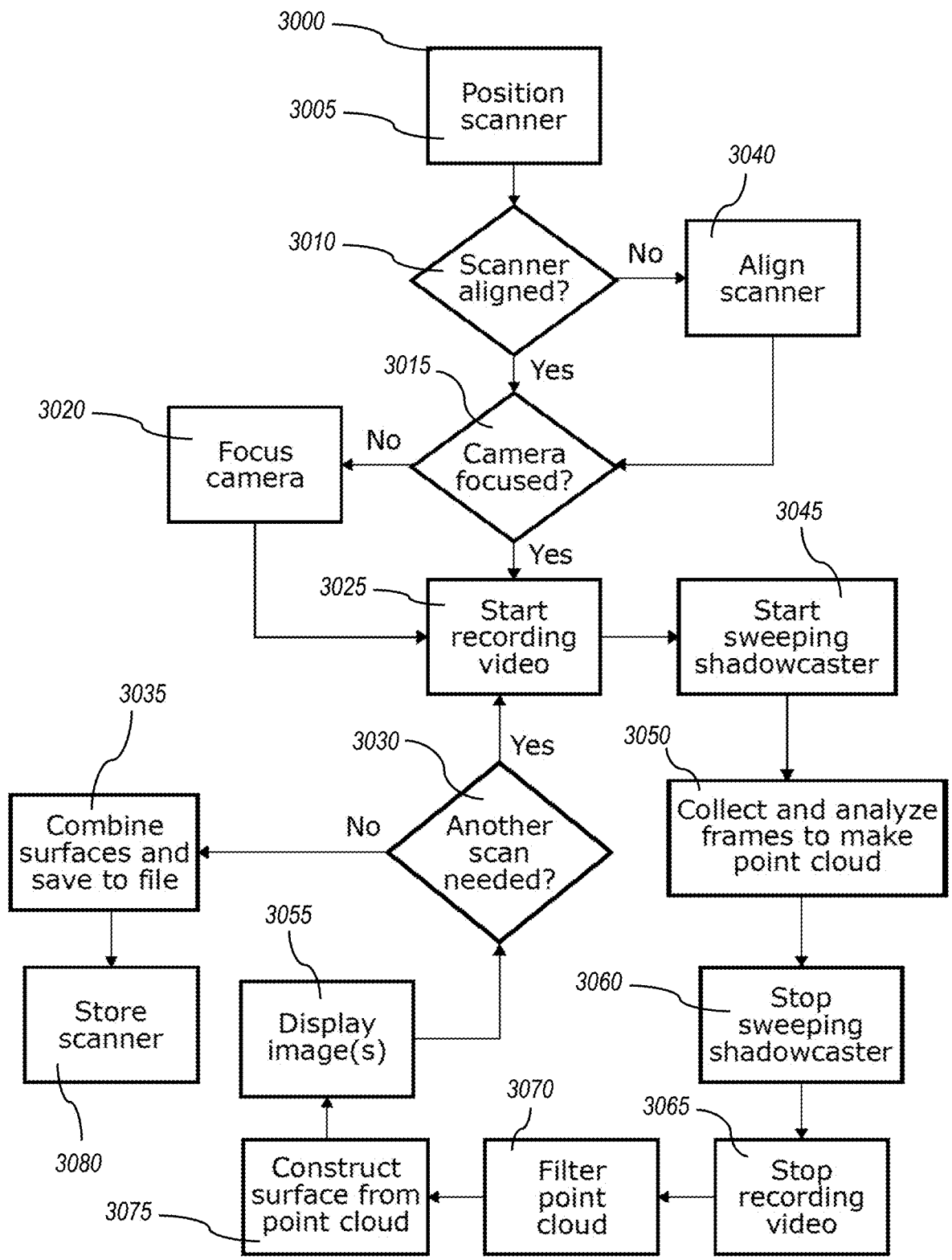
FIG. 30 depicts a flow chart describing the operation of an apparatus of FIG. 24, according to some examples.

Turning to specific and particular applications of the present invention, referring now to the most preferred embodiment of the invention, in FIG. 24, FIG. 25, FIG. 26, FIG. 27, FIG. 28, FIG. 29, and FIG. 30, a Shadow Caster Scanner 2400 is shown. FIG. 24 demonstrates a front perspective view of a Shadow Caster Scanner 2400. FIG. 25 is a rear perspective view of a Shadow Caster Scanner 2400. FIG. 26 is an exploded view of a Shadow Caster Scanner 2400. FIG. 27 is a front perspective view of a filtered shadow caster 2400a of the present invention. FIG. 28 is a front perspective view of bladed shadow caster 2400b of the present invention. FIG. 29 is a front perspective view of a wide bladed shadow caster 2400c of the present invention. FIG. 30 depicts an operation flow chart 3000 describing the operation of a Shadow Caster Scanner 2400.

In further detail, still referring to the invention of FIG. 24, FIG. 25, FIG. 26, FIG. 27, FIG. 28, FIG. 29, and FIG. 30, a Shadow Caster Scanner 2400 comprises an outer housing 2410, said outer housing 2410 comprising: a back panel 2418, said back panel 2418 comprising: a camera opening 2432, a top panel 2412, two side panels 2414, said side panels 2414 comprising: a pivot point 2411, and a base 2416; a shadow caster 2420, said shadow caster 2420 comprising: a front segment 2424, said front segment 2424 being rectangular, two side segments 2422, each said side segment 2422 depending perpendicularly from opposite ends of said front segment 2424, each said side segment 2422 comprising: a triangular shape, and a shoulder mount 2423, each said shoulder mount 2423 comprising: a shoulder screw hole 2421, and a shoulder screw 2428, said shoulder screw 2428 being rotatably attached to said side panel 2414 using a nut 2419 and washers 2413, and a tab 2426, said tab 2426 depending from one said side segment 2422; an actuator assembly 2440, said actuator assembly 2440 comprising: an actuator arm 2442, said actuator arm 2442 depending from said outer housing 2410, an actuator motor 2446, said actuator motor 2446 depending from said actuator arm 2442, and an actuator connector 2444, said actuator connector 2444 depending from said actuator motor 2446 and connecting to said tab 2426 of said shadow caster 2420;

a light source 2450, said light source 2450 being discrete, continuous, linear, and extending between said shoulder screws 2428 of said shoulder mounts 2423 of said side segments 2422 of said shadow caster 2420; a video cameras assembly 2430, said video camera assembly 2430 extending through said camera opening 2432 of said back panel 2418 of said outer housing 2410, said video camera assembly 2430 comprising: a video camera support platform 2436, and a video camera 2434, said video camera 2434 being mounted on said video camera support platform 2436, said video camera 2434 comprising: a camera lens 2435, a camera sync port 2433, a video output port 2439, and a control port 2490; a memory stored in non-transitory computer-readable medium; a processor (not shown), said processor comprising: said computer-readable medium; and a display (not shown); wherein said light source 2450 illuminates said shadow caster 2420 to project high contrast shadows of known geometry, which form said one or more edges of luminosity on said object; wherein said actuator motor 2446 moves said shadow caster 2420 in order to sweep said one or more edges of luminosity across said object; wherein said video camera 2434 detects said one or more edges of luminosity for three-dimensional points on said object and records said three-dimensional points into said memory; wherein said processor forms a three-dimensional data representation from recorded said three-dimensional points; wherein said processor generates said three-dimensional model of said object using said three-dimensional data representation; and wherein said three-dimensional model is displayed on said display using said processor. Alternately, a filtered shadow caster 2420a, shown in FIG. 27, may be used with Shadow Caster Scanner 2400 in place of the shadow caster 2420 and comprises a front segment 2424a, said front segment 2424a being rectangular, two side segments 2422a, each said side segment 2422a depending perpendicularly from opposite ends of said front segment 2424a, each said side segment 2422a comprising: a triangular shape, and a shoulder mount 2423a, each said shoulder mount 2423a comprising: a shoulder screw hole 2421a, and a tab 2426a. The front segment 2424a and two side segments 2422a further comprise a first filter 2423a, a second filter 2425a, and a third filter 2427a, which may filter different colored light or have varying opacities. Although only three filters are shown in the figure, any number of filters could be used. Alternately, a bladed shadow caster 2400b, shown in FIG. 28, may be used with Shadow Caster Scanner 2400 in place of the shadow caster 2420 and comprises a front segment 2424b, said front segment 2424b being rectangular, two side segments 2422b, each said side segment 2422b depending perpendicularly from opposite ends of said front segment 2424b, each said side segment 2422b comprising: a triangular shape, and a shoulder mount 2423b, each said shoulder mount 2423b comprising: a shoulder screw hole 2421b, and a tab 2426b. The front segment 2424b and two side segments 2422b further comprise a first segment 2423b, a second segment 2425b, and a third segment 2427b, for producing more edges of luminosity. Although only three segments are shown in the figure, any number of segments could be used. Alternately, a wide bladed shadow caster 2400c, shown in FIG. 29, may be used with Shadow Caster Scanner 2400 in place of the shadow caster 2420 and comprises a front segment 2424c, two side segments 2422c, each said side segment 2422c depending perpendicularly from opposite ends of said front segment 2424c, each said side segment 2422c comprising: a triangular shape, and a shoulder mount 2423c, each said shoulder mount 2423c comprising: a shoulder screw hole 2421c, and a tab 2426c. The front segment 2424c and two side segments 2422c further comprise a first wide segment 2423c, a second wide segment 2425c, and a third wide segment 2427c, for producing more edges of luminosity. Although only three segments are shown in the figure, any number of segments could be used. In the operation flowchart 3000 described in FIG. 30, the first step in the operation of a Shadow Caster Scanner 2400 comprises positioning the scanner over the subject, in the position scanner step 3005. Next, in the alignment decision step 3010, whether the scanner is aligned with the subject is determined. If the scanner is not aligned, the scanner is then aligned with the subject in the align scanner step 3040. Once the scanner is aligned, whether the camera is focused on the subject is determined in the focus decision step 3015. If the camera is not focused, the camera is then focused in the focus camera step 3020. Once the camera is focused, the camera starts recording video of the subject in the start recording step 3025. Next, in the start sweeping step 3045, the shadow caster begins to sweep edges of luminosity across the subject. Next, frames of the recorded video are collected and analyzed by the processor to make a point cloud in the collect and analyze step 3050. Next, in the stop sweeping step 3060, the shadow caster stops sweeping the edges of luminosity across the subject. Next, the processor filters the point cloud in the filter point cloud step 3070. Next, in the construct surface step 3075, the processor constructs a model of a three-dimensional surface from the filtered point cloud. Next, the model is displayed on the display by the processor in the display image step 3055. Whether another scan is needed is determined in the another scan decision step 3030. If another scan is needed, the start recording step 3025 is repeated, as described above. If another scan is not needed, the modeled surfaces are combined and saved to file in the save file step 3035. Lastly, the scanner is stored after operation in the store scanner step 3080.

The construction details of the invention as shown in FIG. 24, FIG. 25, FIG. 26, FIG. 27, FIG. 28, FIG. 29, and FIG. 30, are as follows. The back panel 2418 of the outer housing 2410 comprises a strong rigid material, such as steel, copper cladding, plastic, high density plastic, silicone, PVC, fiber glass, carbon fiber, composite material, metal, galvanized steel, stainless steel, aluminum, brass, copper, wood, or other like material. The top panel 2412 of the outer housing 2410 comprises a strong rigid material, such as steel, copper cladding, plastic, high density plastic, silicone, PVC, fiber glass, carbon fiber, composite material, metal, galvanized steel, stainless steel, aluminum, brass, copper, wood, or other like material. The side panels 2414 of the outer housing 2410 comprise a strong rigid material, such as steel, copper cladding, plastic, high density plastic, silicone, PVC, fiber glass, carbon fiber, composite material, metal, galvanized steel, stainless steel, aluminum, brass, copper, wood, or other like material. The base 2416 of the outer housing 2410 comprises a strong rigid material, such as steel, copper cladding, plastic, high density plastic, silicone, PVC, fiber glass, carbon fiber, composite material, metal, galvanized steel, stainless steel, aluminum, brass, copper, wood, or other like material. The shadow caster 2420 comprises a strong rigid material, such as steel, copper cladding, plastic, high density plastic, silicone, PVC, fiberglass, carbon fiber, composite material, metal, galvanized steel, stainless steel, aluminum, brass, copper, wood, or other like material, and may further comprise configurable shapes, three-dimensionally-printed shapes, configurable opacity, such as liquid crystal, or the like, or various colored filters. The shoulder screws 2428 comprise a strong rigid material, such as steel, copper cladding, plastic, high density plastic, silicone, PVC, fiberglass, carbon fiber, composite material, metal, galvanized steel, stainless steel, aluminum, brass, copper, wood, or other like material. The nuts 2419 and washers 2413 comprise a strong rigid material, such as steel, copper cladding, plastic, high density plastic, silicone, PVC, fiberglass, carbon fiber, composite material, metal, galvanized steel, stainless steel, aluminum, brass, copper, wood, or other like material. The tab 2426 of the shadow caster 2420 comprises lightweight rigid material, such as steel, copper cladding, plastic, high density plastic, silicone, PVC, fiberglass, carbon fiber, composite material, metal, galvanized steel, stainless steel, aluminum, brass, copper, wood, or other like material. The actuator arm 2442 of the actuator assembly 2440 comprises a strong rigid material, such as steel, copper cladding, plastic, high density plastic, silicone, PVC, fiberglass, carbon fiber, composite material, metal, galvanized steel, stainless steel, aluminum, brass, copper, wood, or other like material. The actuator motor 2446 of the actuator assembly 2440 comprises a linear stepper motor, an electric motor, a hydraulic system, or the like. The actuator connector 2444 of the actuator assembly 2440 comprises a strong rigid material, such as steel, copper cladding, plastic, high density plastic, silicone, PVC, fiberglass, carbon fiber, composite material, metal, galvanized steel, stainless steel, aluminum, brass, copper, wood, or other like material. The light source 2450 comprises an incandescent light, a halogen light, fluorescent light, a linear light, a slitted tube light, an LED, an array of LEDs, a linear array of LEDs, different colored light sources, colored LEDs, lasers, an X-ray source, a UV source, an infrared source, or the like. The video camera support platform 2436 comprises a strong rigid material, such as steel, copper cladding, plastic, high density plastic, silicone, PVC, fiberglass, carbon fiber, composite material, metal, galvanized steel, stainless steel, aluminum, brass, copper, wood, or other like material. The video camera 2434 comprises a digital or analog video camera, or the like. The camera lens 2435 comprises a telephoto lens, a filtered lens, a magnifying lens, a lens with negative focal length, or the like. The memory stored in non-transitory computer-readable medium comprises software, instructions, data, algorithms, or the like. The processor comprises a computer, a mobile phone, a PC, a CPU, or the like. The display comprises a monitor, a screen, a television, an augmented reality headset, a microscope, or the like. The filtered shadow caster 2420*a* comprises configurable opacity, such as liquid crystal, or the like, or various colored filters, or the like, which may filter different colored light or have varying opacities. The bladed shadow caster 2400*b* comprises a strong rigid material, such as steel, copper cladding, plastic, high density plastic, silicone, PVC, fiberglass, carbon fiber, composite material, metal, galvanized steel, stainless steel, aluminum, brass, copper, wood, or other like material, and may further comprise configurable shapes, three-dimensionally-printed shapes, configurable opacity, such as liquid crystal, or the like, or various colored filters, or the like. The wide bladed shadow caster 2400*c* comprises a strong rigid material, such as steel, copper cladding, plastic, high density plastic, silicone, PVC, fiberglass, carbon fiber, composite material, metal, galvanized steel, stainless steel, aluminum, brass, copper, wood, or other like material, and may further comprise configurable shapes, three-dimensionally-printed shapes, configurable opacity, such as liquid crystal, or the like, or various colored filters, or the like.

Figure 31:
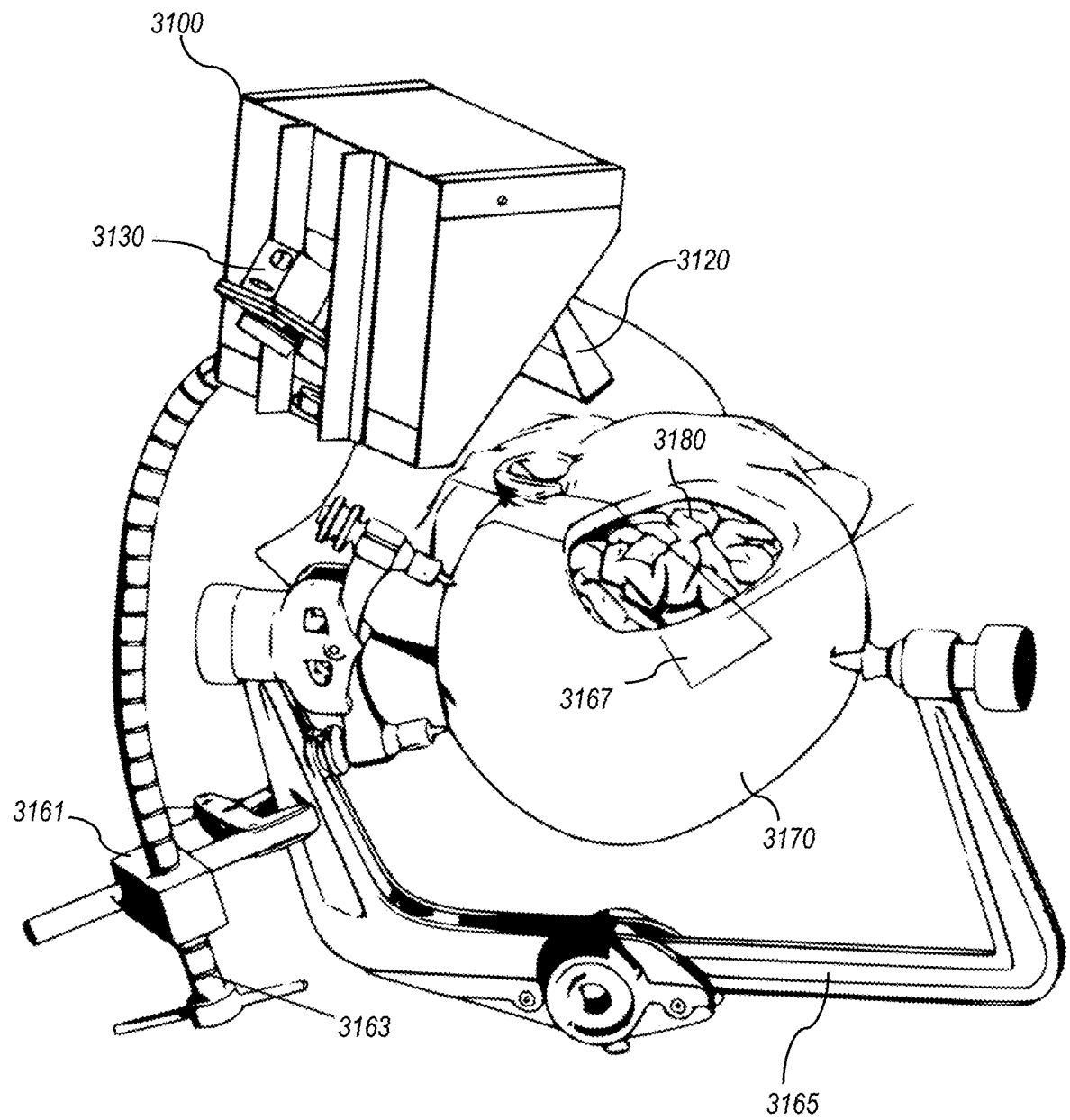
FIG. 31 is a front perspective view of an apparatus of the present invention being used during brain surgery, according to various embodiments.
Figure 32:
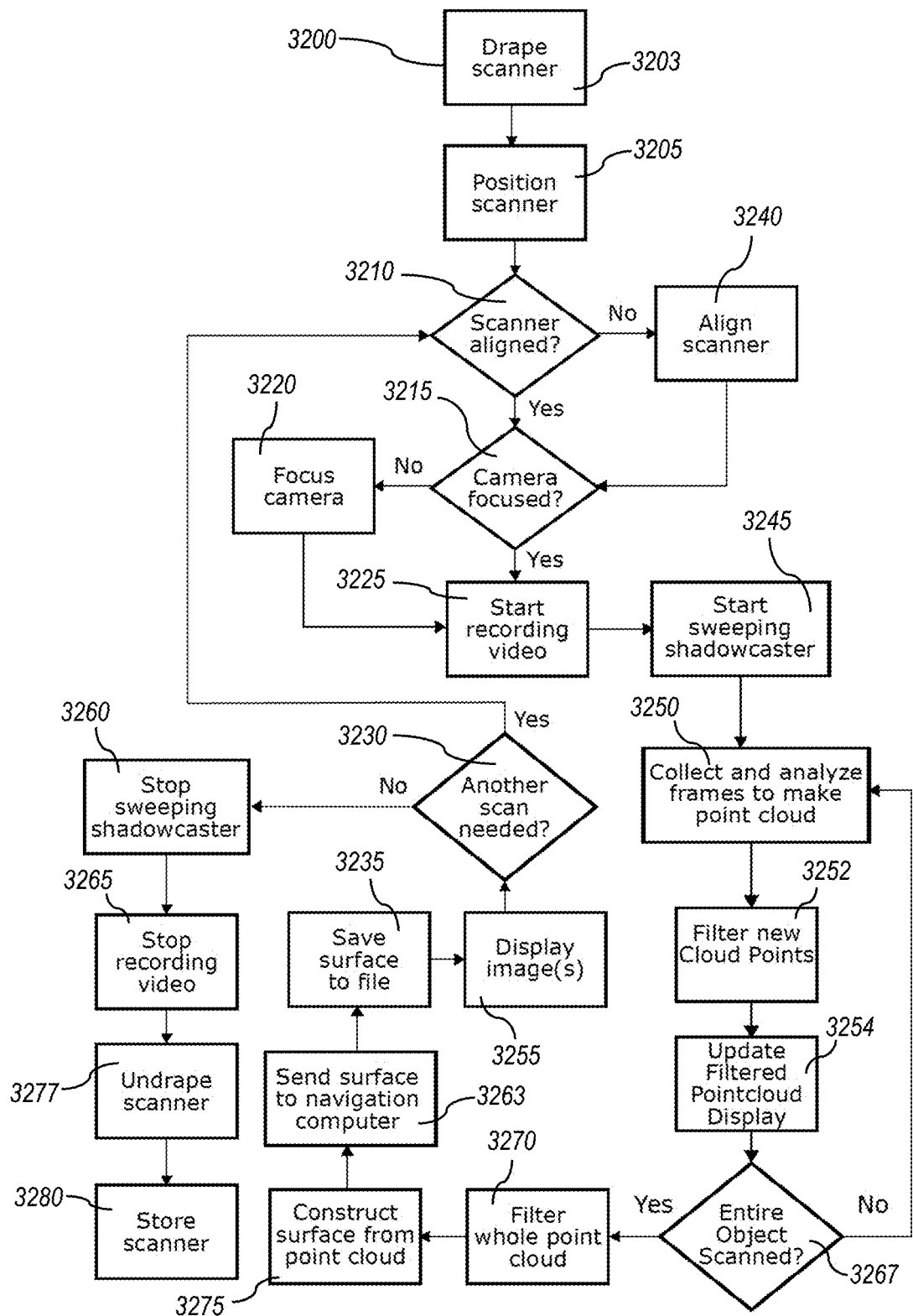
FIG. 32 illustrates a flow chart describing the operation of an apparatus of the present invention being used during brain surgery, according to some examples.
Figure 33:
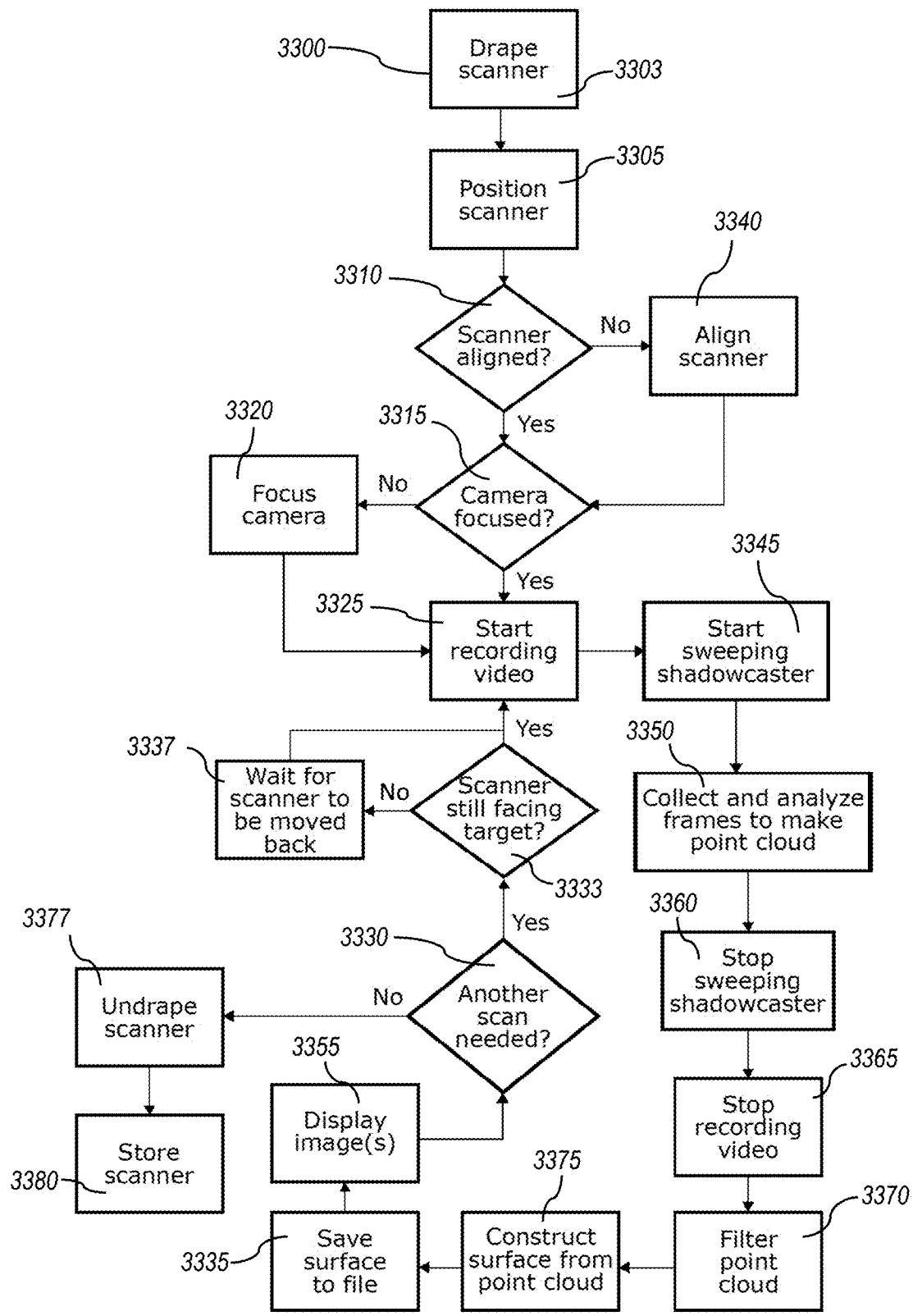
FIG. 33 shows a flow chart describing the operation of an apparatus of the present invention being used during brain surgery, according to some examples.
Figure 34:
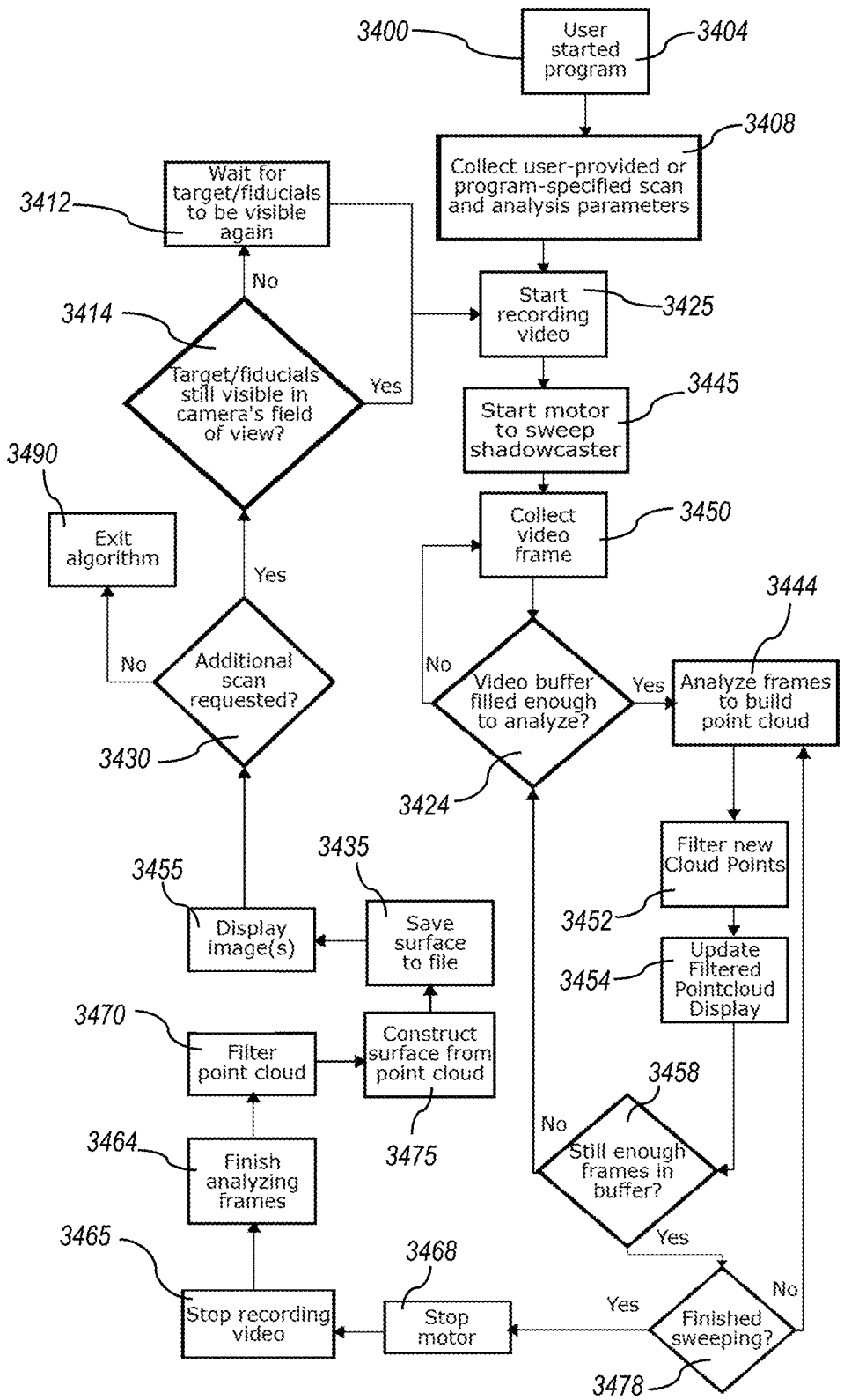
FIG. 34 depicts a flow chart describing the algorithm used by the present invention, according to some examples.
Figure 35:
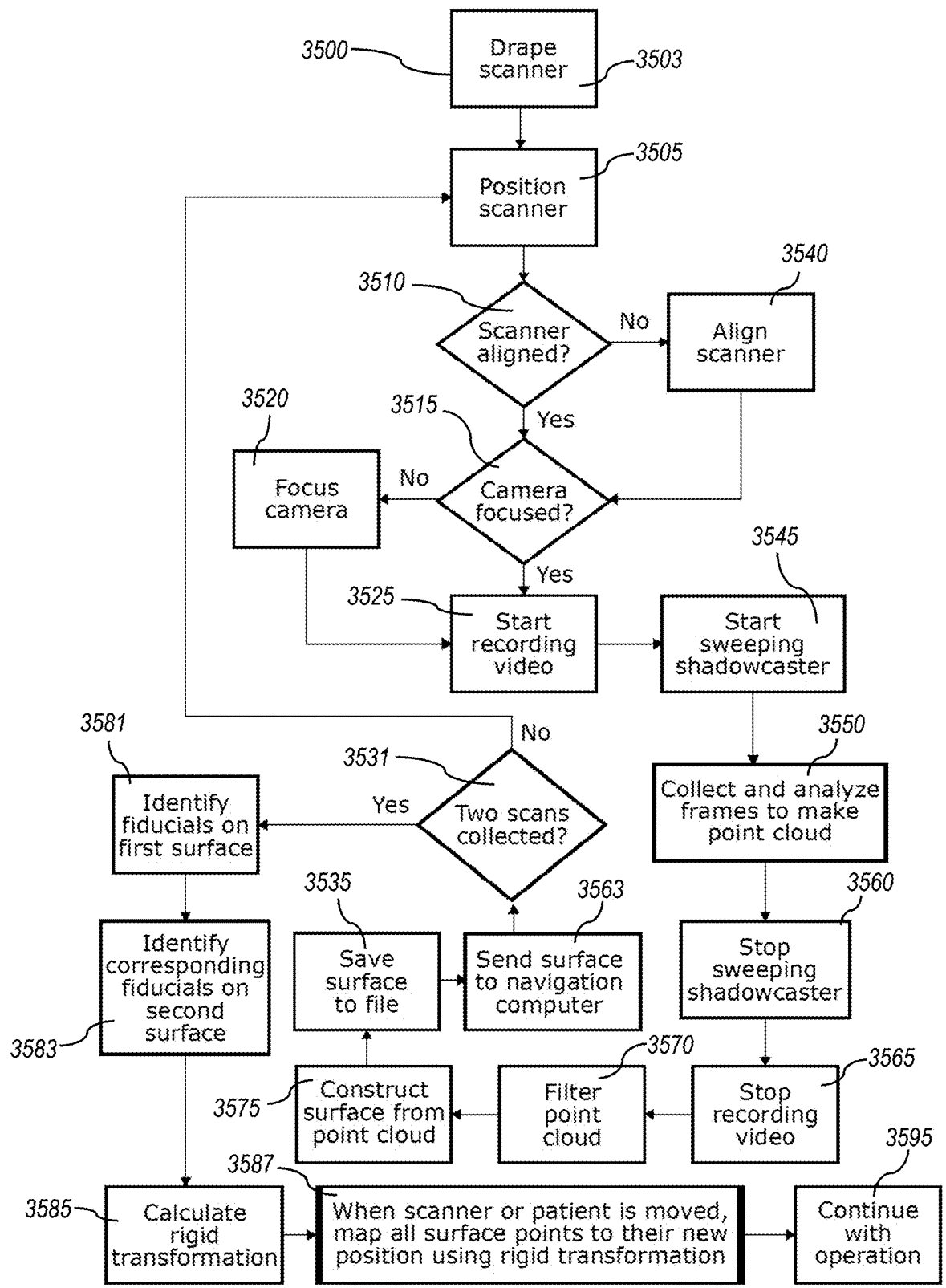
FIG. 35 displays a flow chart describing an apparatus of the present invention being used for patient registration, according to various embodiments.
Figure 36:
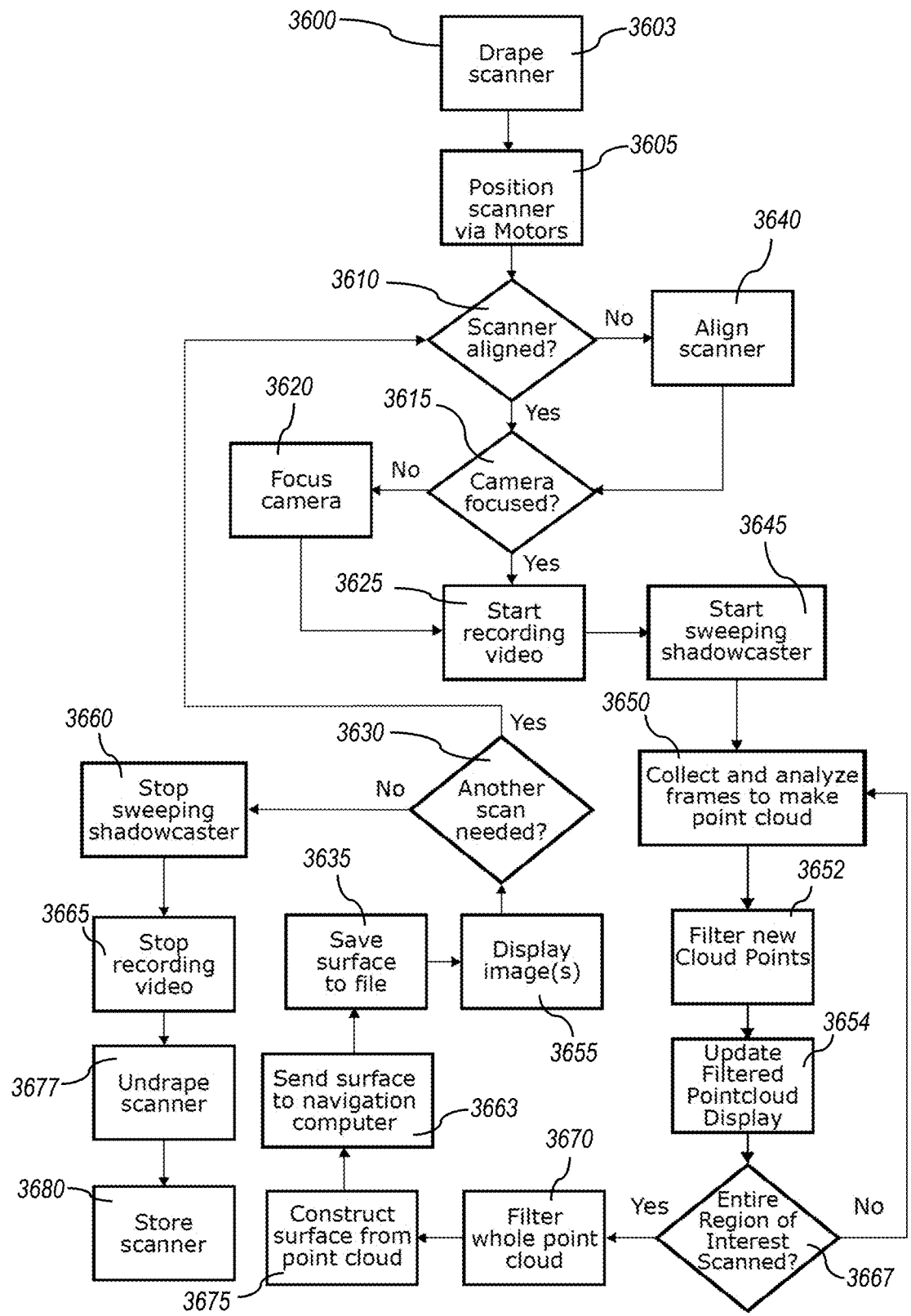
FIG. 36 demonstrates a flow chart describing the operation of an apparatus of the present invention being used during robotic brain surgery, according to some examples.

Referring now to another embodiment of the invention, in FIG. 31, FIG. 32, FIG. 33, FIG. 34, FIG. 35, and FIG. 36, a Surgery Shadow Caster Scanner 3100 is shown being used during surgery. FIG. 31 is a front perspective view of a Surgery Shadow Caster Scanner 3100 being used during brain surgery on a patient 3170. FIG. 32 illustrates an operation flow chart 3200, which describes the operation of a Surgery Shadow Caster Scanner 3100 being used during brain surgery. FIG. 33 shows a side scanner flow chart 3300 describing the operation of a Surgery Shadow Caster Scanner 3100 being used as a side scanner during brain surgery. FIG. 34 depicts an algorithm flow chart 3400 describing the algorithm used by a Surgery Shadow Caster Scanner 3100 being used as a side scanner during brain surgery. FIG. 35 displays a registration flow chart 3500 describing a Surgery Shadow Caster Scanner 3100 being used for patient registration. FIG. 36 demonstrates a robotic flow chart 3600, which describes the operation of a Surgery Shadow Caster Scanner 3100 being used during robotic brain surgery.

In further detail, still referring to the invention of FIG. 31, FIG. 32, FIG. 33, FIG. 34, FIG. 35, and FIG. 36, in FIG. 31, the Surgery Shadow Caster Scanner 3100 is shown casting a shadow 3167 from the shadow caster 3120 across a craniotomy 3180 of a patient 3170 while the video camera 3130 is recording a sweep. A head clamp 3165, right-angle clamp 3161, and lockable flex arm 3163, fixate the position of the Surgery Shadow Caster Scanner 3100 relative to the area being scanned on the patient 3170. In FIG. 32, the operation flow chart 3200 describes the operation of a Surgery Shadow Caster Scanner 3100 being used during brain surgery. The first step in the operation of the Surgery Shadow Caster Scanner 3100 comprises draping the scanner with a custom drape, which is well suited for surgery, which conforms to the exterior of the Surgery Shadow Caster Scanner 3100, and which is capable of protecting the patient 3170 from contamination during surgery, in the drape scanner step 3203. Next, the Surgery Shadow Caster Scanner 3100 is positioned over the subject, in the position scanner step 3205. Next, in the alignment decision step 3210, whether the scanner is aligned with the subject, which in this case is a craniotomy 3180 of a patient 3170, is determined. If the scanner is not aligned, the scanner is then aligned with the subject in the align scanner step 3240. Once the scanner is aligned, whether the camera is focused on the subject is determined in the focus decision step 3215. If the camera is not focused, the camera is then focused in the focus camera step 3220. Once the camera is focused, the camera starts recording video of the subject in the start recording step 3225. Next, in the start sweeping step 3245, the shadow caster begins to sweep edges of luminosity across the subject. Next, frames of the recorded video are collected and analyzed by the processor to make a point cloud in the collect and analyze step 3250. Next, new cloud points are filtered by the processor in the filter new cloud points step 3252. Next, the filtered point cloud display is updated in the update filtered cloud point step 3254. Next, the processor filters the whole point cloud in the filter whole point cloud step 3270. Next, in the construct surface step 3275, the processor constructs a model of a three-dimensional surface from the filtered point cloud. Next, the surface is sent to the surgical navigation computer in the send surface step 3263. The surgical navigation computer comprises a computer that determines where a surgeon's tools are and where the patient is in relation to a common three-dimensional coordinate system. The surgical navigation is used to aid in the surgery. Next, the surface is saved to file in the save file step 3235. Next, the model is displayed on the display by the processor in the display image step 3255. Whether another scan is needed is determined in the another scan decision step 3230.

If another scan is needed, the alignment decision step 3210 is repeated, as described above. Next, in the stop sweeping step 3260, the shadow caster stops sweeping the edges of luminosity across the subject. Next, the camera stops recording video of the subject in the stop recording step 3265. Next, the scanner is undraped in the undrape scanner step 3277. Lastly, the scanner is stored after operation in the store scanner step 3280. In FIG. 33, the side scanner flow chart 3300 describes the operation of a Surgery Shadow Caster Scanner 3100 being used as a side scanner during brain surgery. The first step in the operation of the Surgery Shadow Caster Scanner 3100 as a side scanner comprises draping the scanner with a custom drape, which is well suited for surgery, which conforms to the exterior of the Surgery Shadow Caster Scanner 3100, and which is capable of protecting the patient 3170 from contamination during surgery, in the drape scanner step 3303. Next, the Surgery Shadow Caster Scanner 3100 is positioned at the side of the subject, in the position scanner step 3305. Next, in the alignment decision step 3310, whether the scanner is aligned with the subject is determined. If the scanner is not aligned, the scanner is then aligned with the subject in the align scanner step 3340. Once the scanner is aligned, whether the camera is focused on the subject is determined in the focus decision step 3315. If the camera is not focused, the camera is then focused in the focus camera step 3320. Once the camera is focused, the camera starts recording video of the subject in the start recording step 3325. Next, in the start sweeping step 3345, the shadow caster begins to sweep edges of luminosity across the subject. Next, frames of the recorded video are collected and analyzed by the processor to make a point cloud in the collect and analyze step 3350. Next, in the stop sweeping step 3360, the shadow caster stops sweeping the edges of luminosity across the subject. Next, the camera stops recording video of the subject in the stop recording step 3365. Next, the processor filters the point cloud in the filter point cloud step 3370. Next, in the construct surface step 3375, the processor constructs a model of a three-dimensional surface from the filtered point cloud. Next, the surface is saved to file in the save file step 3335. Next, the model is displayed on the display by the processor in the display image step 3355. Whether another scan is needed is determined in the another scan decision step 3330. If another scan is needed, whether the scanner is still facing the target is determined in the still targeting step 3333. If the scanner is still facing the target, the start recording step 3325 is repeated, as described above. If the scanner is no longer facing the target, then wait until the scanner is moved back in the move back step 3337. Once the scanner is moved back to the target, the start recording step 3325 is repeated, as described above. If another scan is not needed, then the scanner is undraped in the undrape scanner step 3377. Lastly, the scanner is stored after operation in the store scanner step 3380. In FIG. 34, the algorithm flow chart 3400 describes the algorithm used by a Surgery Shadow Caster Scanner 3100 being used as a side scanner during brain surgery. The first step in the algorithm for the Surgery Shadow Caster Scanner 3100 comprises starting the program, in the start program step 3404. Next, user-provided or program-specified scan and analysis parameters are collected in the collect parameters step 3408. Next, the camera starts recording video in the start recording step 3425. Next, in the start sweeping step 3445, the motor is started in order to move the shadow caster and sweep edges of luminosity across the subject. Next, frames of the recorded video are collected in the collect video step 3450. Next, whether the video buffer is filled enough to analyze is determined in the buffer decision step 3424. If the buffer is not filled enough, the collect video step 3450 is repeated, as described above. If the buffer is filled enough to analyze, the video frames are analyzed to build a point cloud in the analyze frames step 3444. Next, new cloud points are filtered by the processor in the filter new cloud points step 3452. Next, the filtered point cloud display is updated in the update filtered point cloud step 3454. Next, whether there are still enough frames in the buffer is determined in the still buffered decision step 3458. If there are not enough frames in the buffer, the buffer decision step 3424 is repeated, as described above. If there are still enough frames in the buffer, whether to finish sweeping is determined in the finish sweeping decision step 3478. If the sweeping is not finished, then the analyze frames step 3444 is repeated, as described above. If the sweeping is finished, then the motor is stopped in the stop motor step 3468. Next, the camera stops recording video of the subject in the stop recording step 3465. Next, analyzing frames is finished in the finish analyzing frames step 3464. Next, the processor filters the point cloud in the filter point cloud step 3470. Next, in the construct surface step 3475, the processor constructs a model of a three-dimensional surface from the filtered point cloud. Next, the surface is saved to file in the save file step 3435. Next, the model is displayed on the display by the processor in the display image step 3455. Whether another scan is requested is determined in the another scan decision step 3430. If another scan is requested, whether the target or fiducials are still visible in the camera's field of view is determined in the still visible step 3414. If the target or fiducials are still visible, the start recording step 3425 is repeated, as described above. If the target or fiducials are not still visible, then wait until the target or fiducials are visible again in the wait step 3412, and, once the target or fiducials are visible again, the start recording step 3425 is repeated, as described above. Lastly, if another scan is not requested, then the user exits the algorithm in the exit algorithm step 3490. In FIG. 35, the registration flow chart 3500 describes a Surgery Shadow Caster Scanner 3100 being used for patient registration. The first step in registering a patient comprises draping the scanner with a custom drape in the drape scanner step 3503. Next, the Surgery Shadow Caster Scanner 3100 is positioned over the subject, in the position scanner step 3505. Next, in the alignment decision step 3510, whether the scanner is aligned with the subject is determined. If the scanner is not aligned, the scanner is then aligned with the subject in the align scanner step 3540. Once the scanner is aligned, whether the camera is focused on the subject is determined in the focus decision step 3515. If the camera is not focused, the camera is then focused in the focus camera step 3520. Once the camera is focused, the camera starts recording video of the subject in the start recording step 3525. Next, in the start sweeping step 3545, the shadow caster begins to sweep edges of luminosity across the subject. Next, frames of the recorded video are collected and analyzed by the processor to make a point cloud in the collect and analyze step 3550. Next, in the stop sweeping step 3560, the shadow caster stops sweeping the edges of luminosity across the subject. Next, the camera stops recording video of the subject in the stop recording step 3565 Next, the processor filters the point cloud in the filter point cloud step 3570. Next, in the construct surface step 3575, the processor constructs a model of a three-dimensional surface from the filtered point cloud. Next, the surface is saved to file in the save file step 3235. Next, the surface is sent to the navigation computer in the send surface step 3563. Next, whether two scans are collected is determined in the two scans decision step 3531. If two scans are not collected, then repeat the position scanner step 3505, as described above. If two scans are collected, then identify fiducials on the first surface in the identify first fiducials step 3581. Next, identify corresponding fiducials on the second surface in the identify second fiducials step 3583. Next, calculate a rigid transformation using the processor in the calculate step 3585. Next, when the scanner or patient is moved, map all surface points to their new position using rigid transformation in the map step 3587. Lastly, continue with the operation in the continue operation step 3595. In FIG. 36, the robotic flow chart 3600 describes the operation of a Surgery Shadow Caster Scanner 3100 being used during robotic brain surgery. The first step in the robotic operation of the Surgery Shadow Caster Scanner 3100 comprises draping the scanner with a custom drape, which is well suited for surgery, which conforms to the exterior of the Surgery Shadow Caster Scanner 3100, and which is capable of protecting the patient 3170 from contamination during surgery, in the drape scanner step 3603. Next, the Surgery Shadow Caster Scanner 3100 is positioned over the subject using robotically controlled motors, in the position scanner step 3605. Next, in the alignment decision step 3610, whether the scanner is aligned with the subject is determined. If the scanner is not aligned, the scanner is then aligned with the subject in the align scanner step 3640. Once the scanner is aligned, whether the camera is focused on the subject is determined in the focus decision step 3615. If the camera is not focused, the camera is then focused in the focus camera step 3620. Once the camera is focused, the camera starts recording video of the subject in the start recording step 3625. Next, in the start sweeping step 3645, the shadow caster begins to sweep edges of luminosity across the subject. Next, frames of the recorded video are collected and analyzed by the processor to make a point cloud in the collect and analyze step 3650. Next, new cloud points are filtered by the processor in the filter new cloud points step 3652. Next, the filtered point cloud display is updated in the update filtered cloud point step 3654. Next, whether the entire region of interest has been scanned is determined in the entire scan decision step 3667. If the entire region of interest has not been scanned, then repeat the collect and analyze step 3650, as described above. If the entire region of interest has been scanned, then the processor filters the whole point cloud in the filter whole point cloud step 3670. Next, in the construct surface step 3675, the processor constructs a model of a three-dimensional surface from the filtered point cloud. Next, the surface is sent to the navigation computer in the send surface step 3663. Next, the surface is saved to file in the save file step 3635. Next, the model is displayed on the display by the processor in the display image step 3655. Whether another scan is needed is determined in the another scan decision step 3630. If another scan is needed, the alignment decision step 3610 is repeated, as described above. If another scan is not needed, the shadow caster stops sweeping the edges of luminosity across the subject in the stop sweeping step 3660. Next, the camera stops recording video of the subject in the stop recording step 3665. Next, the scanner is undraped in the undrape scanner step 3677. Lastly, the scanner is stored after operation in the store scanner step 3680.

The construction details of the invention as shown in FIG. 31, FIG. 32, FIG. 33, FIG. 34, FIG. 35, and FIG. 36, are that a Surgery Shadow Caster Scanner 3100 comprises a strong rigid material, such as steel, copper cladding, plastic, high density plastic, silicone, PVC, fiberglass, carbon fiber, composite material, metal, galvanized steel, stainless steel, aluminum, brass, copper, wood, or other like material. The shadow caster 3120 comprises a strong rigid material, such as steel, copper cladding, plastic, high density plastic, silicone, PVC, fiberglass, carbon fiber, composite material, metal, galvanized steel, stainless steel, aluminum, brass, copper, wood, or other like material, and may further comprise configurable shapes, three-dimensionally-printed shapes, configurable opacity, such as liquid crystal, or the like, or various colored filters, or the like. The video camera 3130 comprises a digital or analog video camera, or the like. The head clamp 3165, right-angle clamp 3161, and lockable flex arm 3163 comprise a strong rigid material, such as steel, copper cladding, plastic, high density plastic, silicone, PVC, fiberglass, carbon fiber, composite material, metal, galvanized steel, stainless steel, aluminum, brass, copper, wood, or other like material.

Figure 37:
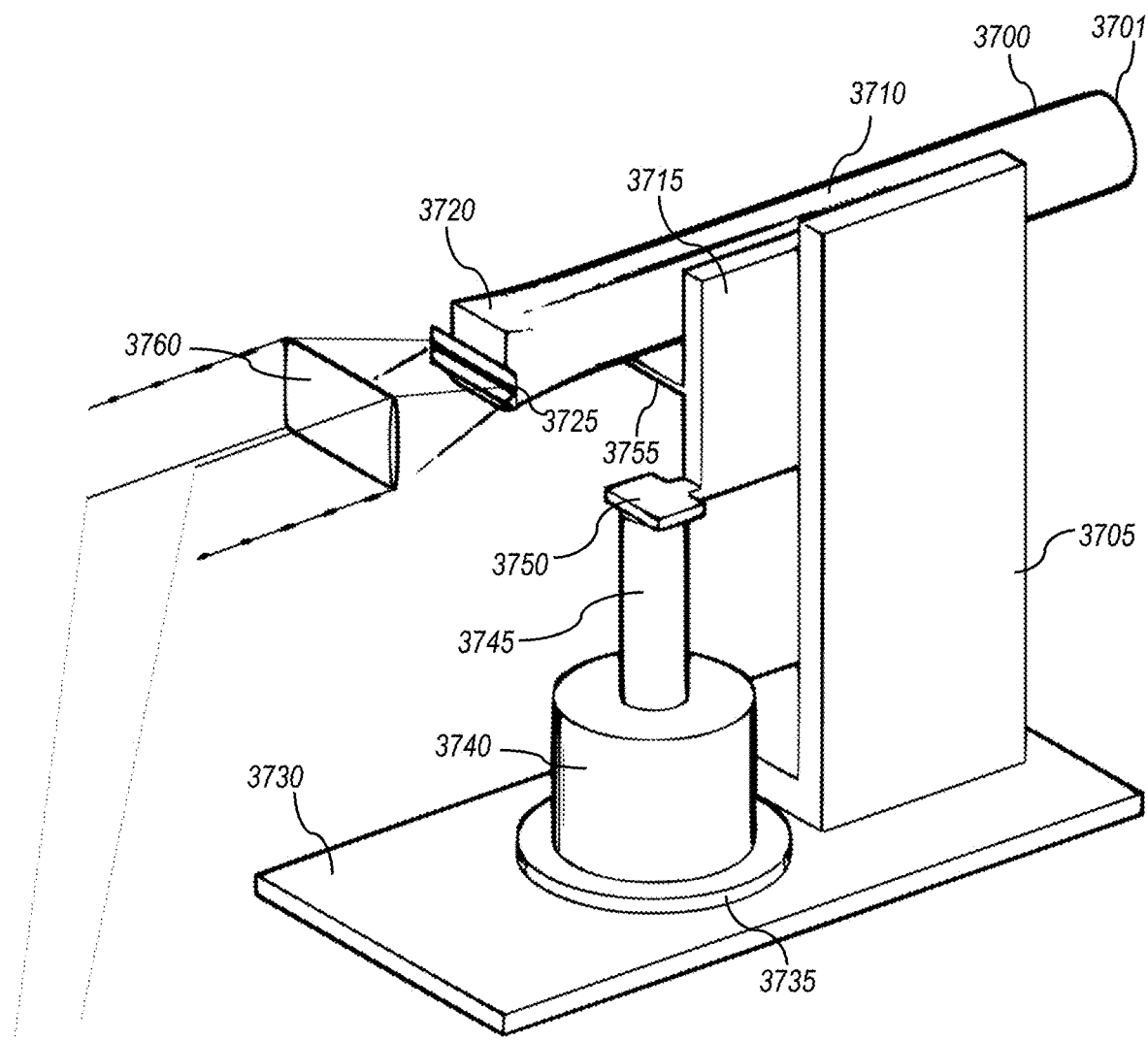
FIG. 37 is a front perspective view of an apparatus of the present invention, according to various embodiments.
Figure 38:
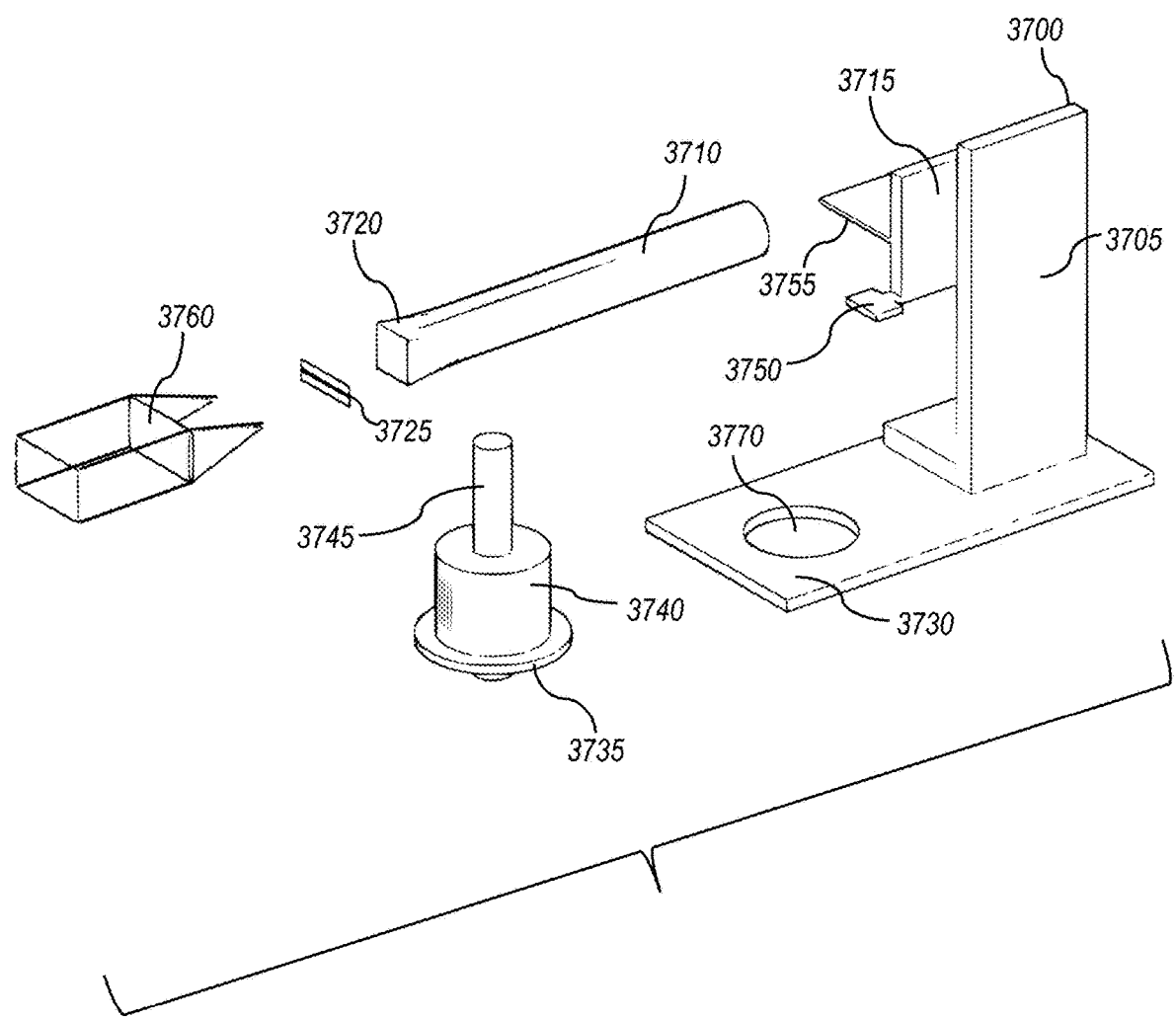
FIG. 38 is an exploded view of an apparatus of FIG. 37, according to some examples.
Figure 39:
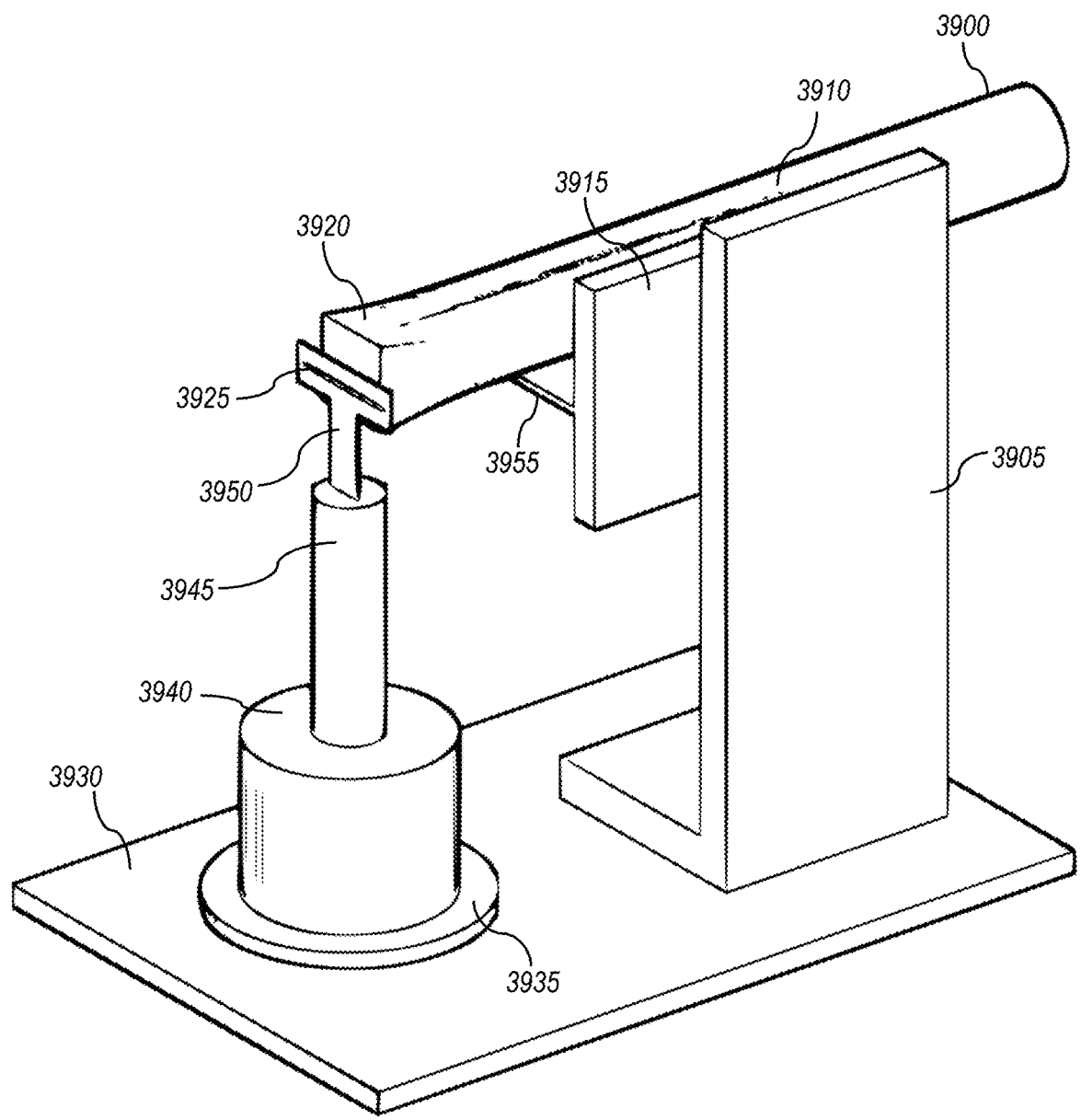
FIG. 39 is a front perspective view of an apparatus of the present invention, according to various embodiments.
Figure 40:
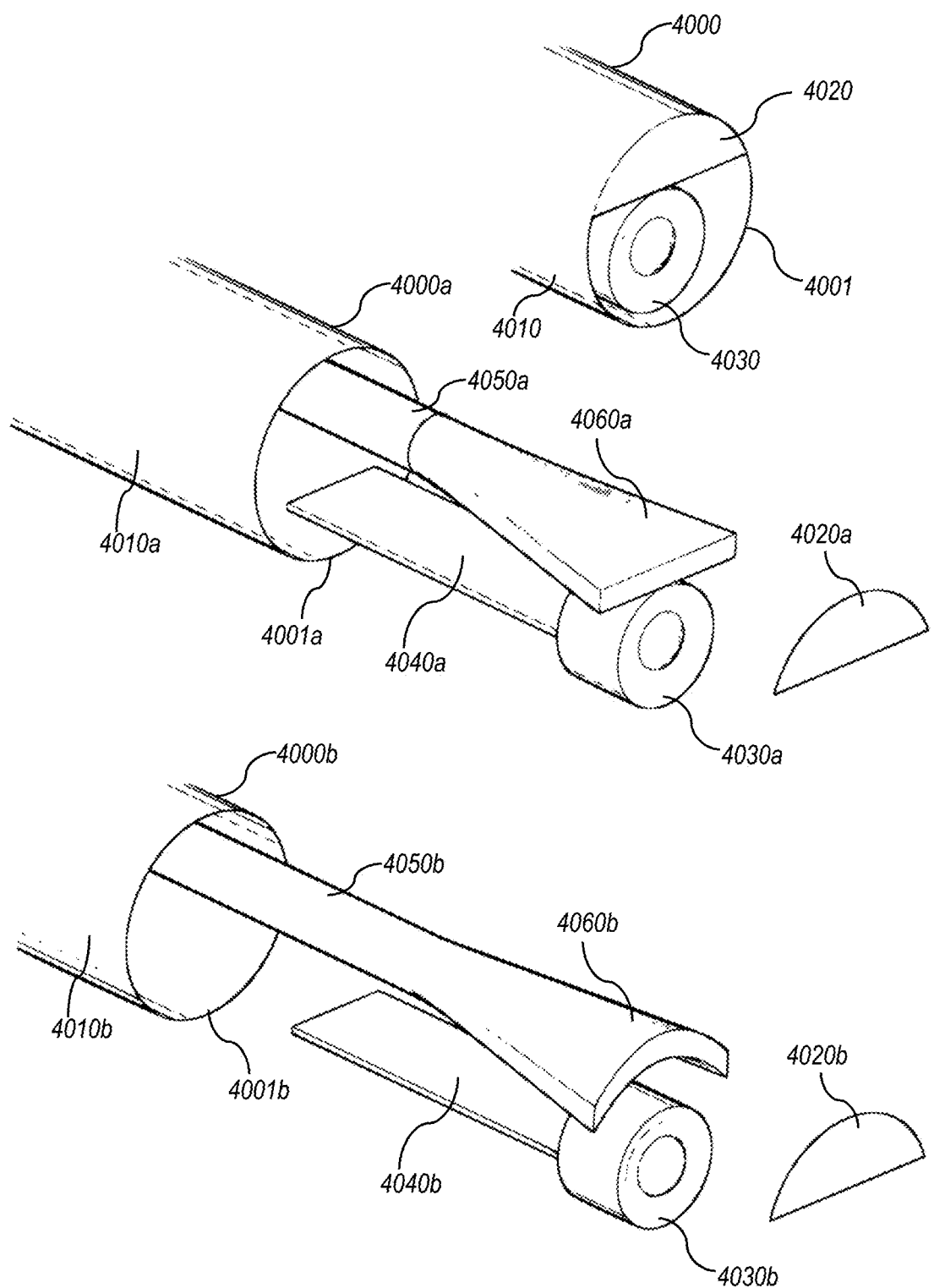
FIG. 40 shows front perspective and exploded views of apparatuses of the present invention mounted in the distal ends of endoscopes, according to various embodiments.
Figure 41:
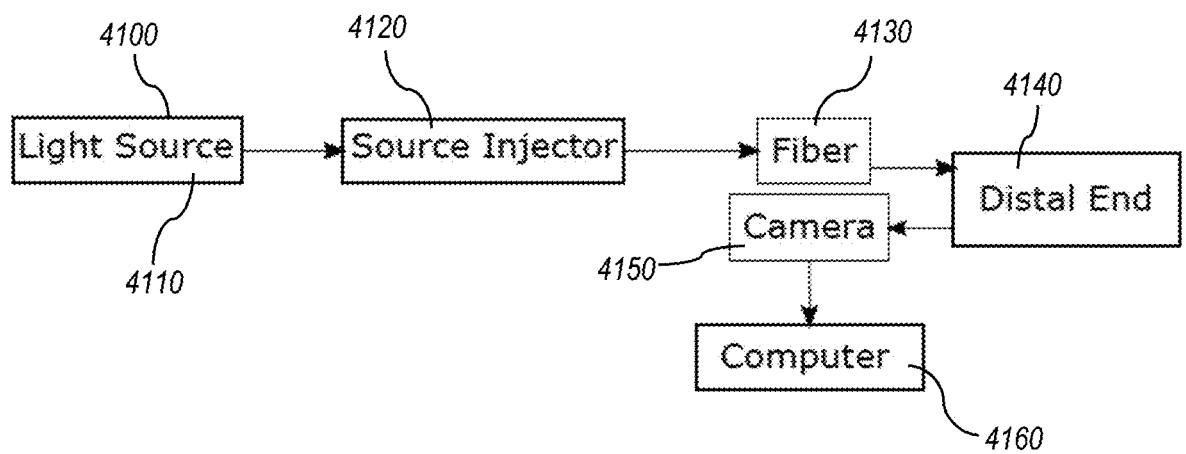
FIG. 41 depicts a block diagram, which describes an apparatus of FIG. 40, according to some examples.
Figure 42:
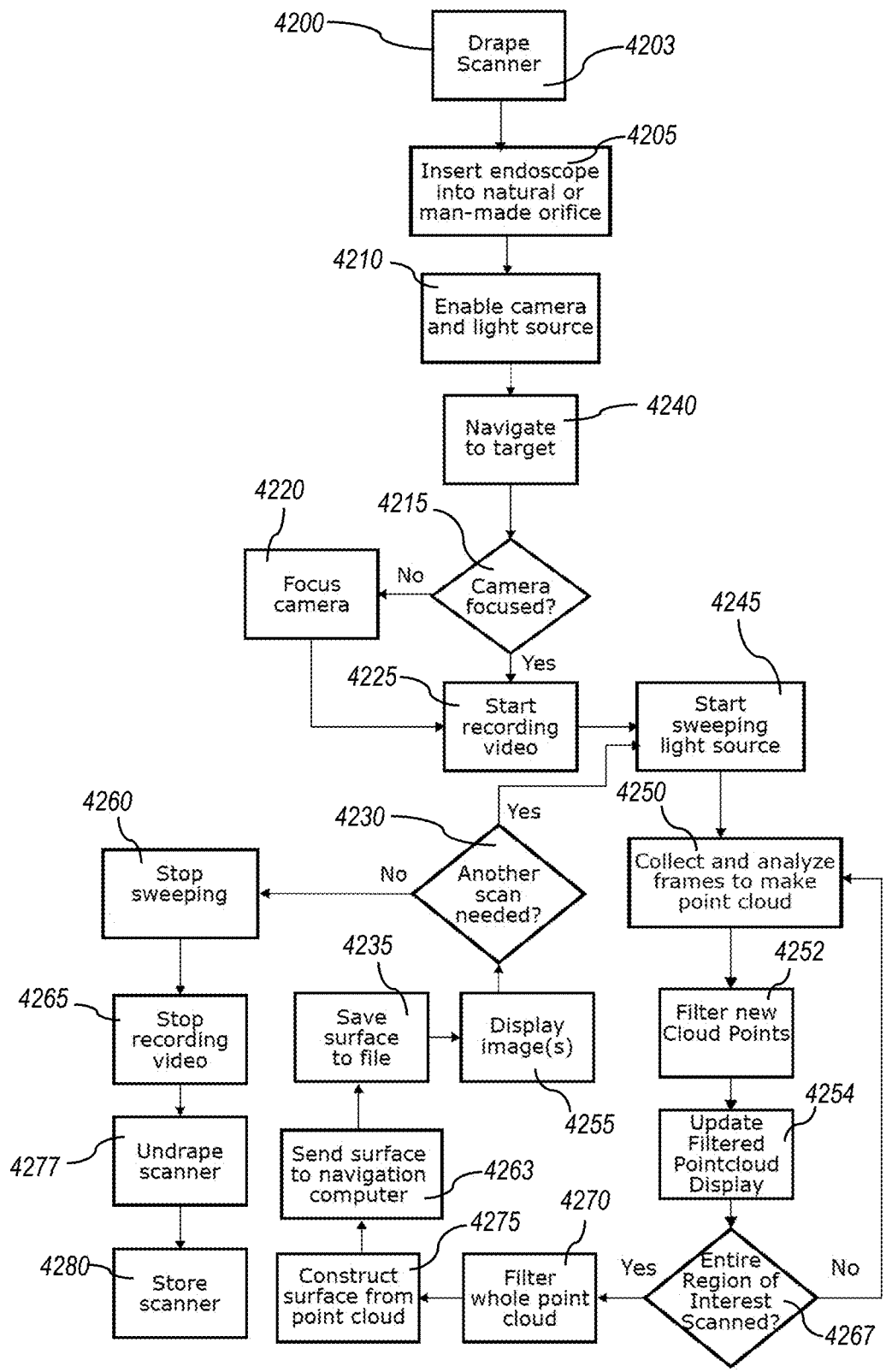
FIG. 42 illustrates a flow chart describing the operation of an endoscope version of an apparatus of the present invention, according to various embodiments.
Figure 43:
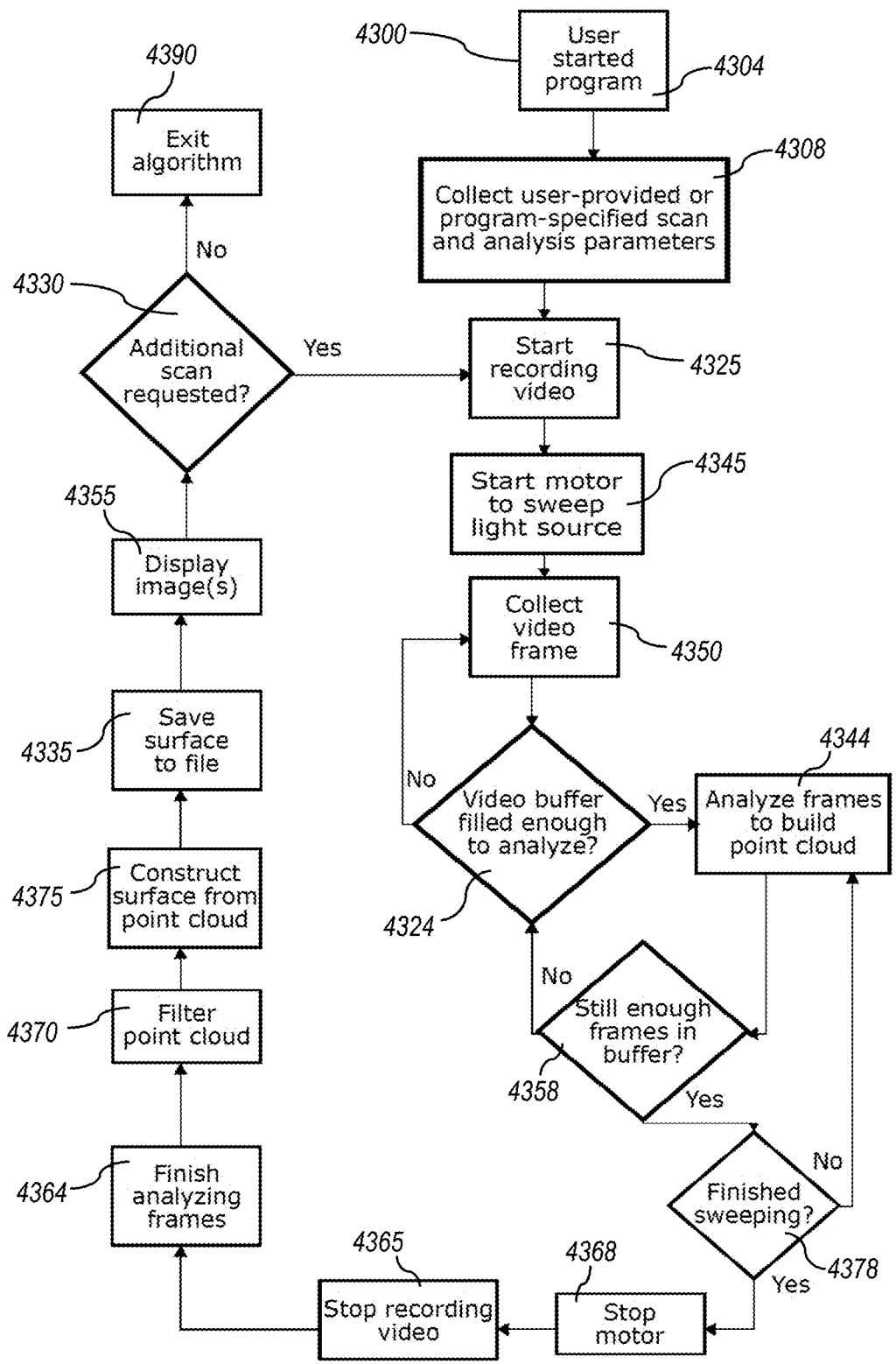
FIG. 43 depicts a flow chart describing the algorithm used by an endoscope version of the present invention, according to some examples.
Figure 44:
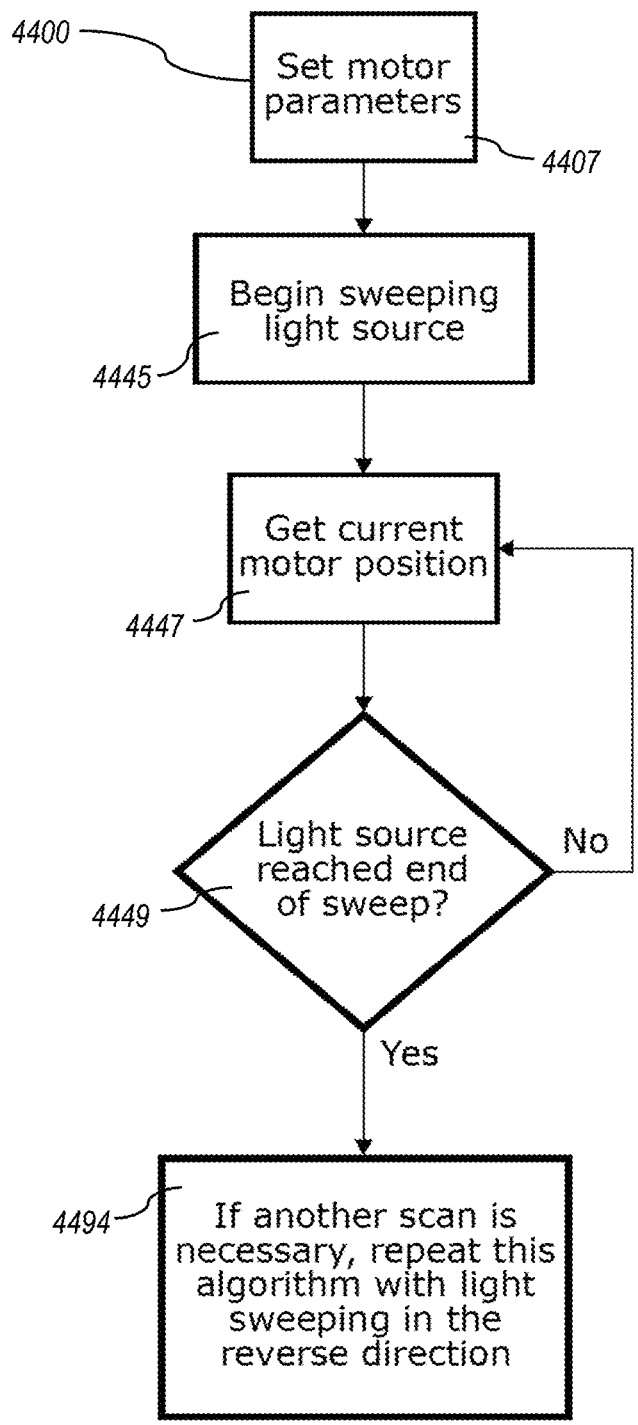
FIG. 44 shows a flow chart, which describes a shadow caster sweep of an endoscope version of an apparatus of the present invention, according to some examples.

Referring now to another embodiment of the invention, in FIG. 37, FIG. 38, FIG. 39, FIG. 40, FIG. 41, FIG. 42, FIG. 43, and FIG. 44, endoscope versions of a shadow caster scanner are shown. FIG. 37 is a front perspective view of an Endoscope Shadow Caster Scanner 3700. FIG. 38 is an exploded view of an Endoscope Shadow Caster Scanner 3700. FIG. 39 is a front perspective view of a Moving Slit Endoscope Shadow Caster Scanner 3900. FIG. 40 shows front perspective and exploded views of the distal ends 4000, 4000a, and 4000b, for an Endoscope Shadow Caster Scanner 3700 and a Moving Slit Endoscope Shadow Caster Scanner 3900. FIG. 41 depicts a light path block diagram 4100, which describes the light path of an Endoscope Shadow Caster Scanner 3700 and a Moving Slit Endoscope Shadow Caster Scanner 3900. FIG. 42 illustrates an endoscope operation flow chart 4200 describing the operation of an Endoscope Shadow Caster Scanner 3700 and a Moving Slit Endoscope Shadow Caster Scanner 3900 during surgery. FIG. 43 depicts an endoscope algorithm flow chart 4300, which describes the algorithm used by an Endoscope Shadow Caster Scanner 3700 and a Moving Slit Endoscope Shadow Caster Scanner 3900. FIG. 44 shows an endoscope sweep flow chart 4400, which describes a shadow caster sweep of an Endoscope Shadow Caster Scanner 3700 and a Moving Slit Endoscope Shadow Caster Scanner 3900.

In further detail, still referring to the invention of FIG. 37, FIG. 38, FIG. 39, FIG. 40, FIG. 41, FIG. 42, FIG. 43, and FIG. 44, in FIG. 37, FIG. 38 and FIG. 40, an Endoscope Shadow Caster Scanner 3700 is shown along with optional distal ends 4001, 4001a, or 4001b. An Endoscope Shadow Caster Scanner 3700 comprises an endoscope body 4000, 4000a, and 4000b, said endoscope body 4000, 4000a, or 4000b comprising: a proximal end 3701, a distal end 4001, 4001a, or 4001b, an endoscope sleeve 4010, 4010a, or 4010b, said endoscope sleeve 4010, 4010a, or 4010b, spanning between said proximal end 3701 and said distal end 4001, 4001a, or 4001b, a tapered fiber optic bundle 4060a and 4060b, said tapered fiber optic bundle 4060a and 4060b being disposed within said endoscope sleeve 4010, 4010a, or 4010b and tapered towards said distal end 4001, 4001a, or 4001b, and an endoscope camera 4030, 4030a, or 4030b, said endoscope camera 4030, 4030a, or 4030b being disposed within said endoscope sleeve 4010, 4010a, or 4010b and facing out said distal end 4001, 4001a, or 4001b; a shadow caster 4020, 4020a, or 4020b, said shadow caster 4020, 4020a, or 4020b being mounted on said distal end 4001, 4001a, or 4001b of said endoscope body 4000, 4000a, or 4000b over said tapered fiber optic bundle 4060a and 4060b, said shadow caster 4020, 4020a, or 4020b comprising: a semi-circular piece; a light launch 3700, said light launch 3700 comprising: a horizontal platform 3730, a vertical stand 3705, said vertical stand distending from said horizontal platform 3730, a stepper motor linear actuator 3740, said stepper motor linear actuator 3740 distending from said horizontal platform 3730, a translating platform 3715, said translating platform 3715 being connected to said stepper motor linear actuator 3740, a light source 3701, said light source 3701 depending from said translating platform 3715, a cylindrical lens 3760, an optic fiber bundle 3710, which may be an image-maintaining optic fiber bundle, said optic fiber bundle 3710 depending from said light source 3701, a square-to-round taper 3720, said square-to-round taper 3720 depending from said optic fiber bundle 3710, and a slit 3725, said slit 3725 being mounted on said square-to-round taper 3720; a memory stored in non-transitory computer-readable medium; a processor (not shown), said processor comprising: said computer-readable medium; and a display (not shown); wherein said light launch 3700 is connected to said proximal end 3701 of said endoscope body 4000, 4000*a*, and 4000*b*; wherein said light source 3701 illuminates said optic fiber bundle 3710, said square-to-round taper 3720, said slit 3725, said tapered fiber optic bundle 4060*a*, and said shadow caster 4020 or 4020*a* to project high contrast shadows of known geometry, which form said one or more edges of luminosity on said object; wherein said stepper motor linear actuator 3740 moves said translating platform 3715 with said light source 3701 in order to sweep said one or more edges of luminosity across said object; wherein said endoscope camera 4030, 4030*a*, or 4030*b* detects said one or more edges of luminosity for three-dimensional points on said object and records said three-dimensional points into said memory; wherein said processor forms a three-dimensional data representation from recorded said three-dimensional points; wherein said processor generates said three-dimensional model of said object using said three-dimensional data representation; and wherein said three-dimensional model is displayed on said display using said processor. In FIG. 39 and FIG. 40, a Moving Slit Endoscope Shadow Caster Scanner 3900 is shown along with optional distal ends 4001, 4001*a*, or 4001*b*. A Moving Slit Endoscope Shadow Caster Scanner 3900 comprises an endoscope body 4000, 4000*a*, and 4000*b*, said endoscope body 4000, 4000*a*, or 4000*b* comprising: a proximal end 3701 (shown in FIG. 37 and FIG. 38), a distal end 4001, 4001*a*, or 4001*b*, an endoscope sleeve 4010, 4010*a*, or 4010*b*, said endoscope sleeve 4010, 4010*a*, or 4010*b*, spanning between said proximal end 3701 and said distal end 4001, 4001*a*, or 4001*b*, a tapered fiber optic bundle 4060*a*, said tapered fiber optic bundle 4060*a* being disposed within said endoscope sleeve 4010 or 4010*a* and tapered towards said distal end 4001, 4001*a*, or 4001*b*, and an endoscope camera 4030, 4030*a*, or 4030*b*, said endoscope camera 4030, 4030*a*, or 4030*b* being disposed within said endoscope sleeve 4010, 4010*a*, or 4010*b* and facing out said distal end 4001, 4001*a*, or 4001*b*; a shadow caster 4020, 4020*a*, or 4020*b*, said shadow caster 4020, 4020*a*, or 4020*b* being mounted on said distal end 4001, 4001*a*, or 4001*b* of said endoscope body 4000, 4000*a*, or 4000*b* over said tapered fiber optic bundle 4060*a*, said shadow caster 4020 or 4020*a* comprising: a semi-circular piece; a light launch 3900, said light launch 3900 comprising: a horizontal platform 3930, a vertical stand 3905, said vertical stand 3905 distending from said horizontal platform 3930, a stepper motor linear actuator 3940, said stepper motor linear actuator 3940 distending from said horizontal platform 3930, a supporting platform 3915, said supporting platform 3915 depending from said vertical stand 3905, a light source (not shown), an optic fiber bundle 3910, said optic fiber bundle 3910 depending from said light source, a square-to-round taper 3920, said square-to-round taper 3920 depending from said optic fiber bundle 3910, and a slit 3925, said slit 3925 being mounted to said stepper motor linear actuator 3940; a memory stored in non-transitory computer-readable medium; a processor (not shown), said processor comprising: said computer-readable medium; and a display (not shown); wherein said light launch 3900 is connected to said light source; wherein said light source illuminates said optic fiber bundle 3910, said square-to-round taper 3920, said slit 3925, said tapered fiber optic bundle 4060*a*, and said shadow caster 4020 or 4020*a* to project high contrast shadows of known geometry, which form said one or more edges of luminosity on said object; wherein said stepper motor linear actuator 3940 moves said slit 3925 in order to sweep said one or more edges of luminosity across said object; wherein said endoscope camera 4030, 4030*a*, or 4030*b* detects said one or more edges of luminosity for three-dimensional points on said object and records said three-dimensional points into said memory; wherein said processor forms a three-dimensional data representation from recorded said three-dimensional points; wherein said processor generates said three-dimensional model of said object using said three-dimensional data representation; and wherein said three-dimensional model is displayed on said display using said processor. In FIG. 41 a light path block diagram 4100 describes the light path of an Endoscope Shadow Caster Scanner 3700 and a Moving Slit Endoscope Shadow Caster Scanner 3900. First, light is emanated from the light source 3701 in the light source step 4110. Next, the light is illuminated through the light launch 3700 and 3900 in the source injector step 4120 where either the light source 3701 is moved or the slit 3925 is moved. Next, the light from the light launch 3700 and 3900 travels down the tapered fiber optic bundle 4060*a* in the fiber step 4130. Next, the light is projected out the distal end distal end 4001, 4001*a*, or 4001*b* of said endoscope body 4000, 4000*a*, or 4000*b* and across the shadow caster 4020, 4020*a*, or 4020*b* in the distal end step 4140. Next, the light and the edges of luminosity are detected by the endoscope camera 4030, 4030*a*, or 4030*b* in the camera step 4150. Lastly, images from the endoscope camera 4030, 4030*a*, or 4030*b* are sent to the processor for processing into a three-dimensional model in the computer step 4160. In FIG. 42, the endoscope operation flow chart 4200 describes the operation of an Endoscope Shadow Caster Scanner 3700 and a Moving Slit Endoscope Shadow Caster Scanner 3900 being used during surgery. The first step in the operation of the Endoscope Shadow Caster Scanner 3700 and the Moving Slit Endoscope Shadow Caster Scanner 3900 comprises draping the scanner with a custom drape, which is well suited for surgery, which conforms to the exterior of the Endoscope Shadow Caster Scanner 3700 or the Moving Slit Endoscope Shadow Caster Scanner 3900, and which is capable of protecting the patient from contamination during surgery, in the drape scanner step 4203. Next, the distal end 4001, 4001*a*, or 4001*b* of the Endoscope Shadow Caster Scanner 3700 or the Moving Slit Endoscope Shadow Caster Scanner 3900 is inserted into a natural or man-made orifice, in the insert scanner step 4205. Next, in the enable step 4210, the light source 3701 and the endoscope camera 4030, 4030*a*, or 4030*b* are enabled. Next the distal end 4001, 4001*a*, or 4001*b* of the Endoscope Shadow Caster Scanner 3700 or the Moving Slit Endoscope Shadow Caster Scanner 3900 is navigated to the target in the navigate step 4240. Next, whether the endoscope camera 4030, 4030*a*, or 4030*b* is focused on the target is determined in the focus decision step 4215. If the endoscope camera 4030, 4030*a*, or 4030*b* is not focused, the endoscope camera 4030, 4030a, or 4030b is then focused in the focus camera step 4220. Once the endoscope camera 4030, 4030a, or 4030b is focused, the endoscope camera 4030, 4030a, or 4030b starts recording video of the target in the start recording step 4225. Next, in the start sweeping step 4245, the edges of luminosity begin to sweep across the subject by either moving the light source 3701 of the Endoscope Shadow Caster Scanner 3700 or the slit 3925 of the Moving Slit Endoscope Shadow Caster Scanner 3900. Next, frames of the recorded video are collected and analyzed by the processor to make a point cloud in the collect and analyze step 4250. Next, new cloud points are filtered by the processor in the filter new cloud points step 4252. Next, the filtered point cloud display is updated in the update filtered cloud point step 4254. Next, whether the entire region of interest has been scanned is determined in the entire scan decision step 4267. If the entire region of interest has not been scanned, then repeat the collect and analyze step 4250, as described above. If the entire region of interest has been scanned, then the processor filters the whole point cloud in the filter whole point cloud step 4270. Next, in the construct surface step 3275, the processor constructs a model of a three-dimensional surface from the filtered point cloud. Next, the surface is sent to the navigation computer in the send surface step 4263. Next, the surface is saved to file in the save file step 4235. Next, the model is displayed on the display by the processor in the display image step 4255. Whether another scan is needed is determined in the another scan decision step 4230. If another scan is needed, the start sweeping step 4245 is repeated, as described above. If another scan is not needed, the edges of luminosity stop sweeping across the subject in the stop sweeping step 4260. Next, the camera stops recording video of the subject in the stop recording step 4265. Next, the scanner is undraped in the undrape scanner step 4277. Lastly, the scanner is stored after operation in the store scanner step 4280. In FIG. 43, the endoscope algorithm flow chart 4300 describes the algorithm used by an Endoscope Shadow Caster Scanner 3700 and a Moving Slit Endoscope Shadow Caster Scanner 3900. The first step in the algorithm for the Endoscope Shadow Caster Scanner 3700 or the Moving Slit Endoscope Shadow Caster Scanner 3900 comprises starting the program, in the start program step 4304. Next, user-provided or program-specified scan and analysis parameters are collected in the collect parameters step 4308. Next, the endoscope camera 4030, 4030a, or 4030b starts recording video in the start recording step 4325. Next, in the start sweeping step 4345, the stepper motor linear actuator 3740 or 3940 is started in order to move the light source 3701 of the Endoscope Shadow Caster Scanner 3700 or the slit 3925 of the Moving Slit Endoscope Shadow Caster Scanner 3900 in order to sweep edges of luminosity across the target. Next, frames of the recorded video are collected in the collect video step 4350. Next, whether the video buffer is filled enough to analyze is determined in the buffer decision step 4324. If the buffer is not filled enough, the collect video step 4350 is repeated, as described above. If the buffer is filled enough to analyze, the video frames are analyzed to build a point cloud in the analyze frames step 4344. Next, whether there are still enough frames in the buffer is determined in the still buffered decision step 4358. If there are not enough frames in the buffer, the buffer decision step 4324 is repeated, as described above. If there are still enough frames in the buffer, whether to finish sweeping is determined in the finish sweeping decision step 4378. If the sweeping is not finished, then the analyze frames step 4344 is repeated, as described above. If the sweeping is finished, then the stepper motor linear actuator 3740 or 3940 is stopped in the stop motor step 4368. Next, the endoscope camera 4030, 4030a, or 4030b stops recording video of the subject in the stop recording step 4365. Next, analyzing frames is finished in the finish analyzing frames step 4364. Next, the processor filters the point cloud in the filter point cloud step 4370. Next, in the construct surface step 4375, the processor constructs a model of a three-dimensional surface from the filtered point cloud. Next, the surface is saved to file in the save file step 4335. Next, the model is displayed on the display by the processor in the display image step 4355. Whether another scan is requested is determined in the another scan decision step 4330. If another scan is requested, the start recording step 4325 is repeated, as described above. Lastly, if another scan is not requested, then the user exits the algorithm in the exit algorithm step 4390. In FIG. 44, an endoscope sweep flow chart 4400 describes a shadow caster sweep of an Endoscope Shadow Caster Scanner 3700 and a Moving Slit Endoscope Shadow Caster Scanner 3900. First, stepper motor linear actuator 3740 or 3940 parameters are set in the set motor parameters step 4407. Next, in the begin sweeping step 4445, the light source 3701 begins sweeping by either moving the light source 3701 of the Endoscope Shadow Caster Scanner 3700 or the slit 3925 of the Moving Slit Endoscope Shadow Caster Scanner 3900. Next, the stepper motor linear actuator 3740 or 3940 position is determined in the get current motor position step 4447. Next, whether the light source reached the end of the sweep is determined in the end sweep decision step 4449. If the light source did not reach the end of the sweep, the get current motor position step 4447 is repeated, as described above. If the light source did reach the end of the sweep and another scan is necessary, the set motor parameters step 4407 is repeated in the reverse direction of the first scan in the repeat algorithm step 4494. In order to use said tapered fiber optic bundle 4060b, the proximal tapered fiber optic bundle 3720 and 3920 must taper to the same shape, e.g. half circle-to-round, as the distal tapered fiber optic bundle 4060b.

The construction details of the invention as shown in FIG. 37, FIG. 38, FIG. 39, FIG. 40, FIG. 41, FIG. 42, FIG. 43, and FIG. 44, are that an endoscope sleeve 4010, 4010a, or 4010b comprises a flexible material, such as plastic, silicone, metal, or the like. The tapered fiber optic bundle 4060a and 4060b comprises optic fibers, glass, plastic, composite material, or the like. The endoscope camera 4030, 4030a, or 4030b comprises a standard endoscope camera, or the like. The shadow caster 4020, 4020a, or 4020b comprises a strong rigid material, such as steel, copper cladding, plastic, high density plastic, silicone, PVC, fiberglass, carbon fiber, composite material, metal, galvanized steel, stainless steel, aluminum, brass, copper, wood, or other like material, and may further comprise configurable shapes, three-dimensionally-printed shapes, configurable opacity, such as liquid crystal, or the like, or various colored filters, or the like. The horizontal platform 3730 and 3930 comprises a strong rigid material, such as steel, copper cladding, plastic, high density plastic, silicone, PVC, fiberglass, carbon fiber, composite material, metal, galvanized steel, stainless steel, aluminum, brass, copper, wood, or other like material. The vertical stand 3705 and 3905 comprises a strong rigid material, such as steel, copper cladding, plastic, high density plastic, silicone, PVC, fiberglass, carbon fiber, composite material, metal, galvanized steel, stainless steel, aluminum, brass, copper, wood, or other like material. The stepper motor linear actuator 3740 and 3940 comprises a linear stepper motor, an electric motor, a hydraulic system, or the like. The translating platform 3715 comprises a strong rigid material, such as steel, copper cladding, plastic, high density plastic, silicone, PVC, fiberglass, carbon fiber, composite material, metal, galvanized steel, stainless steel, aluminum, brass, copper, wood, or other like material. The light source 3701 comprises an incandescent light, a halogen light, fluorescent light, a linear light, a slitted tube light, an LED, an array of LEDs, a linear array of LEDs, different colored light sources, colored LEDs, lasers, an X-ray source, a UV source, an infrared source, or the like. The cylindrical lens 3760 comprises an optical material, such as glass, acrylic, ceramic, or the like. The optic fiber bundle 3710 and 3910 comprises an optical material, such as glass, acrylic, ceramic, or the like. The square-to-round taper 3720 and 3920 comprises glass, plastic, or the like. The slit 3725 comprises an opaque material such as steel, copper cladding, plastic, high density plastic, opaque paint, silicone, PVC, fiberglass, carbon fiber, composite material, metal, galvanized steel, stainless steel, aluminum, brass, copper, wood, or other like material. The memory stored in non-transitory computer-readable medium comprises software, instructions, data, algorithms, or the like. The processor comprises a computer, a mobile phone, a PC, a CPU, or the like. The display comprises a monitor, a screen, a television, an augmented reality headset, a microscope, or the like. The supporting platform 3915 comprises a strong rigid material, such as steel, copper cladding, plastic, high density plastic, silicone, PVC, fiberglass, carbon fiber, composite material, metal, galvanized steel, stainless steel, aluminum, brass, copper, wood, or other like material. The slit 3925 comprises an opaque material such as steel, copper cladding, plastic, high density plastic, opaque paint, silicone, PVC, fiberglass, carbon fiber, composite material, metal, galvanized steel, stainless steel, aluminum, brass, copper, wood, or other like material.

Figure 45:
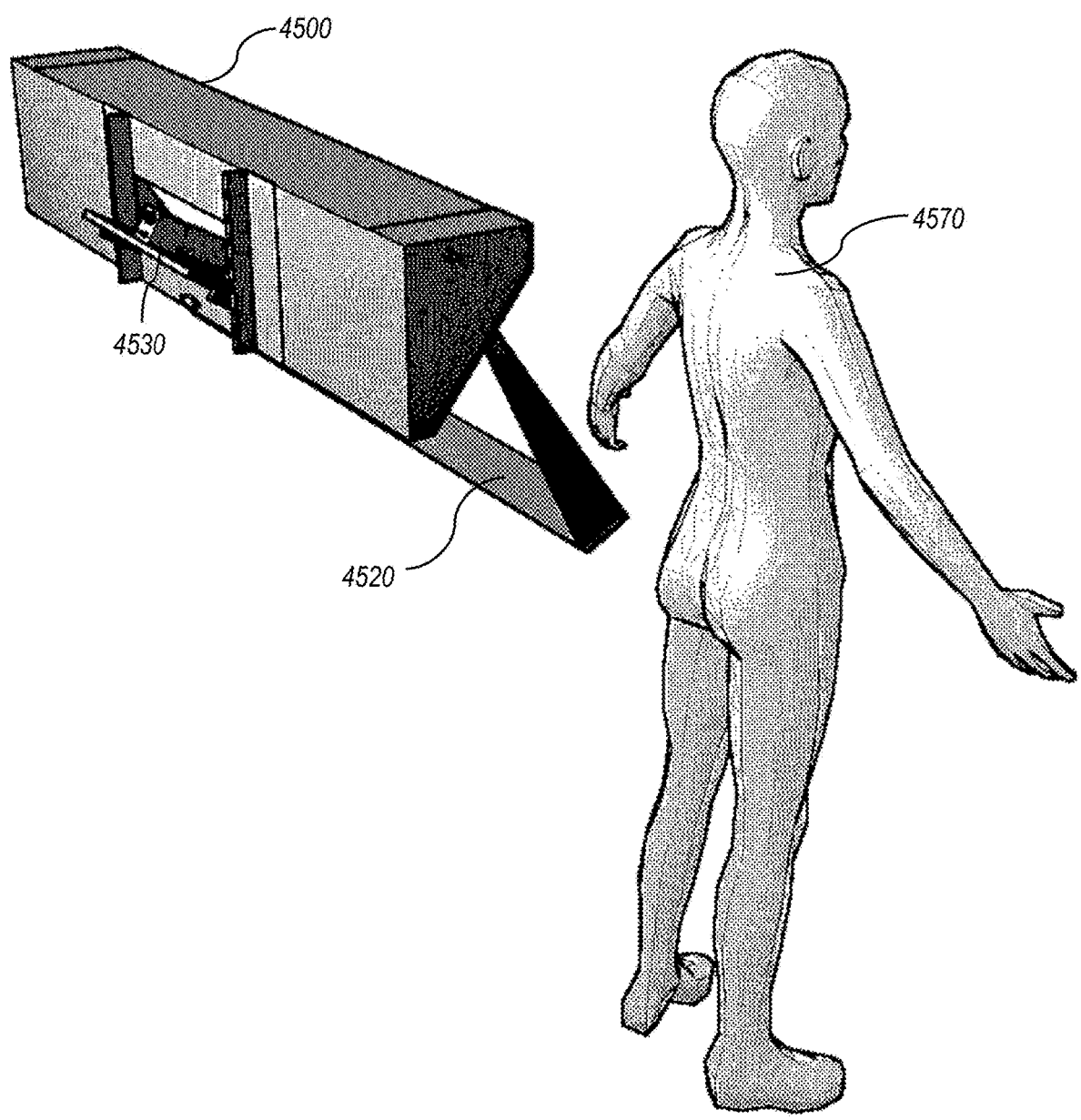
FIG. 45 is a front perspective view of an apparatus of the present invention scanning a person, according to various embodiments.
Figure 46:
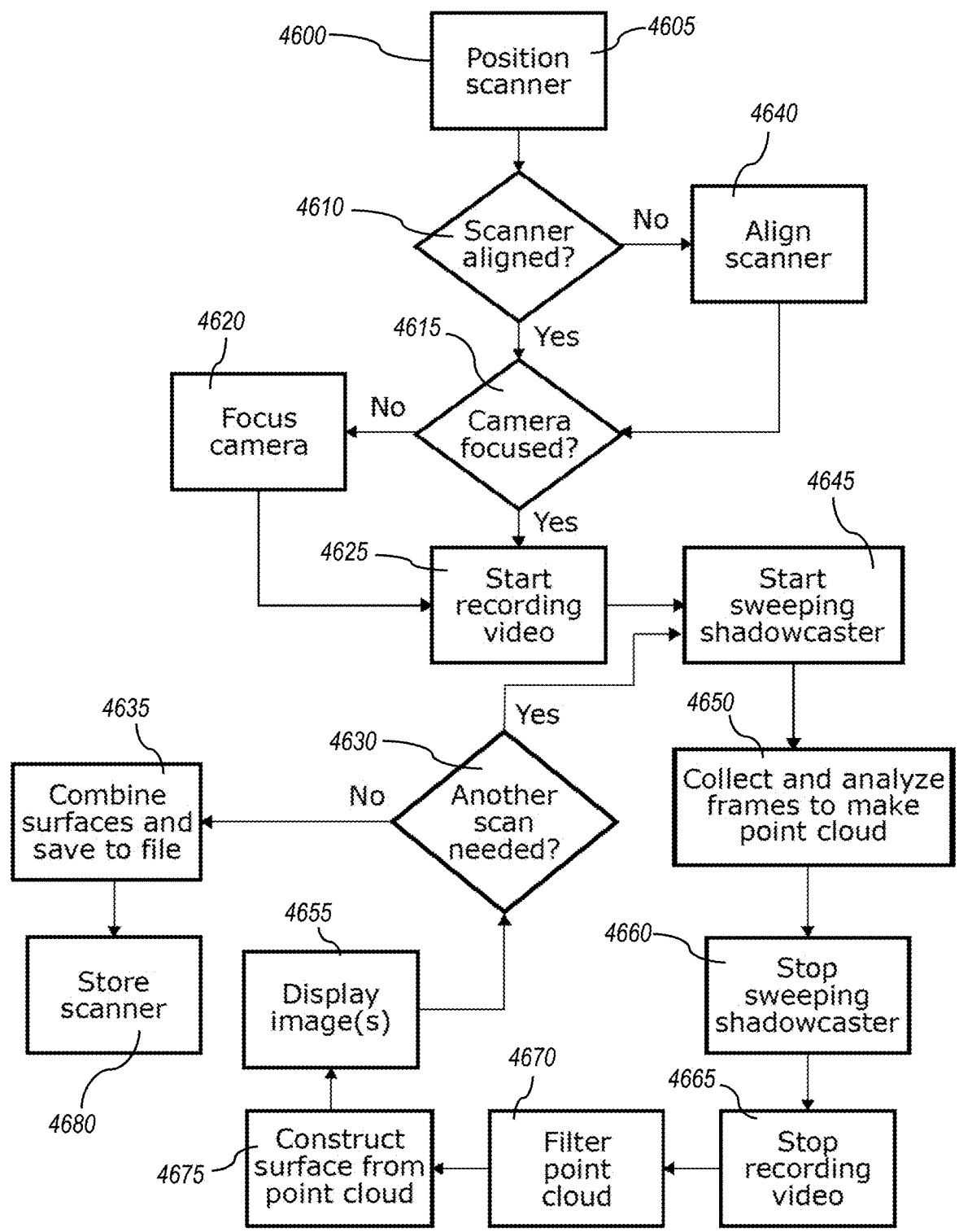
FIG. 46 illustrates a flow chart describing the operation of an apparatus of FIG. 45, according to some examples.

Referring now to another embodiment of the invention, in FIG. 45 and FIG. 46, a Whole Person Shadow Scanner 4500 is shown. FIG. 45 is a front perspective view of an Whole Person Shadow Scanner 4500 scanning a whole person 4570. FIG. 46 shows an whole person operation flow chart 4600 describing the operation of a Whole Person Shadow Scanner 4500.

In further detail, still referring to the invention of FIG. 45 and FIG. 46, the Whole Person Shadow Scanner 4500 is similar in construction to the Shadow Caster Scanner 2400; however, it is scaled and adapted to be able to scan the surface of a whole person 4570, and may be mounted above the whole person 4570, such as on the ceiling of a room. The Whole Person Shadow Scanner 4500 uses a whole person shadow caster 4520 to project edges of luminosity on a whole person 4570 and record the edges of luminosity using a whole person camera 4530. The Whole Person Shadow Scanner 4500 is used for scanning skin or performing dermatological exams and is capable of mapping features on the skin of the whole person 4570, such as moles, freckles, skin lesions, skin cancer, warts, growths, defects, wounds, or the like. Optionally, a person may be placed very close to the Whole Person Shadow Scanner 4500 and/or a smaller embodiment of a like scanner, for higher resolution scans over a smaller region of interest, in order to concentrate on the three-dimensional shape of a single mole, for example. Scans performed at different times may also provide a record of changes in the whole person's 4570 skin, for example, a record of new moles or changing features may be established. Further, use with colored filters may identify different tissues during the scan, such as identifying tumors or cancerous regions. In FIG. 46, the whole person operation flow chart 4600 describes the operation of a Whole Person Shadow Scanner 4500 being used. The first step in the operation of the Whole Person Shadow Scanner 4500 comprises positioned the Whole Person Shadow Scanner 4500 over the whole person 4570, or positioning the whole person 4570 under the Whole Person Shadow Scanner 4500, in the position scanner step 4605. Next, in the alignment decision step 4610, whether the Whole Person Shadow Scanner 4500 is aligned with the subject, which in this case is a whole person 4570, is determined. If the scanner is not aligned, the scanner is then aligned with the subject in the align scanner step 4640. Once the scanner is aligned, whether the camera is focused on the subject is determined in the focus decision step 4615. If the camera is not focused, the camera is then focused in the focus camera step 4620. Once the camera is focused, the camera starts recording video of the subject in the start recording step 4625. Next, in the start sweeping step 4645, the shadow caster begins to sweep edges of luminosity across the subject. Next, frames of the recorded video are collected and analyzed by the processor to make a point cloud in the collect and analyze step 4650. Next, in the stop sweeping step 4660, the shadow caster 4520 stops sweeping the edges of luminosity across the subject. Next, the camera stops recording video of the subject in the stop recording step 4665. Next, the processor filters the point cloud in the filter point cloud step 4670. Next, in the construct surface step 4675, the processor constructs a model of a three-dimensional surface from the filtered point cloud. Next, the model is displayed on the display by the processor in the display image step 4655. Whether another scan is needed is determined in the another scan decision step 4630. If another scan is needed, the start sweeping step 4645 is repeated, as described above. If another scan is not needed, the surfaces are combined and saved to file in the save file step 4635. Lastly, the Whole Person Shadow Scanner 4500 is stored after operation in the store scanner step 4680.

The construction details of the invention as shown in FIG. 45 and FIG. 46 are substantially the same as those of the invention as shown in FIG. 37, FIG. 38, FIG. 39, FIG. 40, FIG. 41, FIG. 42, FIG. 43, and FIG. 44.

Figure 47:
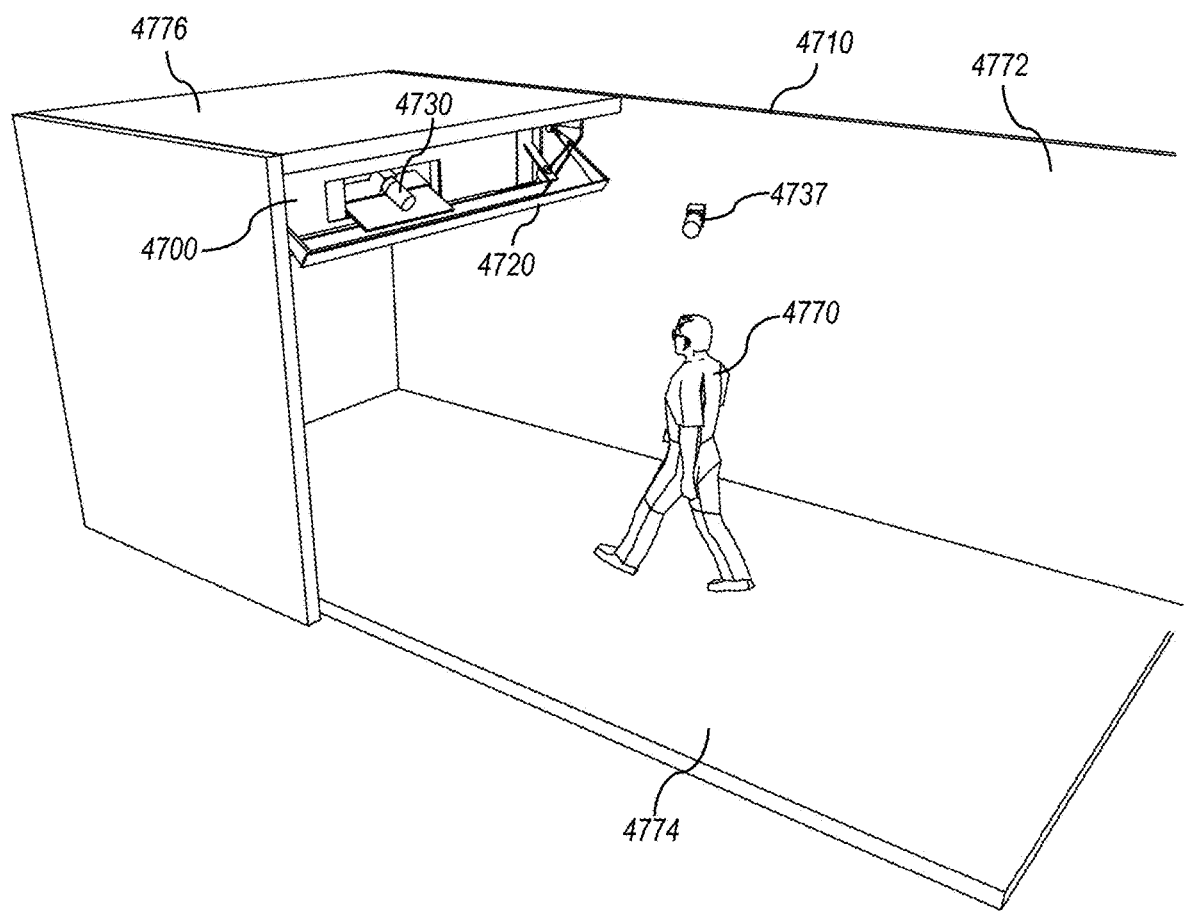
FIG. 47 is a front perspective view of another apparatus of the present invention scanning a walking person, according to various embodiments.
Figure 48:
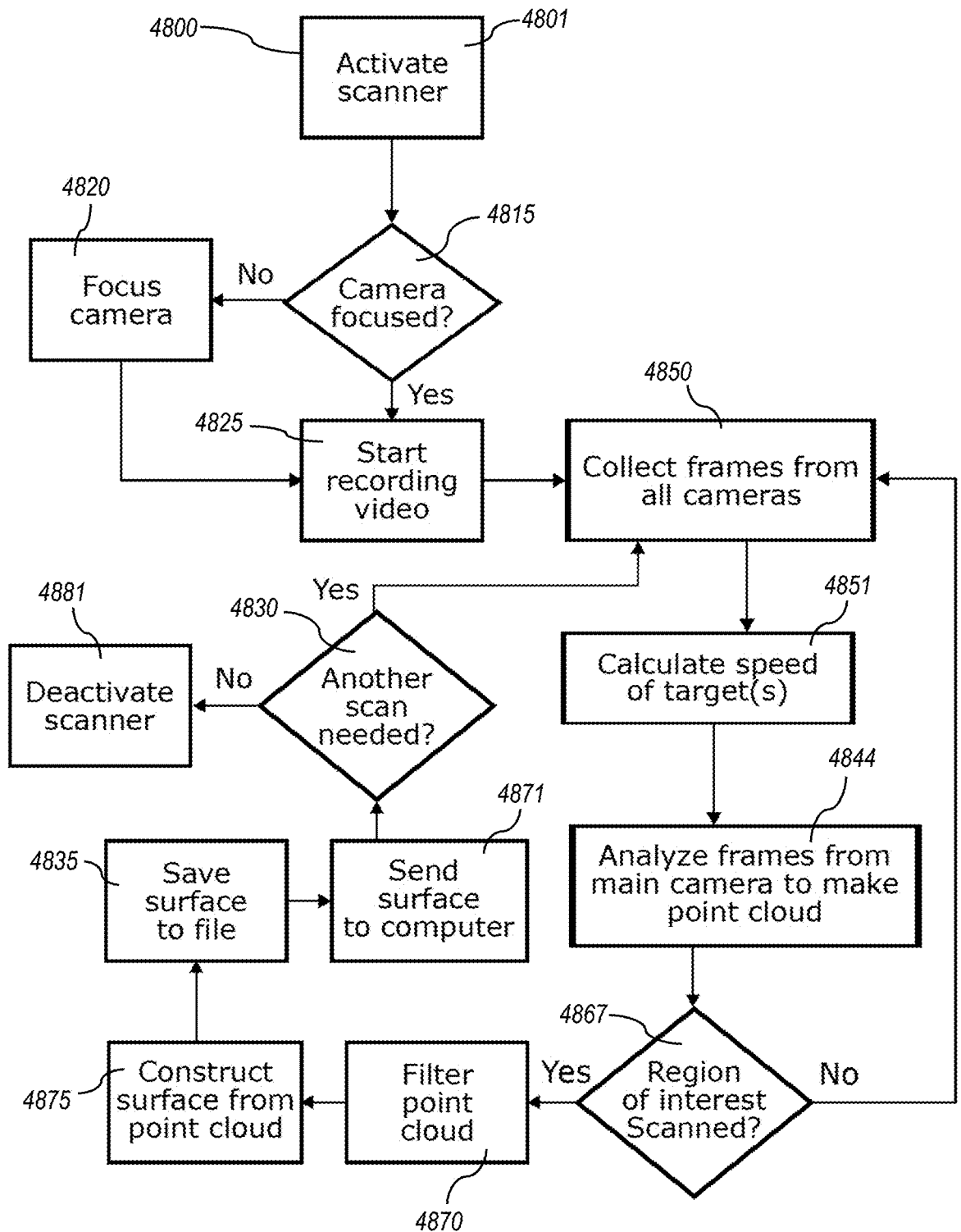
FIG. 48 is a flow chart describing the operation of an apparatus of FIG. 47, according to some examples.

Referring now to another embodiment of the invention, in FIG. 47 and FIG. 48, a Security Shadow Scanner 4700 is shown. FIG. 47 is a front perspective view of a Security Shadow Scanner 4700 scanning a walking person 4770. FIG. 46 depicts an security scanner operation flow chart 4800 describing the operation of a Security Shadow Scanner 4700.

In further detail, still referring to the invention of FIG. 47 and FIG. 48, the Security Shadow Scanner 4700 is similar in construction to the Shadow Caster Scanner 2400; however, it may use the motion of the walking person 4770 to sweep the edges of luminosity and may further comprises one or more additional cameras 4737, which may be mounted on a wall 4772, in order to measure the velocity of the walking person 4770. The Security Shadow Scanner 4700 is scaled and adapted to be able to scan the surface of a walking person 4770, and may be mounted above the walking person 4770, such as on the ceiling 4776 of a room 4710. Other versions may mount the light source in the ceiling of a room. The Security Shadow Scanner 4700 uses a stationary shadow caster 4720 to project edges of luminosity on a walking person 4770 and record the edges of luminosity using a security camera 4730 and, optionally, an additional camera 4737. The additional camera 4737 (and, in fact, both security camera 4730 and additional camera 4737) can detect not only edges of luminosity, but the object itself to help determine the velocity of the object. The Security Shadow Scanner 4700 is used for scanning persons for security risks and may be placed at the entry to a building or at the entry port to a secured area. Further, use with colored filters may identify different features during the scan, such as identifying weapons or contraband. In FIG. 48, the security scanner operation flow chart 4800 describes the operation of a Security Shadow Scanner 4700 being used. The first step in the operation of the Security Shadow Scanner 4700 comprises activating the Security Shadow Scanner 4700 in the activate scanner step 4801. Next, whether the security camera 4730 and, optionally, the additional camera 4737, are focused on the subject is determined in the focus decision step 4815. If the security camera 4730 and, optionally, the additional camera 4737, are not focused, the security camera 4730 and, optionally, the additional camera 4737, are then focused in the focus camera step 4820. Once the security camera 4730 and, optionally, the additional camera 4737, are focused, the security camera 4730 and, optionally, the additional camera 4737, start recording video of the subject as the walking person 4770 walking across the views of the security camera 4730 and, optionally, the additional camera 4737, in the start recording step 4825. Next, frames of the recorded video are collected by the processor in the collect frames step 4850. Next, the speed of the subject, in this case a walking person 4770, is calculated by the processor in the calculate speed step 4851. Next, frames from the security camera 4730 are analyzed using the processor to make a point cloud in the analyze frames step 4844. Next, whether the entire region of interest has been scanned is determined in the entire scan decision step 4867. If the entire region of interest has not been scanned, then repeat the collect frames step 4850, as described above. If the entire region of interest has been scanned, then the processor filters the point cloud in the filter point cloud step 4870. Next, in the construct surface step 4875, the processor constructs a model of a three-dimensional surface from the filtered point cloud. Next, the surface is saved to file in the save file step 4835. Next, the surface is sent to the processor for display in the send surface step 4871. Whether another scan is needed is determined in the another scan decision step 4830. If another scan is needed, the collect frames step 4850 is repeated, as described above. Lastly, if another scan is not needed, the scanner is deactivated in the deactivate scanner step 4881.

The construction details of the invention as shown FIG. 47 and FIG. 48 are substantially the same as those of the invention as shown in FIG. 37, FIG. 38, FIG. 39, FIG. 40, FIG. 41, FIG. 42, FIG. 43, and FIG. 44.

Figure 49:
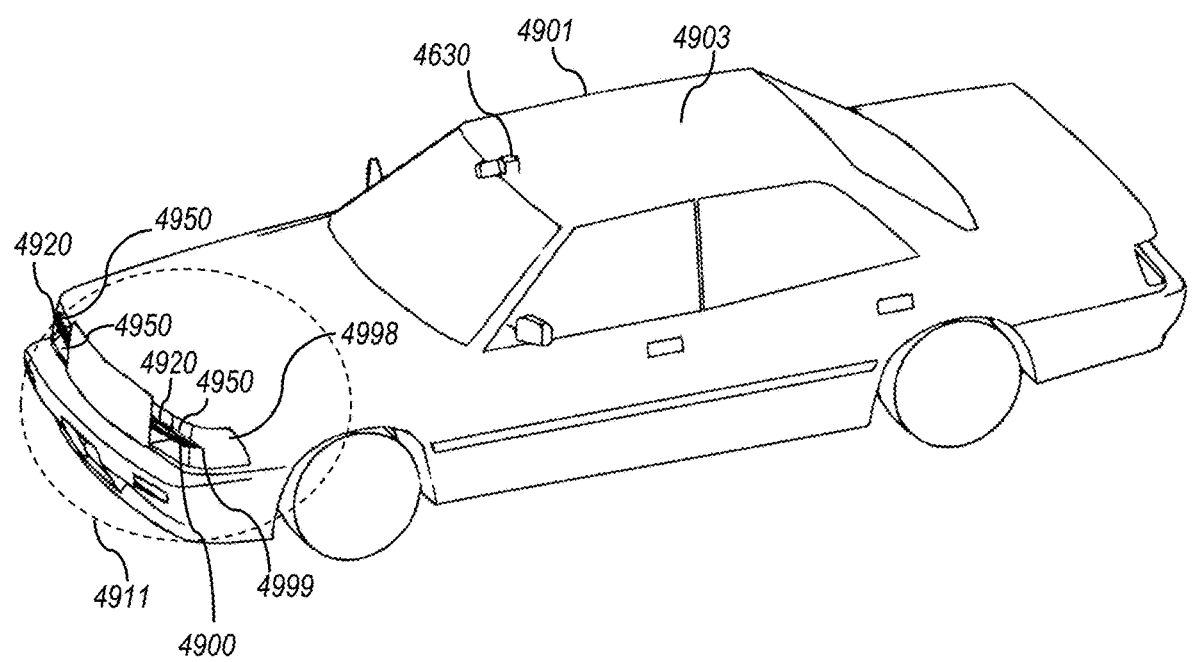
FIG. 49 shows a front perspective view of another apparatus of the present invention incorporated into an automobile, according to various embodiments.
Figure 50:
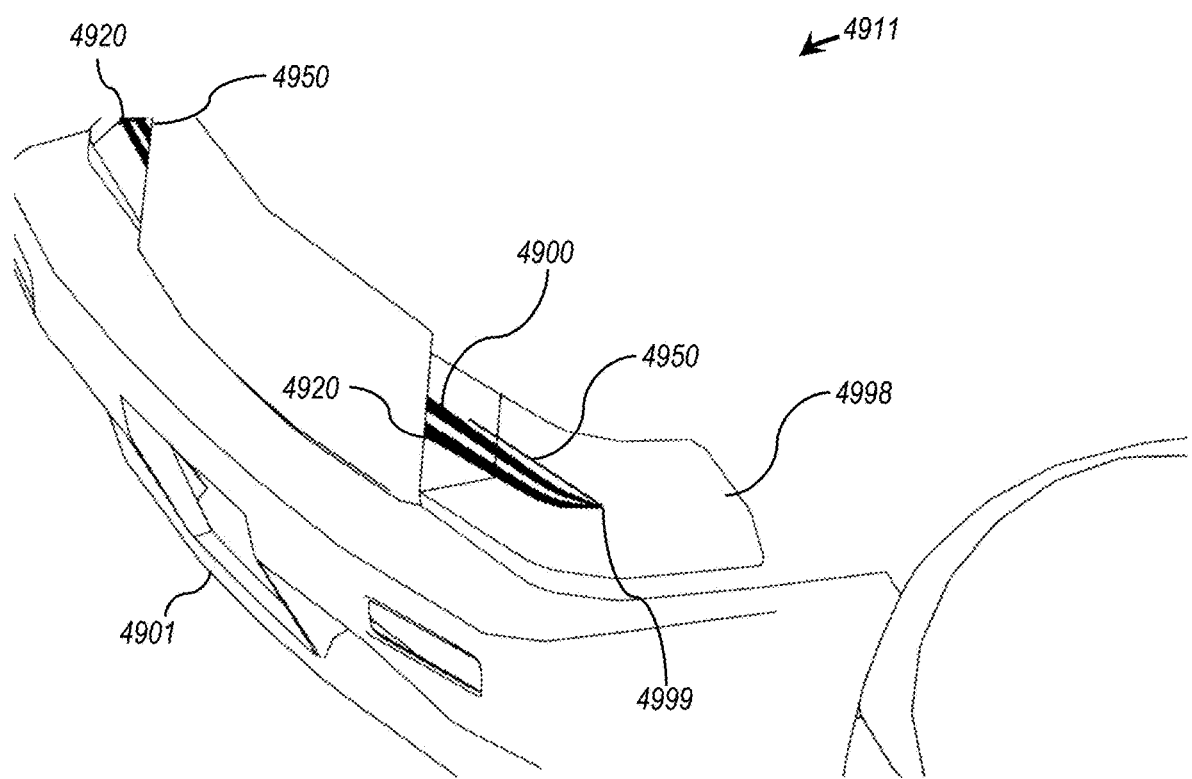
FIG. 50 is a close-up view of the apparatus of FIG. 49, according to some examples.
Figure 51:
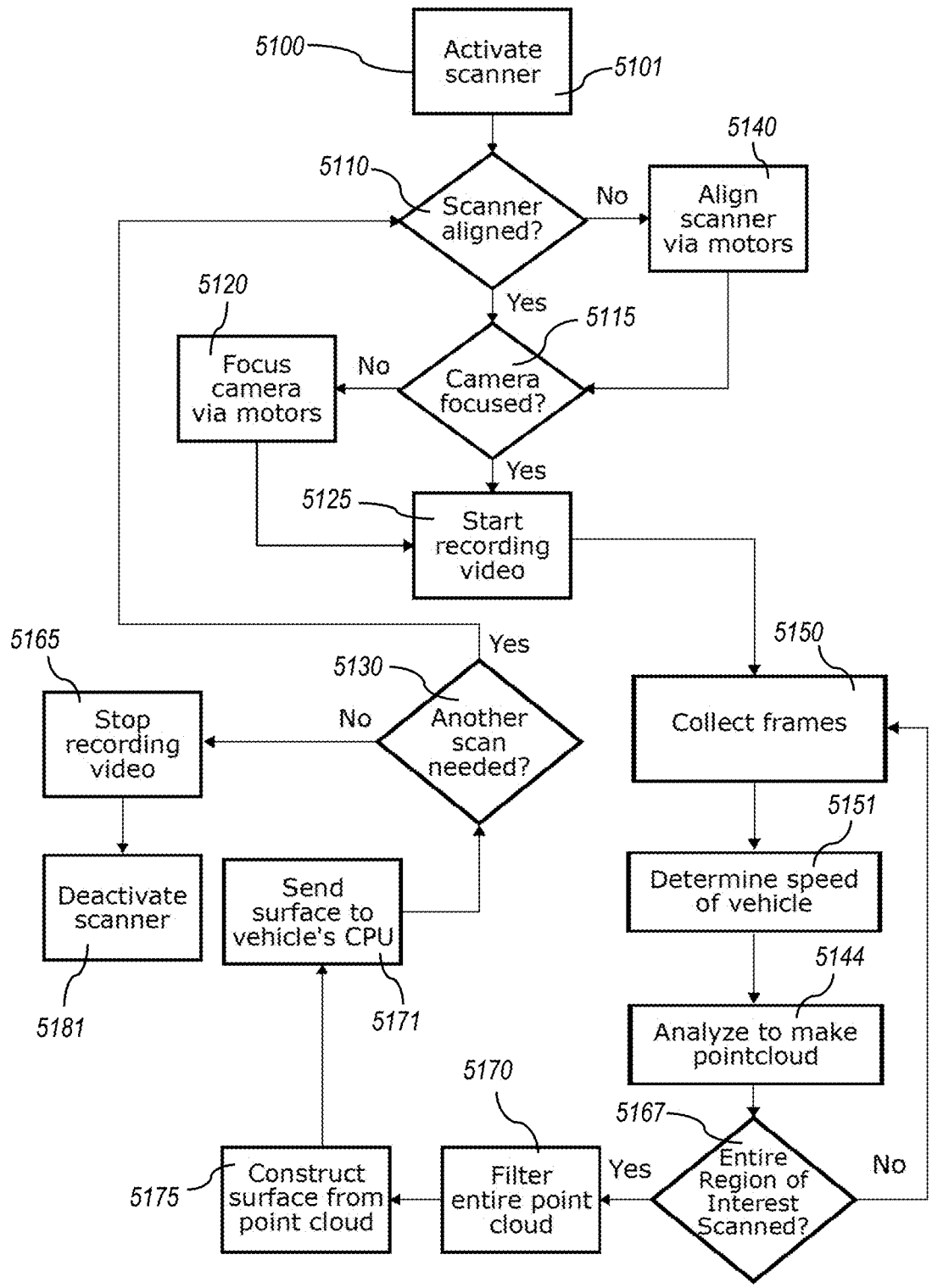
FIG. 51 displays a flow chart describing the operation of an apparatus of FIG. 49, according to some examples.
Figure 52:
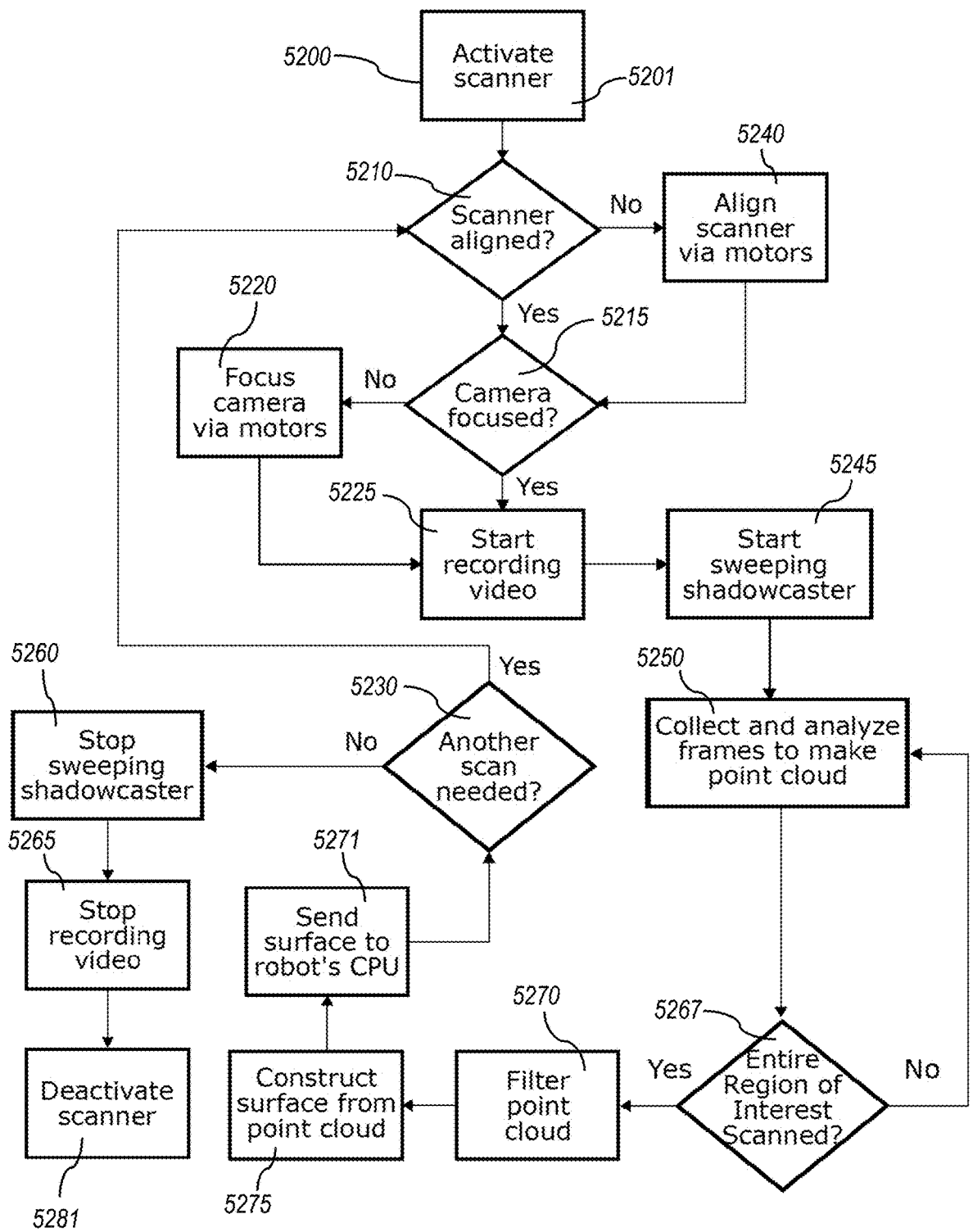
FIG. 52 illustrates a flow chart describing the operation of an apparatus of the present invention incorporated into a robot, according to various embodiments.
Figure 53:
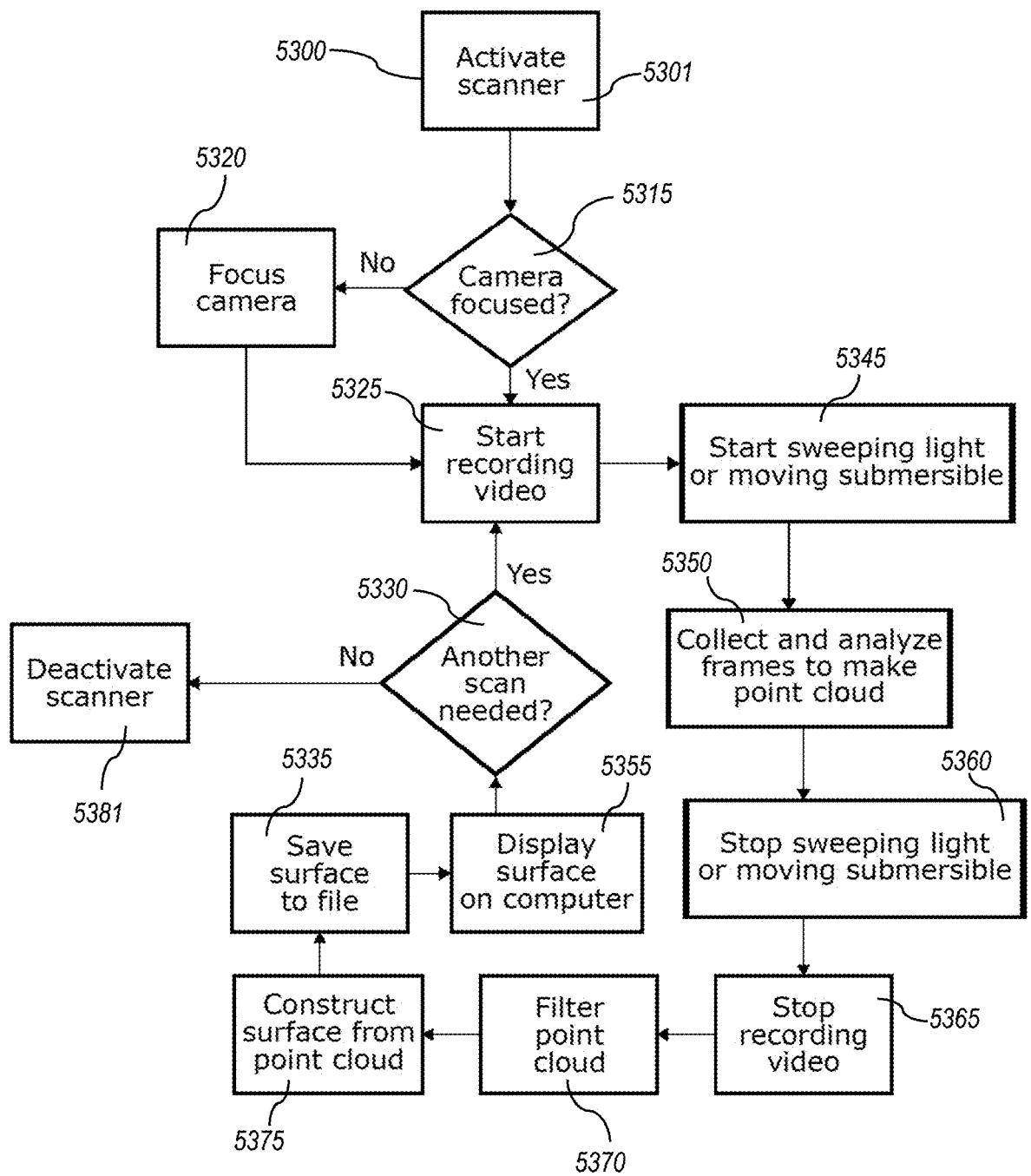
FIG. 53 is a flow chart describing the operation of an apparatus of the present invention incorporated into a submersible, according to various embodiments.

Referring now to another embodiment of the invention, in FIG. 49, FIG. 50, FIG. 51, FIG. 52, and FIG. 53, a Vision Shadow Scanner 4900 is shown. FIG. 49 shows a front perspective view of a Vision Shadow Scanner 4900 incorporated into a vehicle, which is an automobile 4901. FIG. 50 is a close-up view of the indicated area 4911 of FIG. 49. FIG. 51 displays a vision scanner operation flow chart 5100, which describes the operation of a Vision Shadow Scanner 4900 that is incorporated into a vehicle. FIG. 52 illustrates a robot vision scanner operation flow chart 5200, which describes the operation of a Vision Shadow Scanner 4900 that is incorporated into a robot. FIG. 53 is a submersible vision scanner operation flow chart 5300, which describes the operation of a Vision Shadow Scanner 4900 that is incorporated into a submersible.

In further detail, still referring to the invention of FIG. 49, FIG. 50, FIG. 51, FIG. 52, and FIG. 53, in FIG. 49 and FIG. 50, a Vision Shadow Scanner 4900 uses the motion of a moving vehicle to sweep edges of luminosity across the surrounding of the vehicle in order to generate three-dimensional models of the surroundings and comprises shadow casters 4920, which comprise an apex 4999, mounted over a light source 4950, which depends from said apex 4999, over the headlights 4998 of an automobile 4901 or placed inside of an automobile 4901 with the light source 4950 consistent with those described in FIG. 14, a camera 4930 mounted on the roof 4903 of the automobile 4901, and a processor (not shown). In FIG. 51, the vision scanner operation flow chart 5100 describes the operation of a Vision Shadow Scanner 4900 that is incorporated into a vehicle. The first step in the operation of the Vision Shadow Scanner 4900 comprises activating the Vision Shadow Scanner 4900 in the activate scanner step 5101. Next, in the alignment decision step 5110, whether the Vision Shadow Scanner 4900 is aligned is determined. If the Vision Shadow Scanner 4900 is not aligned, the Vision Shadow Scanner 4900 is then aligned using motors in the align scanner step 5140. Once the Vision Shadow Scanner 4900 is aligned, whether the camera 4930 is focused is determined in the focus decision step 5115. If the camera 4930 is not focused, then the camera 4930 is focused using motors in the focus camera step 5120. Once the camera 4930 is focused, the camera 4930 starts recording video of the surroundings of the vehicle, in the start recording step 5125. Next, frames of the recorded video are collected by the processor in the collect frames step 5150. Next, the speed of the vehicle is determined by the processor in the determine speed step 5151. Next, frames from the camera 4930 are analyzed using the processor to make a point cloud in the analyze frames step 5144. Next, whether the entire region of interest has been scanned is determined in the entire scan decision step 5167. If the entire region of interest has not been scanned, then repeat the collect frames step 5150, as described above. If the entire region of interest has been scanned, then the processor filters the entire point cloud in the filter point cloud step 5170. Next, in the construct surface step 5175, the processor constructs a three-dimensional model of the surrounding of the vehicle from the filtered point cloud. Next, the surface is sent to the processor in the send surface step 5171. Next, whether another scan is needed is determined in the another scan decision step 5130. If another scan is needed, the alignment decision step 5110 is repeated, as described above. Next, if another scan is not needed, the camera 4930 stops recording video of the surroundings of the vehicle in the stop recording step 5165. Lastly, the scanner is deactivated in the deactivate scanner step 5181. In FIG. 52, the robot vision scanner operation flow chart 5200 describes the operation of a shadow caster scanner that is incorporated into a robot, which differs from the Vision Shadow Scanner 4900 by actively scanning the surroundings of the robot instead of relying on the speed of the vehicle to sweep the edges of luminosity across the surroundings. The first step in the operation of the scanner, which is incorporated into a robot, comprises activating the scanner in the activate scanner step 5201. Next, in the alignment decision step 5210, whether the scanner is aligned is determined. If the scanner is not aligned, the scanner is then aligned using robotically-controlled motors in the align scanner step 5240. Once the scanner is aligned, whether the camera is focused is determined in the focus decision step 5215. If the camera is not focused, then the camera is focused using robotically-controlled motors in the focus camera step 5220. Once the camera is focused, the camera starts recording video of the surroundings of the robot, in the start recording step 5225. Next, in the start sweeping step 5245, the shadow caster begins to sweep edges of luminosity across the surroundings of the robot. Next, frames of the recorded video are collected and analyzed by the processor to make a point cloud in the collect and analyze frames step 5250. Next, whether the entire region of interest has been scanned is determined in the entire scan decision step 5267. If the entire region of interest has not been scanned, then repeat the collect and analyze frames step 5250, as described above. If the entire region of interest has been scanned, then the processor filters the point cloud in the filter point cloud step 5270. Next, in the construct surface step 5275, the processor constructs a three-dimensional model of the surrounding of the robot from the filtered point cloud. Next, the surface is sent to the robot's processor in the send surface step 5271. Next, whether another scan is needed is determined in the another scan decision step 5230. If another scan is needed, the alignment decision step 5210 is repeated, as described above. Next, if another scan is not needed, the shadow caster stops sweeping the edges of luminosity across the surroundings of the robot in the stop sweeping step 5260. Next, the camera stops recording video of the surroundings of the robot in the stop recording step 5265. Lastly, the scanner is deactivated in the deactivate scanner step 5281. In FIG. 53, the submersible vision scanner operation flow chart 5300 describes the operation of a shadow caster scanner that is incorporated into an underwater submersible. The first step in the operation of the scanner, which is incorporated into a submersible, comprises activating the scanner in the activate scanner step 5301. Next, whether the camera is focused is determined in the focus decision step 5315. If the camera is not focused, then the camera is focused in the focus camera step 5320. Once the camera is focused, the camera starts recording video of the surroundings of the submersible, in the start recording step 5325. Next, in the start sweeping step 5345, the light or moving submersible begins to sweep edges of luminosity across the surroundings of the submersible. Next, frames of the recorded video are collected and analyzed by the processor to make a point cloud in the collect and analyze frames step 5350. Next, the light stops sweeping, or the submersible stops moving, so that the edges of luminosity stop sweeping across the surroundings of the submersible in the stop sweeping step 5360. Next, the processor filters the point cloud in the filter point cloud step 5370. Next, in the construct surface step 5375, the processor constructs a three-dimensional model of the surrounding of the submersible from the filtered point cloud. Next, the surface is saved to file in the save surface step 5335. Next, the surface is displayed on the display by the processor in the display image step 5355. Next, whether another scan is needed is determined in the another scan decision step 5330. If another scan is needed, the start recording step 5325 is repeated, as described above. Lastly, if another scan is not needed, the scanner is deactivated in the deactivate scanner step 5381.

The construction details of the invention as shown FIG. 49, FIG. 50, FIG. 51, FIG. 52, and FIG. 53, are that the shadow casters 4920 comprises a strong rigid material, such as steel, copper cladding, plastic, high density plastic, silicone, PVC, fiberglass, carbon fiber, composite material, metal, galvanized steel, stainless steel, aluminum, brass, copper, wood, or other like material, and may further comprise configurable shapes, three-dimensionally-printed shapes, configurable opacity, such as liquid crystal, or the like, or various colored filters, or the like. The headlights 4998 comprise standard headlights or custom headlights, or the like. The light sources 4950 comprise a linear light or point source, or the like. The automobile 4901 comprises a standard automobile, an autonomous automobile, a remote controlled automobile, a robot, a submersible, or the like. The camera 4930 comprises a digital or analog video camera, or the like.

Figure 54:
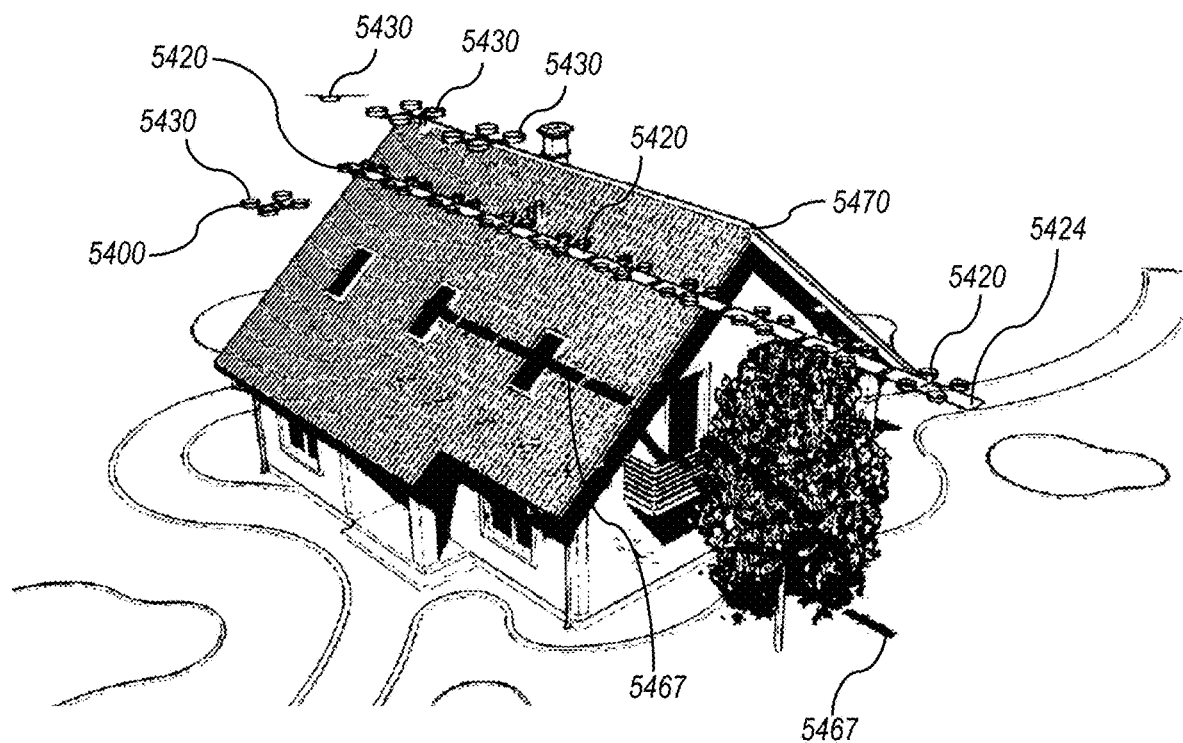
FIG. 54 demonstrates a front perspective view of a system of the present invention, which uses drones, according to various embodiments.
Figure 55:
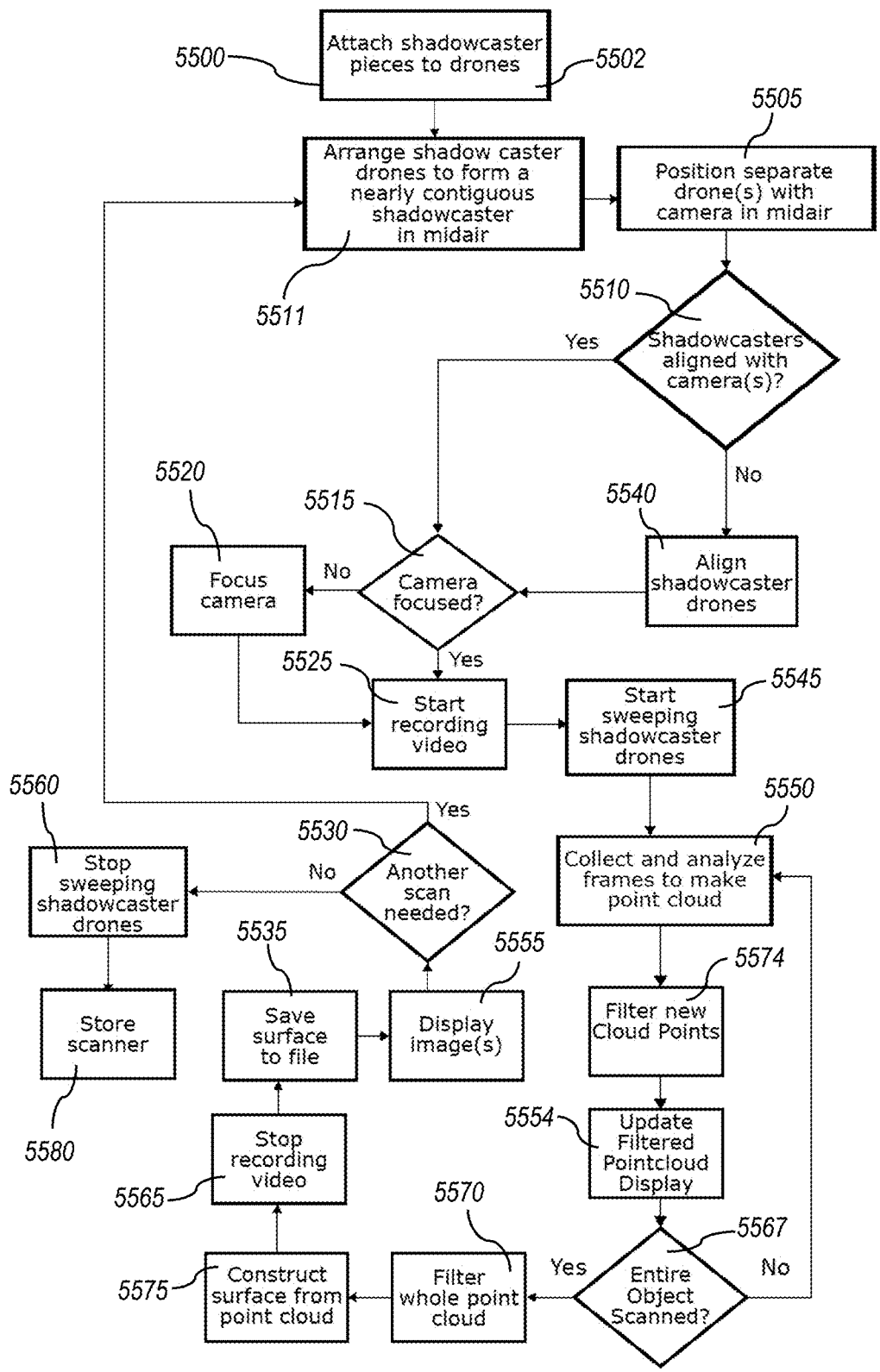
FIG. 55 is a flow chart describing the operation of a system of FIG. 54, according to some examples.
Figure 56:
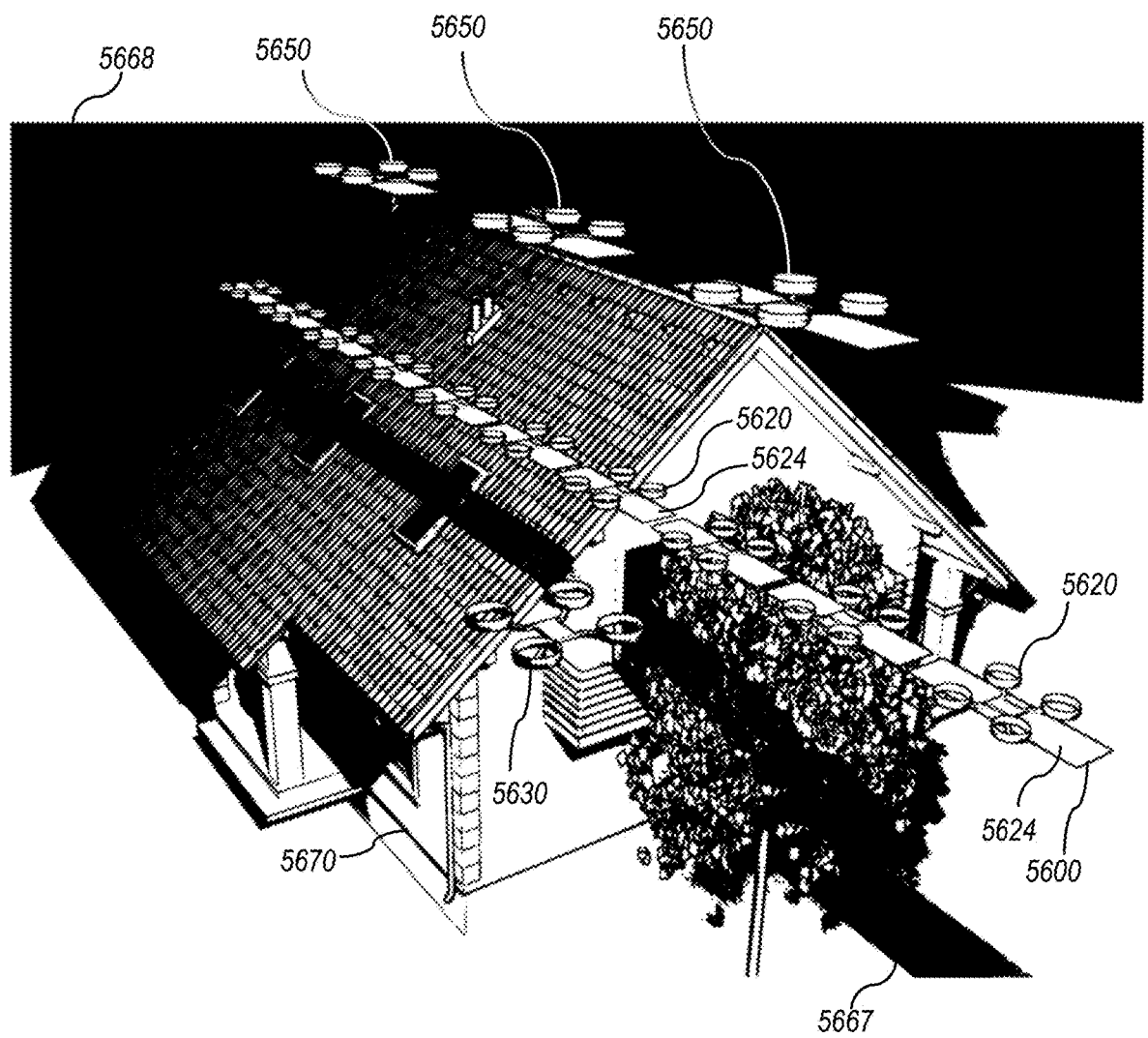
FIG. 56 is a front perspective view of another system of the present invention, which uses drones, according to various embodiments.
Figure 57:
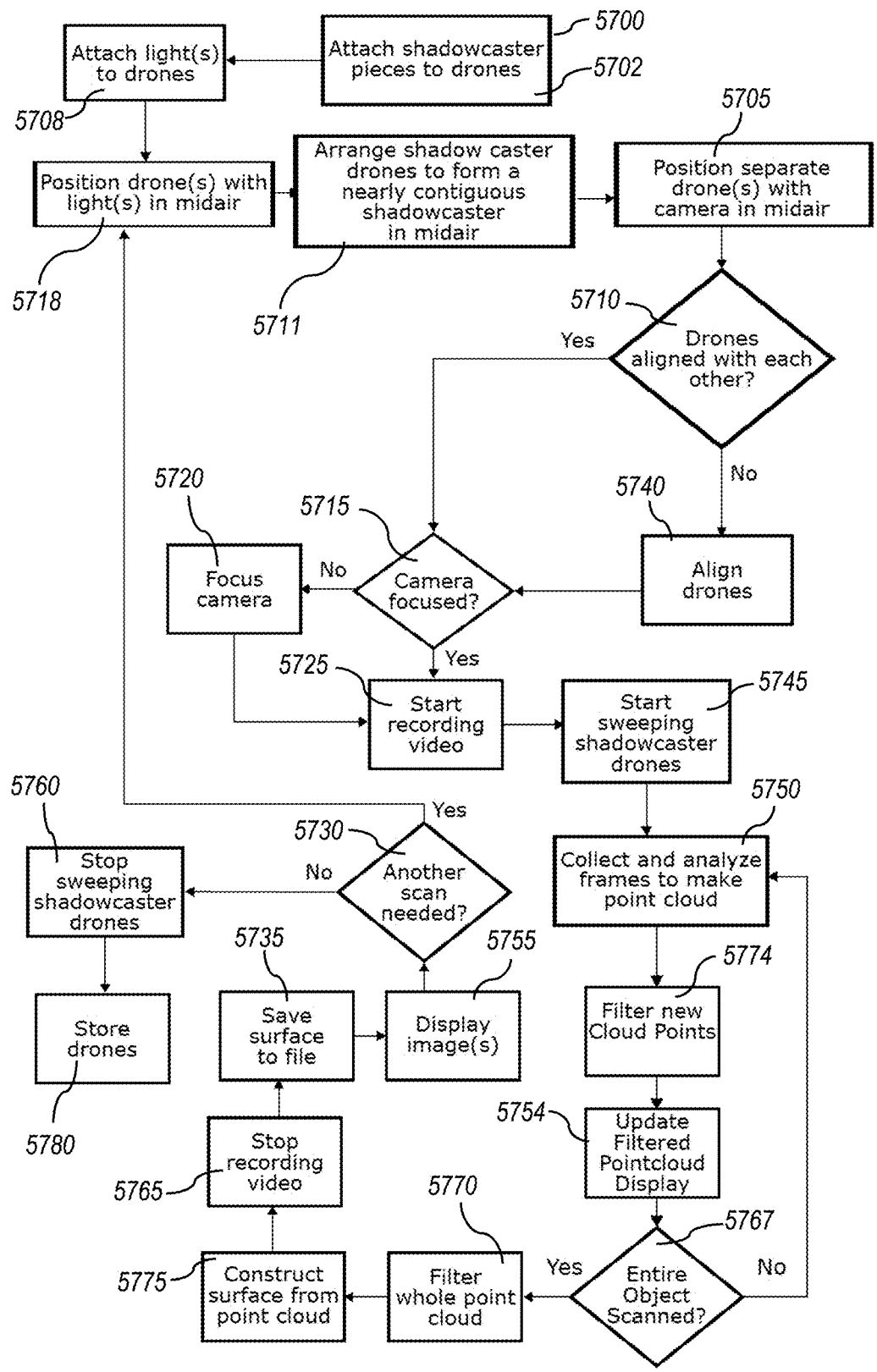
FIG. 57 shows is a flow chart, which describes the operation of a system of FIG. 56, according to some examples.
Figure 58:
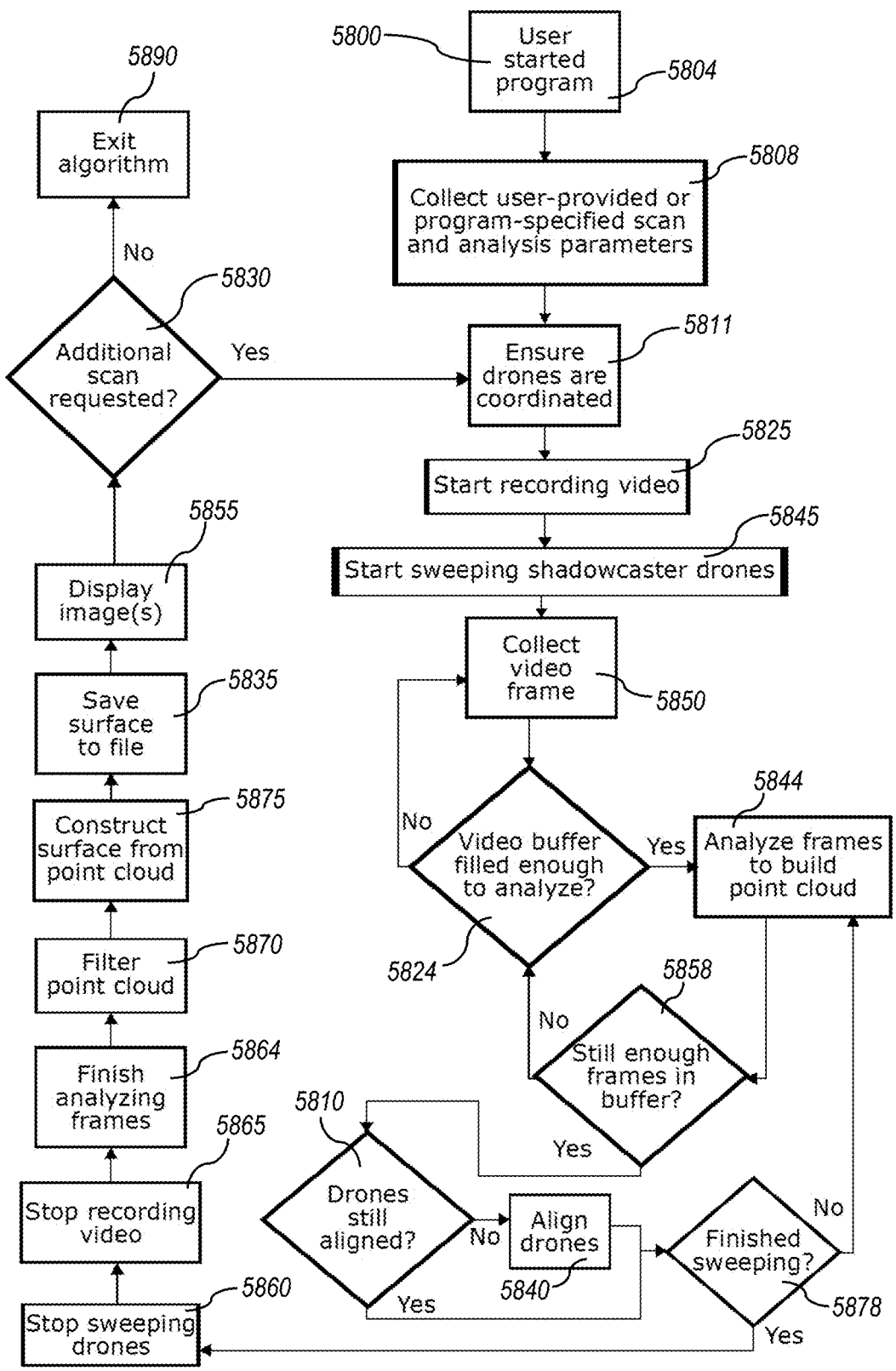
FIG. 58 depicts a flow chart describing the algorithm used by the systems of the present invention, which use drones, according to various embodiments.
Figure 59:
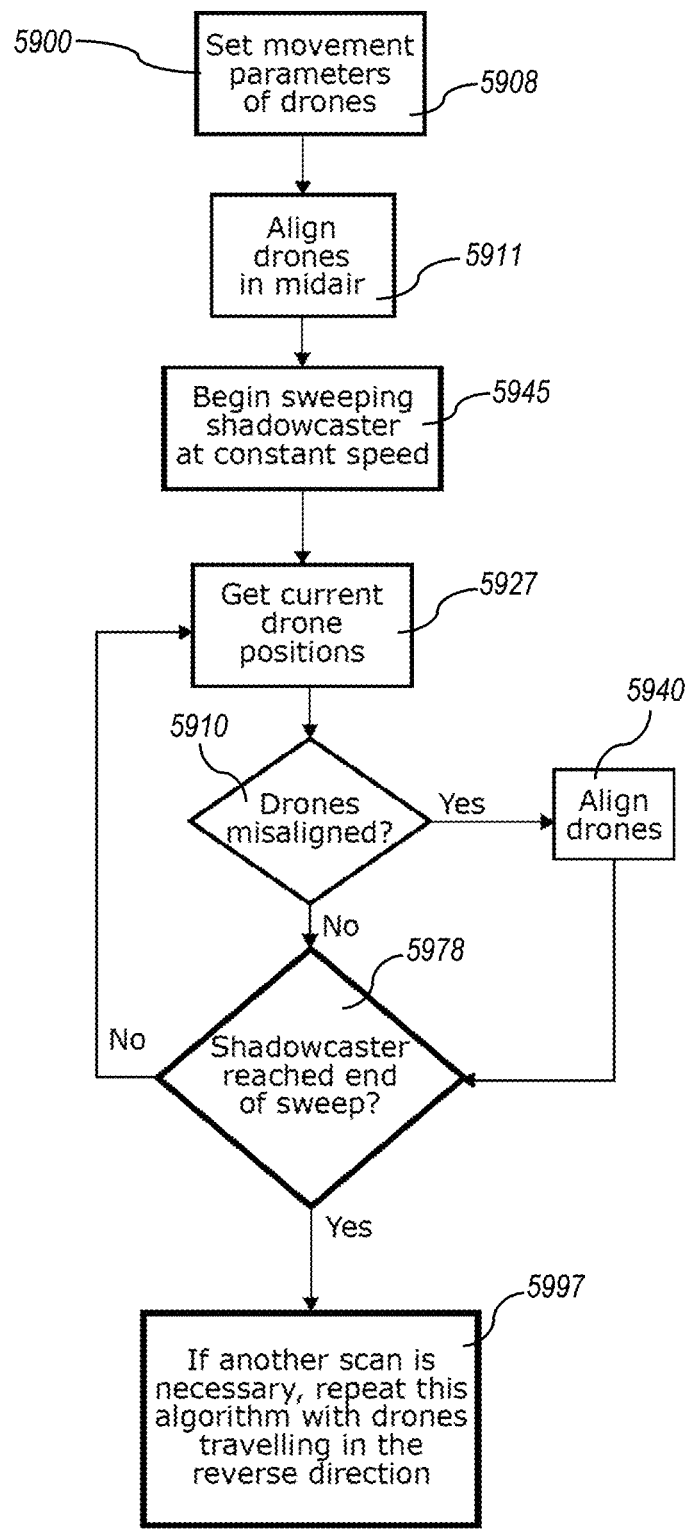
FIG. 59 is a flow chart, which describes a shadow caster sweep of systems of the present invention, which use drones, according to various embodiments.

Referring now to another embodiment of the invention, in FIG. 54, FIG. 55, FIG. 56, FIG. 57, FIG. 58, and FIG. 59, systems of the present invention, which use drones to scan large areas with shadow casters, are shown. FIG. 54 demonstrates a front perspective view of a Sun Drone Shadow Caster Scanner System 5400, which uses drones and the light of the sun to scan a house 5470. FIG. 55 is a sun drone operation flow chart 5500, which describes the operation of a Sun Drone Shadow Caster Scanner System 5400. FIG. 56 is a front perspective view of a Drone Shadow Caster Scanner System 5600, which uses drones with light sources to scan an area. FIG. 57 shows is a drone operation flow chart 5700, which describes the operation of a Drone Shadow Caster Scanner System 5600. FIG. 58 depicts a drone algorithm flow chart 5800, which describes the algorithm used by the Sun Drone Shadow Caster Scanner System 5400 and the Drone Shadow Caster Scanner System 5600. FIG. 59 is a drone sweep flow chart 5900, which describes a shadow caster sweep used by the Sun Drone Shadow Caster Scanner System 5400 and the Drone Shadow Caster Scanner System 5600.

In further detail, still referring to the invention of FIG. 54, FIG. 55, FIG. 56, FIG. 57, FIG. 58, and FIG. 59, in FIG. 54 and FIG. 55 a Sun Drone Shadow Caster Scanner System 5400 comprises a plurality of shadow drones 5420, each said shadow drones 5420 comprising: a drone, said drone comprising: a remote controlled flying vehicle, and a shadow caster 5424, said shadow caster 5424 comprising: a panel, said panel depending from said drone; a plurality of camera drones 5430, each said camera drones comprising: said drone, and a video camera, said video camera depending from said drone; a memory stored in non-transitory computer-readable medium; a processor (not shown), said processor being able to control said shadow drones 5420 and said camera drones 5430, said processor comprising: said computer-readable medium; and a display (not shown); wherein said plurality of shadow drones 5420 are aligned in a flight formation so that said shadow casters 5424 form a substantially continuous collective shadow caster, said collective shadow caster comprising aligned said shadow casters 5424; wherein the sun illuminates said collective shadow caster to project high contrast shadows 5467 of known geometry, which form said one or more edges of luminosity on a house 5470 and its surroundings; wherein aligned said plurality of shadow drones 5420 in said flight formation move in formation across said area in order to sweep said one or more edges of luminosity across said house 5470 and its surroundings; wherein said video cameras of said camera drones 5430 detect said one or more edges of luminosity for three-dimensional points on said house 5470 and its surroundings and records said three-dimensional points into said memory; wherein said processor forms a three-dimensional data representation from recorded said three-dimensional points; wherein said processor generates said three-dimensional model of said house 5470 and its surroundings using said three-dimensional data representation; and wherein said three-dimensional model is displayed on said display using said processor. In FIG. 55, the sun drone operation flow chart 5500 describes the operation of a Sun Drone Shadow Caster Scanner System 5400. The first step in the operation of the Sun Drone Shadow Caster Scanner System 5400 comprises attaching the shadow casters 5424 to the shadow drones 5420 in the attach shadow casters step 5502. Next, in the arrange shadow caster step 5511, the shadow drones 5420 are arranged to form a nearly contiguous shadow caster in midair. Next, the camera drones 5430 are positioned in midair over the shadow drones 5420, in the position camera drones step 5505. Next, in the alignment decision step 5510, whether the shadow drones 5420 are aligned with the camera drones 5430 is determined. If the shadow drones 5420 are not aligned with the camera drones 5430, the drones are aligned in the align drones step 5540. Once the shadow drones 5420 are aligned with the camera drones 5430, whether the camera drones 5430 are focused on the subject is determined in the focus decision step 5515. If the camera drones 5430 are not focused, the camera drones 5430 are then focused in the focus camera step 5520. Once the camera drones 5430 are focused, the camera drones 5430 start recording video of the subject in the start recording step 5525. Next, in the start sweeping step 5545, the shadow drones 5420 begin to sweep edges of luminosity across the subject by flying in unison across and above the subject using the sun as a light source. Next, frames of the recorded video are collected and analyzed by the processor to make a point cloud in the collect and analyze step 5550. Next, new cloud points are filtered by the processor in the filter new cloud points step 5574. Next, the filtered point cloud display is updated in the update filtered cloud point step 5554. Next, whether the entire object has been scanned is determined in the entire scan decision step 5567. If the entire object has not been scanned, then repeat the collect and analyze step 5550, as described above. If the entire object has been scanned, then the processor filters the whole point cloud in the filter whole point cloud step 5570. Next, in the construct surface step 5575, the processor constructs a model of a three-dimensional surface from the filtered point cloud. Next, the surface is saved to file in the save file step 5535. Next, the model is displayed on the display by the processor in the display image step 5555. Whether another scan is needed is determined in the another scan decision step 5530. If another scan is needed, the arrange shadow caster step 5511 is repeated, as described above. If another scan is not needed, the shadow drones 5420 stop sweeping the edges of luminosity across the subject, in the stop sweeping step 5560. Lastly, the drones are stored after operation in the store scanner step 5580. In FIG. 56 and FIG. 57, a Drone Shadow Caster Scanner System 5600 comprises a plurality of shadow drones 5620, each said shadow drones 5620 comprising: a drone, said drone comprising: a remote controlled flying vehicle, and a shadow caster 5624, said shadow caster 5624 comprising: a panel, said panel depending from said drone; a plurality of light drones 5650, each said light drones 5650 comprising: said drone, and a light source, said light source depending from said drone; a plurality of camera drones 5630, each said camera drones 5630 comprising: said drone, and a video camera, said video camera depending from said drone; a memory stored in non-transitory computer-readable medium; a processor (not shown), said processor being able to control said shadow drones 5620, said light drones 5650, and said camera drones 5630, said processor comprising: said computer-readable medium; and a display (not shown); wherein said plurality of shadow drones 5640 are aligned in a flight formation so that said shadow casters 5624 form a substantially continuous collective shadow caster, said collective shadow caster comprising aligned said shadow casters 5624; wherein light drones 5650 illuminate said collective shadow caster to project high contrast shadows 5667 of known geometry, which form said one or more edges of luminosity on the house 5670 and its surroundings; wherein aligned said plurality of shadow drones 5620 in said flight formation move in formation across said house 5670 and its surroundings in order to sweep said one or more edges of luminosity across said house 5670 and its surroundings; wherein said video cameras of said camera drones 5630 detect said one or more edges of luminosity for three-dimensional points on said house 5670 and its surroundings and records said three-dimensional points into said memory; wherein said processor forms a three-dimensional data representation from recorded said three-dimensional points; wherein said processor generates said three-dimensional model of said house 5670 and its surroundings using said three-dimensional data representation; and wherein said three-dimensional model is displayed on said display using said processor. In FIG. 57, the drone operation flow chart 5700 describes the operation of a Drone Shadow Caster Scanner System 5600. The first step in the operation of the Drone Shadow Caster Scanner System 5600 comprises attaching the shadow casters 5624 to the shadow drones 5620 in the attach shadow casters step 5702. Next, lights are attached to the light drones 5650 in the attach light step 5708. Next, the light drones 5650 are positioned in midair in the position light drones step 5718. Next, in the arrange shadow caster step 5711, the shadow drones 5620 are arranged to form a nearly contiguous shadow caster in midair. Next, the camera drones 5630 are positioned in midair over the shadow drones 5620, in the position camera drones step 5705. Next, in the alignment decision step 5710, whether the shadow drones 5420 and light drones 5650 are aligned with the camera drones 5630 is determined. If the shadow drones 5620 and light drones 5650 are not aligned with the camera drones 5630, the drones are aligned in the align drones step 5740. Once the shadow drones 5620 and light drones 5650 are aligned with the camera drones 5630, whether the camera drones 5630 are focused on the subject is determined in the focus decision step 5715. If the camera drones 5630 are not focused, the camera drones 5630 are then focused in the focus camera step 5720. Once the camera drones 5630 are focused, the camera drones 5630 start recording video of the subject in the start recording step 5725. Next, in the start sweeping step 5745, the shadow drones 5620 begin to sweep edges of luminosity across the subject by flying in unison across and above the subject using the light drones 5650 as a light source. Next, frames of the recorded video are collected and analyzed by the processor to make a point cloud in the collect and analyze step 5750. Next, new cloud points are filtered by the processor in the filter new cloud points step 5774. Next, the filtered point cloud display is updated in the update filtered cloud point step 5754. Next, whether the entire object has been scanned is determined in the entire scan decision step 5767. If the entire object has not been scanned, then repeat the collect and analyze step 5750, as described above. If the entire object has been scanned, then the processor filters the whole point cloud in the filter whole point cloud step 5770. Next, in the construct surface step 5775, the processor constructs a model of a three-dimensional surface from the filtered point cloud. Next, the surface is saved to file in the save file step 5735. Next, the model is displayed on the display by the processor in the display image step 5755. Whether another scan is needed is determined in the another scan decision step 5730. If another scan is needed, the position light drones step 5718 is repeated, as described above. If another scan is not needed, the shadow drones 5620 stop sweeping the edges of luminosity across the subject, in the stop sweeping step 5760. Lastly, the drones are stored after operation in the store scanner step 5780. In FIG. 58, the drone algorithm flow chart 5800 describes the algorithm used by the Sun Drone Shadow Caster Scanner System 5400 and the Drone Shadow Caster Scanner System 5600. The first step in the algorithm for the Sun Drone Shadow Caster Scanner System 5400 and the Drone Shadow Caster Scanner System 5600 comprises starting the program, in the start program step 5804. Next, user-provided or program-specified scan and analysis parameters are collected in the collect parameters step 5808. Next, ensure the drones are coordinated in the ensure coordination step 5811. Next, the camera drones 5430 or 5630 start recording video in the start recording step 5825. Next, in the start sweeping step 5845, the shadow drones 5420 or 5620 begin to sweep edges of luminosity across the subject by flying in unison across and above the subject. Next, frames of the recorded video are collected in the collect video step 5850. Next, whether the video buffer is filled enough to analyze is determined in the buffer decision step 5824. If the buffer is not filled enough, the collect video step 5850 is repeated, as described above. If the buffer is filled enough to analyze, the video frames are analyzed to build a point cloud in the analyze frames step 5844. Next, whether there are still enough frames in the buffer is determined in the still buffered decision step 5858. If there are not enough frames in the buffer, the buffer decision step 5824 is repeated, as described above. If there are still enough frames in the buffer, whether the drones are still aligned is determined in the drone alignment decision step 5810. If the drones are not aligned, then the drones are aligned in the align drones step 5840. Once the drones are aligned, whether to finish sweeping is determined in the finish sweeping decision step 5878. If the sweeping is not finished, then the analyze frames step 5844 is repeated, as described above. If the sweeping is finished, then the shadow drones 5420 or 5620 stop sweeping in the stop sweeping step 5860. Next, the camera drones 5430 or 5630 stop recording video of the subject in the stop recording step 5865. Next, analyzing frames is finished in the finish analyzing frames step 5864. Next, the processor filters the point cloud in the filter point cloud step 5870. Next, in the construct surface step 5875, the processor constructs a model of a three-dimensional surface from the filtered point cloud. Next, the surface is saved to file in the save file step 5835. Next, the model is displayed on the display by the processor in the display image step 5855. Whether another scan is requested is determined in the another scan decision step 5830. If another scan is requested, the ensure coordination step 5811 is repeated, as described above. Lastly, if another scan is not requested, then the user exits the algorithm in the exit algorithm step 5890. In FIG. 59, a drone sweep flow chart 5900 describes a shadow caster sweep used by the Sun Drone Shadow Caster Scanner System 5400 and the Drone Shadow Caster Scanner System 5600. First, movement parameters of the drones are set in the set parameters step 5908. Next, the drones are aligned in midair in the align drones step 5911. Next, in the begin sweeping step 5945, the shadow drones 5420 or 5620 begin sweeping by flying in unison over the target area at a constant speed. Next, the drone positions are determined in the get current drone position step 5927. Next, whether the drones are misaligned is determined in the drone misalignment decision step 5910. If the drones are misaligned, then the drones are aligned in the align drones step 5940. Once the drones are not misaligned, then whether the shadow drones 5420 or 5620 reached the end of a sweep is determined in the end of sweep decision step 5978. If the shadow drones 5420 or 5620 did not reach the end of the sweep, then the get current drone position step 5927 is repeated, as described above. If the shadow drones 5420 or 5620 did reach the end of the sweep and another scan is necessary, the set parameters step 5908 is repeated with the drones traveling in the reverse direction of the first scan in the repeat algorithm step 5997.

The construction details of the invention as shown FIG. 54, FIG. 55, FIG. 56, FIG. 57, FIG. 58, and FIG. 59, are that a drone comprises a standard remote controlled flying vehicle, or the like. The shadow caster 5424 and 5624 comprise a lightweight, strong, rigid material, such as steel, copper cladding, plastic, high density plastic, silicone, PVC, fiberglass, carbon fiber, composite material, metal, galvanized steel, stainless steel, aluminum, brass, copper, wood, or other like material, and may further comprise configurable shapes, three-dimensionally-printed shapes, configurable opacity, such as liquid crystal, or the like, or various colored filters, or the like. The video cameras of the camera drones 5430 or 5630 comprise a digital or analog video camera, or the like. The light sources for the light drones 5650 comprise an incandescent light, a halogen light, fluorescent light, a linear light, a slitted tube light, an LED, an array of LEDs, a linear array of LEDs, different colored light sources, colored LEDs, lasers, an X-ray source, a UV source, an infrared source, or the like. The memory stored in non-transitory computer-readable medium comprises software, instructions, data, algorithms, or the like. The processor comprises a computer, a mobile phone, a PC, a CPU, or the like. The display comprises a monitor, a screen, a television, an augmented reality headset, a microscope, or the like.

Figure 60:
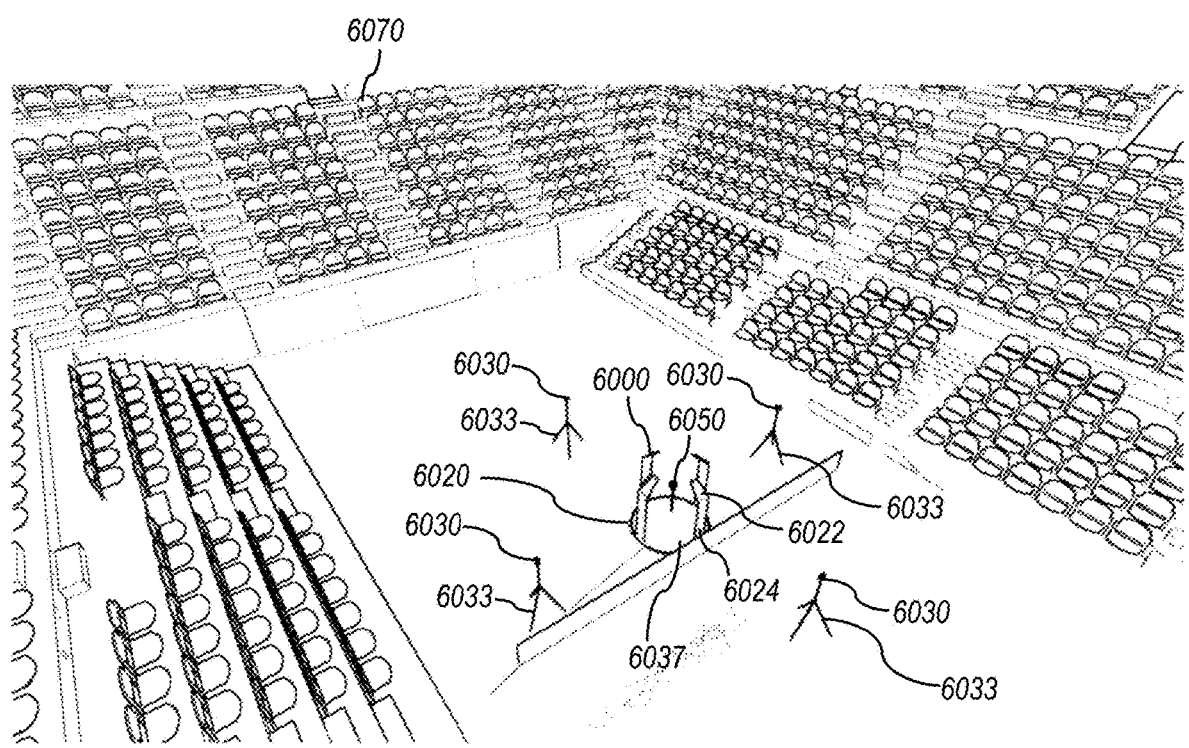
FIG. 60 is a perspective view of another system of the present invention being used to scan a stadium, according to various embodiments.
Figure 61:
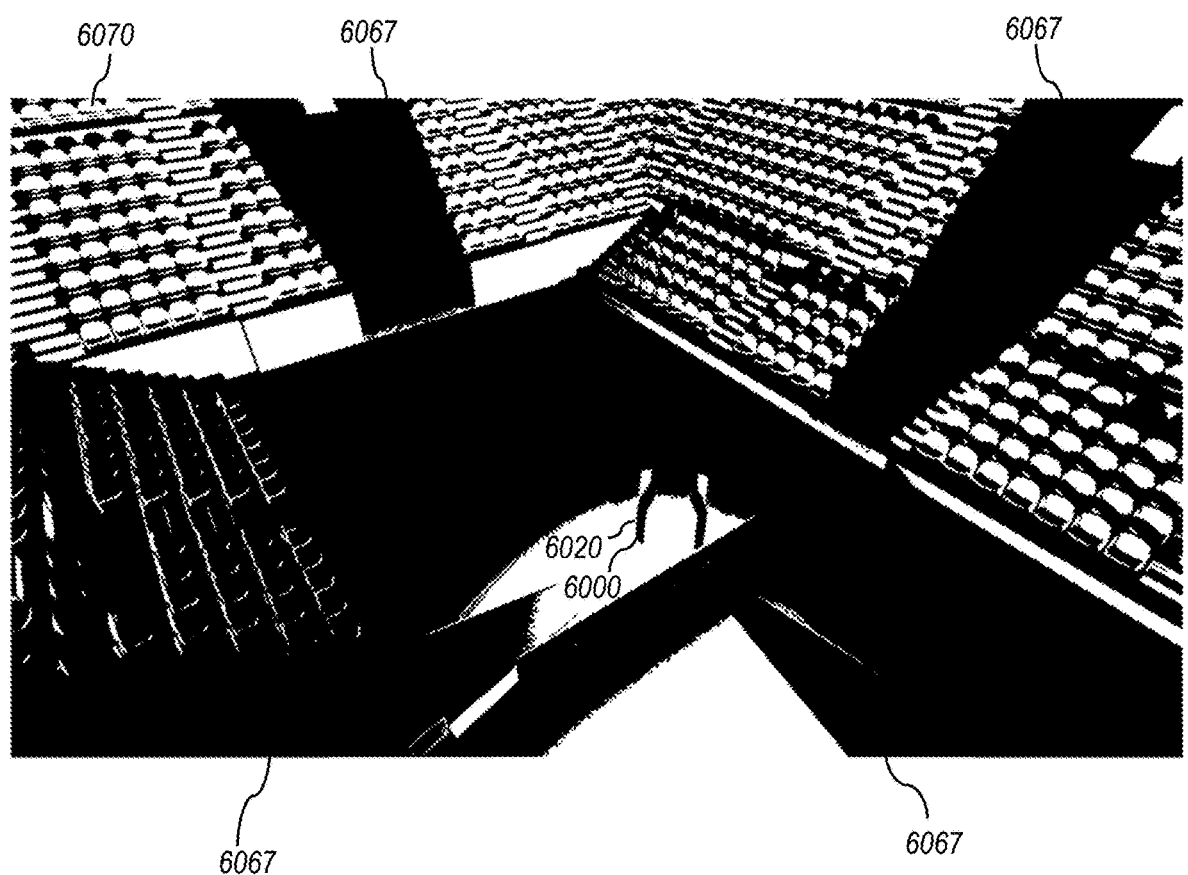
FIG. 61 is a perspective view of a system of FIG. 60 in the process of scanning a stadium, according to some examples.

Referring now to another embodiment of the invention, in FIG. 60 and FIG. 61, a Tripod Shadow Scanner System 6000 is shown. FIG. 60 is a perspective view of a Tripod Shadow Scanner System 6000 in a stadium 6070. FIG. 61 is a perspective view of a Tripod Shadow Scanner System 6000 in the process of scanning a stadium.

In further detail, still referring to the invention of FIG. 60 and FIG. 61, a Tripod Shadow Scanner System 6000 comprises a shadow caster platform 6037, said shadow caster platform 6037 being horizontal and capable of rotation; a light source 6050, said light source 6050 depending from the center of said shadow caster platform 6037; at least one shadow caster 6020, each said shadow caster 6020 depending from said shadow caster platform 6037 around said light source 6050 and comprising: a vertical panel 6024, and an angled panel 6022, said angled panel 6022 being angled towards said light source 6050; a plurality of video cameras 6030, each said video camera 6030 being mounted on a tripod 6033; a memory stored in non-transitory computer-readable medium; a processor (not shown), said processor comprising: said computer-readable medium; and a display (not shown); wherein said plurality of video cameras 6030 are arranged around said shadow caster platform 6037; wherein said light source 6050 illuminates said at least one shadow caster 6020 to project high contrast shadows 6067 of known geometry, which form said one or more edges of luminosity on the stadium 6070; wherein said shadow caster platform 6037 is rotated, thereby rotating said shadow casters 6020 around said light source 6050 in order to sweep said one or more edges of luminosity across said stadium 6070; wherein said plurality of video cameras 6030 detect said one or more edges of luminosity for three-dimensional points on said stadium 6070 and records said three-dimensional points into said memory; wherein said processor forms a three-dimensional data representation from recorded said three-dimensional points; wherein said processor generates said three-dimensional model of said stadium using said three-dimensional data representation; and wherein said three-dimensional model is displayed on said display using said processor. In other version of this embodiment, the shadow caster platform 6037 remained static while the light source 6050, which is directional, rotates.

The construction details of the invention as shown FIG. 60 and FIG. 61, are that a shadow caster platform 6037 comprises a strong rigid material, such as steel, copper cladding, plastic, high density plastic, silicone, PVC, fiber glass, carbon fiber, composite material, metal, galvanized steel, stainless steel, aluminum, brass, copper, wood, or other like material. The light sources 6050 comprises an incandescent light, a halogen light, fluorescent light, a linear light, a slitted tube light, an LED, an array of LEDs, a linear array of LEDs, different colored light sources, colored LEDs, lasers, an X-ray source, a UV source, an infrared source, or the like. The shadow casters 6020 comprise a strong rigid material, such as steel, copper cladding, plastic, high density plastic, silicone, PVC, fiberglass, carbon fiber, composite material, metal, galvanized steel, stainless steel, aluminum, brass, copper, wood, or other like material, and may further comprise configurable shapes, three-dimensionally-printed shapes, configurable opacity, such as liquid crystal, or the like, or various colored filters, or the like. The vertical panel 6024 comprises a strong rigid material, such as steel, copper cladding, plastic, high density plastic, silicone, PVC, fiberglass, carbon fiber, composite material, metal, galvanized steel, stainless steel, aluminum, brass, copper, wood, or other like material, and may further comprise configurable shapes, three-dimensionally-printed shapes, configurable opacity, such as liquid crystal, or the like, or various colored filters, or the like. The angled panel 6022 comprises a strong rigid material, such as steel, copper cladding, plastic, high density plastic, silicone, PVC, fiberglass, carbon fiber, composite material, metal, galvanized steel, stainless steel, aluminum, brass, copper, wood, or other like material, and may further comprise configurable shapes, three-dimensionally-printed shapes, configurable opacity, such as liquid crystal, or the like, or various colored filters, or the like. The video cameras 6030 comprise digital or analog video cameras, or the like. The memory stored in non-transitory computer-readable medium comprises software, instructions, data, algorithms, or the like. The processor comprises a computer, a mobile phone, a PC, a CPU, or the like. The display comprises a monitor, a screen, a television, an augmented reality headset, a microscope, or the like.

Figure 62:
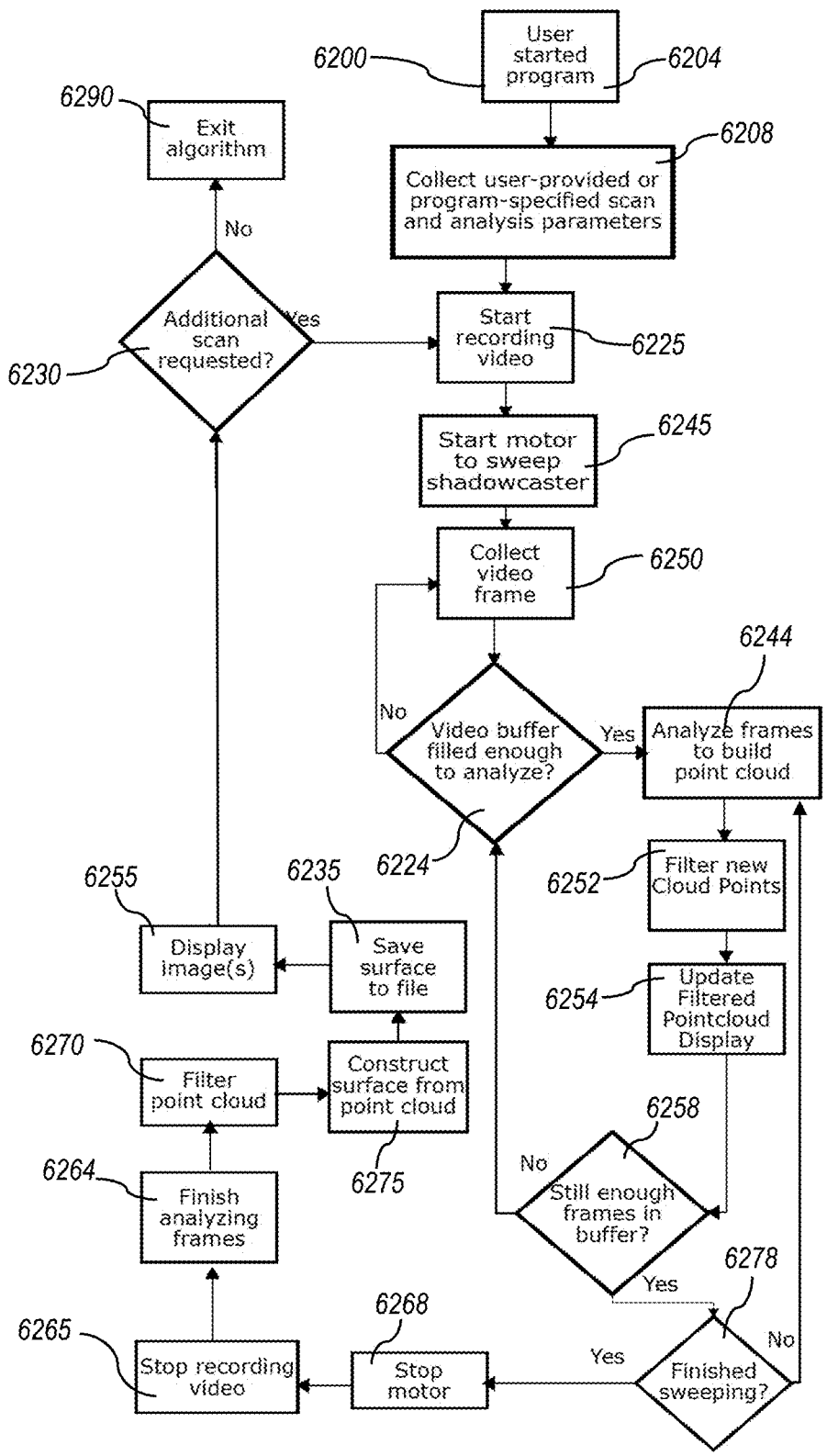
FIG. 62 shows a flow chart describing the algorithm used by embodiments of the present invention, which use a single shadow caster, according to some examples.
Figure 63:
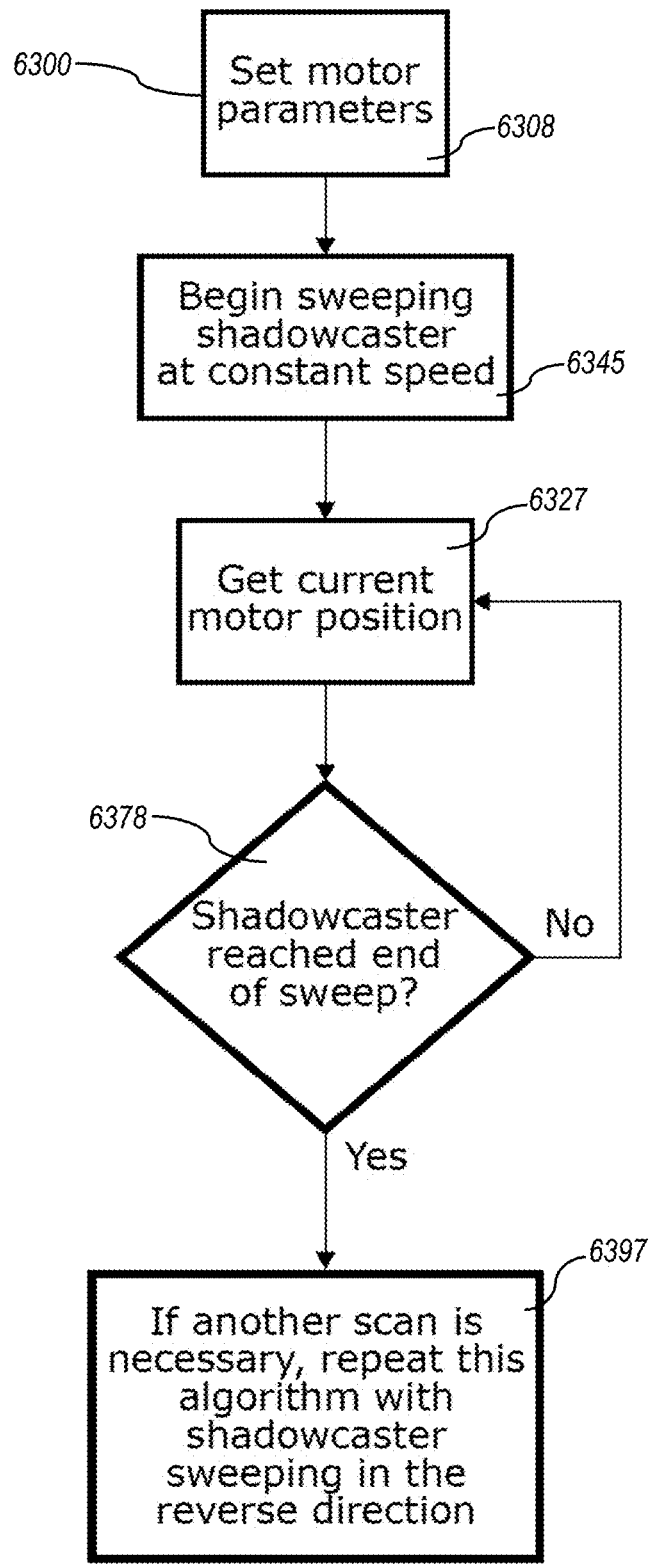
FIG. 63 is a flow chart, which describes a shadow caster sweep used by embodiments of the present invention, which use a single shadow caster, according to some examples.
Figure 64:
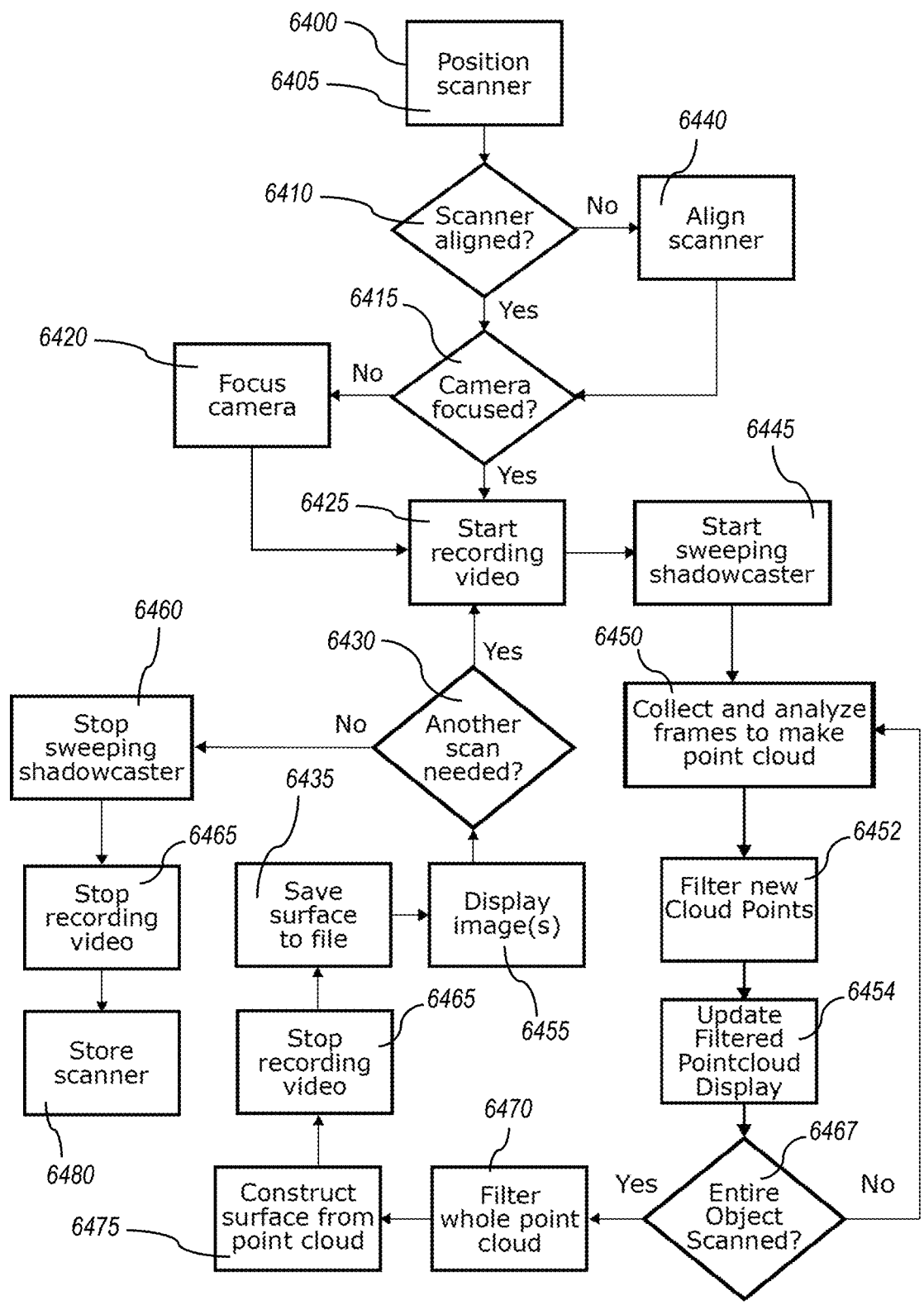
FIG. 64 demonstrates a flow chart describing the operation of an apparatus or system of the present invention, which is used for desktop scanning, according to various embodiments.

Referring now to another embodiment of the invention, in FIG. 62, FIG. 63, and FIG. 64, the algorithm, sweep, and operation, flow charts of a single mobile shadow caster scanner or desktop shadow scanner are shown. FIG. 62 displays an algorithm flow chart 6200 describing the algorithm used by a single mobile shadow caster scanner or desktop shadow scanner, which use a single shadow caster. FIG. 63 is a sweep flow chart 6300, which describes a shadow caster sweep used by a single mobile shadow caster scanner or desktop shadow scanner. FIG. 64 demonstrates an operation flow chart 6400 describing the operation of a single mobile shadow caster scanner or desktop shadow scanner.

In further detail, still referring to the invention of FIG. 62, FIG. 63, and FIG. 64, in FIG. 62, the algorithm flow chart 6200 describes the algorithm used by a single mobile shadow caster scanner or desktop shadow scanner. The first step in the algorithm for a single mobile shadow caster scanner or desktop shadow scanner comprises starting the program, in the start program step 6204. Next, user-provided or program-specified scan and analysis parameters are collected in the collect parameters step 6208. Next, the camera starts recording video in the start recording step 6225. Next, in the start sweeping step 6245, the motor is started in order to move the shadow caster and sweep edges of luminosity across the subject. Next, frames of the recorded video are collected in the collect video step 6250. Next, whether the video buffer is filled enough to analyze is determined in the buffer decision step 6224. If the buffer is not filled enough, the collect video step 6250 is repeated, as described above. If the buffer is filled enough to analyze, the video frames are analyzed to build a point cloud in the analyze frames step 6244. Next, new cloud points are filtered by the processor in the filter new cloud points step 6252. Next, the filtered point cloud display is updated in the update filtered cloud point step 6254. Next, whether there are still enough frames in the buffer is determined in the still buffered decision step 6258. If there are not enough frames in the buffer, the buffer decision step 6224 is repeated, as described above. If there are still enough frames in the buffer, whether to finish sweeping is determined in the finish sweeping decision step 6278. If the sweeping is not finished, then the analyze frames step 6244 is repeated, as described above. If the sweeping is finished, then the motor is stopped in the stop motor step 6268. Next, the camera stops recording video of the subject in the stop recording step 6265. Next, analyzing frames is finished in the finish analyzing frames step 6264. Next, the processor filters the point cloud in the filter point cloud step 6270. Next, in the construct surface step 6275, the processor constructs a model of a three-dimensional surface from the filtered point cloud. Next, the surface is saved to file in the save file step 6235. Next, the model is displayed on the display by the processor in the display image step 6255. Whether another scan is requested is determined in the another scan decision step 6230. If another scan is requested, the start recording step 6225 is repeated, as described above. Lastly, if another scan is not requested, then the user exits the algorithm in the exit algorithm step 6290. In FIG. 63, a sweep flow chart 6300 describes a shadow caster sweep used by a single mobile shadow caster scanner or desktop shadow scanner. First, the motor parameters are set in the set motor parameters step 6308. Next, in the begin sweeping step 6345, the shadow caster begins sweeping edges of luminosity across the subject. Next, the motor position is determined in the get current motor position step 6327. Next, whether the shadow caster reached the end of the sweep is determined in the end sweep decision step 6378. If the shadow caster did not reach the end of the sweep, the get current motor position step 6327 is repeated, as described above. If the shadow caster did reach the end of the sweep and another scan is necessary, the set motor parameters step 6308 is repeated in the reverse direction of the first scan in the repeat algorithm step 6397. In FIG. 64, the operation flow chart 6400 describes the operation of a single mobile shadow caster scanner or desktop shadow scanner. The first step in the operation of a single mobile shadow caster scanner or desktop shadow scanner comprises positioning the scanner over the subject, in the position scanner step 6405. Next, in the alignment decision step 6410, whether the scanner is aligned with the subject is determined. If the scanner is not aligned, the scanner is then aligned with the subject in the align scanner step 6440. Once the scanner is aligned, whether the camera is focused on the subject is determined in the focus decision step 6415. If the camera is not focused, the camera is then focused in the focus camera step 6420. Once the camera is focused, the camera starts recording video of the subject in the start recording step 6425. Next, in the start sweeping step 6445, the shadow caster begins to sweep edges of luminosity across the subject. Next, frames of the recorded video are collected and analyzed by the processor to make a point cloud in the collect and analyze step 6450. Next, new cloud points are filtered by the processor in the filter new cloud points step 6452. Next, the filtered point cloud display is updated in the update filtered cloud point step 6454. Next, whether the entire region of interest has been scanned is determined in the entire scan decision step 6467. If the entire region of interest has not been scanned, then repeat the collect and analyze step 6450, as described above. If the entire region of interest has been scanned, then the processor filters the whole point cloud in the filter whole point cloud step 6470. Next, in the construct surface step 6475, the processor constructs a model of a three-dimensional surface from the filtered point cloud. Next, the surface is saved to file in the save file step 6435. Next, the model is displayed on the display by the processor in the display image step 6455. Whether another scan is needed is determined in the another scan decision step 6430. If another scan is needed, the start recording step 6425 is repeated, as described above. If another scan is not needed, the shadow caster stops sweeping the edges of luminosity across the subject in the stop sweeping step 6460. Next, the camera stops recording video of the subject in the stop recording step 6465. Lastly, the scanner is stored after operation in the store scanner step 6480.

Figure 65:
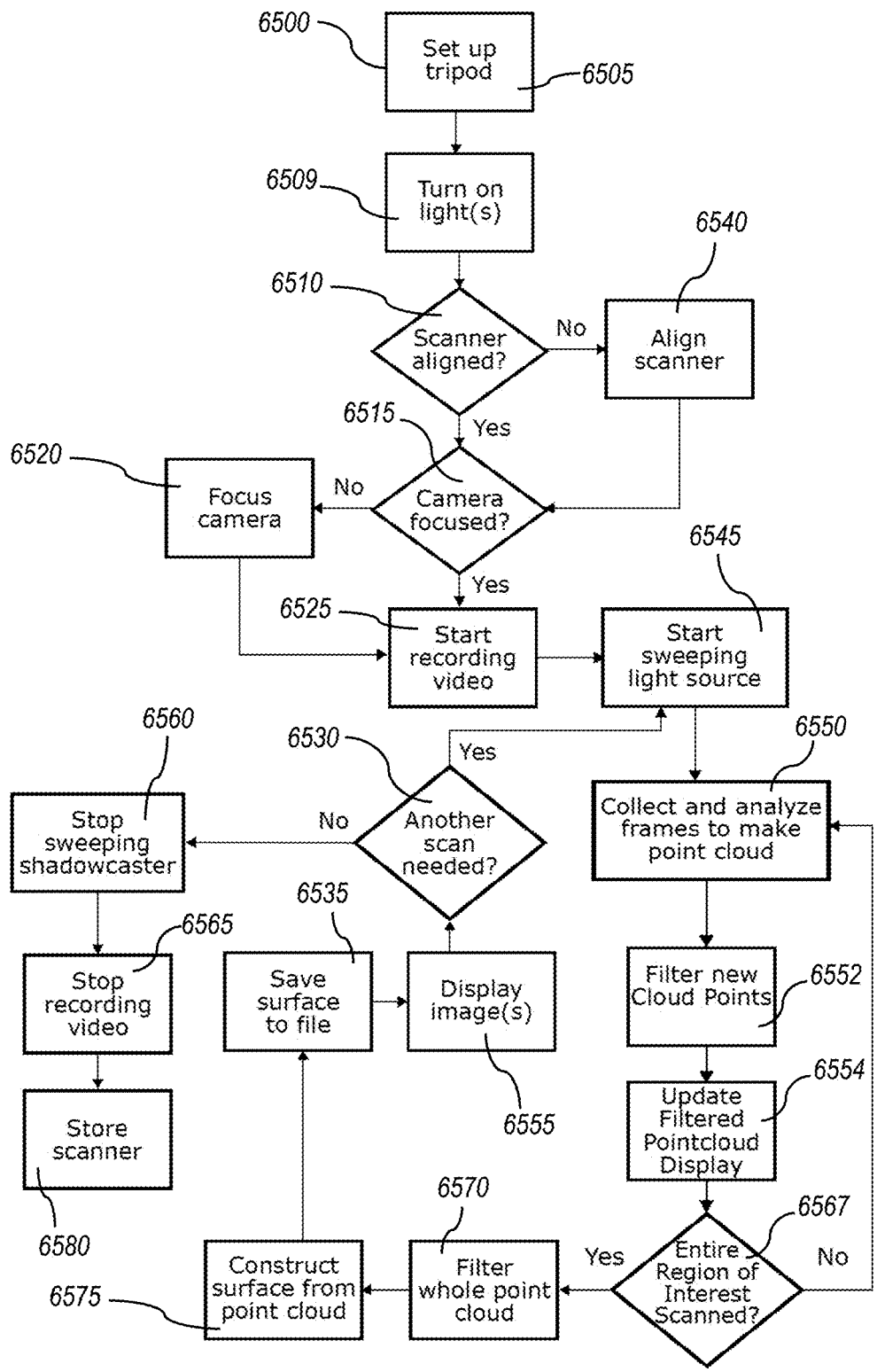
FIG. 65 illustrates a flow chart describing the operation of an apparatus or system of the present invention, which may be used with a tripod for scanning a room, according to various embodiments.
Figure 66:
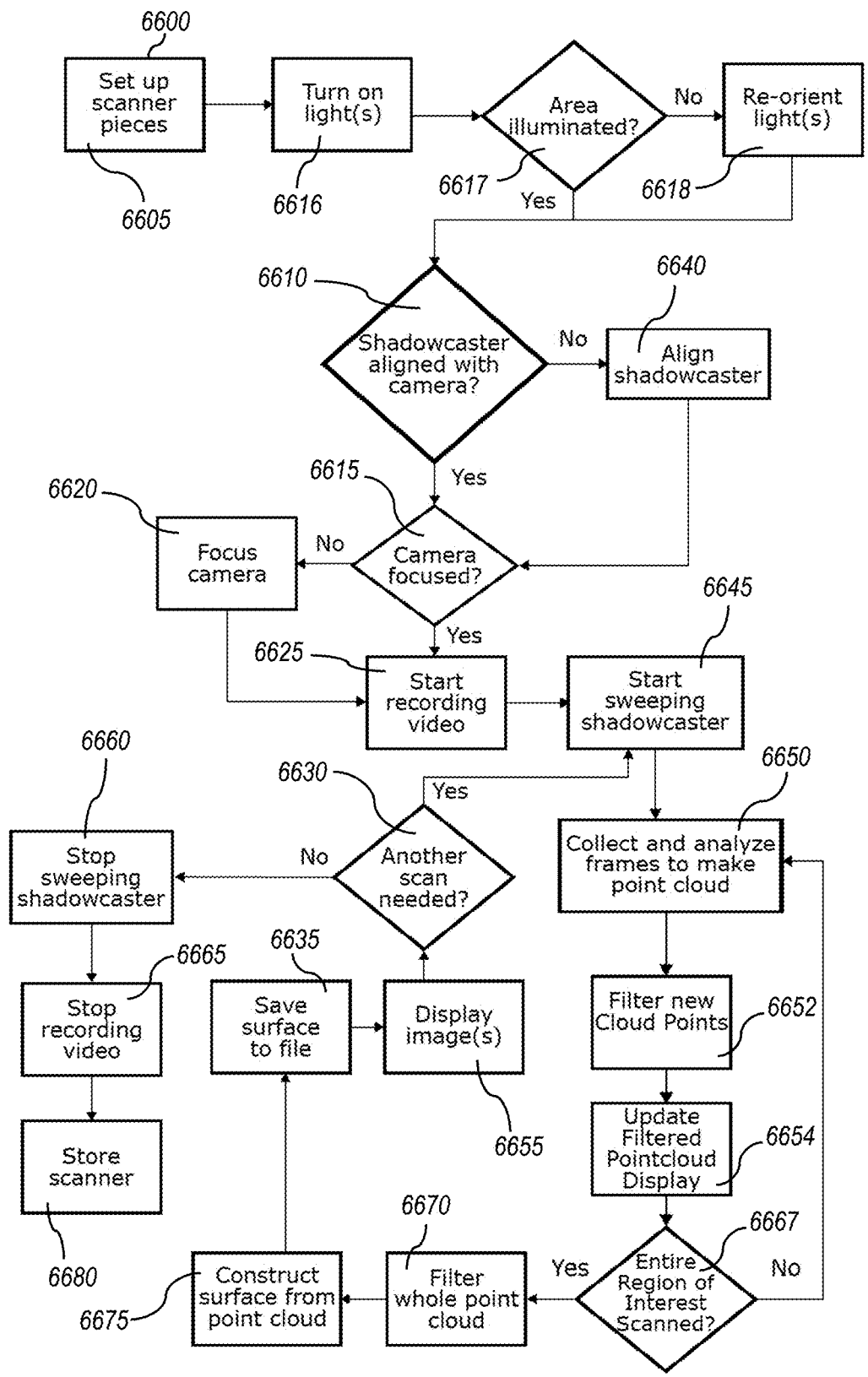
FIG. 66 depicts a flow chart describing the operation of an apparatus or system of the present invention, which may be used with overhead lights for scanning a room, according to various embodiments.

Referring now to another embodiment of the invention, in FIG. 65 and FIG. 66, the operation flow charts of room shadow caster scanners are shown. FIG. 65 illustrates a single tripod room scanner operation flow chart 6500 describing the operation of a shadow caster scanner, which may be used with a tripod, for scanning a room. FIG. 66 depicts a overhead lights room scanner operation flow chart 6600 describing the operation of a shadow caster scanner, which may be used with overhead lights, for scanning a room.

In further detail, still referring to the invention of FIG. 65 and FIG. 66, in FIG. 65, the single tripod room scanner operation flow chart 6500 describes the operation of a shadow caster scanner, which may be used with a tripod, for scanning a room. The first step in the operation of the shadow caster, which may be used with a tripod for scanning a room, comprises setting up the tripod in the room in the position scanner step 6505. Next, the lights are turned on in the light step 6509. Next, in the alignment decision step 6510, whether the scanner is aligned with the room is determined. If the scanner is not aligned, the scanner is then aligned with the room in the align scanner step 6540. Once the scanner is aligned, whether the camera is focused on the room is determined in the focus decision step 6515. If the camera is not focused, the camera is then focused in the focus camera step 6520. Once the camera is focused, the camera starts recording video of the room in the start recording step 6525. Next, in the start sweeping step 6545, the light source begins to sweep edges of luminosity across the room. Next, frames of the recorded video are collected and analyzed by the processor to make a point cloud in the collect and analyze step 6550. Next, new cloud points are filtered by the processor in the filter new cloud points step 6552. Next, the filtered point cloud display is updated in the update filtered cloud point step 6554. Next, whether the entire region of interest has been scanned is determined in the entire scan decision step 6567. If the entire region of interest has not been scanned, then repeat the collect and analyze step 6550, as described above. If the entire region of interest has been scanned, then the processor filters the whole point cloud in the filter whole point cloud step 6570. Next, in the construct surface step 6575, the processor constructs a model of a three-dimensional surface of the room from the filtered point cloud. Next, the surface is saved to file in the save file step 6535. Next, the model is displayed on the display by the processor in the display image step 6555. Whether another scan is needed is determined in the another scan decision step 6530. If another scan is needed, the start sweeping step 6545 is repeated, as described above. If another scan is not needed, the shadow caster stops sweeping the edges of luminosity across the room in the stop sweeping step 6560. Next, the camera stops recording video of the room in the stop recording step 6565. Lastly, the scanner is stored after operation in the store scanner step 6580. In FIG. 66, the overhead lights room scanner operation flow chart 6600 describing the operation of a shadow caster scanner, which may be used with overhead lights, for scanning a room. The first step in the operation of the shadow caster, which may be used with overhead lights for scanning a room, comprises setting up scanner pieces in the room in the set up step 6605. Next, the overhead lights are turned on in the light step 6616. Next, in the illumination decision step 6617, whether the area of the room is illuminated is determined. If the area of the room is not illuminated, then re-orient the lights in the re-orient lights step 6618. Once the area of the room is illuminated, in the alignment decision step 6610, whether the shadow caster is aligned with the camera is determined. If the shadow caster is not aligned with the camera, the shadow caster is then aligned with the camera in the align scanner step 6640. Once the shadow caster is aligned with the camera, whether the camera is focused on the room is determined in the focus decision step 6615. If the camera is not focused, the camera is then focused in the focus camera step 6620. Once the camera is focused, the camera starts recording video of the room in the start recording step 6625. Next, in the start sweeping step 6645, the shadow caster begins to sweep edges of luminosity across the room. Next, frames of the recorded video are collected and analyzed by the processor to make a point cloud in the collect and analyze step 6650. Next, new cloud points are filtered by the processor in the filter new cloud points step 6652. Next, the filtered point cloud display is updated in the update filtered cloud point step 6654. Next, whether the entire region of interest has been scanned is determined in the entire scan decision step 6667. If the entire region of interest has not been scanned, then repeat the collect and analyze step 6650, as described above. If the entire region of interest has been scanned, then the processor filters the whole point cloud in the filter whole point cloud step 6670. Next, in the construct surface step 6675, the processor constructs a model of a three-dimensional surface of the room from the filtered point cloud. Next, the surface is saved to file in the save file step 6635. Next, the model is displayed on the display by the processor in the display image step 6655. Next, whether another scan is needed is determined in the another scan decision step 6630. If another scan is needed, the start sweeping step 6645 is repeated, as described above. If another scan is not needed, the shadow caster stops sweeping the edges of luminosity across the room in the stop sweeping step 6660. Next, the camera stops recording video of the room in the stop recording step 6665. Lastly, the scanner is stored after operation in the store scanner step 6680.

Figure 67:
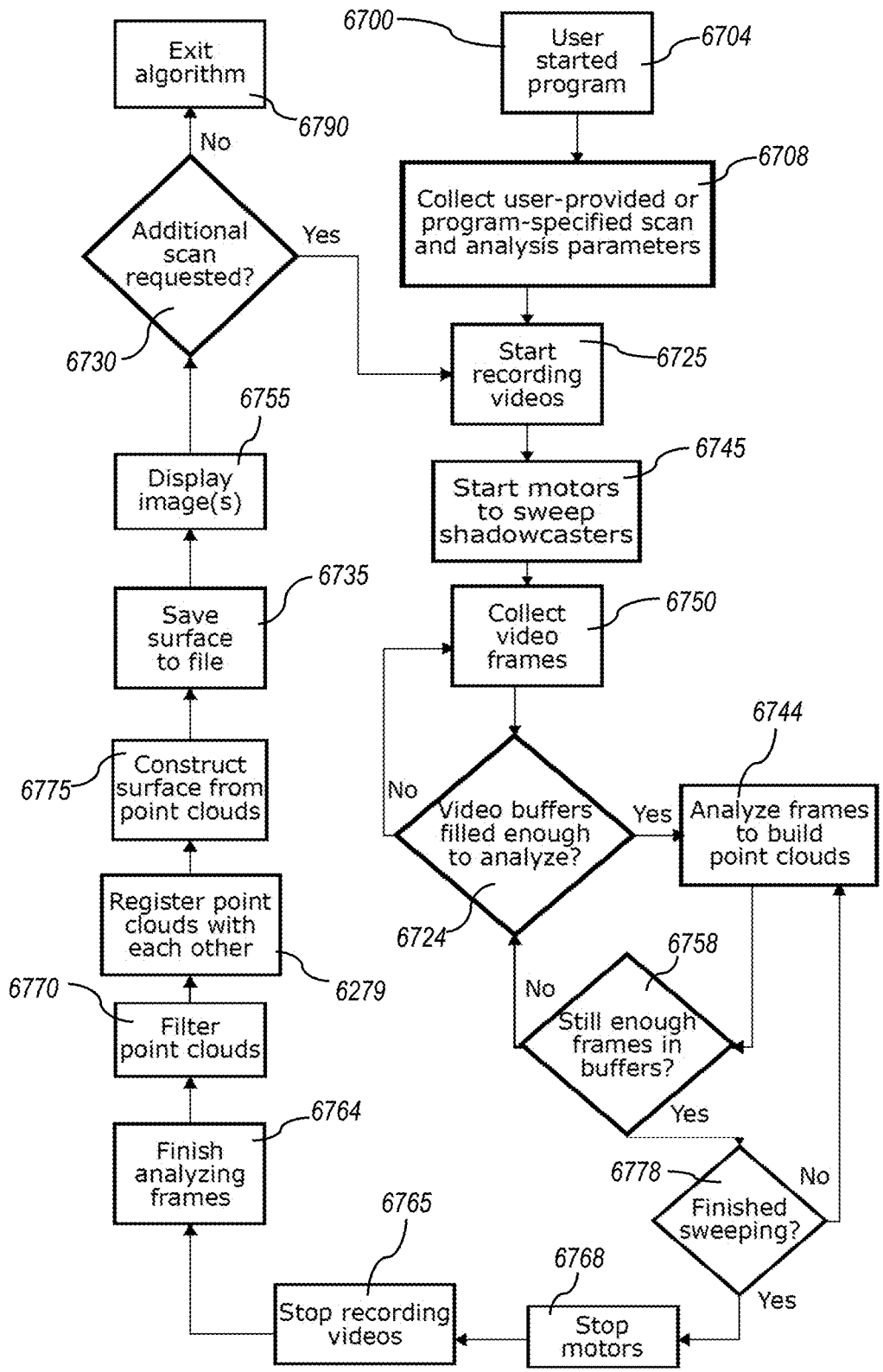
FIG. 67 shows a flow chart describing the algorithm used by embodiments of the present invention, which use a multiple cameras, according to some examples.
Figure 68:
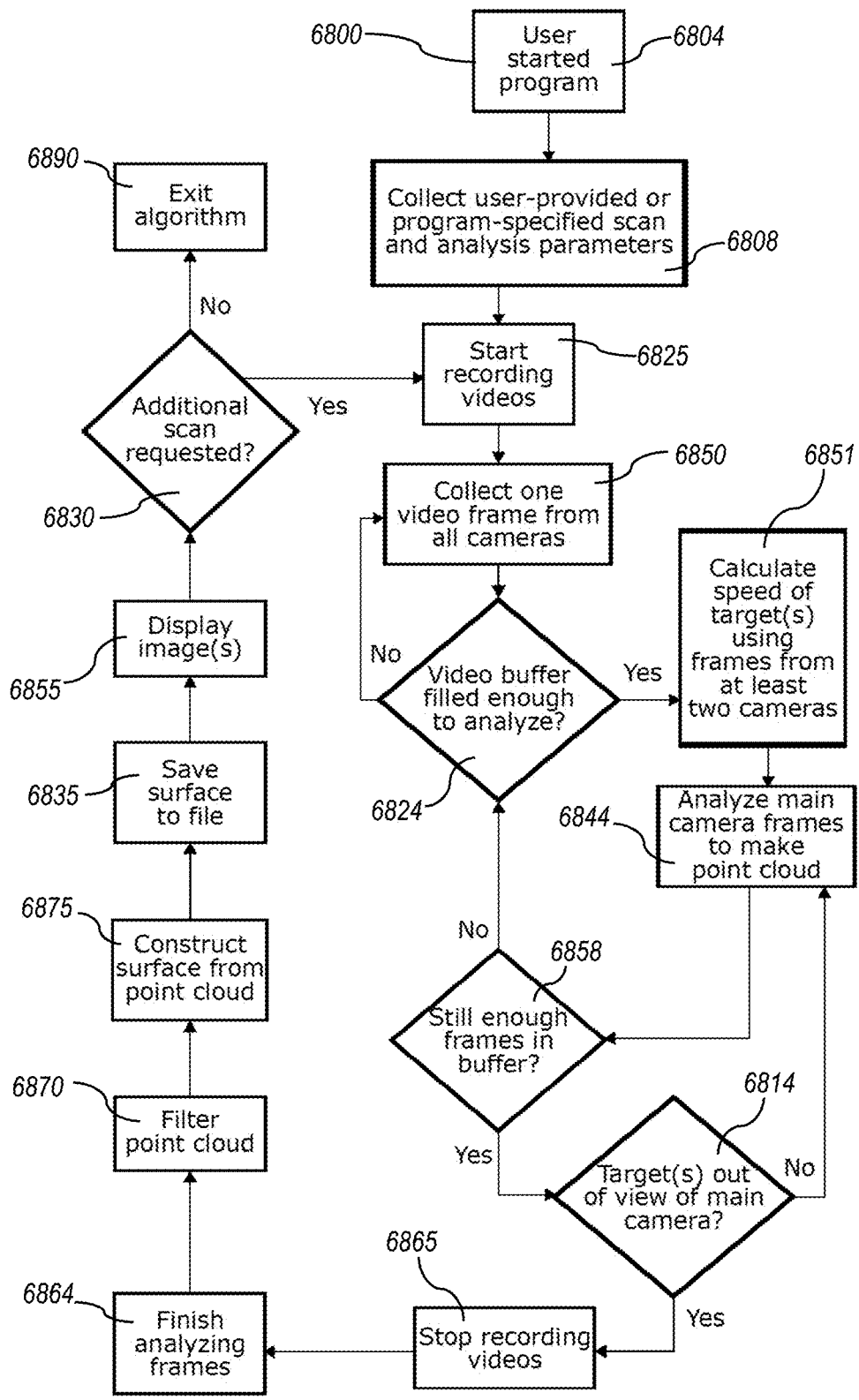
FIG. 68 is a flow chart describing the algorithm used by embodiments of the present invention, which use multiple cameras and a single static shadow caster, according to some examples.

Referring now to another embodiment of the invention, in FIG. 67 and FIG. 68, the algorithm flow charts of multiple camera shadow caster scanners are shown. FIG. 67 displays a multi-camera algorithm flow chart 6700 describing the algorithm used by a multiple camera shadow caster scanner. FIG. 68 illustrates a multi-camera static shadow caster flow chart 6800 describing the algorithm of a multiple camera shadow caster scanner, which uses a single static shadow caster.

In further detail, still referring to the invention of FIG. 67 and FIG. 68, in FIG. 67 a multi-camera algorithm flow chart 6700 describes the algorithm used by a shadow caster scanner, which uses multiple cameras. The first step in the algorithm for a multiple camera shadow caster scanner comprises starting the program, in the start program step 6704. Next, user-provided or program-specified scan and analysis parameters are collected in the collect parameters step 6708. Next, the multiple cameras start recording video in the start recording step 6725. Next, in the start sweeping step 6745, the motor is started in order to move the shadow caster and sweep edges of luminosity across the subject. Next, frames of the recorded video are collected from the multiple cameras in the collect video step 6750. Next, whether the video buffer is filled enough to analyze is determined in the buffer decision step 6724. If the buffer is not filled enough, the collect video step 6750 is repeated, as described above. If the buffer is filled enough to analyze, the video frames collected from the multiple cameras are analyzed to build a point cloud in the analyze frames step 6744. Next, whether there are still enough frames in the buffer is determined in the still buffered decision step 6758. If there are not enough frames in the buffer, the buffer decision step 6724 is repeated, as described above. If there are still enough frames in the buffer, whether to finish sweeping is determined in the finish sweeping decision step 6778. If the sweeping is not finished, then the analyze frames step 6744 is repeated, as described above. If the sweeping is finished, then the motors are stopped in the stop motor step 6768. Next, the multiple cameras stop recording video of the subject in the stop recording step 6765. Next, analyzing frames is finished in the finish analyzing frames step 6764. Next, the processor filters the point cloud in the filter point cloud step 6770. Next, point clouds from the multiple cameras are registered with each other in the register point clouds step 6279. Next, in the construct surface step 6775, the processor constructs a model of a three-dimensional surface from the filtered point clouds. Next, the surface is saved to file in the save file step 6735. Next, the model is displayed on the display by the processor in the display image step 6755. Whether another scan is requested is determined in the another scan decision step 6730. If another scan is requested, the start recording step 6725 is repeated, as described above. Lastly, if another scan is not requested, then the user exits the algorithm in the exit algorithm step 6790. In FIG. 68, the multi-camera static shadow caster flow chart 6800 describes the algorithm of a multiple camera shadow caster scanner, which uses multiple cameras, including a main camera, and a single static shadow caster. The first step in the algorithm for a multiple camera shadow caster scanner, which uses a single static shadow caster, comprises starting the program, in the start program step 6804. Next, user-provided or program-specified scan and analysis parameters are collected in the collect parameters step 6808. Next, the multiple cameras start recording video in the start recording step 6825. Next, one video frame is collected from all cameras in the collect one frame step 6850. Next, whether the video buffer is filled enough to analyze is determined in the buffer decision step 6824. If the buffer is not filled enough, the collect one frame step 6850 is repeated, as described above. If the buffer is filled enough to analyze, then calculate the speed of the target using frames from at least two cameras in the calculate speed step 6851. Next, the main camera video frames are analyzed to build a point cloud in the analyze frames step 6844. Next, whether there are still enough frames in the buffer is determined in the still buffered decision step 6858. If there are not enough frames in the buffer, the buffer decision step 6824 is repeated, as described above. If there are still enough frames in the buffer, then whether the target is out of view of the main camera is determined in the view target decision step 6814. If the target is not out of view of the main camera, then the analyze frames step 6844 is repeated, as described above. If the target is out of view of the main camera, then the multiple cameras stop recording video of the subject in the stop recording step 6865. Next, the processor filters the point cloud in the filter point cloud step 6870. Next, in the construct surface step 6875, the processor constructs a model of a three-dimensional surface from the filtered point cloud. Next, the surface is saved to file in the save file step 6835. Next, the model is displayed on the display by the processor in the display image step 6855. Whether another scan is requested is determined in the another scan decision step 6830. If another scan is requested, the start recording step 6825 is repeated, as described above. Lastly, if another scan is not requested, then the user exits the algorithm in the exit algorithm step 6890.

Figure 69:
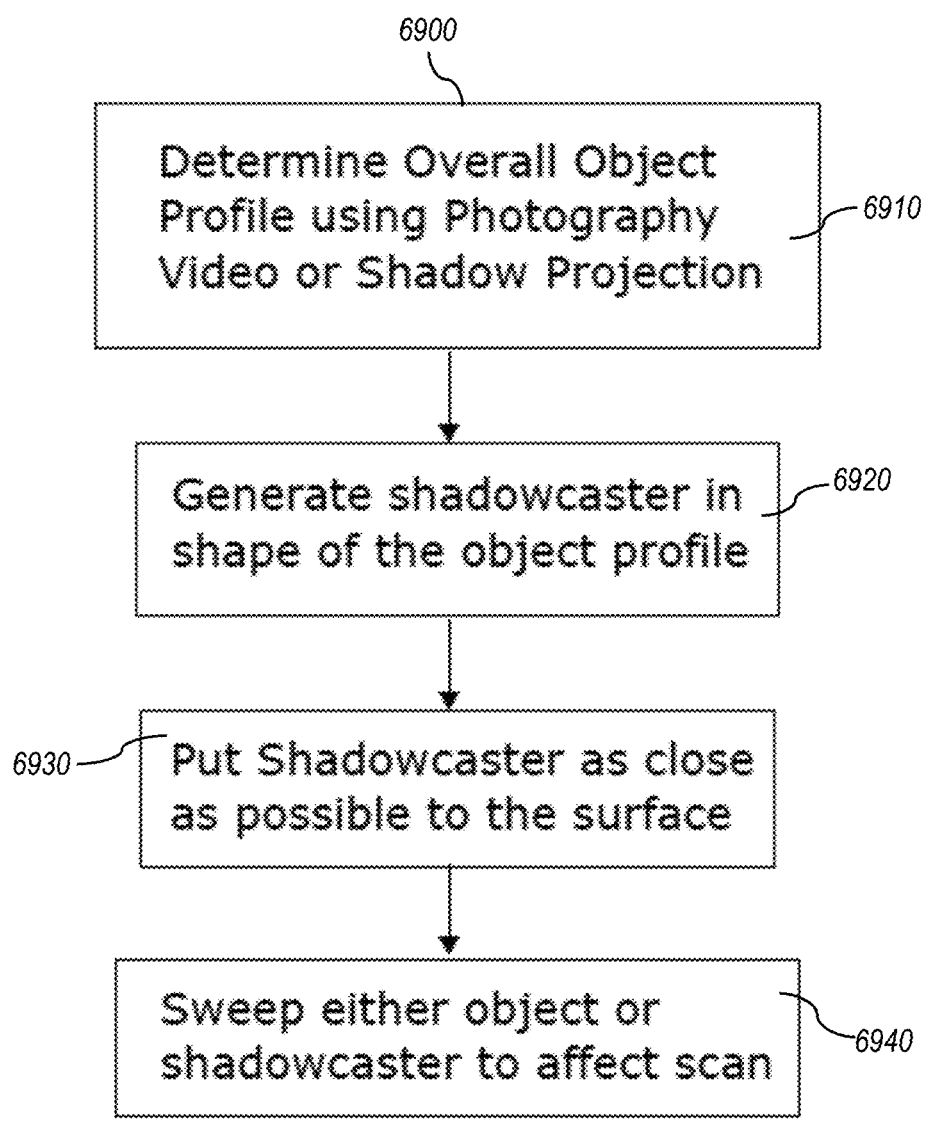
FIG. 69 displays a flow chart describing a method of creating a custom shadow caster, according to some examples.

Referring now to another embodiment of the invention, in FIG. 69, a flow chart describing a method of creating a custom shadow caster is shown.

In further detail, still referring to the invention of FIG. 69, a custom shadow caster flow chart 6900 describes a method of creating a custom-shaped shadow caster. First, in the determine profile step 6910, the overall object profile is determined using photography, video, or shadow projection. Next, in the shape generation step 6920, a custom-shaped shadow caster is generated in the shape of the overall object profile using three-dimensional printing, configurable shadow casters, other means of fabrication, or the like. Next, the custom-shaped shadow caster is placed as close to the surface of the object as possible in the place shadow caster step 6930. Lastly, either the object of the shadow caster sweep edges of luminosity across the object to affect the scan in the sweep object step 6940.

The construction details of the invention as shown in FIG. 69 are that a custom-shaped shadow caster comprises a strong rigid material, such as steel, copper cladding, plastic, high density plastic, silicone, PVC, fiberglass, carbon fiber, composite material, metal, galvanized steel, stainless steel, aluminum, brass, copper, wood, or other like material, and may further comprise configurable shapes, three-dimensionally-printed shapes, configurable opacity, such as liquid crystal, or the like, or various colored filters, or the like, which have be manipulated into the desired form.

Figure 70:
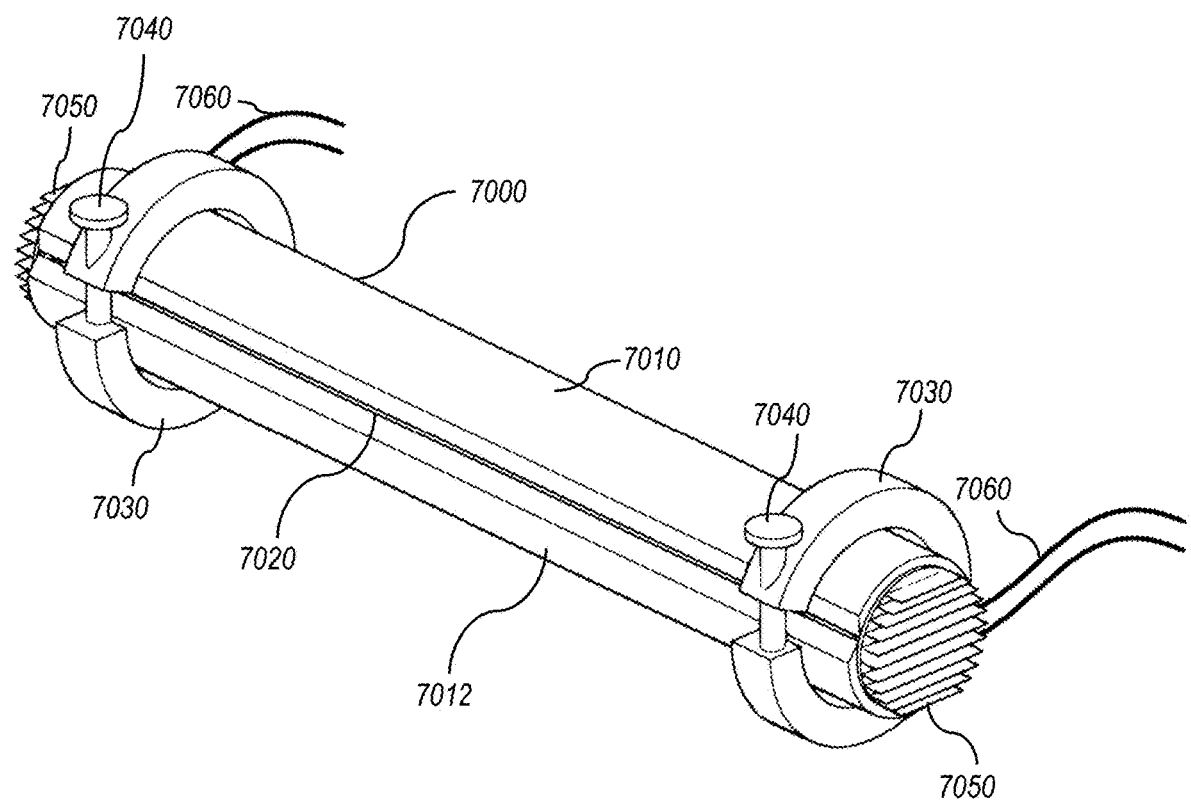
FIG. 70 is a perspective view of an apparatus of the present invention, which is a slitted light source, according to some examples.
Figure 71:
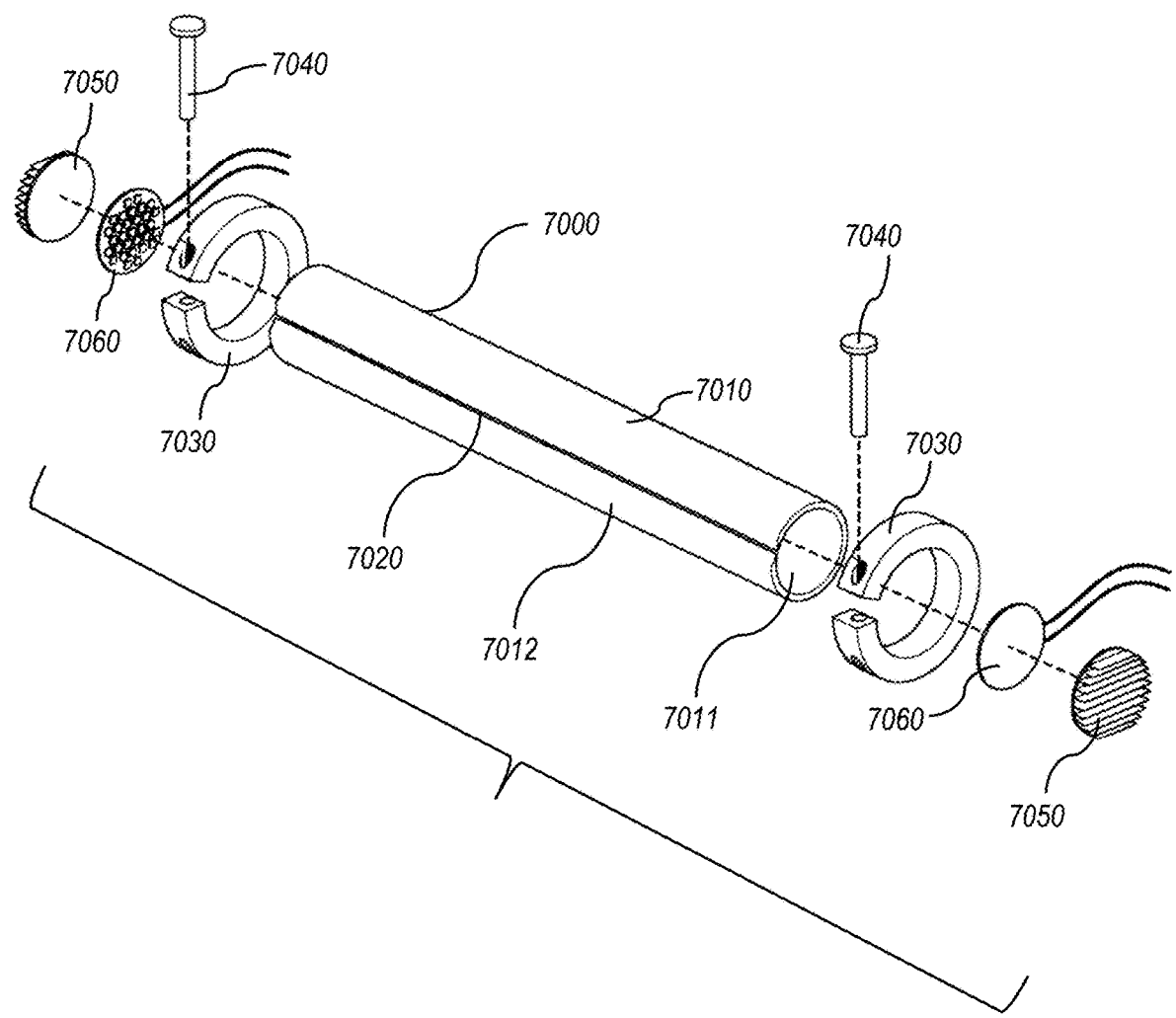
FIG. 71 illustrates an exploded view of the apparatus of FIG. 70, according to some examples.

Referring now to another embodiment of the invention, in FIG. 70 and FIG. 71, a slitted linear light source 7000, which provides improved scanning results with a shadow caster scanner, is shown. FIG. 70 displays a perspective view of a slitted linear light source 7000. FIG. 71 illustrates an exploded view of a slitted linear light source 7000.

In further detail, still referring to the invention of FIG. 70 and FIG. 71, a slitted linear light source 7000 comprises a slitted tube 7010, said slitted tube 7010 comprising: an interior 7011, said interior 7011 being painted white (paint including TiO2), an exterior 7012, said exterior 7012 being opaque, and a slit 7020, said slit 7020 running the length of said slitted tube 7010 and comprising: a width; two light sources 7060, said light sources 7060 depending on opposite ends of said slitted tube 7010; two heat sinks 7050, said heat sinks 7050 depending from said light sources 7060; two clamps 7030, each said clamp 7030 wrapping around said slitted tube and comprising: a screw 7040; wherein said clamps 7030 are capable of adjusting said width of said slit 7020. The slitted tube 7010 allows the escape of light in a very thin form, which improves the accuracy of a shadow caster scanner. This tube could alternatively be any cross-sectional shape as long as light escapes through a slit. The light sources 7060 are an assembly of LEDs. They can also have a refracting element in front of them, but they can also be bare, as depicted. The LEDs could alternatively be in a linear array (as in a strip), laid in the slitted tube 7010 so that they do not shine directly out of the slit 7020 (which may produce a non-uniform illumination). Alternatively, fiber optics can be used to guide light into the slitted tube 7010. This alternative removes the local generation of heat, at the expense of requiring a fiber bundle be attached to the light. The LEDs require have heat sinks. However, for the case of LEDs in a linear array, the slitted tube 7010 itself can be a heat sink. Other version may have a tube inside another tube, and allow for air to flow in the space between the tubes for heat control. The clamps 7030 are used to adjust the width of the slit 7020 by squeezing or releasing the slitted tube 7010, thereby allowing the size of the slit 7020 to be increased or decreased, which increases or decreases the light output, respectively. In variations of this embodiment, as well as in variation of other light sources of the present invention, it may be advantageous to add a single lens or series of lenses that have a net negative optical power (a negative focal length). These lens may be cylindrical and running along the length of the slitted tube 7010. Such lens or lenses would have the effect of reducing the intensity of the light on the object, increasing the angular extent of the light, and changing the effective distance of the light source, depending on the focal length of the lens or lens combination. For a negative lens, it would shift the effective source some amount closer to the object.

The construction details of the invention as shown in FIG. 70 and FIG. 71 are that the slitted tube 7010 comprises a flexible material, such as plastic, metal, composite material, or the like. The light sources 7060 comprise an incandescent light, a fiber optic bundle, a halogen light, fluorescent light, a linear light, a slitted tube light, an LED, an array of LEDs, a linear array of LEDs, different colored light sources, colored LEDs, lasers, an X-ray source, a UV source, an infrared source, or the like. The heat sinks 7050 comprise a heat-conducting material, such as metal, or the like. The clamps 7030 comprise a strong flexible material, such as steel, plastic, high density plastic, silicone, PVC, fiberglass, carbon fiber, composite material, metal, galvanized steel, stainless steel, aluminum, brass, copper, wood, or other like material. The screws 7040 comprise a strong rigid material, such as steel, copper cladding, plastic, high density plastic, silicone, PVC, fiberglass, carbon fiber, composite material, metal, galvanized steel, stainless steel, aluminum, brass, copper, wood, or other like material.

The advantages of the present invention include, without limitation, that the light sources of the present invention involve a minimum of optics, which incur weight and expense, and include the possibility of no lenses, in order to project a sharply contrasted pattern onto the object being scanned; that it does not require optics to optimize a beam of light at a particular distance; that the light sources of the present are relatively inexpensive compared to other technologies, such as lasers; that the light sources of the present invention are well-suited for a large depth of field; that the light sources of the present invention may comprise very bright sources and preserve accuracy if they are far away enough from the shadow caster; that the light sources of the present invention do not rely on a pulsing technology, or phase-detection technology used in schemes that assess distance through time-delay measurements, which may limit the number of simultaneous points measured, as well as the absolute resolution that is limited to the rise-time of typical electronics (100 ps), implying a 0.6-inch resolution in depth (meaning a 0.6 inch change results in an approximately 100 ps delay), and which are sensitive to noise; that the light sources of the present invention may optimally be an "extended" source along one dimension, in other words, a line, which illuminates the object from more angles than competing technology, and, as three-dimensional-scanned surfaces must be simultaneously illuminated and observed, this greater angle of illumination is advantageous, as more of the object can be scanned than typical projection-based scanners; that the hardware of the present invention can be separated among all three elements: light source, shadow caster, and light receiver, and, as such, there can be multiple cameras looking at a single shadow edge from one or more shadow casters; that, because a "point-source" that has a practical width, an extension of such a source, by reproducing it along a line, adds light while improving the scene contrast because the extension adds light, but does so with a reduced "solid angle" of the point light source because it is further away from the edge of the shadow caster, so the linear light source adds brightness while improving the resolution of the light source, on average; that the extended light source does not need to be not contiguous, and there may be more than one light source, as long as they are co-linear; that the light sources of the present invention can all conspire to cast one shadow edge (and, indeed increase its contrast), as this conspiring extends the range of angles while using separate light sources of practical construction, and increases the potential for developing custom illumination geometries for a given task; that a single light source can be used by multiple shadow casters, if they are removed physically from the light, and a single long and bright light at the top of a room can be used more locally by shadow caster-camera systems throughout that room, if they are aligned; that the shadow generation scheme of the present invention can produce large depth-of-field shadows, which retain their sharpness due to a geometric effect, and not an effect caused by lenses, which inherently introduce depth-of field issues, such as with projectors that use lenses, which must be tailored to produce sharp patterns only over a limited range; that, by removing the necessity of an engineered projector, and by removing the specificity of laser single-wavelength operation, the light source of the present invention can be of any wavelength, broad or narrow bandwidth, and use white-light, and a fluorescence-excitation wavelength, in the same scan and use a single camera in alternating "modes;" that the present invention may also use laser light to cast a shadow or cast a shadow into laser-light, which is particularly advantageous for fluorescence measurements during surgery; that, as a matter of spatial resolution, white light used in the present invention has less visible diffraction artifacts, producing a sharper shadow, than does laser light and white light does not suffer the problem of speckle as much as narrow-band laser light does, and this noise source is avoided by the present invention; that the sharp edge, and the large contrast afforded by the shadow in the present invention with its simple single-line geometry allows subsurface scattering measurements to be made on the fly, leading to real-time biomedical applications, such as optical biopsy for detecting skin cancer or cancer surgeries, since determining the margins of healthy versus cancerous tissue is an ongoing challenge; that, in the field of security, these subsurface scattering measurements allow for improved security scanning because it is very difficult to fake subsurface scattering features of a face; that the present invention; that these subsurface scattering measurements are useful to the cosmetics world in computer graphics recreation of actors' faces; that the use of white-light is advantageous over single-frequency sources (laser or lamp) because real-time comparisons of scattering properties may be made for different frequencies of light, such as the blue versus red, for example; that with the present invention it would be possible to use two distinct frequencies, since an array of LEDs may be used, and LEDs of different wavelengths may be interwoven and flash alternately, with the camera optimized in its exposure on each alternate frame to capture the color information; that the side triangle cross sections of the shadow casters of the present invention allow light to be extended laterally, while enabling the application of a shadow-caster very close to the object, while projecting a single, contiguous shadow edge, and these side shadow casters can connect to an intermediate shadow caster, as long as the shadow caster components, together, make a triangular cross-section as viewed along the line as defined by the extended light source; that the segmented shadow casters can speed up scans scalably for object geometries without much complexity by adding additional bands of shadows, so that, during the sweep, for simple objects, these separate shadows will not appear overlapping, and can be independently analyzed with the separation of the shadows depending on the complexity of the object; that the simplicity of the light source of the present invention indicates that any linear light source could serve, including x-rays, with which lensless projection of shadows is relatively easy, although X-ray structured scanning would not usually be particularly feasible, as it usually requires imaging a pattern to the object, and then imaging the scattered light; that typical embodiments of this technology hold the camera and the light source still for improved accuracy with the changes to the scene being due primarily to the shadow edge, meaning that overall the illumination of the object changes very little during the scan, especially for shadow areas that are relatively narrow, allowing for a large signal-to-noise ratio in the generated scan; that typical embodiments of the present invention have the camera, light, and shadow caster, all robustly attached to each other in a pre-calibrated way, so that of there is a loss of calibration, it can be determined again in an autonomous way (albeit with additional hardware such as a calibration stand); that the scanning technology of the present invention may be configured with a variety of tradeoffs including brightness versus accuracy, so that flat items can be scanned with very fine resolution (microscopy), using a specific optimized geometry; that the present invention has improved potential raw accuracy; that large-scale items can be measured with sub-mm accuracy, as long as cameras record the shadow edge; that the shadow can always be made sharp for improved accuracy, if it can be brought close to the item being scanned; that the scanner does not depend on feature-matching, or photogrammetry, in any way and instead depends on triangulation alone, using the aforementioned high signal to noise ratio, providing a single "right" answer, and increasing the certainty of the scan; that the noise in a scan can often be removed in a more automated way than other scanning techniques, which are often marred by banding and other artifacts; that with the present invention there are occasions when noise in the image overwhelms even the contrast afforded by the sharp shadow edge, however, this noise usually takes place many pixels from the shadow edge, and in the triangulation of the data that follows, then, such noise points end up very far removed and sparsely positioned in 3D space, making them easily filtered using a density-threshold algorithm, which calculates the average radius of each point from a certain number of its closest neighbors, and removes those with an average distance greater than a threshold, g resulting in a very clean scan; that object motion may be more easily compensated with the present invention by tracking motion during the scan (perhaps with a separate camera); that the present invention is useful for scanning people, who tend to shift their weight side-to-side, especially when sitting; that the present invention detects for each picture both the color of the object and its 3D coordinate simultaneously, meaning that if the object moves in three dimensions, its accurate color will also be represented, and the simultaneous determination of three dimensional shape, as well as color, is on a pixel-by-pixel basis removes the complex problem of registering the color image on a 3D scan in general, and in the present invention this data is auto-aligned, as it comes from a single camera. Overall, the present invention offers improved scanning quality and accuracy, which is relatively inexpensive, in the generation of three-dimensional models using shadow casters.

In broad embodiment, the present invention relates generally to apparatuses, methods, and systems, for generating one or more edges of luminosity to form three-dimensional models of objects or environments. In broad embodiment, the present invention comprises one or more light sources and one or more shadow casters, which generate one or more edges of luminosity across objects or areas being modeled, one or more means of detecting the one or more edges of luminosity, a means of moving the one or more edges of luminosity relative to the objects or areas being modeled, and a means of generating three-dimensional models of the objects or areas being modeled, as well as related methods and systems. These embodiments are not intended to limit the scope of the present invention.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above described embodiments, methods, and examples, but by all embodiments and methods that are within the scope and spirit of the invention as claimed.

The invention claimed is:
1. An apparatus for generating one or more edges of luminosity to form three-dimensional models of an object, said apparatus comprising:
   one or more light sources;
   one or more shadow casters, said one or more shadow casters comprising:
      a shape with at least one edge, said edge being contained within a plane, which contains said one or more light sources;
   one or more actuators, said actuators being capable of moving said one or more shadow casters;
   one or more image capture devices;
   a memory stored in non-transitory computer-readable medium; and
   a processor, said processor comprising:
      said computer-readable medium;

wherein said one or more light sources illuminate said one or more shadow casters to project sharp shadows of known geometry, which form said one or more edges of luminosity on said object;

wherein said one or more actuators move said one or more shadow casters in order to sweep said one or more edges of luminosity across said object;

wherein said one or more image capture devices capture images of said one or more edges of luminosity on said object and record said images into said memory;

wherein said processor forms a three-dimensional data representation from recorded said images; and wherein said processor generates said three-dimensional model of said object using said three-dimensional data representation.

2. An apparatus for generating one or more edges of luminosity to form three-dimensional models of an object, said apparatus comprising:

one or more light sources;

one or more shadow casters, said one or more shadow casters comprising:
 a shape with at least one edge, said edge being contained within a plane, which contains said one or more light sources;

one or more actuators, said actuators being capable of moving said one or more light sources;

one or more image capture devices;

a memory stored in non-transitory computer-readable medium; and a processor, said processor comprising:
 said computer-readable medium;

wherein said one or more light sources illuminate said one or more shadow casters to project sharp shadows of known geometry, which form said one or more edges of luminosity on said object;

wherein said one or more actuators move said one or more light sources in order to sweep said one or more edges of luminosity across said object;

wherein said one or more image capture devices capture images of said one or more edges of luminosity on said object and record said images into said memory;

wherein said processor forms a three-dimensional data representation from recorded said images; and wherein said processor generates said three-dimensional model of said object using said three-dimensional data representation.

3. An apparatus for generating one or more edges of luminosity to form three-dimensional models of an object, said apparatus comprising:

one or more light sources;

one or more shadow casters, said one or more shadow casters comprising:
 a shape with at least one edge, said edge being contained within a plane, which contains said one or more light sources;

one or more image capture devices;

a memory stored in non-transitory computer-readable medium; and a processor, said processor comprising:
 said computer-readable medium;

wherein said one or more light sources illuminate said one or more shadow casters to project sharp shadows of known geometry, which form said one or more edges of luminosity;

wherein said object moves through said one or more edges of luminosity in order to sweep said one or more edges of luminosity across said object;

wherein said one or more image capture devices detect the motion of said object moving through said one or more edges of luminosity and records said motion into said memory;

wherein said one or more image capture devices capture images of said one or more edges of luminosity on said object moving through said one or more edges of luminosity and record said images into said memory;

wherein said processor calculates the velocity of said object moving through said one or more edges of luminosity from recorded said motion;

wherein said processor forms a three-dimensional data representation from recorded said images and calculated said velocity; and wherein said processor generates said three-dimensional model of said object using said three-dimensional data representation.

4. An apparatus for generating one or more edges of luminosity to form three-dimensional models of the surroundings of an object, said apparatus comprising:

one or more light sources, said one or more light sources being mounted on said object;

one or more shadow casters, said one or more shadow casters being mounted on said object and comprising:
 a shape with at least one edge, said edge being contained within a plane, which contains said one or more light sources;

one or more actuators, said actuators being capable of moving said one or more shadow casters;

one or more image capture devices, said one or more image capture devices being mounted on said object;

a memory stored in non-transitory computer-readable medium; and a processor, said processor comprising:
 said computer-readable medium;

wherein said one or more light sources illuminate said one or more shadow casters to project sharp shadows of known geometry, which form said one or more edges of luminosity on said surroundings of said object;

wherein said one or more actuators move said one or more shadow casters in order to sweep said one or more edges of luminosity across said surroundings of said object;

wherein said one or more image capture devices capture images of said one or more edges of luminosity on said surroundings of said object and record said images into said memory;

wherein said processor forms a three-dimensional data representation from recorded said images;

wherein said processor generates said three-dimensional model of said surroundings of said object using said three-dimensional data representation; and wherein said three-dimensional model is stored in said memory.

5. An apparatus for generating one or more edges of luminosity to form three-dimensional models of the surroundings of an object, said apparatus comprising:

one or more light sources, said one or more light sources being mounted on said object;

one or more shadow casters, said one or more shadow casters being mounted on said object and comprising:
 a shape with at least one edge, said edge being contained within a plane, which contains said one or more light sources;

one or more image capture devices, said one or more image capture devices being mounted on said object;

a memory stored in non-transitory computer-readable medium; and a processor, said processor comprising:
said computer-readable medium;

wherein said one or more light sources illuminate said one or more shadow casters to project sharp shadows of known geometry, which form said one or more edges of luminosity on said surroundings of said object;

wherein said object moves through said surroundings of said object in order to sweep said one or more edges of luminosity across said surroundings of said object;

wherein said one or more image capture devices capture images of said one or more edges of luminosity on said surroundings of said object and record said images into said memory;

wherein said processor forms a three-dimensional data representation from recorded said images;

wherein said processor generates said three-dimensional model of said surroundings of said object using said three-dimensional data representation; and wherein said three-dimensional model is stored in said memory.

6. An apparatus for generating one or more edges of luminosity to form three-dimensional models of an object, said apparatus comprising:
one or more light sources;
one or more image capture devices;
a memory stored in non-transitory computer-readable medium; and
a processor, said processor comprising:
said computer-readable medium;
one or more shadow casters, said one or more shadow casters comprising:
a transparent liquid crystal matrix, said transparent liquid crystal matrix being controllable by said processor and being capable of generating opaque regions, said opaque regions comprising:
a shape with at least one edge, said edge being contained within a plane, which contains said one or more light sources;
wherein said one or more light sources illuminate said one or more shadow casters to project sharp shadows of known geometry, which form said one or more edges of luminosity on said object;
wherein said processor generates a series of said opaque regions on said transparent liquid crystal matrix, which simulates movement of said one or more shadow casters, in order to sweep said one or more edges of luminosity across said object;
wherein said one or more image capture devices capture images of said one or more edges of luminosity on said object and record said images into said memory;
wherein said processor forms a three-dimensional data representation from recorded said images; and
wherein said processor generates said three-dimensional model of said object using said three-dimensional data representation.

7. The apparatus as in any one of claims 1-6, wherein said one or more light sources are discrete or continuous.

8. The apparatus as in any one of claims 1-6, wherein said one or more light sources are linear.

9. The apparatus as in any one of claims 1-6, wherein said one or more light sources comprise one or more arrays of lights.

10. The apparatus as in any one of claims 1-2 and 6, wherein said shape of said one or more shadow casters is based on said object.

11. The apparatus as in any one of claims 1-2 and 4-5, wherein said one or more shadow casters further comprise configurable shapes.

12. The apparatus as in any one of claims 1-5, wherein said one or more shadow casters further comprise configurable opacity.

13. The apparatus as in any one of claims 1-6, wherein said one or more shadow casters further comprise color filters.

14. The apparatus as in one claim 1 or 4, wherein said one or more actuators rotate said one or more shadow casters.

15. The apparatus as in any one of claims 1-3 and 6, said apparatus further comprising an augmented reality headset, wherein said three-dimensional model is displayed in said augmented reality headset.

16. The apparatus of claim 2, wherein said one or more actuators rotate said one or more light sources.

17. The apparatus of claim 3, wherein said apparatus is installed in a room, said room comprising:
a ceiling, said apparatus being mounted on said ceiling.

18. The apparatus of claim 3, wherein said apparatus is installed in a room, said room comprising:
a ceiling, said apparatus and said one or more light sources being mounted on said ceiling.

19. The apparatus as in any one of claim 4 or 5, said apparatus further comprising:
an augmented reality headset;
wherein said three-dimensional model is displayed in said augmented reality headset and overlaid on said surroundings of said object.

20. The apparatus as in any one of claim 4 or 5, wherein said object is an augmented reality headset and said three-dimensional model is displayed in said augmented reality headset and overlaid on said surroundings of said augmented reality headset.

21. The apparatus as in any one of claim 4 or 5, wherein said object is a vehicle.

22. The apparatus as in any one of claim 4 or 5, wherein said object is a robot.

23. The apparatus as in any one of claim 4 or 5, wherein said apparatus and said object are submersible.

24. The apparatus as in any one of claims 1-5, wherein said one or more light sources are linear, and wherein said edge, which shares said plane with said one or more light sources, is parallel to said one or more light sources.

25. The apparatus as in any one of claims 1-3 and 6, said apparatus further comprising a display, wherein said three-dimensional model is displayed on said display.

26. The apparatus as in any one of claims 1-5, wherein said one or more shadow casters further comprise a transparent liquid crystal matrix, said transparent liquid crystal matrix being capable of generating opaque regions.

27. The apparatus as in any one of claims 1-5, wherein said one or more shadow casters further comprise periodic opacity variation.

28. The apparatus of claim 6, wherein said opaque regions of said transparent liquid crystal matrix further comprise regions of varying opacity.

29. The apparatus as in any one of claims 1-6, wherein said one or more shadow casters further comprise a pattern.

30. A method for generating one or more edges of luminosity to form three-dimensional models of an object, said method comprising:
providing one or more light sources;
providing one or more shadow casting elements, said one or more shadow casting elements comprising:

a shape with at least one edge, said edge being contained within a plane, which contains said one or more light sources;
projecting sharp shadows of known geometry to form said one or more edges of luminosity on said object using said one or more light sources and said one or more shadow casting elements;
moving said one or more shadow casting elements in order to move said one or more edges of luminosity across said object;
capturing images of said one or more edges of luminosity on said object;
forming a three-dimensional data representation from captured said images; and
generating said three-dimensional model of said object using said three-dimensional data representation.

31. A method for generating one or more edges of luminosity to form three-dimensional models of an object, said method comprising:
providing one or more light sources;
providing one or more shadow casting elements, said one or more shadow casting elements comprising:
a shape with at least one edge, said edge being contained within a plane, which contains said one or more light sources;
projecting sharp shadows of known geometry to form said one or more edges of luminosity on said object using said one or more light sources and said one or more shadow casting elements;
moving said one or more light sources in order to move said one or more edges of luminosity across said object;
capturing images of said one or more edges of luminosity on said object;
forming a three-dimensional data representation from captured said images; and
generating said three-dimensional model of said object using said three-dimensional data representation.

32. A method for generating one or more edges of luminosity to form three-dimensional models of an object, said method comprising:
providing one or more light sources;
providing one or more shadow casting elements, said one or more shadow casting elements comprising:
a shape with at least one edge, said edge being contained within a plane, which contains said one or more light sources;
projecting sharp shadows of known geometry to form said one or more edges of luminosity using said one or more light sources and said one or more shadow casting elements;
moving said object through said one or more edges of luminosity;
detecting the velocity of said object moving through said one or more edges of luminosity;
capturing images of said one or more edges of luminosity on said object moving through said one or more edges of luminosity;
forming a three-dimensional data representation from detected said velocity and captured said images; and
generating said three-dimensional model of said object using said three-dimensional data representation.

33. A method for generating one or more edges of luminosity to form three-dimensional models of the surroundings of an object, said method comprising:
providing one or more light sources, said one or more light sources being mounted on said object;
providing one or more shadow casting elements, said one or more shadow casting elements being mounted on said object and comprising:
a shape with at least one edge, said edge being contained within a plane, which contains said one or more light sources;
projecting sharp shadows of known geometry to form said one or more edges of luminosity on said surroundings of said object using said one or more light sources and said one or more shadow casting elements;
moving said one or more shadow casting elements in order to move said one or more edges of luminosity across said surroundings of said object;
capturing images of said one or more edges of luminosity on said surroundings of said object;
forming a three-dimensional data representation from captured said images;
generating said three-dimensional model of said surroundings of said object using said three-dimensional data representation; and
storing said three-dimensional model in non-transitory computer-readable medium.

34. A method for generating one or more edges of luminosity to form three-dimensional models of the surroundings of an object, said method comprising:
providing one or more light sources, said one or more light sources being mounted on said object;
providing one or more shadow casting elements, said one or more shadow casting elements being mounted on said object and comprising:
a shape with at least one edge, said edge being contained within a plane, which contains said one or more light sources;
projecting sharp shadows of known geometry to form said one or more edges of luminosity on said surroundings of said object using said one or more light sources and said one or more shadow casting elements;
moving said object in order to move said one or more edges of luminosity across said surroundings of said object;
capturing images of said one or more edges of luminosity on said surroundings of said object;
forming a three-dimensional data representation from captured said images;
generating said three-dimensional model of said surroundings of said object using said three-dimensional data representation; and
storing said three-dimensional model in non-transitory computer-readable medium.

35. A method for generating one or more edges of luminosity to form three-dimensional models of an object, said method comprising:
providing one or more light sources;
providing one or more shadow casting elements, said one or more shadow casting elements comprising:
a transparent liquid crystal matrix, said transparent liquid crystal matrix being capable of generating opaque regions, said opaque regions comprising:
a shape with at least one edge, said edge being contained within a plane, which contains said one or more light sources;
projecting sharp shadows of known geometry to form said one or more edges of luminosity on said object using said one or more light sources and said one or more shadow casting elements;
generating a series of said opaque regions on said transparent liquid crystal matrix, which simulates movement of said one or more shadow casting elements, in order to move said one or more edges of luminosity across said object;

capturing images of said one or more edges of luminosity on said object;

forming a three-dimensional data representation from captured said images; and generating said three-dimensional model of said object using said three-dimensional data representation.

36. The method as in any one of claims 30-35, wherein said one or more light sources are discrete or continuous.

37. The method as in any one of claims 30-35, wherein said one or more light sources are linear.

38. The method as in any one of claims 30-35, wherein said one or more light sources comprise one or more arrays of lights.

39. The method as in any one of claims 30-31 and 35, wherein said shape of said one or more shadow casting elements is based on said object.

40. The method as in any one of claims 30-31 and 33-34, wherein said one or more shadow casting elements comprise configurable shapes.

41. The method as in any one of claims 30-34, wherein said one or more shadow casting elements further comprise configurable opacity.

42. The method as in any one of claims 30-35, wherein said one or more shadow casting elements further comprise color filters.

43. The method as in any one of claims 30-31 and 33, wherein moving said one or more shadow casting elements comprises rotation.

44. The method of claim 32, wherein said object moves through a room, said room comprising:

a ceiling, said one or more shadow casting elements being mounted on said ceiling.

45. The method of claim 32, wherein said object moves through a room, said room comprising:

a ceiling, said one or more shadow casting elements and said one or more light sources being mounted on said ceiling.

46. The method of claim 33, wherein said object is an augmented reality headset, said method furthering comprising:

displaying said three-dimensional model in said augmented reality headset overlaid on said surroundings of said augmented reality headset.

47. The method of claim 34, wherein said object is an augmented reality headset, said method furthering comprising:

displaying said three-dimensional model in said augmented reality headset overlaid on said surroundings of said augmented reality headset.

48. The method as in any one of claims 30-34, wherein said one or more light sources are linear, and wherein said edge, which shares said plane with said one or more light sources, is parallel to said one or more light sources.

49. The method as in any one of claims 30-32 and 35, said method further comprising displaying said three-dimensional model.

50. The method as in any one of claims 30-34, wherein said one or more shadow casting elements further comprise a transparent liquid crystal matrix, said transparent liquid crystal matrix being capable of generating opaque regions.

51. The method as in any one of claims 30-34, wherein said one or more shadow casting elements further comprise periodic opacity variation.

52. The method of claim 35, wherein said opaque regions of said transparent liquid crystal matrix further comprise regions of varying opacity.

53. The method as in any one of claims 30-35, wherein said one or more shadow casting elements further comprise a pattern.

* * * * *